US009969986B2

(12) United States Patent
Akahata et al.

(10) Patent No.: US 9,969,986 B2
(45) **Date of Patent: *May 15, 2018**

(54) VIRUS LIKE PARTICLE COMPRISING MODIFIED ENVELOPE PROTEIN E3

(71) Applicant: VLP Therapeutics, LLC, Wilmington, DE (US)

(72) Inventors: Wataru Akahata, Kensington, MD (US); Ryuji Ueno, Easton, MD (US)

(73) Assignee: VLP Therapeutics, LLC, Wilmington, DE (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/820,785

(22) Filed: Aug. 7, 2015

(65) Prior Publication Data

US 2016/0040134 A1 Feb. 11, 2016

Related U.S. Application Data

(60) Provisional application No. 62/198,949, filed on Jul. 30, 2015, provisional application No. 62/120,569, filed on Feb. 25, 2015, provisional application No. 62/101,514, filed on Jan. 9, 2015, provisional application No. 62/079,128, filed on Nov. 13, 2014, provisional application No. 62/035,037, filed on Aug. 8, 2014.

(51) Int. Cl.

| | |
|---|---|
| ***C12N 7/00*** | (2006.01) |
| ***A61K 39/12*** | (2006.01) |
| ***C07K 14/005*** | (2006.01) |
| ***A61K 39/015*** | (2006.01) |
| *A61K 39/00* | (2006.01) |

(52) U.S. Cl.

CPC ............ *C12N 7/00* (2013.01); *A61K 39/0005* (2013.01); *A61K 39/0011* (2013.01); *A61K 39/015* (2013.01); *A61K 39/12* (2013.01); *C07K 14/005* (2013.01); *A61K 2039/5258* (2013.01); *A61K 2039/58* (2013.01); *A61K 2039/585* (2013.01); *C07K 2319/00* (2013.01); *C07K 2319/40* (2013.01); *C12N 2770/36123* (2013.01); *C12N 2770/36134* (2013.01)

(58) Field of Classification Search

CPC ........... C12N 2770/36123; C12N 2770/36142; C12N 2740/10023; C12N 2799/021; C12N 2799/022; A61K 2039/5258; A61K 2039/505; A61K 38/00; A61K 48/00; A61K 38/177; A61K 39/145; A61K 47/6843; A61K 47/6901; C07K 14/005; C07K 16/1081; C07K 2317/21; C07K 2317/24; Y10S 424/82

See application file for complete search history.

(56) References Cited

U.S. PATENT DOCUMENTS 5,439,809 A 8/1995 Haynes et al.
5,580,773 A 12/1996 Kang et al.
5,629,204 A 5/1997 Honjo et al.
5,698,520 A 12/1997 Honjo et al.
5,939,598 A 8/1999 Kucherlapati et al.
7,101,550 B2 9/2006 Wood et al.
7,595,048 B2 9/2009 Honjo et al.
7,790,181 B2 * 9/2010 Platteborze .......... A61K 39/193 424/204.1
9,249,191 B2 * 2/2016 Ueno .................. C07K 14/005
9,353,353 B2 * 5/2016 Nabel .................... A61K 39/12
9,363,353 B1 6/2016 Chik
2003/0108521 A1 6/2003 Calatrava
2005/0214321 A1 9/2005 Rasochova et al.
2007/0122378 A1 5/2007 Freeman et al.
2009/0298955 A1 12/2009 Handa et al.
2009/0305950 A1 12/2009 Minato et al.
2009/0312190 A1 12/2009 Santiago et al.
2011/0081341 A1 4/2011 Honjo et al.
2011/0207223 A1 8/2011 Tang et al.
2012/0003266 A1 1/2012 Nable et al.
2013/0251744 A1 9/2013 Ueno et al.
2014/0120125 A1 5/2014 Ella et al.
2014/0127247 A1 5/2014 Dubensky, Jr. et al.
2014/0363458 A1 12/2014 Ueno et al.
2015/0017194 A1 1/2015 Akahata et al.
2016/0040134 A1 2/2016 Akahata et al.
2016/0200775 A1 7/2016 Akahata et al.
2016/0303221 A1 * 10/2016 Nabel .................... A61K 39/12

FOREIGN PATENT DOCUMENTS

CN 102321639 A 1/2012
CN 106085974 A 11/2016
JP H04-506301 A 11/1992
JP 2007-512842 A 5/2007
JP 2008-543774 A 12/2008

(Continued)

OTHER PUBLICATIONS

Pushko et al. Virology, 1997, vol. 239, pp. 389-401.*
António Roldao et al., "Virus-like particles in vaccine development", Expert Reviews Vaccines, vol. 9, No. 10, (2010), pp. 1149-1176.
Wataru Akahata et al., "A VLP vaccine for epidemic Chikungunya virus protects non-human primates against infection", Nat Med., Mar. 2010, vol. 16, No. 3, (12 pages total).
International Search Report, issued by International Searching Authority in corresponding International Application No. PCT/JP2015/003997, dated Oct. 27, 2015.
Rodion Gorchakov et al.,"Comparative analysis of the alphavirus-based vectors expressing Rift Valley fever virus glycoproteins", Virology, vol. 366, (2007), pp. 212-225.
Sigrid Elshuber et al., "Cleavage of protein prM is necessary for Infection of BHK-21 cells by tick-borne encephalitis virus", Journal of General Virology, (2003), vol. 84, pp. 183-191.
Simona Ozden et al., "Inhibition of Chikungunya Virus Infection in Cultured Human Muscle Cells by Furin Inhibitors", Journal of Biological Chemistry, vol. 283, No. 32, Aug. 8, 2008. (10 pages total).

(Continued)

*Primary Examiner* — Bao Li
(74) *Attorney, Agent, or Firm* — Sughrue Mion, PLLC

(57) ABSTRACT

A virus like particle comprising a viral structural protein which comprises modified envelope protein E3. The viral structural protein may be that derived from or alphavirus or flavivirus. Especially, the viral structural protein may be derived from Chikungunya virus or Venezuelan equine encephalitis virus.

16 Claims, 11 Drawing Sheets

(56) References Cited

FOREIGN PATENT DOCUMENTS

| | | | | |
|---|---|---|---|---|
| WO | 93/10152 | A1 | | 5/1993 |
| WO | 97/12048 | A1 | | 4/1997 |
| WO | 99/41383 | A1 | | 8/1999 |
| WO | 02/096939 | A2 | | 12/2002 |
| WO | 2004/043399 | A2 | | 5/2004 |
| WO | 2006/040334 | A1 | | 4/2006 |
| WO | 2006/088229 | A1 | | 8/2006 |
| WO | 2007/003384 | A1 | | 1/2007 |
| WO | 2007/059715 | A2 | | 5/2007 |
| WO | 2007/100098 | A1 | | 9/2007 |
| WO | 2008/025067 | A1 | | 3/2008 |
| WO | 2009/079185 | A2 | | 6/2009 |
| WO | 20100062396 | | * | 6/2010 |
| WO | 2011/035004 | A1 | | 3/2011 |
| WO | 2012/006180 | A1 | | 1/2012 |
| WO | 2012/023995 | A1 | | 2/2012 |
| WO | 2012/106356 | A2 | | 8/2012 |
| WO | 2012/123755 | A1 | | 9/2012 |
| WO | 2012/172574 | A1 | | 12/2012 |
| WO | 2013/063248 | A1 | | 5/2013 |
| WO | 2013/122262 | A1 | | 8/2013 |
| WO | 2013/151764 | A1 | | 10/2013 |
| WO | 2015/005500 | A1 | | 1/2015 |
| WO | 2015/139784 | A1 | | 9/2015 |
| WO | 2016/021209 | A1 | | 2/2016 |
| WO | 2016109792 | | | 7/2016 |
| WO | 2016/199936 | A1 | | 12/2016 |
| WO | 2016/210127 | A1 | | 12/2016 |
| WO | 2017/009873 | A1 | | 1/2017 |
| WO | 2017/015463 | A2 | | 1/2017 |

OTHER PUBLICATIONS

Sigrid Elshuber et al., "Resuscitating Mutations in a Furin Cleavage-Deficient Mutant of the Flavivirus Tick-Borne Encephalitis Virus", Journal of Virology, vol. 79, No. 18, Sep. 2005, pp. 11813-11823.

Written Opinion, issued by International Searching Authority in corresponding International Application No. PCT/JP2015/003997, dated Oct. 27, 2015.

Office Action issued in Japanese Application No. 2014-557308 dated Jun. 20, 2017.

Hevey et al., "Marburg Virus Vaccines Based upon Alphavirus Replicons Protect Guinea Pigs and Nonhuman Primates", Virology, 251: 28-37 (1998).

Bonaldo et al., "Surface Expression of an Immunodominant Malaria Protein B Cell Epitope by Yellow Fever Virus", J. Mol. Biol., 315(4):873-885 (2002).

Vuola et al., "Differential Immunogenicity of Various Heterologous Prime-Boost Vaccine Regimens Using DNA and Viral Vectors in Healthy Volunteers", J. Immunol., 174(1):449-455 (2005).

Adams et al., "The expression of hybrid HIV: Ty virus-like particles in yeast", Nature, Sep. 3, 1987; vol. 329 (6134): pp. 68-70.

Agata Y et al., "Expression of the PD-1 antigen on the surface of stimulated mouse T and B lymphocytes", International Immunology, 1996, vol. 8, No. 5, pp. 765-772.

Akahata and Nebel, 2012, "A Specific Domain of the Chikungunya Virus E2 Protein Regulates Particle Formation in Human Cells: Implications for Alphavirus Vaccine Design", Journal of Virology. May 2012, 86 (16) 8879-8883.

Allsopp et al., "Comparison of numerous delivery systems for the induction of cytotoxic T lymphocytes by immunization", Eur. J. Immunol., 1996, vol. 26, pp. 1951-1959.

Arora et al., "Virus-like particles displaying envelope domain III of dengue virus type 2 induce virus-specific antibody response in mice", Vaccine, 2013, vol. 31, p. 873-878.

Atkins G et al., "Therapeutic and prophylactic applications of alphavirus vectors", Expert Reviews in Molecular Medicine, Nov. 2008, vol. 10; (e33) pp. 1-17.

Birkett A et al. "A Modified Hepatitis B Virus Core Particle Containing Multiple Epitopes of the Plasmodium falciparum Circumsporozoite Protein Provides a Highly Immunogenic Malaria Vaccine in Preclinical Analyses in Rodent and Primate Hosts", Infection and Immunity, American Society for Microbiology, vol. 70. No. 12: Dec. 2002. pp. 6860-6870.

Calvo-Calle et al., "A Linear Peptide Containing Minimal T- and B-Cell Epitopes of Plasmodium falciparum Circumsporozoite Protein Elicits Protection against Transgenic Sporozoite Challenge", Infection and Immunity, Dec. 2006. p. 6929-6939. vol. 74, No. 12.

Carvalho et al., "Malaria Vaccine: Candidate Antigens, Mechanisms, Constraints and Prospects", Scand. J. Immunol., Blackwell Science Ltd., Jul. 1, 2002, vol. 56, pp. 327-343.

Chackerian et al., "Determinants of Autoantibody Induction by Conjugated Papillomavirus Virus-Like Particles", The Journal of Immunology, vol. 169, No. 11, 2002, pp. 6120-6126. (7 pages total).

Charoensri et al. "An optimized expression vector for improving the yield of dengue virus-like particles from transfected insect cells" Journal of Virological Methods, vol. 205, 2014 (pp. 116-123).

Crompton et al., "Advances and challenges in malaria vaccine development", Science in medicine, The Journal of Clinical Investigation, Dec. 2010, vol. 120, No. 12, pp. 4168-4178.

Cox et al. "Predicting Zika virus structural biology: Challenges and opportunities for intervention" Antiviral Chemistry and Chemotherapy, vol. 24 (3-4), 2015 (pp. 118-126).

De Wispelaere Melissanne, et al., "Mutagenesis of the DI/DIII Linker in Dengue Virus Envelope Protein Impairs Viral Particle Assembly", Journal of Virology, 2012, vol. 86, No. 13, pp. 7072-7083, ISSN: 0022-538X, Abstract, Fig.1, Fig.8-9, p. 7073.

Dobano C et al., "Alphavirus Replicon Particles Are Highly Immunogenic in the Murine Malaria Model by Homologous or Heterologous Immunization", The Open Vaccine Journal, vol. 1, 2008, pp. 27-37.

Antonio Roldao et al., Expert Reviews, "Virus-like particles in vaccine development", Vaccines 9(10), 1149-1176, 2010.

Federico M., "Virus-like particles show promise as candidates for new vaccine strategies", Future Virology. (2010) 5(4), 371-374.

GenBank: AAB02517.1, "structural polyprotein precursor [Venezuelan equine encephalitis virus]", dated Nov. 17, 2004, retrieved from https://www.ncbi.nlm.nih.gov/protein/AAB02517.1.

GenBank: ADG95942.1, structural polyprotein [Chikungunya virus] http://www.ncbi.nlm.nih.gov/protein/296124572?report=genbank&log$=protalign&blast_rank=2&FilD=PBR7NTOU015. Dec. 28, 2010.

GenBank: AAW78190.1, circumsporozoite protein, partial [Plasmodium falciparum]. Dec. 29, 2006. http://www.ncbi.nlm.nih.gov/protein/58429573?report=genbank&log$=protalign&biast_rank=18&RID=P92DM05R01R.

GenBank "Zika virus strain MR 766, complete genome" AY632535.2, Nov. 23, 2010 (6 pages total) [Retrieved on May 16, 2017] Retrieved from the Internet, URL: <https://www.ncbi.nlm.nih.gov/nuccore/AY632535>.

Ghasparian A et al., "Engineered Synthetic Virus-Like Particles and Their Use in Vaccine Delivery", Chembiochem, 2011, vol. 12, No. 1, pp. 100-109.

Gilbert SC et al., "A protein particle vaccine containing multiple malaria epitopes", Nature Biotechnology, Nov. 1997, vol. 15, No. 12, pp. 1280-1284.

Gregson et al., "Phase I Trial of an Alhydrogel Adjuvanted Hepatitis B Core Virus-Like Particle Containing Epitopes of Plasmodium falciparum Circumsporozoite Protein", PLoS ONE. Feb. 2008, vol. 3, issue 2, e1556, pp. 1-9.

Grgacic E et al., "Virus-like particles: Passport to immune recognition", Methods 40, 2006, 60-65.

Haddow A. D. et al., "Genetic Characterization of Zika Virus Strains: Geographic Expansion of the Asian Lineage" PLOS Neglected Tropical Disease, Feb. 2012, vol. 6, Issue 2, e1477 (7 pages total).

Hsieh Szu-Chia, et al., "A strong endoplasmic reticulum retention signal in the stem-anchor region of envelope glycoprotein of dengue virus type 2 affects the production of virus-like particles", Virology, 2008, vol. 374, No. 2, pp. 338-350, ISSN: 0042-6822.

Spohn et al., "A Virus-Like Particle-Based Vaccine Selectively Targeting Soluble TNF-a Protects from Arthritis without Inducing

(56) References Cited

OTHER PUBLICATIONS

Reactivation of Latent Tuberculosis", The Journal of Immunology, 2007, vol. 178, pp. 7450-7457 (total 8 pages).
Hsieh Szu-Chia et al. "The length of and nonhydrophobic residues in the transmembrane domain of dengue virus envelope protein are critical for its retention and assembly in the endoplasmic reticulum" Journal of Virology, vol. 84 No. 9, Apr. 2010 (pp. 4782-4797).
WHO Dengue vaccine research, "Immunization, Vaccines and Biologicals", http://www.who.int/immunization/research/development/dengue_vaccines/en/ (total 3 pages).
Huang Claire Y.H., et al., "The dengue virus type 2 envelope protein fusion peptide is essential for membrane fusion", Virology, 2010, vol. 396, No. 2, pp. 305-315, ISSN:0042-6822, Table, Fig.5, pp. 310-313.
Jennings G et al., "Immunodrugs: Therapeutic VLP-Based Vaccines for Chronic Diseases", Annu. Rev. Pharmacol. Toxicol., 2009, 49: 303-326.
Jones RM et al., "A Plant-Produced Pfs25 VLP Malaria Vaccine Candidate Induces Persistent Transmission Blocking Antibodies against Plasmodium falciparum in Immunized Mice", PLoS One, Nov. 18, 2013, vol. 8, No. 11, e79538, total 10 pages.
Khetarpal Niyati, et al., "Dengue-specific subviral nanoparticles: design, creation and characterization", Journal of Nanobiotechnology, 2013, vol. 11, No. 15, total 8 pages, ISSN: 1477-3155.
Kostyuchenko V et al., "Structure of the thermally stable Zika virus", Nature, May 19, 2016, vol. 533, pp. 425-428.
Kuo S.C., et al., "Cell-based analysis of Chikungunya virus E1 protein in membrane fusion", Journal of Biomedical Science 2012, 19 (44): pp. 1-12.
Larocca et al., "Vaccine Protection Against Zika Virus from Brazil", Nature, Aug. 25, 2016, 536(7617), 474-478, doi:10.1038/nature18952 (24 pages total).
Lechner F et al., "Virus-like Particles as a Modular System for Novel Vaccines", Intervirology, 2002, vol. 45, pp. 212-217.
Leibl H et al., "Adjuvant/carrier activity of inactivated tick-borne encephalitis virus", Vaccine, 1998, 16(4): pp. 340-345.
Lin et al., "Analysis of Epitopes on Dengue Virus Envelope Protein Recognized by Monoclonal Antibodies and Polyclonal Human Sera by a High Throughput Assay", PLOS, Jan. 2012, 6(1):e1447, total 12 pages.
Malaria Vaccine Program, http://www.globalvaccines.org/content/malaria+vaccine+program/19614, total 4 pages (2012).
McCoy K et al., "Cytotoxic T Lymphocyte-associated Antigen 4 (CTLA-4) Can Regulate Dendritic Cell-induced Activation and Cytotoxicity of CD8+ T Cells Independently of CD4+ T Cell Help", J. Exp. Med., Apr. 5, 1999, vol. 189, No. 7, pp. 1157-1162.
Mellman I et al., "Cancer immunotherapy comes of age", Nature, Dec. 22/29, 2011, 480: pp. 480-489.
Milich D R et al. "Conversion of poorly immunogenic malaria repeat sequences into a highly immunogenic vaccine candidate", Vaccine, Elsevier Science Ltd., vol. 20, 2002, pp. 771-788.
Notka F et al., "Accelerated clearance of SHIV in rhesus monkeys by virus-like particle vaccines is dependent on induction of neutralizing antibodies", Vaccine, 2000, vol. 18, pp. 291-301.
Oliveira G et al., "Safety and Enhanced Immunogenicity of a Hepatitis B Core Practical Plasmodium falciparum Malaria Vaccine Formulated in Adjuvant Montanide ISA 720 in a Phase I Trial", Infection and Immunity, 2005, vol. 73, No. 6, pp. 3587-3597.
Oliveira-Ferreira et al., "Immunogenicity of Ty-VLP bearing a CD8 (+) T cell epitope of the CS protein of P. yoelii: enhanced memory response by boosting with recombinant vaccinia virus", Vaccine, 2000, vol. 18, pp. 1863-1869.
Palomba M et al., "CD8+ T-Cell-Dependent Immunity Following Xenogeneic DNA Immunization against CD20 in a Tumor Challenge Model of B-Cell Lymphoma", Clinical Cancer Research, Jan. 1, 2005, 370(11): pp. 370-379.
Pfeiffer B et al., "A Virosome-Mimotope Approach to Synthetic Vaccine Design and Optimization: Synthesis, Conformation, and Immune Recognition of a Potential Malaria-Vaccine Candidate", Angew. Chem. Int. Ed., 2003, vol. 42, No. 21, pp. 2368-2371 (total 5 pages).
Purdy D et al., "Secretion of noninfectious dengue virus-like particles and identification of amino acids in the stem region involved in intracellular retention of envelope protein" Virology, 2005, vol. 333, No. 2, pp. 239-250, ISSN: 0042-6822, Abstract, Fig.1-4. Table 1, pp. 240, 247-248.
Richner et al. "Modified mRNA vaccines protect against Zika Virus infection" Cell, vol. 168., Mar. 9, 2017 , pp. 1114-1125, (23 pages total).
Roberts W et al., "Vaccination with CD20 peptides induces a biologically active, specific immune response in mice", Blood, May 15, 2002, vol. 99: pp. 3748-3755.
Rodrigues M et al., "Influenza and Vaccinia Viruses Expressing Malaria CD8+T and B Cell Epitopes. Comparison of Their Immunogenicity and Capacity to Induce Protective Immunity", The Journal of I Immunology, Nov. 15, 1994, vol. 153, No. 10, pp. 4636-4648 (total 15 pages).
Rodriguez D et al., "Vaccine Efficacy against Malaria by the Combination of Porcine Parvovirus-Like Particles and Vaccinia Virus Vectors Expressing CS of Plasmodium", PLoS One, Apr. 17, 2012, vol. 7, No. 4, e34445.
Seligman S, "Constancy and diversity in the flavivirus fusion peptide", BioMed Central, Virology Journal 2008, Feb. 14, 2008, total 10 pages. URL: http://www.virologyj.com/content/5/1/27.
Shiratsuchi T. et al., "Replacing adenoviral vector HVR1 with a malaria B cell epitope improves immunogenicity and circumvents preexisting immunity to adenovirus in mice", Journal of Clinical Investigation: vol. 120. No. 10: Oct. 2010: pp. 3688-3701.
Sun S et al., "Structural analyses at pseudo atomic resolution of Chikungunya virus and antibodies show mechanisms of neutralization", eLIFE, Apr. 2, 2013, vol. 2, pp. 1-27.
Taylor et al. "Production of immunogenic West Nile virus-like particles using a herpes simplex virus 1 recombinant vector" Virology, vol. 496, 2016 (pp. 186-193).
Tsai et al., "Complexity of Neutralizing Antibodies against Multiple Dengue Virus Serotypes after Heterotypic Immunization and Secondary Infection Revealed by In-Depth Analysis of Cross-Reactive Antibodies", Journal of Virology, Jul. 2015, vol. 89, No. 14, pp. 7348-7362.
Heinz F et al., "Flaviviruses and flavivirus vaccines", Vaccine 30 (2012) 4301-4306.
Yamaji et al. "Efficient production of Japanese encephalitis virus-like particles by recombinant lepidopteran insect cells" Appl. Microbiol Biotechnol, vol. 97, 2013 (pp. 1071-1079).
Zhang et al., "Vaccination with dengue virus-like particles induces humoral and cellular immune responses in mice", Virology Journal, 2011, 8:333, total 9 pages.
Zika virus fact sheet, updated Sep. 6, 2016; URL:http://www.who.int/mediacentre/factsheets/zika/en/ (5 pages total).
Communication, dated Dec. 20, 2017, issued by the European Patent Office in counterpart European Patent Application No. 15829311.8.
Urakami et al., "Development of a Novel Virus-Like Particle Vaccine Platform That Mimics the Immature Form of Alphavirus," Clinical and Vaccine Immunology, 24(7): e00090-17 (pp. 1-14).

* cited by examiner

VEEV- IDGR ; Replace furin recognition site to Factor Xa recognition motif (IDGR)
VEEV- IEGR ; Replace furin recognition site to Factor Xa recognition motif (IEGR)

SEQUENCE LISTING

```
<160> NUMBER OF SEQ ID NOS: 140

<210> SEQ ID NO 1
<211> LENGTH: 1248
<212> TYPE: PRT
<213> ORGANISM: Chikungunya virus
<220> FEATURE:
<221> NAME/KEY: misc_feature
<222> LOCATION: (749)..(809)
<223> OTHER INFORMATION: 6K

<400> SEQUENCE: 1

Met Glu Phe Ile Pro Thr Gln Thr Phe Tyr Asn Arg Arg Tyr Gln Pro
1               5                   10                  15

Arg Pro Trp Thr Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Lys Gln Lys Gln Gln Ala Pro Gln Asn Asn
65                  70                  75                  80

Thr Asn Gln Lys Lys Gln Pro Pro Lys Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Thr Gly Tyr Ala Cys
        115                 120                 125
```

-continued

```
Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Ile Pro Val Met Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Glu Thr Leu Arg Met Leu Glu Asp Asn Val Met
    290                 295                 300

Arg Pro Gly Tyr Tyr Gln Leu Leu Gln Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
            340                 345                 350

Cys His Ser Pro Val Ala Leu Glu Arg Ile Arg Asn Glu Ala Thr Asp
        355                 360                 365

Gly Thr Leu Lys Ile Gln Val Ser Leu Gln Ile Gly Ile Lys Thr Asp
    370                 375                 380

Asp Ser His Asp Trp Thr Lys Leu Arg Tyr Met Asp Asn His Met Pro
385                 390                 395                 400

Ala Asp Ala Glu Arg Ala Gly Leu Phe Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
        435                 440                 445

Ser Cys Thr His Pro Phe His His Asp Pro Pro Val Ile Gly Arg Glu
    450                 455                 460

Lys Phe His Ser Arg Pro Gln His Gly Lys Glu Leu Pro Cys Ser Thr
465                 470                 475                 480

Tyr Val Gln Ser Thr Ala Ala Thr Thr Glu Glu Ile Glu Val His Met
                485                 490                 495

Pro Pro Asp Thr Pro Asp Arg Thr Leu Met Ser Gln Gln Ser Gly Asn
            500                 505                 510

Val Lys Ile Thr Val Asn Gly Gln Thr Val Arg Tyr Lys Cys Asn Cys
        515                 520                 525

Gly Gly Ser Asn Glu Gly Leu Thr Thr Thr Asp Lys Val Ile Asn Asn
    530                 535                 540

Cys Lys Val Asp Gln Cys His Ala Ala Val Thr Asn His Lys Lys Trp
```

-continued

```
545                 550                 555                 560

Gln Tyr Asn Ser Pro Leu Val Pro Arg Asn Ala Glu Leu Gly Asp Arg
                565                 570                 575

Lys Gly Lys Ile His Ile Pro Phe Pro Leu Ala Asn Val Thr Cys Arg
            580                 585                 590

Val Pro Lys Ala Arg Asn Pro Thr Val Thr Tyr Gly Lys Asn Gln Val
        595                 600                 605

Ile Met Leu Leu Tyr Pro Asp His Pro Thr Leu Leu Ser Tyr Arg Asn
    610                 615                 620

Met Gly Glu Glu Pro Asn Tyr Gln Glu Glu Trp Val Met His Lys Lys
625                 630                 635                 640

Glu Val Val Leu Thr Val Pro Thr Glu Gly Leu Glu Val Thr Trp Gly
                645                 650                 655

Asn Asn Glu Pro Tyr Lys Tyr Trp Pro Gln Leu Ser Thr Asn Gly Thr
            660                 665                 670

Ala His Gly His Pro His Glu Ile Ile Leu Tyr Tyr Tyr Glu Leu Tyr
        675                 680                 685

Pro Thr Met Thr Val Val Val Val Ser Val Ala Thr Phe Ile Leu Leu
    690                 695                 700

Ser Met Val Gly Met Ala Ala Gly Met Cys Met Cys Ala Arg Arg Arg
705                 710                 715                 720

Cys Ile Thr Pro Tyr Glu Leu Thr Pro Gly Ala Thr Val Pro Phe Leu
                725                 730                 735

Leu Ser Leu Ile Cys Cys Ile Arg Thr Ala Lys Ala Ala Thr Tyr Gln
            740                 745                 750

Glu Ala Ala Ile Tyr Leu Trp Asn Glu Gln Gln Pro Leu Phe Trp Leu
        755                 760                 765

Gln Ala Leu Ile Pro Leu Ala Ala Leu Ile Val Leu Cys Asn Cys Leu
    770                 775                 780

Arg Leu Leu Pro Cys Cys Cys Lys Thr Leu Ala Phe Leu Ala Val Met
785                 790                 795                 800

Ser Val Gly Ala His Thr Val Ser Ala Tyr Glu His Val Thr Val Ile
                805                 810                 815

Pro Asn Thr Val Gly Val Pro Tyr Lys Thr Leu Val Asn Arg Pro Gly
            820                 825                 830

Tyr Ser Pro Met Val Leu Glu Met Glu Leu Leu Ser Val Thr Leu Glu
        835                 840                 845

Pro Thr Leu Ser Leu Asp Tyr Ile Thr Cys Glu Tyr Lys Thr Val Ile
    850                 855                 860

Pro Ser Pro Tyr Val Lys Cys Cys Gly Thr Ala Glu Cys Lys Asp Lys
865                 870                 875                 880

Asn Leu Pro Asp Tyr Ser Cys Lys Val Phe Thr Gly Val Tyr Pro Phe
                885                 890                 895

Met Trp Gly Gly Ala Tyr Cys Phe Cys Asp Ala Glu Asn Thr Gln Leu
            900                 905                 910

Ser Glu Ala His Val Glu Lys Ser Glu Ser Cys Lys Thr Glu Phe Ala
        915                 920                 925

Ser Ala Tyr Arg Ala His Thr Ala Ser Ala Ser Ala Lys Leu Arg Val
    930                 935                 940

Leu Tyr Gln Gly Asn Asn Ile Thr Val Thr Ala Tyr Ala Asn Gly Asp
945                 950                 955                 960

His Ala Val Thr Val Lys Asp Ala Lys Phe Ile Val Gly Pro Met Ser
                965                 970                 975
```

```
Ser Ala Trp Thr Pro Phe Asp Asn Lys Ile Val Val Tyr Lys Gly Asp
            980                 985                 990

Val Tyr Asn Met Asp Tyr Pro Pro  Phe Gly Ala Gly Arg  Pro Gly Gln
        995                 1000                1005

Phe Gly  Asp Ile Gln Ser Arg  Thr Pro Glu Ser Lys  Asp Val Tyr
    1010                 1015                1020

Ala Asn  Thr Gln Leu Val Leu  Gln Arg Pro Ala Val  Gly Thr Val
    1025                 1030                1035

His Val  Pro Tyr Ser Gln Ala  Pro Ser Gly Phe Lys  Tyr Trp Leu
    1040                 1045                1050

Lys Glu  Arg Gly Ala Ser Leu  Gln His Thr Ala Pro  Phe Gly Cys
    1055                 1060                1065

Gln Ile  Ala Thr Asn Pro Val  Arg Ala Val Asn Cys  Ala Val Gly
    1070                 1075                1080

Asn Met  Pro Ile Ser Ile Asp  Ile Pro Glu Ala Ala  Phe Thr Arg
    1085                 1090                1095

Val Val  Asp Ala Pro Ser Leu  Thr Asp Met Ser Cys  Glu Val Pro
    1100                 1105                1110

Ala Cys  Thr His Ser Ser Asp  Phe Gly Gly Val Ala  Ile Ile Lys
    1115                 1120                1125

Tyr Ala  Ala Ser Lys Lys Gly  Lys Cys Ala Val His  Ser Met Thr
    1130                 1135                1140

Asn Ala  Val Thr Ile Arg Glu  Ala Glu Ile Glu Val  Glu Gly Asn
    1145                 1150                1155

Ser Gln  Leu Gln Ile Ser Phe  Ser Thr Ala Leu Ala  Ser Ala Glu
    1160                 1165                1170

Phe Arg  Val Gln Val Cys Ser  Thr Gln Val His Cys  Ala Ala Glu
    1175                 1180                1185

Cys His  Pro Pro Lys Asp His  Ile Val Asn Tyr Pro  Ala Ser His
    1190                 1195                1200

Thr Thr  Leu Gly Val Gln Asp  Ile Ser Ala Thr Ala  Met Ser Trp
    1205                 1210                1215

Val Gln  Lys Ile Thr Gly Gly  Val Gly Leu Val Val  Ala Val Ala
    1220                 1225                1230

Ala Leu  Ile Leu Ile Val Val  Leu Cys Val Ser Phe  Ser Arg His
    1235                 1240                1245


<210> SEQ ID NO 2
<211> LENGTH: 1248
<212> TYPE: PRT
<213> ORGANISM: Chikungunya virus
<220> FEATURE:
<221> NAME/KEY: misc_feature
<222> LOCATION: (749)..(809)
<223> OTHER INFORMATION: 6K

<400> SEQUENCE: 2

Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60
```

```
Arg Lys Asn Lys Lys Gln Arg Gln Lys Lys Gln Ala Pro Gln Asn Asp
65                  70                  75                  80

Pro Lys Gln Lys Lys Gln Pro Pro Gln Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Met Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Leu Pro Val Leu Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Ser Thr Leu Arg Met Leu Glu Asp Asn Val Met
    290                 295                 300

Arg Pro Gly Tyr Tyr Gln Leu Leu Lys Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
            340                 345                 350

Cys His Ser Pro Ile Ala Leu Glu Arg Ile Arg Asn Glu Ala Thr Asp
        355                 360                 365

Gly Thr Leu Lys Ile Gln Val Ser Leu Gln Ile Gly Ile Lys Thr Asp
    370                 375                 380

Asp Ser His Asp Trp Thr Lys Leu Arg Tyr Met Asp Ser His Thr Pro
385                 390                 395                 400

Ala Asp Ala Glu Arg Ala Gly Leu Leu Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
        435                 440                 445

Thr Cys Thr His Pro Phe His His Glu Pro Pro Val Ile Gly Arg Glu
    450                 455                 460

Arg Phe His Ser Arg Pro Gln His Gly Lys Glu Leu Pro Cys Ser Thr
465                 470                 475                 480

Tyr Val Gln Ser Thr Ala Ala Thr Ala Glu Glu Ile Glu Val His Met
```

-continued

```
                485                 490                 495

Pro Pro Asp Thr Pro Asp Arg Thr Leu Met Thr Gln Gln Ser Gly Asn
            500                 505                 510

Val Lys Ile Thr Val Asn Gly Gln Thr Val Arg Tyr Lys Cys Asn Cys
        515                 520                 525

Gly Gly Ser Asn Glu Gly Leu Thr Thr Thr Asp Lys Val Ile Asn Asn
    530                 535                 540

Cys Lys Ile Asp Gln Cys His Ala Ala Val Thr Asn His Lys Asn Trp
545                 550                 555                 560

Gln Tyr Asn Ser Pro Leu Val Pro Arg Asn Ala Glu Leu Gly Asp Arg
                565                 570                 575

Lys Gly Lys Ile His Ile Pro Phe Pro Leu Ala Asn Val Thr Cys Arg
            580                 585                 590

Val Pro Lys Ala Arg Asn Pro Thr Val Thr Tyr Gly Lys Asn Gln Val
        595                 600                 605

Thr Met Leu Leu Tyr Pro Asp His Pro Thr Leu Leu Ser Tyr Arg Asn
    610                 615                 620

Met Gly Gln Glu Pro Asn Tyr His Glu Glu Trp Val Thr His Lys Lys
625                 630                 635                 640

Glu Val Thr Leu Thr Val Pro Thr Glu Gly Leu Glu Val Thr Trp Gly
                645                 650                 655

Asn Asn Glu Pro Tyr Lys Tyr Trp Pro Gln Met Ser Thr Asn Gly Thr
            660                 665                 670

Ala His Gly His Pro His Glu Ile Ile Leu Tyr Tyr Tyr Glu Leu Tyr
        675                 680                 685

Pro Thr Met Thr Val Val Ile Val Ser Val Ala Ser Phe Val Leu Leu
    690                 695                 700

Ser Met Val Gly Thr Ala Val Gly Met Cys Val Cys Ala Arg Arg Arg
705                 710                 715                 720

Cys Ile Thr Pro Tyr Glu Leu Thr Pro Gly Ala Thr Val Pro Phe Leu
                725                 730                 735

Leu Ser Leu Leu Cys Cys Val Arg Thr Thr Lys Ala Ala Thr Tyr Tyr
            740                 745                 750

Glu Ala Ala Ala Tyr Leu Trp Asn Glu Gln Gln Pro Leu Phe Trp Leu
        755                 760                 765

Gln Ala Leu Ile Pro Leu Ala Ala Leu Ile Val Leu Cys Asn Cys Leu
    770                 775                 780

Lys Leu Leu Pro Cys Cys Cys Lys Thr Leu Ala Phe Leu Ala Val Met
785                 790                 795                 800

Ser Ile Gly Ala His Thr Val Ser Ala Tyr Glu His Val Thr Val Ile
                805                 810                 815

Pro Asn Thr Val Gly Val Pro Tyr Lys Thr Leu Val Asn Arg Pro Gly
            820                 825                 830

Tyr Ser Pro Met Val Leu Glu Met Glu Leu Gln Ser Val Thr Leu Glu
        835                 840                 845

Pro Thr Leu Ser Leu Asp Tyr Ile Thr Cys Glu Tyr Lys Thr Val Ile
    850                 855                 860

Pro Ser Pro Tyr Val Lys Cys Cys Gly Thr Ala Glu Cys Lys Asp Lys
865                 870                 875                 880

Ser Leu Pro Asp Tyr Ser Cys Lys Val Phe Thr Gly Val Tyr Pro Phe
                885                 890                 895

Met Trp Gly Gly Ala Tyr Cys Phe Cys Asp Ala Glu Asn Thr Gln Leu
            900                 905                 910
```

-continued

```
Ser Glu Ala His Val Glu Lys Ser Glu Ser Cys Lys Thr Glu Phe Ala
        915                 920                 925

Ser Ala Tyr Arg Ala His Thr Ala Ser Ala Ser Ala Lys Leu Arg Val
    930                 935                 940

Leu Tyr Gln Gly Asn Asn Ile Thr Val Ala Ala Tyr Ala Asn Gly Asp
945                 950                 955                 960

His Ala Val Thr Val Lys Asp Ala Lys Phe Val Val Gly Pro Met Ser
                965                 970                 975

Ser Ala Trp Thr Pro Phe Asp Asn Lys Ile Val Val Tyr Lys Gly Asp
            980                 985                 990

Val Tyr Asn Met Asp Tyr Pro Pro  Phe Gly Ala Gly Arg  Pro Gly Gln
        995                 1000                 1005

Phe Gly  Asp Ile Gln Ser Arg  Thr Pro Glu Ser Lys  Asp Val Tyr
    1010                 1015                 1020

Ala Asn  Thr Gln Leu Val Leu  Gln Arg Pro Ala Ala  Gly Thr Val
    1025                 1030                 1035

His Val  Pro Tyr Ser Gln Ala  Pro Ser Gly Phe Lys  Tyr Trp Leu
    1040                 1045                 1050

Lys Glu  Arg Gly Ala Ser Leu  Gln His Thr Ala Pro  Phe Gly Cys
    1055                 1060                 1065

Gln Ile  Ala Thr Asn Pro Val  Arg Ala Val Asn Cys  Ala Val Gly
    1070                 1075                 1080

Asn Ile  Pro Ile Ser Ile Asp  Ile Pro Asp Ala Ala  Phe Thr Arg
    1085                 1090                 1095

Val Val  Asp Ala Pro Ser Val  Thr Asp Met Ser Cys  Glu Val Pro
    1100                 1105                 1110

Ala Cys  Thr His Ser Ser Asp  Phe Gly Gly Val Ala  Ile Ile Lys
    1115                 1120                 1125

Tyr Thr  Ala Ser Lys Lys Gly  Lys Cys Ala Val His  Ser Met Thr
    1130                 1135                 1140

Asn Ala  Val Thr Ile Arg Glu  Ala Asp Val Glu Val  Glu Gly Asn
    1145                 1150                 1155

Ser Gln  Leu Gln Ile Ser Phe  Ser Thr Ala Leu Ala  Ser Ala Glu
    1160                 1165                 1170

Phe Arg  Val Gln Val Cys Ser  Thr Gln Val His Cys  Ala Ala Ala
    1175                 1180                 1185

Cys His  Pro Pro Lys Asp His  Ile Val Asn Tyr Pro  Ala Ser His
    1190                 1195                 1200

Thr Thr  Leu Gly Val Gln Asp  Ile Ser Thr Thr Ala  Met Ser Trp
    1205                 1210                 1215

Val Gln  Lys Ile Thr Gly Gly  Val Gly Leu Ile Val  Ala Val Ala
    1220                 1225                 1230

Ala Leu  Ile Leu Ile Val Val  Leu Cys Val Ser Phe  Ser Arg His
    1235                 1240                 1245
```

<210> SEQ ID NO 3
<211> LENGTH: 1255
<212> TYPE: PRT
<213> ORGANISM: Venezuelan equine encephalitis virus
<220> FEATURE:
<221> NAME/KEY: misc_feature
<222> LOCATION: (758)..(813)
<223> OTHER INFORMATION: 6K

<400> SEQUENCE: 3

-continued

```
Met Phe Pro Phe Gln Pro Met Tyr Pro Met Gln Pro Met Pro Tyr Arg
1               5                   10                  15

Asn Pro Phe Ala Ala Pro Arg Arg Pro Trp Phe Pro Arg Thr Asp Pro
            20                  25                  30

Phe Leu Ala Met Gln Val Gln Glu Leu Thr Arg Ser Met Ala Asn Leu
        35                  40                  45

Thr Phe Lys Gln Arg Arg Asp Ala Pro Pro Glu Gly Pro Ser Ala Ala
    50                  55                  60

Lys Pro Lys Lys Glu Ala Ser Gln Lys Gln Lys Gly Gly Gly Gln Gly
65                  70                  75                  80

Lys Lys Lys Lys Asn Gln Gly Lys Lys Lys Ala Lys Thr Gly Pro Pro
                85                  90                  95

Asn Pro Lys Ala Gln Asn Gly Asn Lys Lys Lys Thr Asn Lys Lys Pro
            100                 105                 110

Gly Lys Arg Gln Arg Met Val Met Lys Leu Glu Ser Asp Lys Thr Phe
        115                 120                 125

Pro Ile Met Leu Glu Gly Lys Ile Asn Gly Tyr Ala Cys Val Val Gly
    130                 135                 140

Gly Lys Leu Phe Arg Pro Met His Val Glu Gly Lys Ile Asp Asn Asp
145                 150                 155                 160

Val Leu Ala Ala Leu Lys Thr Lys Lys Ala Ser Lys Tyr Asp Leu Glu
                165                 170                 175

Tyr Ala Asp Val Pro Gln Asn Met Arg Ala Asp Thr Phe Lys Tyr Thr
            180                 185                 190

His Glu Lys Pro Gln Gly Tyr Tyr Ser Trp His His Gly Ala Val Gln
        195                 200                 205

Tyr Glu Asn Gly Arg Phe Thr Val Pro Lys Gly Val Gly Ala Lys Gly
    210                 215                 220

Asp Ser Gly Arg Pro Ile Leu Asp Asn Gln Gly Arg Val Val Ala Ile
225                 230                 235                 240

Val Leu Gly Gly Val Asn Glu Gly Ser Arg Thr Ala Leu Ser Val Val
                245                 250                 255

Met Trp Asn Glu Lys Gly Val Thr Val Lys Tyr Thr Pro Glu Asn Cys
            260                 265                 270

Glu Gln Trp Ser Leu Val Thr Thr Met Cys Leu Leu Ala Asn Val Thr
        275                 280                 285

Phe Pro Cys Ala Gln Pro Pro Ile Cys Tyr Asp Arg Lys Pro Ala Glu
    290                 295                 300

Thr Leu Ala Met Leu Ser Val Asn Val Asp Asn Pro Gly Tyr Asp Glu
305                 310                 315                 320

Leu Leu Glu Ala Ala Val Lys Cys Pro Gly Arg Lys Arg Arg Ser Thr
                325                 330                 335

Glu Glu Leu Phe Asn Glu Tyr Lys Leu Thr Arg Pro Tyr Met Ala Arg
            340                 345                 350

Cys Ile Arg Cys Ala Val Gly Ser Cys His Ser Pro Ile Ala Ile Glu
        355                 360                 365

Ala Val Lys Ser Asp Gly His Asp Gly Tyr Val Arg Leu Gln Thr Ser
    370                 375                 380

Ser Gln Tyr Gly Leu Asp Ser Ser Gly Asn Leu Lys Gly Arg Thr Met
385                 390                 395                 400

Arg Tyr Asp Met His Gly Thr Ile Lys Glu Ile Pro Leu His Gln Val
                405                 410                 415

Ser Leu Tyr Thr Ser Arg Pro Cys His Ile Val Asp Gly His Gly Tyr
```

```
            420                 425                 430

Phe Leu Leu Ala Arg Cys Pro Ala Gly Asp Ser Ile Thr Met Glu Phe
        435                 440                 445

Lys Lys Asp Ser Val Arg His Ser Cys Ser Val Pro Tyr Glu Val Lys
    450                 455                 460

Phe Asn Pro Val Gly Arg Glu Leu Tyr Thr His Pro Pro Glu His Gly
465                 470                 475                 480

Val Glu Gln Ala Cys Gln Val Tyr Ala His Asp Ala Gln Asn Arg Gly
                485                 490                 495

Ala Tyr Val Glu Met His Leu Pro Gly Ser Glu Val Asp Ser Ser Leu
            500                 505                 510

Val Ser Leu Ser Gly Ser Ser Val Thr Val Thr Pro Pro Asp Gly Thr
        515                 520                 525

Ser Ala Leu Val Glu Cys Glu Cys Gly Gly Thr Lys Ile Ser Glu Thr
    530                 535                 540

Ile Asn Lys Thr Lys Gln Phe Ser Gln Cys Thr Lys Lys Glu Gln Cys
545                 550                 555                 560

Arg Ala Tyr Arg Leu Gln Asn Asp Lys Trp Val Tyr Asn Ser Asp Lys
                565                 570                 575

Leu Pro Lys Ala Ala Gly Ala Thr Leu Lys Gly Lys Leu His Val Pro
            580                 585                 590

Phe Leu Leu Ala Asp Gly Lys Cys Thr Val Pro Leu Ala Pro Glu Pro
        595                 600                 605

Met Ile Thr Phe Gly Phe Arg Ser Val Ser Leu Lys Leu His Pro Lys
    610                 615                 620

Asn Pro Thr Tyr Leu Ile Thr Arg Gln Leu Ala Asp Glu Pro His Tyr
625                 630                 635                 640

Thr His Glu Leu Ile Ser Glu Pro Ala Val Arg Asn Phe Thr Val Thr
                645                 650                 655

Glu Lys Gly Trp Glu Phe Val Trp Gly Asn His Pro Pro Lys Arg Phe
            660                 665                 670

Trp Ala Gln Glu Thr Ala Pro Gly Asn Pro His Gly Leu Pro His Glu
        675                 680                 685

Val Ile Thr His Tyr Tyr His Arg Tyr Pro Met Ser Thr Ile Leu Gly
    690                 695                 700

Leu Ser Ile Cys Ala Ala Ile Ala Thr Val Ser Val Ala Ala Ser Thr
705                 710                 715                 720

Trp Leu Phe Cys Arg Ser Arg Val Ala Cys Leu Thr Pro Tyr Arg Leu
                725                 730                 735

Thr Pro Asn Ala Arg Ile Pro Phe Cys Leu Ala Val Leu Cys Cys Ala
            740                 745                 750

Arg Thr Ala Arg Ala Glu Thr Thr Trp Glu Ser Leu Asp His Leu Trp
        755                 760                 765

Asn Asn Asn Gln Gln Met Phe Trp Ile Gln Leu Leu Ile Pro Leu Ala
    770                 775                 780

Ala Leu Ile Val Val Thr Arg Leu Leu Arg Cys Val Cys Cys Val Val
785                 790                 795                 800

Pro Phe Leu Val Met Ala Gly Ala Ala Gly Ala Gly Ala Tyr Glu His
                805                 810                 815

Ala Thr Thr Met Pro Ser Gln Ala Gly Ile Ser Tyr Asn Thr Ile Val
            820                 825                 830

Asn Arg Ala Gly Tyr Ala Pro Leu Pro Ile Ser Ile Thr Pro Thr Lys
        835                 840                 845
```

-continued

```
Ile Lys Leu Ile Pro Thr Val Asn Leu Glu Tyr Val Thr Cys His Tyr
    850                 855                 860

Lys Thr Gly Met Asp Ser Pro Ala Ile Lys Cys Cys Gly Ser Gln Glu
865                 870                 875                 880

Cys Thr Pro Thr Tyr Arg Pro Asp Glu Gln Cys Lys Val Phe Thr Gly
                885                 890                 895

Val Tyr Pro Phe Met Trp Gly Gly Ala Tyr Cys Phe Cys Asp Thr Glu
            900                 905                 910

Asn Thr Gln Val Ser Lys Ala Tyr Val Met Lys Ser Asp Asp Cys Leu
        915                 920                 925

Ala Asp His Ala Glu Ala Tyr Lys Ala His Thr Ala Ser Val Gln Ala
    930                 935                 940

Phe Leu Asn Ile Thr Val Gly Glu His Ser Ile Val Thr Thr Val Tyr
945                 950                 955                 960

Val Asn Gly Glu Thr Pro Val Asn Phe Asn Gly Val Lys Ile Thr Ala
                965                 970                 975

Gly Pro Leu Ser Thr Ala Trp Thr Pro Phe Asp Arg Lys Ile Val Gln
            980                 985                 990

Tyr Ala Gly Glu Ile Tyr Asn Tyr  Asp Phe Pro Glu Tyr  Gly Ala Gly
        995                 1000                1005

Gln Pro  Gly Ala Phe Gly Asp  Ile Gln Ser Arg Thr  Val Ser Ser
    1010                1015                1020

Ser Asp  Leu Tyr Ala Asn Thr  Asn Leu Val Leu Gln  Arg Pro Lys
    1025                1030                1035

Ala Gly  Ala Ile His Val Pro  Tyr Thr Gln Ala Pro  Ser Gly Phe
    1040                1045                1050

Glu Gln  Trp Lys Lys Asp Lys  Ala Pro Ser Leu Lys  Phe Thr Ala
    1055                1060                1065

Pro Phe  Gly Cys Glu Ile Tyr  Thr Asn Pro Ile Arg  Ala Glu Asn
    1070                1075                1080

Cys Ala  Val Gly Ser Ile Pro  Leu Ala Phe Asp Ile  Pro Asp Ala
    1085                1090                1095

Leu Phe  Thr Arg Val Ser Glu  Thr Pro Thr Leu Ser  Ala Ala Glu
    1100                1105                1110

Cys Thr  Leu Asn Glu Cys Val  Tyr Ser Ser Asp Phe  Gly Gly Ile
    1115                1120                1125

Ala Thr  Val Lys Tyr Ser Ala  Ser Lys Ser Gly Lys  Cys Ala Val
    1130                1135                1140

His Val  Pro Ser Gly Thr Ala  Thr Leu Lys Glu Ala  Ala Val Glu
    1145                1150                1155

Leu Thr  Glu Gln Gly Ser Ala  Thr Ile His Phe Ser  Thr Ala Asn
    1160                1165                1170

Ile His  Pro Glu Phe Arg Leu  Gln Ile Cys Thr Ser  Tyr Val Thr
    1175                1180                1185

Cys Lys  Gly Asp Cys His Pro  Pro Lys Asp His Ile  Val Thr His
    1190                1195                1200

Pro Gln  Tyr His Ala Gln Thr  Phe Thr Ala Ala Val  Ser Lys Thr
    1205                1210                1215

Ala Trp  Thr Trp Leu Thr Ser  Leu Leu Gly Gly Ser  Ala Val Ile
    1220                1225                1230

Ile Ile  Ile Gly Leu Val Leu  Ala Thr Ile Val Ala  Met Tyr Val
    1235                1240                1245
```

Leu Thr Asn Gln Lys His Asn
1250 1255

<210> SEQ ID NO 4
<211> LENGTH: 20
<212> TYPE: PRT
<213> ORGANISM: Artificial Sequence
<220> FEATURE:
<223> OTHER INFORMATION: Synthetic CSP antigen

<400> SEQUENCE: 4

Glu Tyr Leu Asn Lys Ile Gln Asn Ser Leu Ser Thr Glu Trp Ser Pro
1 5 10 15

Cys Ser Val Thr
20

<210> SEQ ID NO 5
<211> LENGTH: 20
<212> TYPE: PRT
<213> ORGANISM: Artificial Sequence
<220> FEATURE:
<223> OTHER INFORMATION: Synthetic CSP antigen

<400> SEQUENCE: 5

Tyr Asn Arg Asn Ile Val Asn Arg Leu Leu Gly Asp Ala Leu Asn Gly
1 5 10 15

Pro Glu Glu Lys
20

<210> SEQ ID NO 6
<211> LENGTH: 18
<212> TYPE: PRT
<213> ORGANISM: Artificial Sequence
<220> FEATURE:
<223> OTHER INFORMATION: Synthetic PD-1 antigen

<400> SEQUENCE: 6

Leu Asn Trp Tyr Arg Met Ser Pro Ser Asn Gln Thr Asp Lys Leu Ala
1 5 10 15

Ala Phe

<210> SEQ ID NO 7
<211> LENGTH: 20
<212> TYPE: PRT
<213> ORGANISM: Artificial Sequence
<220> FEATURE:
<223> OTHER INFORMATION: Synthetic PD-1 antigen

<400> SEQUENCE: 7

Met Leu Asn Trp Tyr Arg Met Ser Pro Ser Asn Gln Thr Asp Lys Leu
1 5 10 15

Ala Ala Phe Ser
20

<210> SEQ ID NO 8
<211> LENGTH: 20
<212> TYPE: PRT
<213> ORGANISM: Artificial Sequence
<220> FEATURE:
<223> OTHER INFORMATION: Synthetic PD-1 antigen

<400> SEQUENCE: 8

Val Leu Asn Trp Tyr Arg Met Ser Pro Ser Asn Gln Thr Asp Lys Leu
1 5 10 15

```
Ala Ala Phe Pro
            20


<210> SEQ ID NO 9
<211> LENGTH: 14
<212> TYPE: PRT
<213> ORGANISM: Artificial Sequence
<220> FEATURE:
<223> OTHER INFORMATION: Synthetic PD-1 antigen

<400> SEQUENCE: 9

Gly Ala Ile Ser Leu His Pro Lys Ala Lys Ile Glu Glu Ser
1               5                   10


<210> SEQ ID NO 10
<211> LENGTH: 15
<212> TYPE: PRT
<213> ORGANISM: Artificial Sequence
<220> FEATURE:
<223> OTHER INFORMATION: Synthetic PD-1 antigen

<400> SEQUENCE: 10

Cys Gly Ala Ile Ser Leu His Pro Lys Ala Lys Ile Glu Glu Cys
1               5                   10                  15


<210> SEQ ID NO 11
<211> LENGTH: 19
<212> TYPE: PRT
<213> ORGANISM: Artificial Sequence
<220> FEATURE:
<223> OTHER INFORMATION: Synthetic PD-1 antigen

<400> SEQUENCE: 11

Val Leu Asn Trp Tyr Arg Met Ser Pro Ser Asn Gln Thr Asp Lys Leu
1               5                   10                  15

Ala Ala Phe


<210> SEQ ID NO 12
<211> LENGTH: 14
<212> TYPE: PRT
<213> ORGANISM: Artificial Sequence
<220> FEATURE:
<223> OTHER INFORMATION: Synthetic PD-1 antigen

<400> SEQUENCE: 12

Gly Ala Ile Ser Leu Ala Pro Lys Ala Gln Ile Lys Glu Ser
1               5                   10


<210> SEQ ID NO 13
<211> LENGTH: 31
<212> TYPE: PRT
<213> ORGANISM: Artificial Sequence
<220> FEATURE:
<223> OTHER INFORMATION: Synthetic PD-1 antigen

<400> SEQUENCE: 13

Arg Asn Asp Ser Gly Thr Tyr Leu Cys Gly Ala Ile Ser Leu Ala Pro
1               5                   10                  15

Lys Ala Gln Ile Lys Glu Ser Leu Arg Ala Glu Leu Arg Val Thr
            20                  25                  30


<210> SEQ ID NO 14
<211> LENGTH: 31
<212> TYPE: PRT
<213> ORGANISM: Artificial Sequence
<220> FEATURE:
```

<223> OTHER INFORMATION: Synthetic PD-1 antigen

<400> SEQUENCE: 14

Arg Asn Asp Ser Gly Ile Tyr Leu Cys Gly Ala Ile Ser Leu His Pro
1               5                   10                  15

Lys Ala Lys Ile Glu Glu Ser Pro Gly Ala Glu Leu Val Val Thr
            20                  25                  30

<210> SEQ ID NO 15
<211> LENGTH: 11
<212> TYPE: PRT
<213> ORGANISM: Artificial Sequence
<220> FEATURE:
<223> OTHER INFORMATION: Synthetic PD-L1 antigen

<400> SEQUENCE: 15

Cys Ile Ile Ser Tyr Gly Gly Ala Asp Tyr Cys
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Synthetic PD-L1 antigen

<400> SEQUENCE: 16

Cys Met Ile Ser Tyr Gly Gly Ala Asp Tyr Cys
1               5                   10

<210> SEQ ID NO 17
<211> LENGTH: 26
<212> TYPE: PRT
<213> ORGANISM: Artificial Sequence
<220> FEATURE:
<223> OTHER INFORMATION: Synthetic PD-L1 antigen

<400> SEQUENCE: 17

Leu Gln Asp Ala Gly Val Tyr Arg Cys Met Ile Ser Tyr Gly Gly Ala
1               5                   10                  15

Asp Tyr Lys Arg Ile Thr Val Lys Val Asn
            20                  25

<210> SEQ ID NO 18
<211> LENGTH: 26
<212> TYPE: PRT
<213> ORGANISM: Artificial Sequence
<220> FEATURE:
<223> OTHER INFORMATION: Synthetic PD-L1 antigen

<400> SEQUENCE: 18

Leu Gln Asp Ala Gly Val Tyr Arg Ala Met Ile Ser Tyr Gly Gly Ala
1               5                   10                  15

Asp Tyr Lys Arg Ile Thr Val Lys Val Asn
            20                  25

<210> SEQ ID NO 19
<211> LENGTH: 21
<212> TYPE: PRT
<213> ORGANISM: Artificial Sequence
<220> FEATURE:
<223> OTHER INFORMATION: Synthetic PD-L1 antigen

<400> SEQUENCE: 19

Asp Leu Ala Ala Leu Ile Val Tyr Trp Glu Met Glu Asp Lys Asn Ile

-continued

```
1               5                   10                  15

Ile Gln Phe Val His
            20


<210> SEQ ID NO 20
<211> LENGTH: 23
<212> TYPE: PRT
<213> ORGANISM: Artificial Sequence
<220> FEATURE:
<223> OTHER INFORMATION: Synthetic PD-L1 antigen

<400> SEQUENCE: 20

Asp Leu Ala Ala Leu Ile Val Tyr Trp Glu Met Glu Asp Lys Asn Ile
1               5                   10                  15

Ile Gln Phe Val His Gly Gly
            20


<210> SEQ ID NO 21
<211> LENGTH: 27
<212> TYPE: PRT
<213> ORGANISM: Artificial Sequence
<220> FEATURE:
<223> OTHER INFORMATION: Synthetic PD-L1 antigen

<400> SEQUENCE: 21

Phe Thr Val Thr Val Pro Lys Asp Leu Tyr Val Val Glu Tyr Gly Ser
1               5                   10                  15

Asn Met Thr Ile Glu Cys Lys Phe Pro Val Glu
            20                  25


<210> SEQ ID NO 22
<211> LENGTH: 26
<212> TYPE: PRT
<213> ORGANISM: Artificial Sequence
<220> FEATURE:
<223> OTHER INFORMATION: Synthetic PD-L1 antigen

<400> SEQUENCE: 22

Leu Gln Asp Ala Gly Val Tyr Cys Cys Ile Ile Ser Tyr Gly Gly Ala
1               5                   10                  15

Asp Tyr Lys Arg Ile Thr Leu Lys Val Asn
            20                  25


<210> SEQ ID NO 23
<211> LENGTH: 26
<212> TYPE: PRT
<213> ORGANISM: Artificial Sequence
<220> FEATURE:
<223> OTHER INFORMATION: Synthetic PD-L1 antigen

<400> SEQUENCE: 23

Leu Gln Asp Ala Gly Val Tyr Ala Ala Ile Ile Ser Tyr Gly Gly Ala
1               5                   10                  15

Asp Tyr Lys Arg Ile Thr Leu Lys Val Asn
            20                  25


<210> SEQ ID NO 24
<211> LENGTH: 21
<212> TYPE: PRT
<213> ORGANISM: Artificial Sequence
<220> FEATURE:
<223> OTHER INFORMATION: Synthetic PD-L1 antigen

<400> SEQUENCE: 24
```

Asp Leu Leu Ala Leu Val Val Tyr Trp Glu Lys Glu Asp Glu Gln Val
1 5 10 15

Ile Gln Phe Val Ala
20

<210> SEQ ID NO 25
<211> LENGTH: 23
<212> TYPE: PRT
<213> ORGANISM: Artificial Sequence
<220> FEATURE:
<223> OTHER INFORMATION: Synthetic PD-L1 antigen

<400> SEQUENCE: 25

Asp Leu Leu Ala Leu Val Val Tyr Trp Glu Lys Glu Asp Glu Gln Val
1 5 10 15

Ile Gln Phe Val Ala Gly Gly
20

<210> SEQ ID NO 26
<211> LENGTH: 27
<212> TYPE: PRT
<213> ORGANISM: Artificial Sequence
<220> FEATURE:
<223> OTHER INFORMATION: Synthetic PD-L1 antigen

<400> SEQUENCE: 26

Phe Thr Ile Thr Ala Pro Lys Asp Leu Tyr Val Val Glu Tyr Gly Ser
1 5 10 15

Asn Val Thr Met Glu Cys Arg Phe Pro Val Glu
20 25

<210> SEQ ID NO 27
<211> LENGTH: 18
<212> TYPE: PRT
<213> ORGANISM: Artificial Sequence
<220> FEATURE:
<223> OTHER INFORMATION: Synthetic CTLA-4 antigen

<400> SEQUENCE: 27

Gly Gly Lys Val Glu Leu Met Tyr Pro Pro Pro Tyr Phe Val Gly Met
1 5 10 15

Gly Gly

<210> SEQ ID NO 28
<211> LENGTH: 19
<212> TYPE: PRT
<213> ORGANISM: Artificial Sequence
<220> FEATURE:
<223> OTHER INFORMATION: Synthetic CTLA-4 antigen

<400> SEQUENCE: 28

Cys Ala Thr Thr Phe Thr Glu Lys Asn Thr Val Gly Phe Leu Asp Tyr
1 5 10 15

Pro Phe Cys

<210> SEQ ID NO 29
<211> LENGTH: 17
<212> TYPE: PRT
<213> ORGANISM: Artificial Sequence
<220> FEATURE:
<223> OTHER INFORMATION: Synthetic CTLA-4 antigen

<400> SEQUENCE: 29

Ala Thr Thr Phe Thr Glu Lys Asn Thr Val Gly Phe Leu Asp Tyr Pro 1 5 10 15

Phe

<210> SEQ ID NO 30
<211> LENGTH: 8401
<212> TYPE: DNA
<213> ORGANISM: Artificial Sequence
<220> FEATURE:
<223> OTHER INFORMATION: Synthetic _CHI 0 antigen (E3) vector

<400> SEQUENCE: 30

```
gaattcccat tgcatacgtt gtatccatat cataatatgt acatttatat tggctcatgt      60
ccaacattac cgccatgttg acattgatta ttgactagtt attaatagta atcaattacg     120
gggtcattag ttcatagccc atatatggag ttccgcgtta cataacttac ggtaaatggc     180
ccgcctggct gaccgcccaa cgacccccgc ccattgacgt caataatgac gtatgttccc     240
atagtaacgc caatagggac tttccattga cgtcaatggg tggagtattt acggtaaact     300
gcccacttgg cagtacatca agtgtatcat atgccaagta cgccccctat tgacgtcaat     360
gacggtaaat ggcccgcctg gcattatgcc cagtacatga ccttatggga ctttcctact     420
tggcagtaca tctacgtatt agtcatcgct attaccatgg tgatgcggtt ttggcagtac     480
atcaatgggc gtggatagcg gtttgactca cggggatttc caagtctcca ccccattgac     540
gtcaatggga gtttgttttg gcaccaaaat caacgggact ttccaaaatg tcgtaacaac     600
tccgccccat tgacgcaaat gggcggtagg cgtgtacggt gggaggtcta tataagcaga     660
gctcgtttag tgaaccgtca gatcgcctgg agacgccatc cacgctgttt tgacctccat     720
agaagacacc gggaccgatc cagcctccgt taacggtgga gggcagtgta gtctgagcag     780
tactcgttgc tgccgcgcgc gccaccagac ataatagctg acagactaac agactgttcc     840
tttccatggg tcttttctgc agtcaccgtc gtcgacacgt gtgatcagat atcgcggccg     900
ccaccatgga gttcatcccg acgcaaactt tctataacag aaggtaccaa ccccgaccct     960
gggccccacg ccctacaatt caagtaatta gacctagacc acgtccacag aggcaggctg    1020
ggcaactcgc ccagctgatc tccgcagtca acaaattgac catgcgcgcg gtacctcaac    1080
agaagcctcg cagaaatcgg aaaaacaaga agcaaaggca gaagaagcag gcgccgcaaa    1140
acgacccaaa gcaaaagaag caaccaccac aaaagaagcc ggctcaaaag aagaagaaac    1200
caggccgtag ggagagaatg tgcatgaaaa ttgaaaatga ttgcatcttc gaagtcaagc    1260
atgaaggcaa agtgatgggc tacgcatgcc tggtggggga taaagtaatg aaaccagcac    1320
atgtgaaggg aactatcgac aatgccgatc tggctaaact ggcctttaag cggtcgtcta    1380
aatacgatct tgaatgtgca cagataccgg tgcacatgaa gtctgatgcc tcgaagttta    1440
cccacgagaa acccgagggg tactataact ggcatcacgg agcagtgcag tattcaggag    1500
gccggttcac tatcccgacg ggtgcaggca agccgggaga cagcggcaga ccgatcttcg    1560
acaacaaagg acgggtggtg gccatcgtcc taggaggggc caacgaaggt gcccgcacgg    1620
ccctctccgt ggtgacgtgg aacaaagaca tcgtcacaaa aattacccct gagggagccg    1680
aagagtggag cctcgccctc ccggtcttgt gcctgttggc aaacactaca ttcccctgct    1740
ctcagccgcc ttgcacaccc tgctgctacg aaaaggaacc ggaaagcacc ttgcgcatgc    1800
ttgaggacaa cgtgatgaga cccggatact accagctact aaaagcatcg ctgacttgct    1860
ctccccactc cggaggagga tccagtacta aggacaattt taatgtctat aaagccacaa    1920
gaccatatct agctcattgt cctgactgcg gagaagggca ttcgtgccac agccctatcg    1980
```

-continued

```
cattggagcg catcagaaat gaagcaacgg acggaacgct gaaaatccag gtctctttgc   2040
agatcgggat aaagacagat gacagccacg attggaccaa gctgcgctat atggatagcc   2100
atacgcccgc ggacgcggag cgagccggat tgcttgtaag gacttcagca ccgtgcacga   2160
tcaccgggac catgggacac tttattctcg cccgatgccc gaaaggagag acgctgacag   2220
tgggatttac ggacagcaga aagatcagcc acacatgcac acacccgttc catcatgaac   2280
cacctgtgat aggtagggag aggttccact ctcgaccaca acatggtaaa gagttacctt   2340
gcagcacgta cgtgcagagc accgctgcca ctgctgagga gatagaggtg catatgcccc   2400
cagatactcc tgaccgcacg ctgatgacgc agcagtctgg caacgtgaag atcacagtta   2460
atgggcagac ggtgcggtac aagtgcaact gcggtggctc aaacgaggga ctgacaacca   2520
cagacaaagt gatcaataac tgcaaaattg atcagtgcca tgctgcagtc actaatcaca   2580
agaattggca atacaactcc cctttagtcc cgcgcaacgc tgaactcggg gaccgtaaag   2640
gaaagatcca catcccattc ccattggcaa acgtgacttg cagagtgcca aaagcaagaa   2700
accctacagt aacttacgga aaaaaccaag tcaccatgct gctgtatcct gaccatccga   2760
cactcttgtc ttaccgtaac atgggacagg aaccaaatta ccacgaggag tgggtgacac   2820
acaagaagga ggttaccttg accgtgccta ctgagggtct ggaggtcact tggggcaaca   2880
acgaaccata caagtactgg ccgcagatgt ctacgaacgg tactgctcat ggtcacccac   2940
atgagataat cttgtactat tatgagctgt accccactat gactgtagtc attgtgtcgg   3000
tggcctcgtt cgtgcttctg tcgatggtgg gcacagcagt gggaatgtgt gtgtgcgcac   3060
ggcgcagatg cattacacca tatgaattaa caccaggagc cactgttccc ttcctgctca   3120
gcctgctatg ctgcgtcaga acgaccaagg cggccacata ttacgaggct gcggcatatc   3180
tatggaacga acagcagccc ctgttctggt tgcaggctct tatcccgctg gccgccttga   3240
tcgtcctgtg caactgtctg aaactcttgc catgctgctg taagaccctg gctttttttag   3300
ccgtaatgag catcggtgcc cacactgtga gcgcgtacga acacgtaaca gtgatcccga   3360
acacggtggg agtaccgtat aagactcttg tcaacagacc gggttacagc cccatggtgt   3420
tggagatgga gctacaatca gtcaccttgg aaccaacact gtcacttgac tacatcacgt   3480
gcgagtacaa aactgtcatc cctctccccgt acgtgaagtg ctgtggtaca gcagagtgca   3540
aggacaagag cctaccagac tacagctgca aggtctttac tggagtctac ccatttatgt   3600
ggggcggcgc ctactgcttt tgcgacgccg aaaatacgca attgagcgag gcacatgtag   3660
agaaatctga atcttgcaaa acagagtttg catcggccta cagagcccac accgcatcgg   3720
cgtcggcgaa gctccgcgtc ctttaccaag gaaacaacat taccgtagct gcctacgcta   3780
acggtgacca tgccgtcaca gtaaaggacg ccaagtttgt cgtgggccca atgtcctccg   3840
cctggacacc ttttgacaac aaaatcgtgg tgtacaaagg cgacgtctac aacatggact   3900
acccaccttt tggcgcagga agaccaggac aatttggtga cattcaaagt cgtacaccgg   3960
aaagtaaaga cgtttatgcc aacactcagt tggtactaca gaggccagca gcaggcacgg   4020
tacatgtacc atactctcag gcaccatctg gcttcaagta ttggctgaag gaacgaggag   4080
catcgctaca gcacacggca ccgttcggtt gccagattgc gacaaacccg gtaagagctg   4140
taaattgcgc tgtggggaac ataccaattt ccatcgacat accggatgcg gcctttacta   4200
gggttgtcga tgcaccctct gtaacggaca tgtcatgcga agtaccagcc tgcactcact   4260
cctccgactt tgggggcgtc gccatcatca aatacacagc tagcaagaaa ggtaaatgtg   4320
```

```
cagtacattc gatgaccaac gccgttacca ttcgagaagc cgacgtagaa gtagagggga   4380
actcccagct gcaaatatcc ttctcaacag ccctggcaag cgccgagttt cgcgtgcaag   4440
tgtgctccac acaagtacac tgcgcagccg catgccaccc tccaaaggac cacatagtca   4500
attacccagc atcacacacc acccttgggg tccaggatat atccacaacg gcaatgtctt   4560
gggtgcagaa gattacggga ggagtaggat taattgttgc tgttgctgcc ttaattttaa   4620
ttgtggtgct atgcgtgtcg tttagcaggc actaaggatc tagatctgct gtgccttcta   4680
gttgccagcc atctgttgtt tgcccctccc ccgtgccttc cttgaccctg gaaggtgcca   4740
ctcccactgt cctttcctaa taaaatgagg aaattgcatc gcattgtctg agtaggtgtc   4800
attctattct ggggggtggg gtggggcagg acagcaaggg ggaggattgg gaagacaata   4860
gcaggcatgc tggggatgcg gtgggctcta tgggtaccca ggtgctgaag aattgacccg   4920
gttcctcctg ggccagaaag aagcaggcac atccccttct ctgtgacaca ccctgtccac   4980
gcccctggtt cttagttcca gccccactca taggacactc atagctcagg agggctccgc   5040
cttcaatccc acccgctaaa gtacttggag cggtctctcc ctccctcatc agcccaccaa   5100
accaaaccta gcctccaaga gtgggaagaa attaaagcaa gataggctat taagtgcaga   5160
gggagagaaa atgcctccaa catgtgagga agtaatgaga gaaatcatag aattttaagg   5220
ccatgattta aggccatcat ggcctaagct tgaaaggaga taggatcaaa gcttggcgta   5280
atcatggtca tagctgtttc ctgtgtgaaa ttgttatccg ctcacaattc cacacaacat   5340
acgagccgga agcataaagt gtaaagcctg gggtgcctaa tgagtgagct aactcacatt   5400
aattgcgttg cgctcactgc ccgctttcca gtcgggaaac ctgtcgtgcc agctgcatta   5460
atgaatcggc caacgcgcgg ggagaggcgg tttgcgtatt gggcgctctt ccgcttcctc   5520
gctcactgac tcgctgcgct cggtcgttcg gctgcggcga gcggtatcag ctcactcaaa   5580
ggcggtaata cggttatcca cagaatcagg ggataacgca ggaaagaaca tgtgagcaaa   5640
aggccagcaa aaggccagga accgtaaaaa ggccgcgttg ctggcgtttt tccataggct   5700
ccgcccccct gacgagcatc acaaaaatcg acgctcaagt cagaggtggc gaaacccgac   5760
aggactataa agataccagg cgtttccccc tggaagctcc ctcgtgcgct ctcctgttcc   5820
gaccctgccg cttaccggat acctgtccgc ctttctccct tcgggaagcg tggcgctttc   5880
tcatagctca cgctgtaggt atctcagttc ggtgtaggtc gttcgctcca agctgggctg   5940
tgtgcacgaa ccccccgttc agcccgaccg ctgcgcctta tccggtaact atcgtcttga   6000
gtccaacccg gtaagacacg acttatcgcc actggcagca gccactggta acaggattag   6060
cagagcgagg tatgtaggcg gtgctacaga gttcttgaag tggtggccta actacggcta   6120
cactagaaga acagtatttg gtatctgcgc tctgctgaag ccagttacct tcggaaaaag   6180
agttggtagc tcttgatccg gcaaacaaac caccgctggt agcggtggtt tttttgtttg   6240
caagcagcag attacgcgca gaaaaaaagg atctcaagaa gatcctttga tcttttctac   6300
ggggtctgac gctcagtgga acgaaaactc acgttaaggg attttggtca tgagattatc   6360
aaaaaggatc ttcacctaga tccttttaaa ttaaaaatga agttttaaat caatctaaag   6420
tatatatgag taaacttggt ctgacagtta ccaatgctta atcagtgagg cacctatctc   6480
agcgatctgt ctatttcgtt catccatagt tgcctgactc cccgtcgtgt agataactac   6540
gatacgggag ggcttaccat ctggccccag tgctgcaatg ataccgcgag aaccacgctc   6600
accggctcca gatttatcag caataaacca gccagccgga agggccgagc gcagaagtgg   6660
tcctgcaact ttatccgcct ccatccagtc tattaattgt tgccgggaag ctagagtaag   6720
```

-continued

```
tagttcgcca gttaatagtt tgcgcaacgt tgttgccatt gctacaggca tcgtggtgtc   6780

acgctcgtcg tttggtatgg cttcattcag ctccggttcc caacgatcaa ggcgagttac   6840

atgatccccc atgttgtgca aaaaagcggt tagctccttc ggtcctccga tcgttgtcag   6900

aagtaagttg gccgcagtgt tatcactcat ggttatggca gcactgcata attctcttac   6960

tgtcatgcca tccgtaagat gcttttctgt gactggtgag tactcaacca agtcattctg   7020

agaatagtgt atgcggcgac cgagttgctc ttgcccggcg tcaatacggg ataataccgc   7080

gccacatagc agaactttaa aagtgctcat cattggaaaa cgttcttcgg ggcgaaaact   7140

ctcaaggatc ttaccgctgt tgagatccag ttcgatgtaa cccactcgtg cacccaactg   7200

atcttcagca tcttttactt tcaccagcgt ttctgggtga gcaaaaacag gaaggcaaaa   7260

tgccgcaaaa aagggaataa gggcgacacg gaaatgttga atactcatac tcttcctttt   7320

tcaatattat tgaagcattt atcagggtta ttgtctcatg agcggataca tatttgaatg   7380

tatttagaaa aataaacaaa taggggttcc gcgcacattt ccccgaaaag tgccacctga   7440

cgtctaagaa accattatta tcatgacatt aacctataaa aataggcgta tcacgaggcc   7500

ctttcgggtc gcgcgtttcg gtgatgacgg tgaaaacctc tgacacatgc agctcccgtt   7560

gacggtcaca gcttgtctgt aagcggatgc cgggagcaga caagcccgtc agggcgcgtc   7620

agcgggtgtt ggcgggtgtc ggggctggct taactatgcg gcatcagagc agattgtact   7680

gagagtgcac cataaaattg taaacgttaa tattttgtta aaattcgcgt taaatttttg   7740

ttaaatcagc tcatttttta accaataggc cgaaatcggc aaaatccctt ataaatcaaa   7800

agaatagccc gagatagggt tgagtgttgt tccagtttgg aacaagagtc cactattaaa   7860

gaacgtggac tccaacgtca aagggcgaaa aaccgtctat cagggcgatg gcccactacg   7920

tgaaccatca cccaaatcaa gttttttggg gtcgaggtgc cgtaaagcac taaatcggaa   7980

ccctaaaggg agcccccgat ttagagcttg acggggaaag ccggcgaacg tggcgagaaa   8040

ggaagggaag aaagcgaaag gagcgggcgc tagggcgctg gcaagtgtag cggtcacgct   8100

gcgcgtaacc accacacccg ccgcgcttaa tgcgccgcta cagggcgcgt actatggttg   8160

ctttgacgta tgcggtgtga aataccgcac agatgcgtaa ggagaaaata ccgcatcagg   8220

cgccattcgc cattcaggct gcgcaactgt tgggaagggc gatcggtgcg ggcctcttcg   8280

ctattacgcc agctggcgaa aggggggatgt gctgcaaggc gattaagttg ggtaacgcca   8340

gggttttccc agtcacgacg ttgtaaaacg acggccagtg aattccatgg tctcaacttt   8400

c                                                                   8401


<210> SEQ ID NO 31
<211> LENGTH: 261
<212> TYPE: PRT
<213> ORGANISM: Artificial Sequence
<220> FEATURE:
<223> OTHER INFORMATION: Synthetic CHIKV Capsid (37997 strain)

<400> SEQUENCE: 31

Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
```

```
    50                  55                  60

Arg Lys Asn Lys Lys Gln Arg Gln Lys Lys Gln Ala Pro Gln Asn Asp
65                  70                  75                  80

Pro Lys Gln Lys Lys Gln Pro Pro Gln Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Met Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp
            260


<210> SEQ ID NO 32
<211> LENGTH: 439
<212> TYPE: PRT
<213> ORGANISM: Artificial Sequence
<220> FEATURE:
<223> OTHER INFORMATION: Synthetic CHIKV E1 (37997 strain)

<400> SEQUENCE: 32

Tyr Glu His Val Thr Val Ile Pro Asn Thr Val Gly Val Pro Tyr Lys
1               5                   10                  15

Thr Leu Val Asn Arg Pro Gly Tyr Ser Pro Met Val Leu Glu Met Glu
            20                  25                  30

Leu Gln Ser Val Thr Leu Glu Pro Thr Leu Ser Leu Asp Tyr Ile Thr
        35                  40                  45

Cys Glu Tyr Lys Thr Val Ile Pro Ser Pro Tyr Val Lys Cys Cys Gly
    50                  55                  60

Thr Ala Glu Cys Lys Asp Lys Ser Leu Pro Asp Tyr Ser Cys Lys Val
65                  70                  75                  80

Phe Thr Gly Val Tyr Pro Phe Met Trp Gly Gly Ala Tyr Cys Phe Cys
                85                  90                  95

Asp Ala Glu Asn Thr Gln Leu Ser Glu Ala His Val Glu Lys Ser Glu
            100                 105                 110

Ser Cys Lys Thr Glu Phe Ala Ser Ala Tyr Arg Ala His Thr Ala Ser
        115                 120                 125

Ala Ser Ala Lys Leu Arg Val Leu Tyr Gln Gly Asn Asn Ile Thr Val
    130                 135                 140

Ala Ala Tyr Ala Asn Gly Asp His Ala Val Thr Val Lys Asp Ala Lys
```

145 150 155 160

Phe Val Val Gly Pro Met Ser Ser Ala Trp Thr Pro Phe Asp Asn Lys
165 170 175

Ile Val Val Tyr Lys Gly Asp Val Tyr Asn Met Asp Tyr Pro Pro Phe
180 185 190

Gly Ala Gly Arg Pro Gly Gln Phe Gly Asp Ile Gln Ser Arg Thr Pro
195 200 205

Glu Ser Lys Asp Val Tyr Ala Asn Thr Gln Leu Val Leu Gln Arg Pro
210 215 220

Ala Ala Gly Thr Val His Val Pro Tyr Ser Gln Ala Pro Ser Gly Phe
225 230 235 240

Lys Tyr Trp Leu Lys Glu Arg Gly Ala Ser Leu Gln His Thr Ala Pro
245 250 255

Phe Gly Cys Gln Ile Ala Thr Asn Pro Val Arg Ala Val Asn Cys Ala
260 265 270

Val Gly Asn Ile Pro Ile Ser Ile Asp Ile Pro Asp Ala Ala Phe Thr
275 280 285

Arg Val Val Asp Ala Pro Ser Val Thr Asp Met Ser Cys Glu Val Pro
290 295 300

Ala Cys Thr His Ser Ser Asp Phe Gly Gly Val Ala Ile Ile Lys Tyr
305 310 315 320

Thr Ala Ser Lys Lys Gly Lys Cys Ala Val His Ser Met Thr Asn Ala
325 330 335

Val Thr Ile Arg Glu Ala Asp Val Glu Val Glu Gly Asn Ser Gln Leu
340 345 350

Gln Ile Ser Phe Ser Thr Ala Leu Ala Ser Ala Glu Phe Arg Val Gln
355 360 365

Val Cys Ser Thr Gln Val His Cys Ala Ala Ala Cys His Pro Pro Lys
370 375 380

Asp His Ile Val Asn Tyr Pro Ala Ser His Thr Thr Leu Gly Val Gln
385 390 395 400

Asp Ile Ser Thr Thr Ala Met Ser Trp Val Gln Lys Ile Thr Gly Gly
405 410 415

Val Gly Leu Ile Val Ala Val Ala Ala Leu Ile Leu Ile Val Val Leu
420 425 430

Cys Val Ser Phe Ser Arg His
435

<210> SEQ ID NO 33
<211> LENGTH: 483
<212> TYPE: PRT
<213> ORGANISM: Artificial Sequence
<220> FEATURE:
<223> OTHER INFORMATION: Synthetic CHIKV E3-insert-E2 (37997 strain)
<220> FEATURE:
<221> NAME/KEY: NON_CONS
<222> LOCATION: (60)..(61)
<223> OTHER INFORMATION: antigen will be inserted

<400> SEQUENCE: 33

Ser Leu Ala Leu Pro Val Leu Cys Leu Leu Ala Asn Thr Thr Phe Pro
1 5 10 15

Cys Ser Gln Pro Pro Cys Thr Pro Cys Cys Tyr Glu Lys Glu Pro Glu
20 25 30

Ser Thr Leu Arg Met Leu Glu Asp Asn Val Met Arg Pro Gly Tyr Tyr
35 40 45

-continued

```
Gln Leu Leu Lys Ala Ser Leu Thr Cys Ser Pro His Ser Thr Lys Asp
    50                  55                  60

Asn Phe Asn Val Tyr Lys Ala Thr Arg Pro Tyr Leu Ala His Cys Pro
65                  70                  75                  80

Asp Cys Gly Glu Gly His Ser Cys His Ser Pro Ile Ala Leu Glu Arg
                85                  90                  95

Ile Arg Asn Glu Ala Thr Asp Gly Thr Leu Lys Ile Gln Val Ser Leu
            100                 105                 110

Gln Ile Gly Ile Lys Thr Asp Asp Ser His Asp Trp Thr Lys Leu Arg
        115                 120                 125

Tyr Met Asp Ser His Thr Pro Ala Asp Ala Glu Arg Ala Gly Leu Leu
    130                 135                 140

Val Arg Thr Ser Ala Pro Cys Thr Ile Thr Gly Thr Met Gly His Phe
145                 150                 155                 160

Ile Leu Ala Arg Cys Pro Lys Gly Glu Thr Leu Thr Val Gly Phe Thr
                165                 170                 175

Asp Ser Arg Lys Ile Ser His Thr Cys Thr His Pro Phe His His Glu
            180                 185                 190

Pro Pro Val Ile Gly Arg Glu Arg Phe His Ser Arg Pro Gln His Gly
        195                 200                 205

Lys Glu Leu Pro Cys Ser Thr Tyr Val Gln Ser Thr Ala Ala Thr Ala
    210                 215                 220

Glu Glu Ile Glu Val His Met Pro Pro Asp Thr Pro Asp Arg Thr Leu
225                 230                 235                 240

Met Thr Gln Gln Ser Gly Asn Val Lys Ile Thr Val Asn Gly Gln Thr
                245                 250                 255

Val Arg Tyr Lys Cys Asn Cys Gly Gly Ser Asn Glu Gly Leu Thr Thr
            260                 265                 270

Thr Asp Lys Val Ile Asn Asn Cys Lys Ile Asp Gln Cys His Ala Ala
        275                 280                 285

Val Thr Asn His Lys Asn Trp Gln Tyr Asn Ser Pro Leu Val Pro Arg
    290                 295                 300

Asn Ala Glu Leu Gly Asp Arg Lys Gly Lys Ile His Ile Pro Phe Pro
305                 310                 315                 320

Leu Ala Asn Val Thr Cys Arg Val Pro Lys Ala Arg Asn Pro Thr Val
                325                 330                 335

Thr Tyr Gly Lys Asn Gln Val Thr Met Leu Leu Tyr Pro Asp His Pro
            340                 345                 350

Thr Leu Leu Ser Tyr Arg Asn Met Gly Gln Glu Pro Asn Tyr His Glu
        355                 360                 365

Glu Trp Val Thr His Lys Lys Glu Val Thr Leu Thr Val Pro Thr Glu
    370                 375                 380

Gly Leu Glu Val Thr Trp Gly Asn Asn Glu Pro Tyr Lys Tyr Trp Pro
385                 390                 395                 400

Gln Met Ser Thr Asn Gly Thr Ala His Gly His Pro His Glu Ile Ile
                405                 410                 415

Leu Tyr Tyr Tyr Glu Leu Tyr Pro Thr Met Thr Val Val Ile Val Ser
            420                 425                 430

Val Ala Ser Phe Val Leu Leu Ser Met Val Gly Thr Ala Val Gly Met
        435                 440                 445

Cys Val Cys Ala Arg Arg Arg Cys Ile Thr Pro Tyr Glu Leu Thr Pro
    450                 455                 460

Gly Ala Thr Val Pro Phe Leu Leu Ser Leu Leu Cys Cys Val Arg Thr
```

465 470 475 480

Thr Lys Ala

<210> SEQ ID NO 34
<211> LENGTH: 8422
<212> TYPE: DNA
<213> ORGANISM: Artificial Sequence
<220> FEATURE:
<223> OTHER INFORMATION: Synthetic _VEEV 0.66 vector

<400> SEQUENCE: 34
gaattcccat tgcatacgtt gtatccatat cataatatgt acatttatat tggctcatgt 60
ccaacattac cgccatgttg acattgatta ttgactagtt attaatagta atcaattacg 120
gggtcattag ttcatagccc atatatggag ttccgcgtta cataacttac ggtaaatggc 180
ccgcctggct gaccgcccaa cgacccccgc ccattgacgt caataatgac gtatgttccc 240
atagtaacgc caatagggac tttccattga cgtcaatggg tggagtattt acggtaaact 300
gcccacttgg cagtacatca agtgtatcat atgccaagta cgccccctat tgacgtcaat 360
gacggtaaat ggcccgcctg gcattatgcc cagtacatga ccttatggga ctttcctact 420
tggcagtaca tctacgtatt agtcatcgct attaccatgg tgatgcggtt ttggcagtac 480
atcaatgggc gtggatagcg gtttgactca cggggatttc caagtctcca ccccattgac 540
gtcaatggga gtttgttttg gcaccaaaat caacgggact ttccaaaatg tcgtaacaac 600
tccgccccat tgacgcaaat gggcggtagg cgtgtacggt gggaggtcta tataagcaga 660
gctcgtttag tgaaccgtca gatcgcctgg agacgccatc cacgctgttt tgacctccat 720
agaagacacc gggaccgatc cagcctccgt taacggtgga gggcagtgta gtctgagcag 780
tactcgttgc tgccgcgcgc gccaccagac ataatagctg acagactaac agactgttcc 840
tttccatggg tcttttctgc agtcaccgtc gtcgacacgt gtgatcagat atcgcggccg 900
ccaccatgtt cccgttccag ccaatgtatc cgatgcagcc aatgccctat cgcaacccgt 960
tcgcggcccc gcgcaggccc tggttcccca gaaccgaccc ttttctggcg atgcaggtgc 1020
aggaattaac ccgctcgatg gctaacctga cgttcaagca acgccgggac gcgccacctg 1080
aggggccatc cgctaataaa ccgaagaagg aggcctcgca aaaacagaaa gggggaggcc 1140
aagggaagaa gaagaagaac caagggaaga agaaggctaa gacagggccg cctaatccga 1200
aggcacagaa tggaaacaag aagaagacca acaagaaacc aggcaagaga cagcgcatgg 1260
tcatgaaatt ggaatctgac aagacgttcc caatcatgtt ggaagggaag ataaacggct 1320
acgcttgtgt ggtcggaggg aagttattca ggccgatgca tgtggaaggc aagatcgaca 1380
acgacgttct ggccgcgctt aagacgaaga aagcatccaa atacgatctt gagtatgcag 1440
atgtgccaca gaacatgcgg gccgatacat tcaaatacac ccatgagaaa ccccaaggct 1500
attacagctg gcatcatgga gcagtccaat atgaaaatgg gcgtttcacg gtgccgaaag 1560
gagttggggc caagggagac agcggacgac ccattctgga taaccaggga cgggtggtcg 1620
ctattgtgct gggaggtgtg aatgaaggat ctaggacagc cctttcagtc gtcatgtgga 1680
acgagaaggg agttaccgtg aagtatactc cagagaactg cgagcaatgg tcactagtga 1740
ccaccatgtg tctgctcgcc aatgtgacgt tcccatgtgc tcaaccacca atttgctacg 1800
acagaaaacc agcagagact ttggccatgc tcagcgttaa cgttgacaac ccgggctacg 1860
atgagctgct ggaagcagct gttaagtgcc ccgggtccgg aggtggatcc tccaccgagg 1920
agctgtttaa tgagtataag ctaacgcgcc cttacatggc cagatgcatc agatgtgcag 1980

```
ttgggagctg ccatagtcca atagcaatcg aggcagtaaa gagcgacggg cacgacggtt   2040
atgttagact tcagacttcc tcgcagtatg gcctggattc ctccggcaac ttaaagggca   2100
ggaccatgcg gtatgacatg cacgggacca ttaaagagat accactacat caagtgtcac   2160
tctatacatc tcgcccgtgt cacattgtgg atgggcacgg ttatttcctg ctagccaggt   2220
gcccggcagg ggactccatc accatggaat ttaagaaaga ttccgtcaga cactcctgct   2280
cggtgccgta tgaagtgaaa tttaatcctg taggcagaga actctatact catcccccag   2340
aacacggagt agagcaagcg tgccaagtct acgcacatga tgcacagaac agaggagctt   2400
atgtcgagat gcacctcccg ggctcagaag tggacagcag tttggtttcc ttgagcggca   2460
gttcagtcac cgtgacacct cctgatggga ctagcgccct ggtggaatgc gagtgtggcg   2520
gcacaaagat ctccgagacc atcaacaaga caaaacagtt cagccagtgc acaaagaagg   2580
agcagtgcag agcatatcgg ctgcagaacg ataagtgggt gtataattct gacaaactgc   2640
ccaaagcagc gggagccacc ttaaaaggaa aactgcatgt cccattcttg ctggcagacg   2700
gcaaatgcac cgtgcctcta gcaccagaac ctatgataac cttcggtttc agatcagtgt   2760
cactgaaact gcaccctaag aatcccacat atctaatcac ccgccaactt gctgatgagc   2820
ctcactacac gcacgagctc atatctgaac cagctgttag gaattttacc gtcaccgaaa   2880
aagggtggga gtttgtatgg ggaaaccacc cgccgaaaag gttttgggca caggaaacag   2940
cacccggaaa tccacatggg ctaccgcacg aggtgataac tcattattac cacagatacc   3000
ctatgtccac catcctgggt ttgtcaattt gtgccgccat tgcaaccgtt tccgttgcag   3060
cgtctacctg gctgttttgc agatcaagag ttgcgtgcct aactccttac cggctaacac   3120
ctaacgctag gataccattt tgtctggctg tgctttgctg cgcccgcact gcccgggccg   3180
agaccacctg ggagtccttg gatcacctat ggaacaataa ccaacagatg ttctggattc   3240
aattgctgat ccctctggcc gccttgatcg tagtgactcg cctgctcagg tgcgtgtgct   3300
gtgtcgtgcc tttttagtc atggccggcg ccgcaggcgc cggcgcctac gagcacgcga   3360
ccacgatgcc gagccaagcg ggaatctcgt ataacactat agtcaacaga gcaggctacg   3420
caccactccc tatcagcata acaccaacaa agatcaagct gatacctaca gtgaacttgg   3480
agtacgtcac ctgccactac aaaacaggaa tggattcacc agccatcaaa tgctgcggat   3540
ctcaggaatg cactccaact tacaggcctg atgaacagtg caaagtcttc acaggggttt   3600
acccgttcat gtggggtggt gcatattgct tttgcgacac tgagaacacc caagtcagca   3660
aggcctacgt aatgaaatct gacgactgcc ttgcggatca tgctgaagca tataaagcgc   3720
acacagcctc agtgcaggcg ttcctcaaca tcacagtggg agaacactct attgtgacta   3780
ccgtgtatgt gaatggagaa actcctgtga atttcaatgg ggtcaaaata actgcaggtc   3840
cgctttccac agcttggaca ccctttgatc gcaaaatcgt gcagtatgcc ggggagatct   3900
ataattatga ttttcctgag tatggggcag gacaaccagg agcatttgga gatatacaat   3960
ccagaacagt ctcaagctct gatctgtatg ccaataccaa cctagtgctg cagagaccca   4020
aagcaggagc gatccacgtg ccatacactc aggcaccttc gggttttgag caatggaaga   4080
aagataaagc tccatcattg aaatttaccg cccctttcgg atgcgaaata tatacaaacc   4140
ccattcgcgc cgaaaactgt gctgtagggt caattccatt agcctttgac attcccgacg   4200
ccttgttcac cagggtgtca gaaacaccga cactttcagc ggccgaatgc actcttaacg   4260
agtgcgtgta ttcttccgac tttggtggga tcgccacggt caagtactcg gccagcaagt   4320
```

```
caggcaagtg cgcagtccat gtgccatcag ggactgctac cctaaaagaa gcagcagtcg   4380
agctaaccga gcaagggtcg gcgactatcc atttctcgac cgcaaatatc cacccggagt   4440
tcaggctcca aatatgcaca tcatatgtta cgtgcaaagg tgattgtcac cccccgaaag   4500
accatattgt gacacaccct cagtatcacg cccaaacatt tacagccgcg gtgtcaaaaa   4560
ccgcgtggac gtggttaaca tccctgctgg gaggatcagc cgtaattatt ataattggct   4620
tggtgctggc tactattgtg gccatgtacg tgctgaccaa ccagaaacat aattaaggat   4680
ctagatctgc tgtgccttct agttgccagc catctgttgt ttgcccctcc cccgtgcctt   4740
ccttgaccct ggaaggtgcc actcccactg tcctttccta ataaaatgag gaaattgcat   4800
cgcattgtct gagtaggtgt cattctattc tggggggtgg ggtggggcag gacagcaagg   4860
gggaggattg ggaagacaat agcaggcatg ctggggatgc ggtgggctct atgggtaccc   4920
aggtgctgaa gaattgaccc ggttcctcct gggccagaaa gaagcaggca catccccttc   4980
tctgtgacac accctgtcca cgcccctggt tcttagttcc agccccactc ataggacact   5040
catagctcag gagggctccg ccttcaatcc cacccgctaa agtacttgga gcggtctctc   5100
cctccctcat cagcccacca aaccaaacct agcctccaag agtgggaaga aattaaagca   5160
agataggcta ttaagtgcag agggagagaa aatgcctcca acatgtgagg aagtaatgag   5220
agaaatcata gaattttaag gccatgattt aaggccatca tggcctaagc ttgaaaggag   5280
ataggatcaa agcttggcgt aatcatggtc atagctgttt cctgtgtgaa attgttatcc   5340
gctcacaatt ccacacaaca tacgagccgg aagcataaag tgtaaagcct ggggtgccta   5400
atgagtgagc taactcacat taattgcgtt gcgctcactg cccgctttcc agtcgggaaa   5460
cctgtcgtgc cagctgcatt aatgaatcgg ccaacgcgcg gggagaggcg gtttgcgtat   5520
tgggcgctct tccgcttcct cgctcactga ctcgctgcgc tcggtcgttc ggctgcggcg   5580
agcggtatca gctcactcaa aggcggtaat acggttatcc acagaatcag gggataacgc   5640
aggaaagaac atgtgagcaa aaggccagca aaaggccagg aaccgtaaaa aggccgcgtt   5700
gctggcgttt ttccataggc tccgcccccc tgacgagcat cacaaaaatc gacgctcaag   5760
tcagaggtgg cgaaacccga caggactata aagataccag gcgtttcccc ctggaagctc   5820
cctcgtgcgc tctcctgttc cgaccctgcc gcttaccgga tacctgtccg cctttctccc   5880
ttcgggaagc gtggcgcttt ctcatagctc acgctgtagg tatctcagtt cggtgtaggt   5940
cgttcgctcc aagctgggct gtgtgcacga accccccgtt cagcccgacc gctgcgcctt   6000
atccggtaac tatcgtcttg agtccaaccc ggtaagacac gacttatcgc cactggcagc   6060
agccactggt aacaggatta gcagagcgag gtatgtaggc ggtgctacag agttcttgaa   6120
gtggtggcct aactacggct acactagaag aacagtattt ggtatctgcg ctctgctgaa   6180
gccagttacc ttcggaaaaa gagttggtag ctcttgatcc ggcaaacaaa ccaccgctgg   6240
tagcggtggt ttttttgttt gcaagcagca gattacgcgc agaaaaaaag gatctcaaga   6300
agatcctttg atcttttcta cggggtctga cgctcagtgg aacgaaaact cacgttaagg   6360
gattttggtc atgagattat caaaaaggat cttcacctag atccttttaa attaaaaatg   6420
aagttttaaa tcaatctaaa gtatatatga gtaaacttgg tctgacagtt accaatgctt   6480
aatcagtgag gcacctatct cagcgatctg tctatttcgt tcatccatag ttgcctgact   6540
ccccgtcgtg tagataacta cgatacggga gggcttacca tctggcccca gtgctgcaat   6600
gataccgcga gaaccacgct caccggctcc agatttatca gcaataaacc agccagccgg   6660
aagggccgag cgcagaagtg gtcctgcaac tttatccgcc tccatccagt ctattaattg   6720
```

ttgccgggaa gctagagtaa gtagttcgcc agttaatagt ttgcgcaacg ttgttgccat 6780
tgctacaggc atcgtggtgt cacgctcgtc gtttggtatg gcttcattca gctccggttc 6840
ccaacgatca aggcgagtta catgatcccc catgttgtgc aaaaaagcgg ttagctcctt 6900
cggtcctccg atcgttgtca gaagtaagtt ggccgcagtg ttatcactca tggttatggc 6960
agcactgcat aattctctta ctgtcatgcc atccgtaaga tgcttttctg tgactggtga 7020
gtactcaacc aagtcattct gagaatagtg tatgcggcga ccgagttgct cttgcccggc 7080
gtcaatacgg gataataccg cgccacatag cagaacttta aaagtgctca tcattggaaa 7140
acgttcttcg gggcgaaaac tctcaaggat cttaccgctg ttgagatcca gttcgatgta 7200
acccactcgt gcacccaact gatcttcagc atcttttact ttcaccagcg tttctgggtg 7260
agcaaaaaca ggaaggcaaa atgccgcaaa aaagggaata agggcgacac ggaaatgttg 7320
aatactcata ctcttccttt ttcaatatta ttgaagcatt tatcagggtt attgtctcat 7380
gagcggatac atatttgaat gtatttagaa aaataaacaa ataggggttc cgcgcacatt 7440
tccccgaaaa gtgccacctg acgtctaaga aaccattatt atcatgacat taacctataa 7500
aaataggcgt atcacgaggc cctttcgggt cgcgcgtttc ggtgatgacg gtgaaaacct 7560
ctgacacatg cagctcccgt tgacggtcac agcttgtctg taagcggatg ccgggagcag 7620
acaagcccgt cagggcgcgt cagcgggtgt tggcgggtgt cggggctggc ttaactatgc 7680
ggcatcagag cagattgtac tgagagtgca ccataaaatt gtaaacgtta atattttgtt 7740
aaaattcgcg ttaaattttt gttaaatcag ctcatttttt aaccaatagg ccgaaatcgg 7800
caaaatccct tataaatcaa aagaatagcc cgagataggg ttgagtgttg ttccagtttg 7860
gaacaagagt ccactattaa agaacgtgga ctccaacgtc aaagggcgaa aaaccgtcta 7920
tcagggcgat ggcccactac gtgaaccatc acccaaatca agttttttgg ggtcgaggtg 7980
ccgtaaagca ctaaatcgga accctaaagg gagcccccga tttagagctt gacggggaaa 8040
gccggcgaac gtggcgagaa aggaagggaa gaaagcgaaa ggagcgggcg ctagggcgct 8100
ggcaagtgta gcggtcacgc tgcgcgtaac caccacaccc gccgcgctta atgcgccgct 8160
acagggcgcg tactatggtt gctttgacgt atgcggtgtg aaataccgca cagatgcgta 8220
aggagaaaat accgcatcag gcgccattcg ccattcaggc tgcgcaactg ttgggaaggg 8280
cgatcggtgc gggcctcttc gctattacgc cagctggcga aagggggatg tgctgcaagg 8340
cgattaagtt gggtaacgcc agggttttcc cagtcacgac gttgtaaaac gacggccagt 8400
gaattccatg gtctcaactt tc 8422

<210> SEQ ID NO 35
<211> LENGTH: 275
<212> TYPE: PRT
<213> ORGANISM: Artificial Sequence
<220> FEATURE:
<223> OTHER INFORMATION: Synthetic VEEV Capsid

<400> SEQUENCE: 35

Met Phe Pro Phe Gln Pro Met Tyr Pro Met Gln Pro Met Pro Tyr Arg
1               5                   10                  15

Asn Pro Phe Ala Ala Pro Arg Arg Pro Trp Phe Pro Arg Thr Asp Pro
            20                  25                  30

Phe Leu Ala Met Gln Val Gln Glu Leu Thr Arg Ser Met Ala Asn Leu
        35                  40                  45

Thr Phe Lys Gln Arg Arg Asp Ala Pro Pro Glu Gly Pro Ser Ala Asn

```
    50                  55                  60

Lys Pro Lys Lys Glu Ala Ser Gln Lys Gln Lys Gly Gly Gly Gln Gly
65                  70                  75                  80

Lys Lys Lys Lys Asn Gln Gly Lys Lys Lys Ala Lys Thr Gly Pro Pro
                85                  90                  95

Asn Pro Lys Ala Gln Asn Gly Asn Lys Lys Lys Thr Asn Lys Lys Pro
            100                 105                 110

Gly Lys Arg Gln Arg Met Val Met Lys Leu Glu Ser Asp Lys Thr Phe
        115                 120                 125

Pro Ile Met Leu Glu Gly Lys Ile Asn Gly Tyr Ala Cys Val Val Gly
    130                 135                 140

Gly Lys Leu Phe Arg Pro Met His Val Glu Gly Lys Ile Asp Asn Asp
145                 150                 155                 160

Val Leu Ala Ala Leu Lys Thr Lys Lys Ala Ser Lys Tyr Asp Leu Glu
                165                 170                 175

Tyr Ala Asp Val Pro Gln Asn Met Arg Ala Asp Thr Phe Lys Tyr Thr
            180                 185                 190

His Glu Lys Pro Gln Gly Tyr Tyr Ser Trp His His Gly Ala Val Gln
        195                 200                 205

Tyr Glu Asn Gly Arg Phe Thr Val Pro Lys Gly Val Gly Ala Lys Gly
    210                 215                 220

Asp Ser Gly Arg Pro Ile Leu Asp Asn Gln Gly Arg Val Val Ala Ile
225                 230                 235                 240

Val Leu Gly Gly Val Asn Glu Gly Ser Arg Thr Ala Leu Ser Val Val
                245                 250                 255

Met Trp Asn Glu Lys Gly Val Thr Val Lys Tyr Thr Pro Glu Asn Cys
            260                 265                 270

Glu Gln Trp
        275


<210> SEQ ID NO 36
<211> LENGTH: 442
<212> TYPE: PRT
<213> ORGANISM: Artificial Sequence
<220> FEATURE:
<223> OTHER INFORMATION: Synthetic VEEV E1

<400> SEQUENCE: 36

Tyr Glu His Ala Thr Thr Met Pro Ser Gln Ala Gly Ile Ser Tyr Asn
1               5                   10                  15

Thr Ile Val Asn Arg Ala Gly Tyr Ala Pro Leu Pro Ile Ser Ile Thr
            20                  25                  30

Pro Thr Lys Ile Lys Leu Ile Pro Thr Val Asn Leu Glu Tyr Val Thr
        35                  40                  45

Cys His Tyr Lys Thr Gly Met Asp Ser Pro Ala Ile Lys Cys Cys Gly
    50                  55                  60

Ser Gln Glu Cys Thr Pro Thr Tyr Arg Pro Asp Glu Gln Cys Lys Val
65                  70                  75                  80

Phe Thr Gly Val Tyr Pro Phe Met Trp Gly Gly Ala Tyr Cys Phe Cys
                85                  90                  95

Asp Thr Glu Asn Thr Gln Val Ser Lys Ala Tyr Val Met Lys Ser Asp
            100                 105                 110

Asp Cys Leu Ala Asp His Ala Glu Ala Tyr Lys Ala His Thr Ala Ser
        115                 120                 125

Val Gln Ala Phe Leu Asn Ile Thr Val Gly Glu His Ser Ile Val Thr
```

-continued

```
    130                 135                 140

Thr Val Tyr Val Asn Gly Glu Thr Pro Val Asn Phe Asn Gly Val Lys
145                 150                 155                 160

Ile Thr Ala Gly Pro Leu Ser Thr Ala Trp Thr Pro Phe Asp Arg Lys
                165                 170                 175

Ile Val Gln Tyr Ala Gly Glu Ile Tyr Asn Tyr Asp Phe Pro Glu Tyr
            180                 185                 190

Gly Ala Gly Gln Pro Gly Ala Phe Gly Asp Ile Gln Ser Arg Thr Val
        195                 200                 205

Ser Ser Ser Asp Leu Tyr Ala Asn Thr Asn Leu Val Leu Gln Arg Pro
    210                 215                 220

Lys Ala Gly Ala Ile His Val Pro Tyr Thr Gln Ala Pro Ser Gly Phe
225                 230                 235                 240

Glu Gln Trp Lys Lys Asp Lys Ala Pro Ser Leu Lys Phe Thr Ala Pro
                245                 250                 255

Phe Gly Cys Glu Ile Tyr Thr Asn Pro Ile Arg Ala Glu Asn Cys Ala
            260                 265                 270

Val Gly Ser Ile Pro Leu Ala Phe Asp Ile Pro Asp Ala Leu Phe Thr
        275                 280                 285

Arg Val Ser Glu Thr Pro Thr Leu Ser Ala Ala Glu Cys Thr Leu Asn
    290                 295                 300

Glu Cys Val Tyr Ser Ser Asp Phe Gly Gly Ile Ala Thr Val Lys Tyr
305                 310                 315                 320

Ser Ala Ser Lys Ser Gly Lys Cys Ala Val His Val Pro Ser Gly Thr
                325                 330                 335

Ala Thr Leu Lys Glu Ala Ala Val Glu Leu Thr Glu Gln Gly Ser Ala
            340                 345                 350

Thr Ile His Phe Ser Thr Ala Asn Ile His Pro Glu Phe Arg Leu Gln
        355                 360                 365

Ile Cys Thr Ser Tyr Val Thr Cys Lys Gly Asp Cys His Pro Pro Lys
    370                 375                 380

Asp His Ile Val Thr His Pro Gln Tyr His Ala Gln Thr Phe Thr Ala
385                 390                 395                 400

Ala Val Ser Lys Thr Ala Trp Thr Trp Leu Thr Ser Leu Leu Gly Gly
                405                 410                 415

Ser Ala Val Ile Ile Ile Ile Gly Leu Val Leu Ala Thr Ile Val Ala
            420                 425                 430

Met Tyr Val Leu Thr Asn Gln Lys His Asn
        435                 440
```

<210> SEQ ID NO 37
<211> LENGTH: 478
<212> TYPE: PRT
<213> ORGANISM: Artificial Sequence
<220> FEATURE:
<223> OTHER INFORMATION: Synthetic VEEV E3-insert-E2
<220> FEATURE:
<221> NAME/KEY: NON_CONS
<222> LOCATION: (61)..(62)
<223> OTHER INFORMATION: antigen will be inserted

<400> SEQUENCE: 37

```
Ser Leu Val Thr Thr Met Cys Leu Leu Ala Asn Val Thr Phe Pro Cys
1               5                   10                  15

Ala Gln Pro Pro Ile Cys Tyr Asp Arg Lys Pro Ala Glu Thr Leu Ala
            20                  25                  30
```

```
Met Leu Ser Val Asn Val Asp Asn Pro Gly Tyr Asp Glu Leu Leu Glu
        35                  40                  45

Ala Ala Val Lys Cys Pro Gly Ser Thr Glu Glu Leu Phe Asn Glu Tyr
    50                  55                  60

Lys Leu Thr Arg Pro Tyr Met Ala Arg Cys Ile Arg Cys Ala Val Gly
65                  70                  75                  80

Ser Cys His Ser Pro Ile Ala Ile Glu Ala Val Lys Ser Asp Gly His
                85                  90                  95

Asp Gly Tyr Val Arg Leu Gln Thr Ser Ser Gln Tyr Gly Leu Asp Ser
            100                 105                 110

Ser Gly Asn Leu Lys Gly Arg Thr Met Arg Tyr Asp Met His Gly Thr
        115                 120                 125

Ile Lys Glu Ile Pro Leu His Gln Val Ser Leu Tyr Thr Ser Arg Pro
    130                 135                 140

Cys His Ile Val Asp Gly His Gly Tyr Phe Leu Leu Ala Arg Cys Pro
145                 150                 155                 160

Ala Gly Asp Ser Ile Thr Met Glu Phe Lys Lys Asp Ser Val Arg His
                165                 170                 175

Ser Cys Ser Val Pro Tyr Glu Val Lys Phe Asn Pro Val Gly Arg Glu
            180                 185                 190

Leu Tyr Thr His Pro Pro Glu His Gly Val Glu Gln Ala Cys Gln Val
        195                 200                 205

Tyr Ala His Asp Ala Gln Asn Arg Gly Ala Tyr Val Glu Met His Leu
    210                 215                 220

Pro Gly Ser Glu Val Asp Ser Ser Leu Val Ser Leu Ser Gly Ser Ser
225                 230                 235                 240

Val Thr Val Thr Pro Pro Asp Gly Thr Ser Ala Leu Val Glu Cys Glu
                245                 250                 255

Cys Gly Gly Thr Lys Ile Ser Glu Thr Ile Asn Lys Thr Lys Gln Phe
            260                 265                 270

Ser Gln Cys Thr Lys Lys Glu Gln Cys Arg Ala Tyr Arg Leu Gln Asn
        275                 280                 285

Asp Lys Trp Val Tyr Asn Ser Asp Lys Leu Pro Lys Ala Ala Gly Ala
    290                 295                 300

Thr Leu Lys Gly Lys Leu His Val Pro Phe Leu Leu Ala Asp Gly Lys
305                 310                 315                 320

Cys Thr Val Pro Leu Ala Pro Glu Pro Met Ile Thr Phe Gly Phe Arg
                325                 330                 335

Ser Val Ser Leu Lys Leu His Pro Lys Asn Pro Thr Tyr Leu Ile Thr
            340                 345                 350

Arg Gln Leu Ala Asp Glu Pro His Tyr Thr His Glu Leu Ile Ser Glu
        355                 360                 365

Pro Ala Val Arg Asn Phe Thr Val Thr Glu Lys Gly Trp Glu Phe Val
    370                 375                 380

Trp Gly Asn His Pro Pro Lys Arg Phe Trp Ala Gln Glu Thr Ala Pro
385                 390                 395                 400

Gly Asn Pro His Gly Leu Pro His Glu Val Ile Thr His Tyr Tyr His
                405                 410                 415

Arg Tyr Pro Met Ser Thr Ile Leu Gly Leu Ser Ile Cys Ala Ala Ile
            420                 425                 430

Ala Thr Val Ser Val Ala Ala Ser Thr Trp Leu Phe Cys Arg Ser Arg
        435                 440                 445

Val Ala Cys Leu Thr Pro Tyr Arg Leu Thr Pro Asn Ala Arg Ile Pro
```

```
    450                 455                 460

Phe Cys Leu Ala Val Leu Cys Cys Ala Arg Thr Ala Arg Ala
465                 470                 475


<210> SEQ ID NO 38
<211> LENGTH: 3822
<212> TYPE: DNA
<213> ORGANISM: Artificial Sequence
<220> FEATURE:
<223> OTHER INFORMATION: Synthetic Expression vector for CHIKV viral
      structural protein containing CSP repeat antigen 74 in E3

<400> SEQUENCE: 38

atggagttca tcccgacgca aactttctat aacagaaggt accaaccccg accctgggcc     60

ccacgcccta caattcaagt aattagacct agaccacgtc cacagaggca ggctgggcaa    120

ctcgcccagc tgatctccgc agtcaacaaa ttgaccatgc gcgcggtacc tcaacagaag    180

cctcgcagaa atcggaaaaa caagaagcaa aggcagaaga agcaggcgcc gcaaaacgac    240

ccaaagcaaa agaagcaacc accacaaaag aagccggctc aaaagaagaa gaaaccaggc    300

cgtagggaga gaatgtgcat gaaaattgaa aatgattgca tcttcgaagt caagcatgaa    360

ggcaaagtga tgggctacgc atgcctggtg ggggataaag taatgaaacc agcacatgtg    420

aagggaacta tcgacaatgc cgatctggct aaactggcct ttaagcggtc gtctaaatac    480

gatcttgaat gtgcacagat accggtgcac atgaagtctg atgcctcgaa gtttacccac    540

gagaaacccg aggggtacta taactggcat cacggagcag tgcagtattc aggaggccgg    600

ttcactatcc cgacgggtgc aggcaagccg ggagacagcg gcagaccgat cttcgacaac    660

aaaggacggg tggtggccat cgtcctagga ggggccaacg aaggtgcccg cacggccctc    720

tccgtggtga cgtggaacaa agacatcgtc acaaaaatta cccctgaggg agccgaagag    780

tggagcctcg ccctcccggt cttgtgcctg ttggcaaaca ctacattccc ctgctctcag    840

ccgccttgca caccctgctg ctacgaaaag gaaccggaaa gcaccttgcg catgcttgag    900

gacaacgtga tgagacccgg atactaccag ctactaaaag catcgctgac ttgctctccc    960

cactccggag gaaacccgaa tgccaatccc aacgcgaacc ccaatgctaa cccaaatgcc   1020

aacccaaacg ccaaccccaa cgctggtgga tccagtacta aggacaattt taatgtctat   1080

aaagccacaa gaccatatct agctcattgt cctgactgcg gagaagggca ttcgtgccac   1140

agccctatcg cattggagcg catcagaaat gaagcaacgg acggaacgct gaaaatccag   1200

gtctctttgc agatcgggat aaagacagat gacagccacg attggaccaa gctgcgctat   1260

atggatagcc atacgcccgc ggacgcggag cgagccggat tgcttgtaag gacttcagca   1320

ccgtgcacga tcaccgggac catgggacac tttattctcg cccgatgccc gaaaggagag   1380

acgctgacag tgggatttac ggacagcaga aagatcagcc acacatgcac acacccgttc   1440

catcatgaac cacctgtgat aggtagggag aggttccact ctcgaccaca acatggtaaa   1500

gagttacctt gcagcacgta cgtgcagagc accgctgcca ctgctgagga gatagaggtg   1560

catatgcccc cagatactcc tgaccgcacg ctgatgacgc agcagtctgg caacgtgaag   1620

atcacagtta atgggcagac ggtgcggtac aagtgcaact gcggtggctc aaacgaggga   1680

ctgacaacca cagacaaagt gatcaataac tgcaaaattg atcagtgcca tgctgcagtc   1740

actaatcaca agaattggca atacaactcc cctttagtcc cgcgcaacgc tgaactcggg   1800

gaccgtaaag gaaagatcca catcccattc ccattggcaa acgtgacttg cagagtgcca   1860

aaagcaagaa accctacagt aacttacgga aaaaaccaag tcaccatgct gctgtatcct   1920
```

-continued gaccatccga cactcttgtc ttaccgtaac atgggacagg aaccaaatta ccacgaggag 1980
tgggtgacac acaagaagga ggttaccttg accgtgccta ctgagggtct ggaggtcact 2040
tggggcaaca acgaaccata caagtactgg ccgcagatgt ctacgaacgg tactgctcat 2100
ggtcacccac atgagataat cttgtactat tatgagctgt accccactat gactgtagtc 2160
attgtgtcgg tggcctcgtt cgtgcttctg tcgatggtgg gcacagcagt gggaatgtgt 2220
gtgtgcgcac ggcgcagatg cattacacca tatgaattaa caccaggagc cactgttccc 2280
ttcctgctca gcctgctatg ctgcgtcaga acgaccaagg cggccacata ttacgaggct 2340
gcggcatatc tatggaacga acagcagccc ctgttctggt tgcaggctct tatcccgctg 2400
gccgccttga tcgtcctgtg caactgtctg aaactcttgc catgctgctg taagaccctg 2460 gctttttag ccgtaatgag catcggtgcc cacactgtga gcgcgtacga acacgtaaca 2520
gtgatcccga acacggtggg agtaccgtat aagactcttg tcaacagacc gggttacagc 2580
cccatggtgt tggagatgga gctacaatca gtcaccttgg aaccaacact gtcacttgac 2640
tacatcacgt gcgagtacaa aactgtcatc ccctccccgt acgtgaagtg ctgtggtaca 2700
gcagagtgca aggacaagag cctaccagac tacagctgca aggtctttac tggagtctac 2760
ccatttatgt ggggcggcgc ctactgcttt tgcgacgccg aaaatacgca attgagcgag 2820
gcacatgtag agaaatctga atcttgcaaa acagagtttg catcggccta cagagcccac 2880
accgcatcgg cgtcggcgaa gctccgcgtc ctttaccaag gaaacaacat taccgtagct 2940
gcctacgcta acggtgacca tgccgtcaca gtaaaggacg ccaagtttgt cgtgggccca 3000
atgtcctccg cctggacacc ttttgacaac aaaatcgtgg tgtacaaagg cgacgtctac 3060
aacatggact acccaccttt tggcgcagga agaccaggac aatttggtga cattcaaagt 3120
cgtacaccgg aaagtaaaga cgtttatgcc aacactcagt tggtactaca gaggccagca 3180
gcaggcacgg tacatgtacc atactctcag gcaccatctg gcttcaagta ttggctgaag 3240
gaacgaggag catcgctaca gcacacggca ccgttcggtt gccagattgc gacaaacccg 3300
gtaagagctg taaattgcgc tgtggggaac ataccaattt ccatcgacat accggatgcg 3360
gcctttacta gggttgtcga tgcaccctct gtaacggaca tgtcatgcga agtaccagcc 3420
tgcactcact cctccgactt tgggggcgtc gccatcatca aatacacagc tagcaagaaa 3480
ggtaaatgtg cagtacattc gatgaccaac gccgttacca ttcgagaagc cgacgtagaa 3540
gtagagggga actcccagct gcaaatatcc ttctcaacag ccctggcaag cgccgagttt 3600
cgcgtgcaag tgtgctccac acaagtacac tgcgcagccg catgccaccc tccaaaggac 3660
cacatagtca attacccagc atcacacacc acccttgggg tccaggatat atccacaacg 3720
gcaatgtctt gggtgcagaa gattacggga ggagtaggat taattgttgc tgttgctgcc 3780
ttaattttaa ttgtggtgct atgcgtgtcg tttagcaggc ac 3822

<210> SEQ ID NO 39
<211> LENGTH: 3843
<212> TYPE: DNA
<213> ORGANISM: Artificial Sequence
<220> FEATURE:
<223> OTHER INFORMATION: Synthetic Expression vector for VEEV viral structural protein containing CSP repeat antigen 74 in E3 (74.66)

<400> SEQUENCE: 39
atgttcccgt tccagccaat gtatccgatg cagccaatgc cctatcgcaa cccgttcgcg 60
gccccgcgca ggccctggtt ccccagaacc gacccttttc tggcgatgca ggtgcaggaa 120

-continued

```
ttaacccgct cgatggctaa cctgacgttc aagcaacgcc gggacgcgcc acctgagggg    180
ccatccgcta ataaaccgaa gaaggaggcc tcgcaaaaac agaaaggggg aggccaaggg    240
aagaagaaga agaaccaagg gaagaagaag gctaagacag ggccgcctaa tccgaaggca    300
cagaatggaa acaagaagaa gaccaacaag aaaccaggca agagacagcg catggtcatg    360
aaattggaat ctgacaagac gttcccaatc atgttggaag ggaagataaa cggctacgct    420
tgtgtggtcg gagggaagtt attcaggccg atgcatgtgg aaggcaagat cgacaacgac    480
gttctggccg cgcttaagac gaagaaagca tccaaatacg atcttgagta tgcagatgtg    540
ccacagaaca tgcgggccga tacattcaaa tacacccatg agaaacccca aggctattac    600
agctggcatc atggagcagt ccaatatgaa aatgggcgtt tcacggtgcc gaaaggagtt    660
ggggccaagg gagacagcgg acgacccatt ctggataacc agggacgggt ggtcgctatt    720
gtgctgggag gtgtgaatga aggatctagg acagcccttt cagtcgtcat gtggaacgag    780
aagggagtta ccgtgaagta tactccagag aactgcgagc aatggtcact agtgaccacc    840
atgtgtctgc tcgccaatgt gacgttccca tgtgctcaac caccaatttg ctacgacaga    900
aaaccagcag agactttggc catgctcagc gttaacgttg acaacccggg ctacgatgag    960
ctgctggaag cagctgttaa gtgccccggg tccggaggaa acccgaatgc caatcccaac   1020
gcgaacccca atgctaaccc aaatgccaac ccaaacgcca accccaacgc tggtggatcc   1080
tccaccgagg agctgtttaa tgagtataag ctaacgcgcc cttacatggc cagatgcatc   1140
agatgtgcag ttgggagctg ccatagtcca atagcaatcg aggcagtaaa gagcgacggg   1200
cacgacggtt atgttagact tcagacttcc tcgcagtatg gcctggattc ctccggcaac   1260
ttaaagggca ggaccatgcg gtatgacatg cacgggacca ttaaagagat accactacat   1320
caagtgtcac tctatacatc tcgcccgtgt cacattgtgg atgggcacgg ttatttcctg   1380
ctagccaggt gcccggcagg ggactccatc accatggaat ttaagaaaga ttccgtcaga   1440
cactcctgct cggtgccgta tgaagtgaaa tttaatcctg taggcagaga actctatact   1500
catcccccag aacacggagt agagcaagcg tgccaagtct acgcacatga tgcacagaac   1560
agaggagctt atgtcgagat gcacctcccg ggctcagaag tggacagcag tttggtttcc   1620
ttgagcggca gttcagtcac cgtgacacct cctgatggga ctagcgccct ggtggaatgc   1680
gagtgtggcg gcacaaagat ctccgagacc atcaacaaga caaaacagtt cagccagtgc   1740
acaaagaagg agcagtgcag agcatatcgg ctgcagaacg ataagtgggt gtataattct   1800
gacaaactgc ccaaagcagc gggagccacc ttaaaaggaa aactgcatgt cccattcttg   1860
ctggcagacg gcaaatgcac cgtgcctcta gcaccagaac ctatgataac cttcggtttc   1920
agatcagtgt cactgaaact gcaccctaag aatcccacat atctaatcac ccgccaactt   1980
gctgatgagc ctcactacac gcacgagctc atatctgaac cagctgttag gaattttacc   2040
gtcaccgaaa aagggtggga gtttgtatgg ggaaaccacc cgccgaaaag gttttgggca   2100
caggaaacag cacccggaaa tccacatggg ctaccgcacg aggtgataac tcattattac   2160
cacagatacc ctatgtccac catcctgggt ttgtcaattt gtgccgccat tgcaaccgtt   2220
tccgttgcag cgtctacctg gctgttttgc agatcaagag ttgcgtgcct aactccttac   2280
cggctaacac ctaacgctag gataccattt tgtctggctg tgctttgctg cgcccgcact   2340
gcccgggccg agaccacctg ggagtccttg gatcacctat ggaacaataa ccaacagatg   2400
ttctggattc aattgctgat ccctctggcc gccttgatcg tagtgactcg cctgctcagg   2460
```

```
tgcgtgtgct gtgtcgtgcc ttttttagtc atggccggcg ccgcaggcgc cggcgcctac   2520

gagcacgcga ccacgatgcc gagccaagcg ggaatctcgt ataacactat agtcaacaga   2580

gcaggctacg caccactccc tatcagcata acaccaacaa agatcaagct gatacctaca   2640

gtgaacttgg agtacgtcac ctgccactac aaaacaggaa tggattcacc agccatcaaa   2700

tgctgcggat ctcaggaatg cactccaact tacaggcctg atgaacagtg caaagtcttc   2760

acaggggttt acccgttcat gtggggtggt gcatattgct tttgcgacac tgagaacacc   2820

caagtcagca aggcctacgt aatgaaatct gacgactgcc ttgcggatca tgctgaagca   2880

tataaagcgc acacagcctc agtgcaggcg ttcctcaaca tcacagtggg agaacactct   2940

attgtgacta ccgtgtatgt gaatggagaa actcctgtga atttcaatgg ggtcaaaata   3000

actgcaggtc cgctttccac agcttggaca ccctttgatc gcaaaatcgt gcagtatgcc   3060

ggggagatct ataattatga ttttcctgag tatggggcag gacaaccagg agcatttgga   3120

gatatacaat ccagaacagt ctcaagctct gatctgtatg ccaataccaa cctagtgctg   3180

cagagaccca aagcaggagc gatccacgtg ccatacactc aggcaccttc gggttttgag   3240

caatggaaga aagataaagc tccatcattg aaatttaccg cccctttcgg atgcgaaata   3300

tatacaaacc ccattcgcgc cgaaaactgt gctgtagggt caattccatt agcctttgac   3360

attcccgacg ccttgttcac cagggtgtca gaaacaccga cactttcagc ggccgaatgc   3420

actcttaacg agtgcgtgta ttcttccgac tttggtggga tcgccacggt caagtactcg   3480

gccagcaagt caggcaagtg cgcagtccat gtgccatcag ggactgctac cctaaaagaa   3540

gcagcagtcg agctaaccga gcaagggtcg gcgactatcc atttctcgac cgcaaatatc   3600

cacccggagt tcaggctcca aatatgcaca tcatatgtta cgtgcaaagg tgattgtcac   3660

cccccgaaag accatattgt gacacaccct cagtatcacg cccaaacatt tacagccgcg   3720

gtgtcaaaaa ccgcgtggac gtggttaaca tccctgctgg gaggatcagc cgtaattatt   3780

ataattggct tggtgctggc tactattgtg gccatgtacg tgctgaccaa ccagaaacat   3840

aat                                                                  3843
```

```
<210> SEQ ID NO 40
<211> LENGTH: 3789
<212> TYPE: DNA
<213> ORGANISM: Artificial Sequence
<220> FEATURE:
<223> OTHER INFORMATION: Synthetic Expression vector for CHIKV viral
      structural protein containing mouse PD-1 antigen “274” in E3

<400> SEQUENCE: 40
```

```
atggagttca tcccgacgca aactttctat aacagaaggt accaaccccg accctgggcc     60

ccacgcccta caattcaagt aattagacct agaccacgtc cacagaggca ggctgggcaa    120

ctcgcccagc tgatctccgc agtcaacaaa ttgaccatgc gcgcggtacc tcaacagaag    180

cctcgcagaa atcggaaaaa caagaagcaa aggcagaaga agcaggcgcc gcaaaacgac    240

ccaaagcaaa agaagcaacc accacaaaag aagccggctc aaaagaagaa gaaaccaggc    300

cgtagggaga gaatgtgcat gaaaattgaa aatgattgca tcttcgaagt caagcatgaa    360

ggcaaagtga tgggctacgc atgcctggtg ggggataaag taatgaaacc agcacatgtg    420

aagggaacta tcgacaatgc cgatctggct aaactggcct ttaagcggtc gtctaaatac    480

gatcttgaat gtgcacagat accggtgcac atgaagtctg atgcctcgaa gtttacccac    540

gagaaacccg aggggtacta taactggcat cacggagcag tgcagtattc aggaggccgg    600
```

-continued

```
ttcactatcc cgacgggtgc aggcaagccg ggagacagcg gcagaccgat cttcgacaac    660
aaaggacggg tggtggccat cgtcctagga ggggccaacg aaggtgcccg cacggccctc    720
tccgtggtga cgtggaacaa agacatcgtc acaaaaatta cccctgaggg agccgaagag    780
tggagcctcg ccctcccggt cttgtgcctg ttggcaaaca ctacattccc ctgctctcag    840
ccgccttgca caccctgctg ctacgaaaag gaaccggaaa gcaccttgcg catgcttgag    900
gacaacgtga tgagacccgg atactaccag ctactaaaag catcgctgac ttgctctccc    960
cactccggag gcggcgccat cagcctgcac cccaaggcca agatcgagga atctggatcc   1020
agtactaagg acaattttaa tgtctataaa gccacaagac catatctagc tcattgtcct   1080
gactgcggag aagggcattc gtgccacagc cctatcgcat tggagcgcat cagaaatgaa   1140
gcaacggacg gaacgctgaa aatccaggtc tctttgcaga tcgggataaa gacagatgac   1200
agccacgatt ggaccaagct gcgctatatg gatagccata cgcccgcgga cgcggagcga   1260
gccggattgc ttgtaaggac ttcagcaccg tgcacgatca ccgggaccat gggacacttt   1320
attctcgccc gatgcccgaa aggagagacg ctgacagtgg gatttacgga cagcagaaag   1380
atcagccaca catgcacaca cccgttccat catgaaccac ctgtgatagg tagggagagg   1440
ttccactctc gaccacaaca tggtaaagag ttaccttgca gcacgtacgt gcagagcacc   1500
gctgccactg ctgaggagat agaggtgcat atgcccccag atactcctga ccgcacgctg   1560
atgacgcagc agtctggcaa cgtgaagatc acagttaatg ggcagacggt gcggtacaag   1620
tgcaactgcg gtggctcaaa cgagggactg acaaccacag acaaagtgat caataactgc   1680
aaaattgatc agtgccatgc tgcagtcact aatcacaaga attggcaata caactcccct   1740
ttagtcccgc gcaacgctga actcggggac cgtaaaggaa agatccacat cccattccca   1800
ttggcaaacg tgacttgcag agtgccaaaa gcaagaaacc ctacagtaac ttacggaaaa   1860
aaccaagtca ccatgctgct gtatcctgac catccgacac tcttgtctta ccgtaacatg   1920
ggacaggaac caaattacca cgaggagtgg gtgacacaca agaaggaggt taccttgacc   1980
gtgcctactg agggtctgga ggtcacttgg ggcaacaacg aaccatacaa gtactggccg   2040
cagatgtcta cgaacggtac tgctcatggt cacccacatg agataatctt gtactattat   2100
gagctgtacc ccactatgac tgtagtcatt gtgtcggtgg cctcgttcgt gcttctgtcg   2160
atggtgggca cagcagtggg aatgtgtgtg tgcgcacggc gcagatgcat tacaccatat   2220
gaattaacac caggagccac tgttcccttc ctgctcagcc tgctatgctg cgtcagaacg   2280
accaaggcgg ccacatatta cgaggctgcg gcatatctat ggaacgaaca gcagcccctg   2340
ttctggttgc aggctcttat cccgctggcc gccttgatcg tcctgtgcaa ctgtctgaaa   2400
ctcttgccat gctgctgtaa gaccctggct tttttagccg taatgagcat cggtgcccac   2460
actgtgagcg cgtacgaaca cgtaacagtg atcccgaaca cggtgggagt accgtataag   2520
actcttgtca acagaccggg ttacagcccc atggtgttgg agatggagct acaatcagtc   2580
accttggaac caacactgtc acttgactac atcacgtgcg agtacaaaac tgtcatcccc   2640
tccccgtacg tgaagtgctg tggtacagca gagtgcaagg acaagagcct accagactac   2700
agctgcaagg tctttactgg agtctaccca tttatgtggg gcggcgccta ctgcttttgc   2760
gacgccgaaa atacgcaatt gagcgaggca catgtagaga aatctgaatc ttgcaaaaca   2820
gagtttgcat cggcctacag agcccacacc gcatcggcgt cggcgaagct ccgcgtcctt   2880
taccaaggaa acaacattac cgtagctgcc tacgctaacg gtgaccatgc cgtcacagta   2940
aaggacgcca agtttgtcgt gggcccaatg tcctccgcct ggacaccttt tgacaacaaa   3000
```

```
atcgtggtgt acaaaggcga cgtctacaac atggactacc caccttttgg cgcaggaaga   3060

ccaggacaat ttggtgacat tcaaagtcgt acaccggaaa gtaaagacgt ttatgccaac   3120

actcagttgg tactacagag gccagcagca ggcacggtac atgtaccata ctctcaggca   3180

ccatctggct tcaagtattg gctgaaggaa cgaggagcat cgctacagca cacggcaccg   3240

ttcggttgcc agattgcgac aaacccggta agagctgtaa attgcgctgt ggggaacata   3300

ccaatttcca tcgacatacc ggatgcggcc tttactaggg ttgtcgatgc accctctgta   3360

acggacatgt catgcgaagt accagcctgc actcactcct ccgactttgg gggcgtcgcc   3420

atcatcaaat acacagctag caagaaaggt aaatgtgcag tacattcgat gaccaacgcc   3480

gttaccattc gagaagccga cgtagaagta gaggggaact cccagctgca aatatccttc   3540

tcaacagccc tggcaagcgc cgagtttcgc gtgcaagtgt gctccacaca agtacactgc   3600

gcagccgcat gccaccctcc aaaggaccac atagtcaatt acccagcatc acacaccacc   3660

cttggggtcc aggatatatc cacaacggca atgtcttggg tgcagaagat tacgggagga   3720

gtaggattaa ttgttgctgt tgctgcctta attttaattg tggtgctatg cgtgtcgttt   3780

agcaggcac                                                           3789
```

<210> SEQ ID NO 41
<211> LENGTH: 3810
<212> TYPE: DNA
<213> ORGANISM: Artificial Sequence
<220> FEATURE:
<223> OTHER INFORMATION: Synthetic Expression vector for VEEV viral structural protein comprising mouse PD-1 antigen “274” in E3 (274.66)

<400> SEQUENCE: 41

```
atgttcccgt tccagccaat gtatccgatg cagccaatgc cctatcgcaa cccgttcgcg     60

gccccgcgca ggccctggtt ccccagaacc gaccctttc tggcgatgca ggtgcaggaa    120

ttaacccgct cgatggctaa cctgacgttc aagcaacgcc gggacgcgcc acctgagggg    180

ccatccgcta ataaaccgaa gaaggaggcc tcgcaaaaac agaaaggggg aggccaaggg    240

aagaagaaga agaaccaagg gaagaagaag gctaagacag ggccgcctaa tccgaaggca    300

cagaatggaa acaagaagaa gaccaacaag aaaccaggca agagacagcg catggtcatg    360

aaattggaat ctgacaagac gttcccaatc atgttggaag ggaagataaa cggctacgct    420

tgtgtggtcg gagggaagtt attcaggccg atgcatgtgg aaggcaagat cgacaacgac    480

gttctggccg cgcttaagac gaagaaagca tccaaatacg atcttgagta tgcagatgtg    540

ccacagaaca tgcgggccga tacattcaaa tacacccatg agaaacccca aggctattac    600

agctggcatc atggagcagt ccaatatgaa aatgggcgtt tcacggtgcc gaaaggagtt    660

ggggccaagg gagacagcgg acgacccatt ctggataacc agggacgggt ggtcgctatt    720

gtgctgggag gtgtgaatga aggatctagg acagcccttt cagtcgtcat gtggaacgag    780

aagggagtta ccgtgaagta tactccagag aactgcgagc aatggtcact agtgaccacc    840

atgtgtctgc tcgccaatgt gacgttccca tgtgctcaac caccaatttg ctacgacaga    900

aaaccagcag agactttggc catgctcagc gttaacgttg acaacccggg ctacgatgag    960

ctgctggaag cagctgttaa gtgccccggg tccggaggcg gcgccatcag cctgcacccc   1020

aaggccaaga tcgaggaatc tggatcctcc accgaggagc tgtttaatga gtataagcta   1080

acgcgccctt acatggccag atgcatcaga tgtgcagttg ggagctgcca tagtccaata   1140
```

-continued

```
gcaatcgagg cagtaaagag cgacgggcac gacggttatg ttagacttca gacttcctcg   1200
cagtatggcc tggattcctc cggcaactta aagggcagga ccatgcggta tgacatgcac   1260
gggaccatta aagagatacc actacatcaa gtgtcactct atacatctcg cccgtgtcac   1320
attgtggatg ggcacggtta tttcctgcta gccaggtgcc cggcagggga ctccatcacc   1380
atggaattta agaaagattc cgtcagacac tcctgctcgg tgccgtatga agtgaaattt   1440
aatcctgtag gcagagaact ctatactcat cccccagaac acggagtaga gcaagcgtgc   1500
caagtctacg cacatgatgc acagaacaga ggagcttatg tcgagatgca cctcccgggc   1560
tcagaagtgg acagcagttt ggtttccttg agcggcagtt cagtcaccgt gacacctcct   1620
gatgggacta gcgccctggt ggaatgcgag tgtggcggca caaagatctc cgagaccatc   1680
aacaagacaa aacagttcag ccagtgcaca aagaaggagc agtgcagagc atatcggctg   1740
cagaacgata agtgggtgta taattctgac aaactgccca aagcagcggg agccacctta   1800
aaaggaaaac tgcatgtccc attcttgctg gcagacggca aatgcaccgt gcctctagca   1860
ccagaaccta tgataacctt cggtttcaga tcagtgtcac tgaaactgca ccctaagaat   1920
cccacatatc taatcacccg ccaacttgct gatgagcctc actacacgca cgagctcata   1980
tctgaaccag ctgttaggaa ttttaccgtc accgaaaaag ggtgggagtt tgtatgggga   2040
aaccacccgc cgaaaaggtt ttgggcacag gaaacagcac ccggaaatcc acatgggcta   2100
ccgcacgagg tgataactca ttattaccac agatacccta tgtccaccat cctgggtttg   2160
tcaatttgtg ccgccattgc aaccgtttcc gttgcagcgt ctacctggct gttttgcaga   2220
tcaagagttg cgtgcctaac tccttaccgg ctaacaccta acgctaggat accattttgt   2280
ctggctgtgc tttgctgcgc ccgcactgcc cgggccgaga ccacctggga gtccttggat   2340
cacctatgga acaataacca acagatgttc tggattcaat tgctgatccc tctggccgcc   2400
ttgatcgtag tgactcgcct gctcaggtgc gtgtgctgtg tcgtgccttt tttagtcatg   2460
gccggcgccg caggcgccgg cgcctacgag cacgcgacca cgatgccgag ccaagcggga   2520
atctcgtata acactatagt caacagagca ggctacgcac cactccctat cagcataaca   2580
ccaacaaaga tcaagctgat acctacagtg aacttggagt acgtcacctg ccactacaaa   2640
acaggaatgg attcaccagc catcaaatgc tgcggatctc aggaatgcac tccaacttac   2700
aggcctgatg aacagtgcaa agtcttcaca ggggtttacc cgttcatgtg ggtggtgca    2760
tattgctttt gcgacactga gaacacccaa gtcagcaagg cctacgtaat gaaatctgac   2820
gactgccttg cggatcatgc tgaagcatat aaagcgcaca cagcctcagt gcaggcgttc   2880
ctcaacatca cagtgggaga acactctatt gtgactaccg tgtatgtgaa tggagaaact   2940
cctgtgaatt tcaatggggt caaaataact gcaggtccgc tttccacagc ttggacaccc   3000
tttgatcgca aaatcgtgca gtatgccggg gagatctata attatgattt tcctgagtat   3060
ggggcaggac aaccaggagc atttggagat atacaatcca gaacagtctc aagctctgat   3120
ctgtatgcca ataccaacct agtgctgcag agacccaaag caggagcgat ccacgtgcca   3180
tacactcagg caccttcggg ttttgagcaa tggaagaaag ataaagctcc atcattgaaa   3240
tttaccgccc ctttcggatg cgaaatatat acaaacccca ttcgcgccga aaactgtgct   3300
gtagggtcaa ttccattagc ctttgacatt cccgacgcct tgttcaccag ggtgtcagaa   3360
acaccgacac tttcagcggc cgaatgcact cttaacgagt gcgtgtattc ttccgacttt   3420
ggtgggatcg ccacggtcaa gtactcggcc agcaagtcag gcaagtgcgc agtccatgtg   3480
ccatcaggga ctgctaccct aaaagaagca gcagtcgagc taaccgagca agggtcggcg   3540
```

actatccatt tctcgaccgc aaatatccac ccggagttca ggctccaaat atgcacatca 3600
tatgttacgt gcaaaggtga ttgtcacccc ccgaaagacc atattgtgac acaccctcag 3660
tatcacgccc aaacatttac agccgcggtg tcaaaaaccg cgtggacgtg gttaacatcc 3720
ctgctgggag gatcagccgt aattattata attggcttgg tgctggctac tattgtggcc 3780
atgtacgtgc tgaccaacca gaaacataat 3810

<210> SEQ ID NO 42
<211> LENGTH: 3783
<212> TYPE: DNA
<213> ORGANISM: Artificial Sequence
<220> FEATURE:
<223> OTHER INFORMATION: Synthetic Expression vector for CHIKV viral structural protein containing mouse PDL1 antigen “299” in E3

<400> SEQUENCE: 42
atggagttca tcccgacgca aactttctat aacagaaggt accaaccccg accctgggcc 60
ccacgcccta caattcaagt aattagacct agaccacgtc cacagaggca ggctgggcaa 120
ctcgcccagc tgatctccgc agtcaacaaa ttgaccatgc gcgcggtacc tcaacagaag 180
cctcgcagaa atcggaaaaa caagaagcaa aggcagaaga agcaggcgcc gcaaaacgac 240
ccaaagcaaa agaagcaacc accacaaaag aagccggctc aaaagaagaa gaaaccaggc 300
cgtagggaga gaatgtgcat gaaaattgaa aatgattgca tcttcgaagt caagcatgaa 360
ggcaaagtga tgggctacgc atgcctggtg ggggataaag taatgaaacc agcacatgtg 420
aagggaacta tcgacaatgc cgatctggct aaactggcct ttaagcggtc gtctaaatac 480
gatcttgaat gtgcacagat accggtgcac atgaagtctg atgcctcgaa gtttacccac 540
gagaaacccg aggggtacta taactggcat cacggagcag tgcagtattc aggaggccgg 600
ttcactatcc cgacgggtgc aggcaagccg ggagacagcg gcagaccgat cttcgacaac 660
aaaggacggg tggtggccat cgtcctagga ggggccaacg aaggtgcccg cacggccctc 720
tccgtggtga cgtggaacaa agacatcgtc acaaaaatta cccctgaggg agccgaagag 780
tggagcctcg ccctcccggt cttgtgcctg ttggcaaaca ctacattccc ctgctctcag 840
ccgccttgca caccctgctg ctacgaaaag gaaccggaaa gcaccttgcg catgcttgag 900
gacaacgtga tgagacccgg atactaccag ctactaaaag catcgctgac ttgctctccc 960
cactccggag gctgcatcat cagctacggc ggagccgact actgcggcgg atccagtact 1020
aaggacaatt ttaatgtcta taaagccaca agaccatatc tagctcattg tcctgactgc 1080
ggagaagggc attcgtgcca cagccctatc gcattggagc gcatcagaaa tgaagcaacg 1140
gacggaacgc tgaaaatcca ggtctctttg cagatcggga taaagacaga tgacagccac 1200
gattggacca agctgcgcta tatggatagc catacgcccg cggacgcgga gcgagccgga 1260
ttgcttgtaa ggacttcagc accgtgcacg atcaccggga ccatgggaca ctttattctc 1320
gcccgatgcc cgaaaggaga gacgctgaca gtgggattta cggacagcag aaagatcagc 1380
cacacatgca cacacccgtt ccatcatgaa ccacctgtga taggtaggga gaggttccac 1440
tctcgaccac aacatggtaa agagttacct tgcagcacgt acgtgcagag caccgctgcc 1500
actgctgagg agatagaggt gcatatgccc ccagatactc ctgaccgcac gctgatgacg 1560
cagcagtctg gcaacgtgaa gatcacagtt aatgggcaga cggtgcggta caagtgcaac 1620
tgcggtggct caaacgaggg actgacaacc acagacaaag tgatcaataa ctgcaaaatt 1680
gatcagtgcc atgctgcagt cactaatcac aagaattggc aatacaactc ccctttagtc 1740
ccgcgcaacg ctgaactcgg ggaccgtaaa ggaaagatcc acatcccatt cccattggca 1800
aacgtgactt gcagagtgcc aaaagcaaga aaccctacag taacttacgg aaaaaaccaa 1860
gtcaccatgc tgctgtatcc tgaccatccg acactcttgt cttaccgtaa catgggacag 1920
gaaccaaatt accacgagga gtgggtgaca cacaagaagg aggttacctt gaccgtgcct 1980
actgagggtc tggaggtcac ttggggcaac aacgaaccat acaagtactg gccgcagatg 2040
tctacgaacg gtactgctca tggtcaccca catgagataa tcttgtacta ttatgagctg 2100
taccccacta tgactgtagt cattgtgtcg gtggcctcgt tcgtgcttct gtcgatggtg 2160
ggcacagcag tgggaatgtg tgtgtgcgca cggcgcagat gcattacacc atatgaatta 2220
acaccaggag ccactgttcc cttcctgctc agcctgctat gctgcgtcag aacgaccaag 2280
gcggccacat attacgaggc tgcggcatat ctatggaacg aacagcagcc cctgttctgg 2340
ttgcaggctc ttatcccgct ggccgccttg atcgtcctgt gcaactgtct gaaactcttg 2400
ccatgctgct gtaagaccct ggcttttta gccgtaatga gcatcggtgc ccacactgtg 2460
agcgcgtacg aacacgtaac agtgatcccg aacacggtgg gagtaccgta taagactctt 2520
gtcaacagac cgggttacag ccccatggtg ttggagatgg agctacaatc agtcaccttg 2580
gaaccaacac tgtcacttga ctacatcacg tgcgagtaca aaactgtcat cccctccccg 2640
tacgtgaagt gctgtggtac agcagagtgc aaggacaaga gcctaccaga ctacagctgc 2700
aaggtcttta ctggagtcta cccatttatg tggggcggcg cctactgctt ttgcgacgcc 2760
gaaaatacgc aattgagcga ggcacatgta gagaaatctg aatcttgcaa aacagagttt 2820
gcatcggcct acagagccca caccgcatcg gcgtcggcga agctccgcgt cctttaccaa 2880
ggaaacaaca ttaccgtagc tgcctacgct aacggtgacc atgccgtcac agtaaaggac 2940
gccaagtttg tcgtgggccc aatgtcctcc gcctggacac cttttgacaa caaaatcgtg 3000
gtgtacaaag gcgacgtcta caacatggac tacccacctt ttggcgcagg aagaccagga 3060
caatttggtg acattcaaag tcgtacaccg gaaagtaaag acgtttatgc caacactcag 3120
ttggtactac agaggccagc agcaggcacg gtacatgtac catactctca ggcaccatct 3180
ggcttcaagt attggctgaa ggaacgagga gcatcgctac agcacacggc accgttcggt 3240
tgccagattg cgacaaaccc ggtaagagct gtaaattgcg ctgtggggaa cataccaatt 3300
tccatcgaca taccggatgc ggcctttact agggttgtcg atgcaccctc tgtaacggac 3360
atgtcatgcg aagtaccagc ctgcactcac tcctccgact ttgggggcgt cgccatcatc 3420
aaatacacag ctagcaagaa aggtaaatgt gcagtacatt cgatgaccaa cgccgttacc 3480
attcgagaag ccgacgtaga agtagagggg aactcccagc tgcaaatatc cttctcaaca 3540
gccctggcaa gcgccgagtt tcgcgtgcaa gtgtgctcca cacaagtaca ctgcgcagcc 3600
gcatgccacc ctccaaagga ccacatagtc aattacccag catcacacac cacccttggg 3660
gtccaggata tatccacaac ggcaatgtct tgggtgcaga agattacggg aggagtagga 3720
ttaattgttg ctgttgctgc cttaatttta attgtggtgc tatgcgtgtc gtttagcagg 3780
cac 3783

<210> SEQ ID NO 43
<211> LENGTH: 3804
<212> TYPE: DNA
<213> ORGANISM: Artificial Sequence
<220> FEATURE:
<223> OTHER INFORMATION: Synthetic Expression vector for VEEV viral
structural protein containing mouse PDL1 antigen in E3 (299.66)

<400> SEQUENCE: 43
atgttcccgt tccagccaat gtatccgatg cagccaatgc cctatcgcaa cccgttcgcg 60
gccccgcgca ggccctggtt ccccagaacc gacccttttc tggcgatgca ggtgcaggaa 120
ttaacccgct cgatggctaa cctgacgttc aagcaacgcc gggacgcgcc acctgagggg 180
ccatccgcta ataaaccgaa gaaggaggcc tcgcaaaaac agaaaggggg aggccaaggg 240
aagaagaaga agaaccaagg gaagaagaag gctaagacag ggccgcctaa tccgaaggca 300
cagaatggaa acaagaagaa gaccaacaag aaaccaggca agagacagcg catggtcatg 360
aaattggaat ctgacaagac gttcccaatc atgttggaag ggaagataaa cggctacgct 420
tgtgtggtcg gagggaagtt attcaggccg atgcatgtgg aaggcaagat cgacaacgac 480
gttctggccg cgcttaagac gaagaaagca tccaaatacg atcttgagta tgcagatgtg 540
ccacagaaca tgcgggccga tacattcaaa tacacccatg agaaacccca aggctattac 600
agctggcatc atggagcagt ccaatatgaa aatgggcgtt tcacggtgcc gaaaggagtt 660
ggggccaagg gagacagcgg acgacccatt ctggataacc agggacgggt ggtcgctatt 720
gtgctgggag gtgtgaatga aggatctagg acagcccttt cagtcgtcat gtggaacgag 780
aagggagtta ccgtgaagta tactccagag aactgcgagc aatggtcact agtgaccacc 840
atgtgtctgc tcgccaatgt gacgttccca tgtgctcaac caccaatttg ctacgacaga 900
aaaccagcag agactttggc catgctcagc gttaacgttg acaacccggg ctacgatgag 960
ctgctggaag cagctgttaa gtgccccggg tccggaggct gcatcatcag ctacggcgga 1020
gccgactact gcggcggatc ctccaccgag gagctgttta atgagtataa gctaacgcgc 1080
ccttacatgg ccagatgcat cagatgtgca gttgggagct gccatagtcc aatagcaatc 1140
gaggcagtaa agagcgacgg gcacgacggt tatgttagac ttcagacttc ctcgcagtat 1200
ggcctggatt cctccggcaa cttaaagggc aggaccatgc ggtatgacat gcacgggacc 1260
attaaagaga taccactaca tcaagtgtca ctctatacat ctcgcccgtg tcacattgtg 1320
gatgggcacg gttatttcct gctagccagg tgcccggcag gggactccat caccatggaa 1380
tttaagaaag attccgtcag acactcctgc tcggtgccgt atgaagtgaa atttaatcct 1440
gtaggcagag aactctatac tcatcccccca gaacacggag tagagcaagc gtgccaagtc 1500
tacgcacatg atgcacagaa cagaggagct tatgtcgaga tgcacctccc gggctcagaa 1560
gtggacagca gtttggtttc cttgagcggc agttcagtca ccgtgacacc tcctgatggg 1620
actagcgccc tggtggaatg cgagtgtggc ggcacaaaga tctccgagac catcaacaag 1680
acaaaacagt tcagccagtg cacaaagaag gagcagtgca gagcatatcg gctgcagaac 1740
gataagtggg tgtataattc tgacaaactg cccaaagcag cgggagccac cttaaaagga 1800
aaactgcatg tcccattctt gctggcagac ggcaaatgca ccgtgcctct agcaccagaa 1860
cctatgataa ccttcggttt cagatcagtg tcactgaaac tgcaccctaa gaatcccaca 1920
tatctaatca cccgccaact tgctgatgag cctcactaca cgcacgagct catatctgaa 1980
ccagctgtta ggaattttac cgtcaccgaa aaagggtggg agtttgtatg ggggaaaccac 2040 ccgccgaaaa ggttttgggc acaggaaaca gcacccggaa atccacatgg gctaccgcac 2100
gaggtgataa ctcattatta ccacagatac cctatgtcca ccatcctggg tttgtcaatt 2160
tgtgccgcca ttgcaaccgt ttccgttgca gcgtctacct ggctgttttg cagatcaaga 2220
gttgcgtgcc taactcctta ccggctaaca cctaacgcta ggataccatt ttgtctggct 2280

```
gtgctttgct gcgcccgcac tgcccgggcc gagaccacct gggagtcctt ggatcaccta   2340
tggaacaata accaacagat gttctggatt caattgctga tccctctggc cgccttgatc   2400
gtagtgactc gcctgctcag gtgcgtgtgc tgtgtcgtgc ctttttttagt catggccggc   2460
gccgcaggcg ccggcgccta cgagcacgcg accacgatgc cgagccaagc gggaatctcg   2520
tataacacta tagtcaacag agcaggctac gcaccactcc ctatcagcat aacaccaaca   2580
aagatcaagc tgatacctac agtgaacttg gagtacgtca cctgccacta caaaacagga   2640
atggattcac cagccatcaa atgctgcgga tctcaggaat gcactccaac ttacaggcct   2700
gatgaacagt gcaaagtctt cacaggggtt tacccgttca tgtggggtgg tgcatattgc   2760
ttttgcgaca ctgagaacac ccaagtcagc aaggcctacg taatgaaatc tgacgactgc   2820
cttgcggatc atgctgaagc atataaagcg cacacagcct cagtgcaggc gttcctcaac   2880
atcacagtgg gagaacactc tattgtgact accgtgtatg tgaatggaga aactcctgtg   2940
aatttcaatg gggtcaaaat aactgcaggt ccgctttcca cagcttggac accctttgat   3000
cgcaaaatcg tgcagtatgc cggggagatc tataattatg attttcctga gtatggggca   3060
ggacaaccag gagcatttgg agatatacaa tccagaacag tctcaagctc tgatctgtat   3120
gccaatacca acctagtgct gcagagaccc aaagcaggag cgatccacgt gccatacact   3180
caggcacctt cgggttttga gcaatggaag aaagataaag ctccatcatt gaaatttacc   3240
gccccctttcg gatgcgaaat atatacaaac cccattcgcg ccgaaaactg tgctgtaggg   3300
tcaattccat tagcctttga cattcccgac gccttgttca ccagggtgtc agaaacaccg   3360
acactttcag cggccgaatg cactcttaac gagtgcgtgt attcttccga ctttggtggg   3420
atcgccacgg tcaagtactc ggccagcaag tcaggcaagt gcgcagtcca tgtgccatca   3480
gggactgcta ccctaaaaga agcagcagtc gagctaaccg agcaagggtc ggcgactatc   3540
catttctcga ccgcaaatat ccacccggag ttcaggctcc aaatatgcac atcatatgtt   3600
acgtgcaaag gtgattgtca ccccccgaaa gaccatattg tgacacaccc tcagtatcac   3660
gcccaaacat ttacagccgc ggtgtcaaaa accgcgtgga cgtggttaac atccctgctg   3720
ggaggatcag ccgtaattat tataattggc ttggtgctgg ctactattgt ggccatgtac   3780
gtgctgacca accagaaaca taat                                          3804
```

<210> SEQ ID NO 44
<211> LENGTH: 3804
<212> TYPE: DNA
<213> ORGANISM: Artificial Sequence
<220> FEATURE:
<223> OTHER INFORMATION: Synthetic Expression vector for CHIKV viral structural protein comprising mouse CTLA4_Ver2 antigen in E3

<400> SEQUENCE: 44

```
atggagttca tcccgacgca aactttctat aacagaaggt accaaccccg accctgggcc     60
ccacgcccta caattcaagt aattagacct agaccacgtc cacagaggca ggctgggcaa    120
ctcgcccagc tgatctccgc agtcaacaaa ttgaccatgc gcgcggtacc tcaacagaag    180
cctcgcagaa atcggaaaaa caagaagcaa aggcagaaga agcaggcgcc gcaaaacgac    240
ccaaagcaaa agaagcaacc accacaaaag aagccggctc aaaagaagaa gaaaccaggc    300
cgtagggaga gaatgtgcat gaaaattgaa aatgattgca tcttcgaagt caagcatgaa    360
ggcaaagtga tgggctacgc atgcctggtg ggggataaag taatgaaacc agcacatgtg    420
aagggaacta tcgacaatgc cgatctggct aaactggcct ttaagcggtc gtctaaatac    480
```

-continued

```
gatcttgaat gtgcacagat accggtgcac atgaagtctg atgcctcgaa gtttacccac    540
gagaaacccg aggggtacta taactggcat cacggagcag tgcagtattc aggaggccgg    600
ttcactatcc cgacgggtgc aggcaagccg ggagacagcg gcagaccgat cttcgacaac    660
aaaggacggg tggtggccat cgtcctagga ggggccaacg aaggtgcccg cacggccctc    720
tccgtggtga cgtggaacaa agacatcgtc acaaaaatta cccctgaggg agccgaagag    780
tggagcctcg ccctcccggt cttgtgcctg ttggcaaaca ctacattccc ctgctctcag    840
ccgccttgca caccctgctg ctacgaaaag gaaccggaaa gcaccttgcg catgcttgag    900
gacaacgtga tgagacccgg atactaccag ctactaaaag catcgctgac ttgctctccc    960
cactccggag gcggcggcaa ggtggaactc atgtacccac cgccatactt tgtgggcatg   1020
ggcggcggcg gatccagtac taaggacaat tttaatgtct ataaagccac aagaccatat   1080
ctagctcatt gtcctgactg cggagaaggg cattcgtgcc acagccctat cgcattggag   1140
cgcatcagaa atgaagcaac ggacggaacg ctgaaaatcc aggtctcttt gcagatcggg   1200
ataaagacag atgacagcca cgattggacc aagctgcgct atatggatag ccatacgccc   1260
gcggacgcgg agcgagccgg attgcttgta aggacttcag caccgtgcac gatcaccggg   1320
accatgggac actttattct cgcccgatgc ccgaaaggag agacgctgac agtgggattt   1380
acggacagca gaaagatcag ccacacatgc acacacccgt tccatcatga accacctgtg   1440
ataggtaggg agaggttcca ctctcgacca caacatggta aagagttacc ttgcagcacg   1500
tacgtgcaga gcaccgctgc cactgctgag gagatagagg tgcatatgcc cccagatact   1560
cctgaccgca cgctgatgac gcagcagtct ggcaacgtga agatcacagt taatgggcag   1620
acggtgcggt acaagtgcaa ctgcggtggc tcaaacgagg gactgacaac cacagacaaa   1680
gtgatcaata actgcaaaat tgatcagtgc catgctgcag tcactaatca caagaattgg   1740
caatacaact cccctttagt cccgcgcaac gctgaactcg gggaccgtaa aggaaagatc   1800
cacatcccat tcccattggc aaacgtgact tgcagagtgc caaaagcaag aaaccctaca   1860
gtaacttacg gaaaaaacca agtcaccatg ctgctgtatc ctgaccatcc gacactcttg   1920
tcttaccgta acatgggaca ggaaccaaat taccacgagg agtgggtgac acacaagaag   1980
gaggttacct tgaccgtgcc tactgagggt ctggaggtca cttggggcaa caacgaacca   2040
tacaagtact ggccgcagat gtctacgaac ggtactgctc atggtcaccc acatgagata   2100
atcttgtact attatgagct gtaccccact atgactgtag tcattgtgtc ggtggcctcg   2160
ttcgtgcttc tgtcgatggt gggcacagca gtgggaatgt gtgtgtgcgc acggcgcaga   2220
tgcattacac catatgaatt aacaccagga gccactgttc ccttcctgct cagcctgcta   2280
tgctgcgtca gaacgaccaa ggcggccaca tattacgagg ctgcggcata tctatggaac   2340
gaacagcagc ccctgttctg gttgcaggct cttatcccgc tggccgcctt gatcgtcctg   2400
tgcaactgtc tgaaactctt gccatgctgc tgtaagaccc tggctttttt agccgtaatg   2460
agcatcggtg cccacactgt gagcgcgtac gaacacgtaa cagtgatccc gaacacggtg   2520
ggagtaccgt ataagactct tgtcaacaga ccgggttaca gccccatggt gttggagatg   2580
gagctacaat cagtcacctt ggaaccaaca ctgtcacttg actacatcac gtgcgagtac   2640
aaaactgtca tcccctcccc gtacgtgaag tgctgtggta cagcagagtg caaggacaag   2700
agcctaccag actacagctg caaggtcttt actggagtct acccatttat gtggggcggc   2760
gcctactgct tttgcgacgc cgaaaatacg caattgagcg aggcacatgt agagaaatct   2820
gaatcttgca aaacagagtt tgcatcggcc tacagagccc acaccgcatc ggcgtcggcg   2880
```

```
aagctccgcg tcctttacca aggaaacaac attaccgtag ctgcctacgc taacggtgac   2940
catgccgtca cagtaaagga cgccaagttt gtcgtgggcc caatgtcctc cgcctggaca   3000
ccttttgaca acaaaatcgt ggtgtacaaa ggcgacgtct acaacatgga ctacccacct   3060
tttggcgcag gaagaccagg acaatttggt gacattcaaa gtcgtacacc ggaaagtaaa   3120
gacgtttatg ccaacactca gttggtacta cagaggccag cagcaggcac ggtacatgta   3180
ccatactctc aggcaccatc tggcttcaag tattggctga aggaacgagg agcatcgcta   3240
cagcacacgg caccgttcgg ttgccagatt gcgacaaacc cggtaagagc tgtaaattgc   3300
gctgtgggga acataccaat ttccatcgac ataccggatg cggcctttac tagggttgtc   3360
gatgcaccct ctgtaacgga catgtcatgc gaagtaccag cctgcactca ctcctccgac   3420
tttgggggcg tcgccatcat caaatacaca gctagcaaga aaggtaaatg tgcagtacat   3480
tcgatgacca acgccgttac cattcgagaa gccgacgtag aagtagaggg gaactcccag   3540
ctgcaaatat ccttctcaac agccctggca agcgccgagt ttcgcgtgca agtgtgctcc   3600
acacaagtac actgcgcagc cgcatgccac cctccaaagg accacatagt caattaccca   3660
gcatcacaca ccacccttgg ggtccaggat atatccacaa cggcaatgtc ttgggtgcag   3720
aagattacgg gaggagtagg attaattgtt gctgttgctg ccttaatttt aattgtggtg   3780
ctatgcgtgt cgtttagcag gcac                                          3804
```

```
<210> SEQ ID NO 45
<211> LENGTH: 3825
<212> TYPE: DNA
<213> ORGANISM: Artificial Sequence
<220> FEATURE:
<223> OTHER INFORMATION: Synthetic Expression vector for VEEV viral
      structural protein comprising mouse CTLA4ver2 antigen in E3

<400> SEQUENCE: 45
```

```
atgttcccgt tccagccaat gtatccgatg cagccaatgc cctatcgcaa cccgttcgcg     60
gccccgcgca ggccctggtt ccccagaacc gacccttttc tggcgatgca ggtgcaggaa    120
ttaacccgct cgatggctaa cctgacgttc aagcaacgcc gggacgcgcc acctgagggg    180
ccatccgcta ataaaccgaa gaaggaggcc tcgcaaaaac agaaaggggg aggccaaggg    240
aagaagaaga agaaccaagg gaagaagaag gctaagacag ggccgcctaa tccgaaggca    300
cagaatggaa acaagaagaa gaccaacaag aaaccaggca agagacagcg catggtcatg    360
aaattggaat ctgacaagac gttcccaatc atgttggaag ggaagataaa cggctacgct    420
tgtgtggtcg gagggaagtt attcaggccg atgcatgtgg aaggcaagat cgacaacgac    480
gttctggccg cgcttaagac gaagaaagca tccaaatacg atcttgagta tgcagatgtg    540
ccacagaaca tgcgggccga tacattcaaa tacacccatg agaaacccca aggctattac    600
agctggcatc atggagcagt ccaatatgaa aatgggcgtt tcacggtgcc gaaaggagtt    660
ggggccaagg gagacagcgg acgacccatt ctggataacc agggacgggt ggtcgctatt    720
gtgctgggag gtgtgaatga aggatctagg acagcccttt cagtcgtcat gtggaacgag    780
aagggagtta ccgtgaagta tactccagag aactgcgagc aatggtcact agtgaccacc    840
atgtgtctgc tcgccaatgt gacgttccca tgtgctcaac caccaatttg ctacgacaga    900
aaaccagcag agactttggc catgctcagc gttaacgttg acaacccggg ctacgatgag    960
ctgctggaag cagctgttaa gtgccccggg tccggaggcg gcggcaaggt ggaactcatg   1020
tacccaccgc catactttgt gggcatgggc ggcggcggat cctccaccga ggagctgttt   1080
```

-continued aatgagtata agctaacgcg cccttacatg gccagatgca tcagatgtgc agttgggagc 1140
tgccatagtc caatagcaat cgaggcagta aagagcgacg ggcacgacgg ttatgttaga 1200
cttcagactt cctcgcagta tggcctggat tcctccggca acttaaaggg caggaccatg 1260
cggtatgaca tgcacgggac cattaaagag ataccactac atcaagtgtc actctataca 1320
tctcgcccgt gtcacattgt ggatgggcac ggttatttcc tgctagccag gtgcccggca 1380
ggggactcca tcaccatgga atttaagaaa gattccgtca gacactcctg ctcggtgccg 1440
tatgaagtga aatttaatcc tgtaggcaga gaactctata ctcatccccc agaacacgga 1500
gtagagcaag cgtgccaagt ctacgcacat gatgcacaga acagaggagc ttatgtcgag 1560
atgcacctcc cgggctcaga agtggacagc agtttggttt ccttgagcgg cagttcagtc 1620
accgtgacac ctcctgatgg gactagcgcc ctggtggaat gcgagtgtgg cggcacaaag 1680
atctccgaga ccatcaacaa gacaaaacag ttcagccagt gcacaaagaa ggagcagtgc 1740
agagcatatc ggctgcagaa cgataagtgg gtgtataatt ctgacaaact gcccaaagca 1800
gcgggagcca ccttaaaagg aaaactgcat gtcccattct tgctggcaga cggcaaatgc 1860
accgtgcctc tagcaccaga acctatgata accttcggtt tcagatcagt gtcactgaaa 1920
ctgcacccta agaatcccac atatctaatc acccgccaac ttgctgatga gcctcactac 1980
acgcacgagc tcatatctga accagctgtt aggaatttta ccgtcaccga aaaagggtgg 2040
gagtttgtat ggggaaacca cccgccgaaa aggttttggg cacaggaaac agcacccgga 2100
aatccacatg ggctaccgca cgaggtgata actcattatt accacagata ccctatgtcc 2160
accatcctgg gtttgtcaat ttgtgccgcc attgcaaccg tttccgttgc agcgtctacc 2220
tggctgtttt gcagatcaag agttgcgtgc ctaactcctt accggctaac acctaacgct 2280
aggataccat tttgtctggc tgtgctttgc tgcgcccgca ctgcccgggc cgagaccacc 2340
tgggagtcct tggatcacct atggaacaat aaccaacaga tgttctggat tcaattgctg 2400
atccctctgg ccgccttgat cgtagtgact cgcctgctca ggtgcgtgtg ctgtgtcgtg 2460 cctttttag tcatggccgg cgccgcaggc gccggcgcct acgagcacgc gaccacgatg 2520
ccgagccaag cgggaatctc gtataacact atagtcaaca gagcaggcta cgcaccactc 2580
cctatcagca taacaccaac aaagatcaag ctgataccta cagtgaactt ggagtacgtc 2640
acctgccact acaaaacagg aatggattca ccagccatca aatgctgcgg atctcaggaa 2700
tgcactccaa cttacaggcc tgatgaacag tgcaaagtct tcacaggggt ttacccgttc 2760
atgtggggtg gtgcatattg cttttgcgac actgagaaca cccaagtcag caaggcctac 2820
gtaatgaaat ctgacgactg ccttgcggat catgctgaag catataaagc gcacacagcc 2880
tcagtgcagg cgttcctcaa catcacagtg ggagaacact ctattgtgac taccgtgtat 2940
gtgaatggag aaactcctgt gaatttcaat ggggtcaaaa taactgcagg tccgctttcc 3000
acagcttgga caccctttga tcgcaaaatc gtgcagtatg ccggggagat ctataattat 3060
gattttcctg agtatggggc aggacaacca ggagcatttg gagatataca atccagaaca 3120
gtctcaagct ctgatctgta tgccaatacc aacctagtgc tgcagagacc caaagcagga 3180
gcgatccacg tgccatacac tcaggcacct tcgggttttg agcaatggaa gaaagataaa 3240
gctccatcat tgaaatttac cgcccctttc ggatgcgaaa tatatacaaa ccccattcgc 3300
gccgaaaact gtgctgtagg gtcaattcca ttagcctttg acattcccga cgccttgttc 3360
accagggtgt cagaaacacc gacactttca gcggccgaat gcactcttaa cgagtgcgtg 3420

```
tattcttccg actttggtgg gatcgccacg gtcaagtact cggccagcaa gtcaggcaag   3480

tgcgcagtcc atgtgccatc agggactgct accctaaaag aagcagcagt cgagctaacc   3540

gagcaagggt cggcgactat ccatttctcg accgcaaata tccacccgga gttcaggctc   3600

caaatatgca catcatatgt tacgtgcaaa ggtgattgtc accccccgaa agaccatatt   3660

gtgacacacc ctcagtatca cgcccaaaca tttacagccg cggtgtcaaa aaccgcgtgg   3720

acgtggttaa catccctgct gggaggatca gccgtaatta ttataattgg cttggtgctg   3780

gctactattg tggccatgta cgtgctgacc aaccagaaac ataat                   3825
```

<210> SEQ ID NO 46
<211> LENGTH: 351
<212> TYPE: PRT
<213> ORGANISM: Artificial Sequence
<220> FEATURE:
<223> OTHER INFORMATION: Synthetic CHIKV E3-Malaria-E2

<400> SEQUENCE: 46

```
Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Arg Gln Lys Lys Gln Ala Pro Gln Asn Asp
65                  70                  75                  80

Pro Lys Gln Lys Lys Gln Pro Pro Gln Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Met Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Leu Pro Val Leu Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Ser Thr Leu Arg Met Leu Glu Asp Asn Val Met
```

```
    290                 295                 300

Arg Pro Gly Tyr Tyr Gln Leu Leu Lys Ala Ser Leu Thr Cys Ser Pro
305                 310                 315                 320

His Ser Gly Gly Asn Pro Asn Ala Asn Pro Asn Ala Asn Pro Asn Ala
                325                 330                 335

Asn Pro Asn Ala Asn Pro Asn Ala Asn Pro Asn Ala Gly Gly Ser
            340                 345                 350


<210> SEQ ID NO 47
<211> LENGTH: 502
<212> TYPE: PRT
<213> ORGANISM: Artificial Sequence
<220> FEATURE:
<223> OTHER INFORMATION: Synthetic CHIKV E3-PD-1-E2

<400> SEQUENCE: 47

Ser Leu Ala Leu Pro Val Leu Cys Leu Leu Ala Asn Thr Thr Phe Pro
1               5                   10                  15

Cys Ser Gln Pro Pro Cys Thr Pro Cys Cys Tyr Glu Lys Glu Pro Glu
            20                  25                  30

Ser Thr Leu Arg Met Leu Glu Asp Asn Val Met Arg Pro Gly Tyr Tyr
        35                  40                  45

Gln Leu Leu Lys Ala Ser Leu Thr Cys Ser Pro His Ser Gly Gly Gly
    50                  55                  60

Ala Ile Ser Leu His Pro Lys Ala Lys Ile Glu Glu Ser Gly Ser Ser
65                  70                  75                  80

Thr Lys Asp Asn Phe Asn Val Tyr Lys Ala Thr Arg Pro Tyr Leu Ala
                85                  90                  95

His Cys Pro Asp Cys Gly Glu Gly His Ser Cys His Ser Pro Ile Ala
            100                 105                 110

Leu Glu Arg Ile Arg Asn Glu Ala Thr Asp Gly Thr Leu Lys Ile Gln
        115                 120                 125

Val Ser Leu Gln Ile Gly Ile Lys Thr Asp Asp Ser His Asp Trp Thr
    130                 135                 140

Lys Leu Arg Tyr Met Asp Ser His Thr Pro Ala Asp Ala Glu Arg Ala
145                 150                 155                 160

Gly Leu Leu Val Arg Thr Ser Ala Pro Cys Thr Ile Thr Gly Thr Met
                165                 170                 175

Gly His Phe Ile Leu Ala Arg Cys Pro Lys Gly Glu Thr Leu Thr Val
            180                 185                 190

Gly Phe Thr Asp Ser Arg Lys Ile Ser His Thr Cys Thr His Pro Phe
        195                 200                 205

His His Glu Pro Pro Val Ile Gly Arg Glu Arg Phe His Ser Arg Pro
    210                 215                 220

Gln His Gly Lys Glu Leu Pro Cys Ser Thr Tyr Val Gln Ser Thr Ala
225                 230                 235                 240

Ala Thr Ala Glu Glu Ile Glu Val His Met Pro Pro Asp Thr Pro Asp
                245                 250                 255

Arg Thr Leu Met Thr Gln Gln Ser Gly Asn Val Lys Ile Thr Val Asn
            260                 265                 270

Gly Gln Thr Val Arg Tyr Lys Cys Asn Cys Gly Gly Ser Asn Glu Gly
        275                 280                 285

Leu Thr Thr Thr Asp Lys Val Ile Asn Asn Cys Lys Ile Asp Gln Cys
    290                 295                 300

His Ala Ala Val Thr Asn His Lys Asn Trp Gln Tyr Asn Ser Pro Leu
```

305 310 315 320

Val Pro Arg Asn Ala Glu Leu Gly Asp Arg Lys Gly Lys Ile His Ile
325 330 335

Pro Phe Pro Leu Ala Asn Val Thr Cys Arg Val Pro Lys Ala Arg Asn
340 345 350

Pro Thr Val Thr Tyr Gly Lys Asn Gln Val Thr Met Leu Leu Tyr Pro
355 360 365

Asp His Pro Thr Leu Leu Ser Tyr Arg Asn Met Gly Gln Glu Pro Asn
370 375 380

Tyr His Glu Glu Trp Val Thr His Lys Lys Glu Val Thr Leu Thr Val
385 390 395 400

Pro Thr Glu Gly Leu Glu Val Thr Trp Gly Asn Asn Glu Pro Tyr Lys
405 410 415

Tyr Trp Pro Gln Met Ser Thr Asn Gly Thr Ala His Gly His Pro His
420 425 430

Glu Ile Ile Leu Tyr Tyr Tyr Glu Leu Tyr Pro Thr Met Thr Val Val
435 440 445

Ile Val Ser Val Ala Ser Phe Val Leu Leu Ser Met Val Gly Thr Ala
450 455 460

Val Gly Met Cys Val Cys Ala Arg Arg Arg Cys Ile Thr Pro Tyr Glu
465 470 475 480

Leu Thr Pro Gly Ala Thr Val Pro Phe Leu Leu Ser Leu Leu Cys Cys
485 490 495

Val Arg Thr Thr Lys Ala
500

<210> SEQ ID NO 48
<211> LENGTH: 500
<212> TYPE: PRT
<213> ORGANISM: Artificial Sequence
<220> FEATURE:
<223> OTHER INFORMATION: Synthetic CHIKV E3-PD-L1-E2

<400> SEQUENCE: 48

Ser Leu Ala Leu Pro Val Leu Cys Leu Leu Ala Asn Thr Thr Phe Pro
1 5 10 15

Cys Ser Gln Pro Pro Cys Thr Pro Cys Cys Tyr Glu Lys Glu Pro Glu
20 25 30

Ser Thr Leu Arg Met Leu Glu Asp Asn Val Met Arg Pro Gly Tyr Tyr
35 40 45

Gln Leu Leu Lys Ala Ser Leu Thr Cys Ser Pro His Ser Gly Gly Cys
50 55 60

Ile Ile Ser Tyr Gly Gly Ala Asp Tyr Cys Gly Gly Ser Ser Thr Lys
65 70 75 80

Asp Asn Phe Asn Val Tyr Lys Ala Thr Arg Pro Tyr Leu Ala His Cys
85 90 95

Pro Asp Cys Gly Glu Gly His Ser Cys His Ser Pro Ile Ala Leu Glu
100 105 110

Arg Ile Arg Asn Glu Ala Thr Asp Gly Thr Leu Lys Ile Gln Val Ser
115 120 125

Leu Gln Ile Gly Ile Lys Thr Asp Asp Ser His Asp Trp Thr Lys Leu
130 135 140

Arg Tyr Met Asp Ser His Thr Pro Ala Asp Ala Glu Arg Ala Gly Leu
145 150 155 160

Leu Val Arg Thr Ser Ala Pro Cys Thr Ile Thr Gly Thr Met Gly His 165 170 175

Phe Ile Leu Ala Arg Cys Pro Lys Gly Glu Thr Leu Thr Val Gly Phe
180 185 190

Thr Asp Ser Arg Lys Ile Ser His Thr Cys Thr His Pro Phe His His
195 200 205

Glu Pro Pro Val Ile Gly Arg Glu Arg Phe His Ser Arg Pro Gln His
210 215 220

Gly Lys Glu Leu Pro Cys Ser Thr Tyr Val Gln Ser Thr Ala Ala Thr
225 230 235 240

Ala Glu Glu Ile Glu Val His Met Pro Pro Asp Thr Pro Asp Arg Thr
245 250 255

Leu Met Thr Gln Gln Ser Gly Asn Val Lys Ile Thr Val Asn Gly Gln
260 265 270

Thr Val Arg Tyr Lys Cys Asn Cys Gly Gly Ser Asn Glu Gly Leu Thr
275 280 285

Thr Thr Asp Lys Val Ile Asn Asn Cys Lys Ile Asp Gln Cys His Ala
290 295 300

Ala Val Thr Asn His Lys Asn Trp Gln Tyr Asn Ser Pro Leu Val Pro
305 310 315 320

Arg Asn Ala Glu Leu Gly Asp Arg Lys Gly Lys Ile His Ile Pro Phe
325 330 335

Pro Leu Ala Asn Val Thr Cys Arg Val Pro Lys Ala Arg Asn Pro Thr
340 345 350

Val Thr Tyr Gly Lys Asn Gln Val Thr Met Leu Leu Tyr Pro Asp His
355 360 365

Pro Thr Leu Leu Ser Tyr Arg Asn Met Gly Gln Glu Pro Asn Tyr His
370 375 380

Glu Glu Trp Val Thr His Lys Lys Glu Val Thr Leu Thr Val Pro Thr
385 390 395 400

Glu Gly Leu Glu Val Thr Trp Gly Asn Asn Glu Pro Tyr Lys Tyr Trp
405 410 415

Pro Gln Met Ser Thr Asn Gly Thr Ala His Gly His Pro His Glu Ile
420 425 430

Ile Leu Tyr Tyr Tyr Glu Leu Tyr Pro Thr Met Thr Val Val Ile Val
435 440 445

Ser Val Ala Ser Phe Val Leu Leu Ser Met Val Gly Thr Ala Val Gly
450 455 460

Met Cys Val Cys Ala Arg Arg Arg Cys Ile Thr Pro Tyr Glu Leu Thr
465 470 475 480

Pro Gly Ala Thr Val Pro Phe Leu Leu Ser Leu Leu Cys Cys Val Arg
485 490 495

Thr Thr Lys Ala
500

<210> SEQ ID NO 49
<211> LENGTH: 507
<212> TYPE: PRT
<213> ORGANISM: Artificial Sequence
<220> FEATURE:
<223> OTHER INFORMATION: Synthetic CHIKV E3-CTLA-4-E2

<400> SEQUENCE: 49

Ser Leu Ala Leu Pro Val Leu Cys Leu Leu Ala Asn Thr Thr Phe Pro
1 5 10 15

Cys Ser Gln Pro Pro Cys Thr Pro Cys Cys Tyr Glu Lys Glu Pro Glu

```
            20                  25                  30

Ser Thr Leu Arg Met Leu Glu Asp Asn Val Met Arg Pro Gly Tyr Tyr
        35                  40                  45

Gln Leu Leu Lys Ala Ser Leu Thr Cys Ser Pro His Ser Gly Gly Gly
    50                  55                  60

Gly Lys Val Glu Leu Met Tyr Pro Pro Pro Tyr Phe Val Gly Met Gly
65                  70                  75                  80

Gly Gly Gly Ser Ser Thr Lys Asp Asn Phe Asn Val Tyr Lys Ala Thr
                85                  90                  95

Arg Pro Tyr Leu Ala His Cys Pro Asp Cys Gly Glu Gly His Ser Cys
            100                 105                 110

His Ser Pro Ile Ala Leu Glu Arg Ile Arg Asn Glu Ala Thr Asp Gly
        115                 120                 125

Thr Leu Lys Ile Gln Val Ser Leu Gln Ile Gly Ile Lys Thr Asp Asp
    130                 135                 140

Ser His Asp Trp Thr Lys Leu Arg Tyr Met Asp Ser His Thr Pro Ala
145                 150                 155                 160

Asp Ala Glu Arg Ala Gly Leu Leu Val Arg Thr Ser Ala Pro Cys Thr
                165                 170                 175

Ile Thr Gly Thr Met Gly His Phe Ile Leu Ala Arg Cys Pro Lys Gly
            180                 185                 190

Glu Thr Leu Thr Val Gly Phe Thr Asp Ser Arg Lys Ile Ser His Thr
        195                 200                 205

Cys Thr His Pro Phe His His Glu Pro Pro Val Ile Gly Arg Glu Arg
    210                 215                 220

Phe His Ser Arg Pro Gln His Gly Lys Glu Leu Pro Cys Ser Thr Tyr
225                 230                 235                 240

Val Gln Ser Thr Ala Ala Thr Ala Glu Glu Ile Glu Val His Met Pro
                245                 250                 255

Pro Asp Thr Pro Asp Arg Thr Leu Met Thr Gln Gln Ser Gly Asn Val
            260                 265                 270

Lys Ile Thr Val Asn Gly Gln Thr Val Arg Tyr Lys Cys Asn Cys Gly
        275                 280                 285

Gly Ser Asn Glu Gly Leu Thr Thr Thr Asp Lys Val Ile Asn Asn Cys
    290                 295                 300

Lys Ile Asp Gln Cys His Ala Ala Val Thr Asn His Lys Asn Trp Gln
305                 310                 315                 320

Tyr Asn Ser Pro Leu Val Pro Arg Asn Ala Glu Leu Gly Asp Arg Lys
                325                 330                 335

Gly Lys Ile His Ile Pro Phe Pro Leu Ala Asn Val Thr Cys Arg Val
            340                 345                 350

Pro Lys Ala Arg Asn Pro Thr Val Thr Tyr Gly Lys Asn Gln Val Thr
        355                 360                 365

Met Leu Leu Tyr Pro Asp His Pro Thr Leu Leu Ser Tyr Arg Asn Met
    370                 375                 380

Gly Gln Glu Pro Asn Tyr His Glu Glu Trp Val Thr His Lys Lys Glu
385                 390                 395                 400

Val Thr Leu Thr Val Pro Thr Glu Gly Leu Glu Val Thr Trp Gly Asn
                405                 410                 415

Asn Glu Pro Tyr Lys Tyr Trp Pro Gln Met Ser Thr Asn Gly Thr Ala
            420                 425                 430

His Gly His Pro His Glu Ile Ile Leu Tyr Tyr Tyr Glu Leu Tyr Pro
        435                 440                 445
```

```
Thr Met Thr Val Val Ile Val Ser Val Ala Ser Phe Val Leu Leu Ser
    450                 455                 460

Met Val Gly Thr Ala Val Gly Met Cys Val Cys Ala Arg Arg Arg Cys
465                 470                 475                 480

Ile Thr Pro Tyr Glu Leu Thr Pro Gly Ala Thr Val Pro Phe Leu Leu
                485                 490                 495

Ser Leu Leu Cys Cys Val Arg Thr Thr Lys Ala
            500                 505
```

```
<210> SEQ ID NO 50
<211> LENGTH: 508
<212> TYPE: PRT
<213> ORGANISM: Artificial Sequence
<220> FEATURE:
<223> OTHER INFORMATION: Synthetic VEEV E3-malaria-E2(74.66)

<400> SEQUENCE: 50

Ser Leu Val Thr Thr Met Cys Leu Leu Ala Asn Val Thr Phe Pro Cys
1               5                   10                  15

Ala Gln Pro Pro Ile Cys Tyr Asp Arg Lys Pro Ala Glu Thr Leu Ala
            20                  25                  30

Met Leu Ser Val Asn Val Asp Asn Pro Gly Tyr Asp Glu Leu Leu Glu
        35                  40                  45

Ala Ala Val Lys Cys Pro Gly Ser Gly Gly Asn Pro Asn Ala Asn Pro
    50                  55                  60

Asn Ala Asn Pro Asn Ala Asn Pro Asn Ala Asn Pro Asn Ala Asn Pro
65                  70                  75                  80

Asn Ala Gly Gly Ser Ser Thr Glu Glu Leu Phe Asn Glu Tyr Lys Leu
                85                  90                  95

Thr Arg Pro Tyr Met Ala Arg Cys Ile Arg Cys Ala Val Gly Ser Cys
            100                 105                 110

His Ser Pro Ile Ala Ile Glu Ala Val Lys Ser Asp Gly His Asp Gly
        115                 120                 125

Tyr Val Arg Leu Gln Thr Ser Ser Gln Tyr Gly Leu Asp Ser Ser Gly
    130                 135                 140

Asn Leu Lys Gly Arg Thr Met Arg Tyr Asp Met His Gly Thr Ile Lys
145                 150                 155                 160

Glu Ile Pro Leu His Gln Val Ser Leu Tyr Thr Ser Arg Pro Cys His
                165                 170                 175

Ile Val Asp Gly His Gly Tyr Phe Leu Leu Ala Arg Cys Pro Ala Gly
            180                 185                 190

Asp Ser Ile Thr Met Glu Phe Lys Lys Asp Ser Val Arg His Ser Cys
        195                 200                 205

Ser Val Pro Tyr Glu Val Lys Phe Asn Pro Val Gly Arg Glu Leu Tyr
    210                 215                 220

Thr His Pro Pro Glu His Gly Val Glu Gln Ala Cys Gln Val Tyr Ala
225                 230                 235                 240

His Asp Ala Gln Asn Arg Gly Ala Tyr Val Glu Met His Leu Pro Gly
                245                 250                 255

Ser Glu Val Asp Ser Ser Leu Val Ser Leu Ser Gly Ser Ser Val Thr
            260                 265                 270

Val Thr Pro Pro Asp Gly Thr Ser Ala Leu Val Glu Cys Glu Cys Gly
        275                 280                 285

Gly Thr Lys Ile Ser Glu Thr Ile Asn Lys Thr Lys Gln Phe Ser Gln
    290                 295                 300
```

Cys Thr Lys Lys Glu Gln Cys Arg Ala Tyr Arg Leu Gln Asn Asp Lys
305 310 315 320

Trp Val Tyr Asn Ser Asp Lys Leu Pro Lys Ala Ala Gly Ala Thr Leu
325 330 335

Lys Gly Lys Leu His Val Pro Phe Leu Leu Ala Asp Gly Lys Cys Thr
340 345 350

Val Pro Leu Ala Pro Glu Pro Met Ile Thr Phe Gly Phe Arg Ser Val
355 360 365

Ser Leu Lys Leu His Pro Lys Asn Pro Thr Tyr Leu Ile Thr Arg Gln
370 375 380

Leu Ala Asp Glu Pro His Tyr Thr His Glu Leu Ile Ser Glu Pro Ala
385 390 395 400

Val Arg Asn Phe Thr Val Thr Glu Lys Gly Trp Glu Phe Val Trp Gly
405 410 415

Asn His Pro Pro Lys Arg Phe Trp Ala Gln Glu Thr Ala Pro Gly Asn
420 425 430

Pro His Gly Leu Pro His Glu Val Ile Thr His Tyr Tyr His Arg Tyr
435 440 445

Pro Met Ser Thr Ile Leu Gly Leu Ser Ile Cys Ala Ala Ile Ala Thr
450 455 460

Val Ser Val Ala Ala Ser Thr Trp Leu Phe Cys Arg Ser Arg Val Ala
465 470 475 480

Cys Leu Thr Pro Tyr Arg Leu Thr Pro Asn Ala Arg Ile Pro Phe Cys
485 490 495

Leu Ala Val Leu Cys Cys Ala Arg Thr Ala Arg Ala
500 505

<210> SEQ ID NO 51
<211> LENGTH: 497
<212> TYPE: PRT
<213> ORGANISM: Artificial Sequence
<220> FEATURE:
<223> OTHER INFORMATION: Synthetic VEEV E3-PD-1-E2

<400> SEQUENCE: 51

Ser Leu Val Thr Thr Met Cys Leu Leu Ala Asn Val Thr Phe Pro Cys
1 5 10 15

Ala Gln Pro Pro Ile Cys Tyr Asp Arg Lys Pro Ala Glu Thr Leu Ala
20 25 30

Met Leu Ser Val Asn Val Asp Asn Pro Gly Tyr Asp Glu Leu Leu Glu
35 40 45

Ala Ala Val Lys Cys Pro Gly Ser Gly Gly Gly Ala Ile Ser Leu His
50 55 60

Pro Lys Ala Lys Ile Glu Glu Ser Gly Ser Ser Thr Glu Glu Leu Phe
65 70 75 80

Asn Glu Tyr Lys Leu Thr Arg Pro Tyr Met Ala Arg Cys Ile Arg Cys
85 90 95

Ala Val Gly Ser Cys His Ser Pro Ile Ala Ile Glu Ala Val Lys Ser
100 105 110

Asp Gly His Asp Gly Tyr Val Arg Leu Gln Thr Ser Ser Gln Tyr Gly
115 120 125

Leu Asp Ser Ser Gly Asn Leu Lys Gly Arg Thr Met Arg Tyr Asp Met
130 135 140

His Gly Thr Ile Lys Glu Ile Pro Leu His Gln Val Ser Leu Tyr Thr
145 150 155 160

```
Ser Arg Pro Cys His Ile Val Asp Gly His Gly Tyr Phe Leu Leu Ala
                165                 170                 175

Arg Cys Pro Ala Gly Asp Ser Ile Thr Met Glu Phe Lys Lys Asp Ser
            180                 185                 190

Val Arg His Ser Cys Ser Val Pro Tyr Glu Val Lys Phe Asn Pro Val
        195                 200                 205

Gly Arg Glu Leu Tyr Thr His Pro Pro Glu His Gly Val Glu Gln Ala
    210                 215                 220

Cys Gln Val Tyr Ala His Asp Ala Gln Asn Arg Gly Ala Tyr Val Glu
225                 230                 235                 240

Met His Leu Pro Gly Ser Glu Val Asp Ser Ser Leu Val Ser Leu Ser
                245                 250                 255

Gly Ser Ser Val Thr Val Thr Pro Pro Asp Gly Thr Ser Ala Leu Val
            260                 265                 270

Glu Cys Glu Cys Gly Gly Thr Lys Ile Ser Glu Thr Ile Asn Lys Thr
        275                 280                 285

Lys Gln Phe Ser Gln Cys Thr Lys Lys Glu Gln Cys Arg Ala Tyr Arg
    290                 295                 300

Leu Gln Asn Asp Lys Trp Val Tyr Asn Ser Asp Lys Leu Pro Lys Ala
305                 310                 315                 320

Ala Gly Ala Thr Leu Lys Gly Lys Leu His Val Pro Phe Leu Leu Ala
                325                 330                 335

Asp Gly Lys Cys Thr Val Pro Leu Ala Pro Glu Pro Met Ile Thr Phe
            340                 345                 350

Gly Phe Arg Ser Val Ser Leu Lys Leu His Pro Lys Asn Pro Thr Tyr
        355                 360                 365

Leu Ile Thr Arg Gln Leu Ala Asp Glu Pro His Tyr Thr His Glu Leu
    370                 375                 380

Ile Ser Glu Pro Ala Val Arg Asn Phe Thr Val Thr Glu Lys Gly Trp
385                 390                 395                 400

Glu Phe Val Trp Gly Asn His Pro Pro Lys Arg Phe Trp Ala Gln Glu
                405                 410                 415

Thr Ala Pro Gly Asn Pro His Gly Leu Pro His Glu Val Ile Thr His
            420                 425                 430

Tyr Tyr His Arg Tyr Pro Met Ser Thr Ile Leu Gly Leu Ser Ile Cys
        435                 440                 445

Ala Ala Ile Ala Thr Val Ser Val Ala Ala Ser Thr Trp Leu Phe Cys
    450                 455                 460

Arg Ser Arg Val Ala Cys Leu Thr Pro Tyr Arg Leu Thr Pro Asn Ala
465                 470                 475                 480

Arg Ile Pro Phe Cys Leu Ala Val Leu Cys Cys Ala Arg Thr Ala Arg
                485                 490                 495

Ala


<210> SEQ ID NO 52
<211> LENGTH: 495
<212> TYPE: PRT
<213> ORGANISM: Artificial Sequence
<220> FEATURE:
<223> OTHER INFORMATION: Synthetic VEEV E3-PD-L1-E2

<400> SEQUENCE: 52

Ser Leu Val Thr Thr Met Cys Leu Leu Ala Asn Val Thr Phe Pro Cys
1               5                   10                  15
```

-continued

```
Ala Gln Pro Pro Ile Cys Tyr Asp Arg Lys Pro Ala Glu Thr Leu Ala
            20                  25                  30

Met Leu Ser Val Asn Val Asp Asn Pro Gly Tyr Asp Glu Leu Leu Glu
        35                  40                  45

Ala Ala Val Lys Cys Pro Gly Ser Gly Gly Cys Ile Ile Ser Tyr Gly
    50                  55                  60

Gly Ala Asp Tyr Cys Gly Gly Ser Ser Thr Glu Glu Leu Phe Asn Glu
65                  70                  75                  80

Tyr Lys Leu Thr Arg Pro Tyr Met Ala Arg Cys Ile Arg Cys Ala Val
                85                  90                  95

Gly Ser Cys His Ser Pro Ile Ala Ile Glu Ala Val Lys Ser Asp Gly
            100                 105                 110

His Asp Gly Tyr Val Arg Leu Gln Thr Ser Ser Gln Tyr Gly Leu Asp
        115                 120                 125

Ser Ser Gly Asn Leu Lys Gly Arg Thr Met Arg Tyr Asp Met His Gly
    130                 135                 140

Thr Ile Lys Glu Ile Pro Leu His Gln Val Ser Leu Tyr Thr Ser Arg
145                 150                 155                 160

Pro Cys His Ile Val Asp Gly His Gly Tyr Phe Leu Leu Ala Arg Cys
                165                 170                 175

Pro Ala Gly Asp Ser Ile Thr Met Glu Phe Lys Lys Asp Ser Val Arg
            180                 185                 190

His Ser Cys Ser Val Pro Tyr Glu Val Lys Phe Asn Pro Val Gly Arg
        195                 200                 205

Glu Leu Tyr Thr His Pro Pro Glu His Gly Val Glu Gln Ala Cys Gln
    210                 215                 220

Val Tyr Ala His Asp Ala Gln Asn Arg Gly Ala Tyr Val Glu Met His
225                 230                 235                 240

Leu Pro Gly Ser Glu Val Asp Ser Ser Leu Val Ser Leu Ser Gly Ser
                245                 250                 255

Ser Val Thr Val Thr Pro Pro Asp Gly Thr Ser Ala Leu Val Glu Cys
            260                 265                 270

Glu Cys Gly Gly Thr Lys Ile Ser Glu Thr Ile Asn Lys Thr Lys Gln
        275                 280                 285

Phe Ser Gln Cys Thr Lys Lys Glu Gln Cys Arg Ala Tyr Arg Leu Gln
    290                 295                 300

Asn Asp Lys Trp Val Tyr Asn Ser Asp Lys Leu Pro Lys Ala Ala Gly
305                 310                 315                 320

Ala Thr Leu Lys Gly Lys Leu His Val Pro Phe Leu Leu Ala Asp Gly
                325                 330                 335

Lys Cys Thr Val Pro Leu Ala Pro Glu Pro Met Ile Thr Phe Gly Phe
            340                 345                 350

Arg Ser Val Ser Leu Lys Leu His Pro Lys Asn Pro Thr Tyr Leu Ile
        355                 360                 365

Thr Arg Gln Leu Ala Asp Glu Pro His Tyr Thr His Glu Leu Ile Ser
    370                 375                 380

Glu Pro Ala Val Arg Asn Phe Thr Val Thr Glu Lys Gly Trp Glu Phe
385                 390                 395                 400

Val Trp Gly Asn His Pro Pro Lys Arg Phe Trp Ala Gln Glu Thr Ala
                405                 410                 415

Pro Gly Asn Pro His Gly Leu Pro His Glu Val Ile Thr His Tyr Tyr
            420                 425                 430

His Arg Tyr Pro Met Ser Thr Ile Leu Gly Leu Ser Ile Cys Ala Ala
```

```
        435                 440                 445

Ile Ala Thr Val Ser Val Ala Ala Ser Thr Trp Leu Phe Cys Arg Ser
    450                 455                 460

Arg Val Ala Cys Leu Thr Pro Tyr Arg Leu Thr Pro Asn Ala Arg Ile
465                 470                 475                 480

Pro Phe Cys Leu Ala Val Leu Cys Cys Ala Arg Thr Ala Arg Ala
                485                 490                 495


<210> SEQ ID NO 53
<211> LENGTH: 502
<212> TYPE: PRT
<213> ORGANISM: Artificial Sequence
<220> FEATURE:
<223> OTHER INFORMATION: Synthetic VEEV E3-CTLA-4-E2

<400> SEQUENCE: 53

Ser Leu Val Thr Thr Met Cys Leu Leu Ala Asn Val Thr Phe Pro Cys
1               5                   10                  15

Ala Gln Pro Pro Ile Cys Tyr Asp Arg Lys Pro Ala Glu Thr Leu Ala
            20                  25                  30

Met Leu Ser Val Asn Val Asp Asn Pro Gly Tyr Asp Glu Leu Leu Glu
        35                  40                  45

Ala Ala Val Lys Cys Pro Gly Ser Gly Gly Gly Gly Lys Val Glu Leu
    50                  55                  60

Met Tyr Pro Pro Pro Tyr Phe Val Gly Met Gly Gly Gly Gly Ser Ser
65                  70                  75                  80

Thr Glu Glu Leu Phe Asn Glu Tyr Lys Leu Thr Arg Pro Tyr Met Ala
                85                  90                  95

Arg Cys Ile Arg Cys Ala Val Gly Ser Cys His Ser Pro Ile Ala Ile
            100                 105                 110

Glu Ala Val Lys Ser Asp Gly His Asp Gly Tyr Val Arg Leu Gln Thr
        115                 120                 125

Ser Ser Gln Tyr Gly Leu Asp Ser Ser Gly Asn Leu Lys Gly Arg Thr
    130                 135                 140

Met Arg Tyr Asp Met His Gly Thr Ile Lys Glu Ile Pro Leu His Gln
145                 150                 155                 160

Val Ser Leu Tyr Thr Ser Arg Pro Cys His Ile Val Asp Gly His Gly
                165                 170                 175

Tyr Phe Leu Leu Ala Arg Cys Pro Ala Gly Asp Ser Ile Thr Met Glu
            180                 185                 190

Phe Lys Lys Asp Ser Val Arg His Ser Cys Ser Val Pro Tyr Glu Val
        195                 200                 205

Lys Phe Asn Pro Val Gly Arg Glu Leu Tyr Thr His Pro Pro Glu His
    210                 215                 220

Gly Val Glu Gln Ala Cys Gln Val Tyr Ala His Asp Ala Gln Asn Arg
225                 230                 235                 240

Gly Ala Tyr Val Glu Met His Leu Pro Gly Ser Glu Val Asp Ser Ser
                245                 250                 255

Leu Val Ser Leu Ser Gly Ser Ser Val Thr Val Thr Pro Pro Asp Gly
            260                 265                 270

Thr Ser Ala Leu Val Glu Cys Glu Cys Gly Gly Thr Lys Ile Ser Glu
        275                 280                 285

Thr Ile Asn Lys Thr Lys Gln Phe Ser Gln Cys Thr Lys Lys Glu Gln
    290                 295                 300

Cys Arg Ala Tyr Arg Leu Gln Asn Asp Lys Trp Val Tyr Asn Ser Asp
```

305 310 315 320

Lys Leu Pro Lys Ala Ala Gly Ala Thr Leu Lys Gly Lys Leu His Val
325 330 335

Pro Phe Leu Leu Ala Asp Gly Lys Cys Thr Val Pro Leu Ala Pro Glu
340 345 350

Pro Met Ile Thr Phe Gly Phe Arg Ser Val Ser Leu Lys Leu His Pro
355 360 365

Lys Asn Pro Thr Tyr Leu Ile Thr Arg Gln Leu Ala Asp Glu Pro His
370 375 380

Tyr Thr His Glu Leu Ile Ser Glu Pro Ala Val Arg Asn Phe Thr Val
385 390 395 400

Thr Glu Lys Gly Trp Glu Phe Val Trp Gly Asn His Pro Pro Lys Arg
405 410 415

Phe Trp Ala Gln Glu Thr Ala Pro Gly Asn Pro His Gly Leu Pro His
420 425 430

Glu Val Ile Thr His Tyr Tyr His Arg Tyr Pro Met Ser Thr Ile Leu
435 440 445

Gly Leu Ser Ile Cys Ala Ala Ile Ala Thr Val Ser Val Ala Ala Ser
450 455 460

Thr Trp Leu Phe Cys Arg Ser Arg Val Ala Cys Leu Thr Pro Tyr Arg
465 470 475 480

Leu Thr Pro Asn Ala Arg Ile Pro Phe Cys Leu Ala Val Leu Cys Cys
485 490 495

Ala Arg Thr Ala Arg Ala
500

<210> SEQ ID NO 54
<211> LENGTH: 3747
<212> TYPE: DNA
<213> ORGANISM: Artificial Sequence
<220> FEATURE:
<223> OTHER INFORMATION: Synthetic CHIKV

<400> SEQUENCE: 54
atggagttca tcccgacgca aactttctat aacagaaggt accaaccccg accctgggcc 60
ccacgcccta caattcaagt aattagacct agaccacgtc cacagaggca ggctgggcaa 120
ctcgcccagc tgatctccgc agtcaacaaa ttgaccatgc gcgcggtacc tcaacagaag 180
cctcgcagaa atcggaaaaa caagaagcaa aggcagaaga agcaggcgcc gcaaaacgac 240
ccaaagcaaa agaagcaacc accacaaaag aagccggctc aaaagaagaa gaaaccaggc 300
cgtagggaga gaatgtgcat gaaaattgaa aatgattgca tcttcgaagt caagcatgaa 360
ggcaaagtga tgggctacgc atgcctggtg ggggataaag taatgaaacc agcacatgtg 420
aagggaacta tcgacaatgc cgatctggct aaactggcct ttaagcggtc gtctaaatac 480
gatcttgaat gtgcacagat accggtgcac atgaagtctg atgcctcgaa gtttacccac 540
gagaaacccg aggggtacta taactggcat cacggagcag tgcagtattc aggaggccgg 600
ttcactatcc cgacgggtgc aggcaagccg ggagacagcg gcagaccgat cttcgacaac 660
aaaggacggg tggtggccat cgtcctagga ggggccaacg aaggtgcccg cacggccctc 720
tccgtggtga cgtggaacaa agacatcgtc acaaaaatta cccctgaggg agccgaagag 780
tggagcctcg ccctcccggt cttgtgcctg ttggcaaaca ctacattccc ctgctctcag 840
ccgccttgca caccctgctg ctacgaaaag gaaccggaaa gcaccttgcg catgcttgag 900
gacaacgtga tgagacccgg atactaccag ctactaaaag catcgctgac ttgctctccc 960
cactccggag gcggatccag tactaaggac aattttaatg tctataaagc cacaagacca 1020
tatctagctc attgtcctga ctgcggagaa gggcattcgt gccacagccc tatcgcattg 1080
gagcgcatca gaaatgaagc aacggacgga acgctgaaaa tccaggtctc tttgcagatc 1140
gggataaaga cagatgacag ccacgattgg accaagctgc gctatatgga tagccatacg 1200
cccgcggacg cggagcgagc cggattgctt gtaaggactt cagcaccgtg cacgatcacc 1260
gggaccatgg gacactttat tctcgcccga tgcccgaaag gagagacgct gacagtggga 1320
tttacggaca gcagaaagat cagccacaca tgcacacacc cgttccatca tgaaccacct 1380
gtgataggta gggagaggtt ccactctcga ccacaacatg gtaaagagtt accttgcagc 1440
acgtacgtgc agagcaccgc tgccactgct gaggagatag aggtgcatat gcccccagat 1500
actcctgacc gcacgctgat gacgcagcag tctggcaacg tgaagatcac agttaatggg 1560
cagacggtgc ggtacaagtg caactgcggt ggctcaaacg agggactgac aaccacagac 1620
aaagtgatca ataactgcaa aattgatcag tgccatgctg cagtcactaa tcacaagaat 1680
tggcaataca actccccttt agtcccgcgc aacgctgaac tcggggaccg taaaggaaag 1740
atccacatcc cattcccatt ggcaaacgtg acttgcagag tgccaaaagc aagaaaccct 1800
acagtaactt acggaaaaaa ccaagtcacc atgctgctgt atcctgacca tccgacactc 1860
ttgtcttacc gtaacatggg acaggaacca aattaccacg aggagtgggt gacacacaag 1920
aaggaggtta ccttgaccgt gcctactgag ggtctggagg tcacttgggg caacaacgaa 1980
ccatacaagt actggccgca gatgtctacg aacggtactg ctcatggtca cccacatgag 2040
ataatcttgt actattatga gctgtacccc actatgactg tagtcattgt gtcggtggcc 2100
tcgttcgtgc ttctgtcgat ggtgggcaca gcagtgggaa tgtgtgtgtg cgcacggcgc 2160
agatgcatta caccatatga attaacacca ggagccactg ttcccttcct gctcagcctg 2220
ctatgctgcg tcagaacgac caaggcggcc acatattacg aggctgcggc atatctatgg 2280
aacgaacagc agcccctgtt ctggttgcag gctcttatcc cgctggccgc cttgatcgtc 2340
ctgtgcaact gtctgaaact cttgccatgc tgctgtaaga ccctggcttt tttagccgta 2400
atgagcatcg gtgcccacac tgtgagcgcg tacgaacacg taacagtgat cccgaacacg 2460
gtgggagtac cgtataagac tcttgtcaac agaccgggtt acagccccat ggtgttggag 2520
atggagctac aatcagtcac cttggaacca acactgtcac ttgactacat cacgtgcgag 2580
tacaaaactg tcatcccctc cccgtacgtg aagtgctgtg gtacagcaga gtgcaaggac 2640
aagagcctac cagactacag ctgcaaggtc tttactggag tctacccatt tatgtggggc 2700
ggcgcctact gcttttgcga cgccgaaaat acgcaattga gcgaggcaca tgtagagaaa 2760
tctgaatctt gcaaaacaga gtttgcatcg gcctacagag cccacaccgc atcggcgtcg 2820
gcgaagctcc gcgtccttta ccaaggaaac aacattaccg tagctgccta cgctaacggt 2880
gaccatgccg tcacagtaaa ggacgccaag tttgtcgtgg gcccaatgtc ctccgcctgg 2940
acaccttttg acaacaaaat cgtggtgtac aaaggcgacg tctacaacat ggactaccca 3000
ccttttggcg caggaagacc aggacaattt ggtgacattc aaagtcgtac accggaaagt 3060
aaagacgttt atgccaacac tcagttggta ctacagaggc cagcagcagg cacggtacat 3120
gtaccatact ctcaggcacc atctggcttc aagtattggc tgaaggaacg aggagcatcg 3180
ctacagcaca cggcaccgtt cggttgccag attgcgacaa acccggtaag agctgtaaat 3240
tgcgctgtgg ggaacatacc aatttccatc gacataccgg atgcggcctt tactagggtt 3300
gtcgatgcac cctctgtaac ggacatgtca tgcgaagtac cagcctgcac tcactcctcc 3360
gactttgggg gcgtcgccat catcaaatac acagctagca agaaaggtaa atgtgcagta 3420
cattcgatga ccaacgccgt taccattcga gaagccgacg tagaagtaga ggggaactcc 3480
cagctgcaaa tatccttctc aacagccctg gcaagcgccg agtttcgcgt gcaagtgtgc 3540
tccacacaag tacactgcgc agccgcatgc caccctccaa aggaccacat agtcaattac 3600
ccagcatcac acaccaccct tggggtccag gatatatcca caacggcaat gtcttgggtg 3660
cagaagatta cgggaggagt aggattaatt gttgctgttg ctgccttaat tttaattgtg 3720
gtgctatgcg tgtcgtttag caggcac 3747

<210> SEQ ID NO 55
<211> LENGTH: 3768
<212> TYPE: DNA
<213> ORGANISM: Artificial Sequence
<220> FEATURE:
<223> OTHER INFORMATION: Synthetic VEEV

<400> SEQUENCE: 55
atgttcccgt tccagccaat gtatccgatg cagccaatgc cctatcgcaa cccgttcgcg 60
gccccgcgca ggccctggtt ccccagaacc gacccttttc tggcgatgca ggtgcaggaa 120
ttaacccgct cgatggctaa cctgacgttc aagcaacgcc gggacgcgcc acctgagggg 180
ccatccgcta ataaaccgaa gaaggaggcc tcgcaaaaac agaaaggggg aggccaaggg 240
aagaagaaga agaaccaagg gaagaagaag gctaagacag ggccgcctaa tccgaaggca 300
cagaatggaa acaagaagaa gaccaacaag aaaccaggca agagacagcg catggtcatg 360
aaattggaat ctgacaagac gttcccaatc atgttggaag ggaagataaa cggctacgct 420
tgtgtggtcg gagggaagtt attcaggccg atgcatgtgg aaggcaagat cgacaacgac 480
gttctggccg cgcttaagac gaagaaagca tccaaatacg atcttgagta tgcagatgtg 540
ccacagaaca tgcgggccga tacattcaaa tacacccatg agaaacccca aggctattac 600
agctggcatc atggagcagt ccaatatgaa aatgggcgtt tcacggtgcc gaaaggagtt 660
ggggccaagg gagacagcgg acgacccatt ctggataacc agggacgggt ggtcgctatt 720
gtgctgggag gtgtgaatga aggatctagg acagcccttt cagtcgtcat gtggaacgag 780
aagggagtta ccgtgaagta tactccagag aactgcgagc aatggtcact agtgaccacc 840
atgtgtctgc tcgccaatgt gacgttccca tgtgctcaac caccaatttg ctacgacaga 900
aaaccagcag agactttggc catgctcagc gttaacgttg acaacccggg ctacgatgag 960
ctgctggaag cagctgttaa gtgccccggg tccggaggtg gatcctccac cgaggagctg 1020
tttaatgagt ataagctaac gcgcccttac atggccagat gcatcagatg tgcagttggg 1080
agctgccata gtccaatagc aatcgaggca gtaaagagcg acgggcacga cggttatgtt 1140
agacttcaga cttcctcgca gtatggcctg gattcctccg gcaacttaaa gggcaggacc 1200
atgcggtatg acatgcacgg gaccattaaa gagataccac tacatcaagt gtcactctat 1260
acatctcgcc cgtgtcacat tgtggatggg cacggttatt tcctgctagc caggtgcccg 1320
gcaggggact ccatcaccat ggaatttaag aaagattccg tcagacactc ctgctcggtg 1380
ccgtatgaag tgaaatttaa tcctgtaggc agagaactct atactcatcc cccagaacac 1440
ggagtagagc aagcgtgcca agtctacgca catgatgcac agaacagagg agcttatgtc 1500
gagatgcacc tcccgggctc agaagtggac agcagtttgg tttccttgag cggcagttca 1560
gtcaccgtga cacctcctga tgggactagc gccctggtgg aatgcgagtg tggcggcaca 1620
aagatctccg agaccatcaa caagacaaaa cagttcagcc agtgcacaaa gaaggagcag 1680
tgcagagcat atcggctgca gaacgataag tgggtgtata attctgacaa actgcccaaa 1740
gcagcgggag ccaccttaaa aggaaaactg catgtcccat tcttgctggc agacggcaaa 1800
tgcaccgtgc ctctagcacc agaacctatg ataaccttcg gtttcagatc agtgtcactg 1860
aaactgcacc ctaagaatcc cacatatcta atcacccgcc aacttgctga tgagcctcac 1920
tacacgcacg agctcatatc tgaaccagct gttaggaatt ttaccgtcac cgaaaaaggg 1980
tgggagtttg tatggggaaa ccacccgccg aaaaggtttt gggcacagga aacagcaccc 2040
ggaaatccac atgggctacc gcacgaggtg ataactcatt attaccacag ataccctatg 2100
tccaccatcc tgggtttgtc aatttgtgcc gccattgcaa ccgtttccgt tgcagcgtct 2160
acctggctgt tttgcagatc aagagttgcg tgcctaactc cttaccggct aacacctaac 2220
gctaggatac cattttgtct ggctgtgctt tgctgcgccc gcactgcccg ggccgagacc 2280
acctgggagt ccttggatca cctatggaac aataaccaac agatgttctg gattcaattg 2340
ctgatccctc tggccgcctt gatcgtagtg actcgcctgc tcaggtgcgt gtgctgtgtc 2400
gtgccttttt tagtcatggc cggcgccgca ggcgccggcg cctacgagca cgcgaccacg 2460
atgccgagcc aagcgggaat ctcgtataac actatagtca acagagcagg ctacgcacca 2520
ctccctatca gcataacacc aacaaagatc aagctgatac ctacagtgaa cttggagtac 2580
gtcacctgcc actacaaaac aggaatggat tcaccagcca tcaaatgctg cggatctcag 2640
gaatgcactc caacttacag gcctgatgaa cagtgcaaag tcttcacagg ggtttacccg 2700
ttcatgtggg gtggtgcata ttgcttttgc gacactgaga acacccaagt cagcaaggcc 2760
tacgtaatga aatctgacga ctgccttgcg gatcatgctg aagcatataa agcgcacaca 2820
gcctcagtgc aggcgttcct caacatcaca gtgggagaac actctattgt gactaccgtg 2880
tatgtgaatg gagaaactcc tgtgaatttc aatggggtca aaataactgc aggtccgctt 2940
tccacagctt ggacaccctt tgatcgcaaa atcgtgcagt atgccgggga gatctataat 3000
tatgattttc ctgagtatgg ggcaggacaa ccaggagcat ttggagatat acaatccaga 3060
acagtctcaa gctctgatct gtatgccaat accaacctag tgctgcagag acccaaagca 3120
ggagcgatcc acgtgccata cactcaggca ccttcgggtt ttgagcaatg gaagaaagat 3180
aaagctccat cattgaaatt taccgcccct ttcggatgcg aaatatatac aaaccccatt 3240
cgcgccgaaa actgtgctgt agggtcaatt ccattagcct ttgacattcc cgacgccttg 3300
ttcaccaggg tgtcagaaac accgacactt tcagcggccg aatgcactct taacgagtgc 3360
gtgtattctt ccgactttgg tgggatcgcc acggtcaagt actcggccag caagtcaggc 3420
aagtgcgcag tccatgtgcc atcagggact gctaccctaa aagaagcagc agtcgagcta 3480
accgagcaag ggtcggcgac tatccatttc tcgaccgcaa atatccaccc ggagttcagg 3540
ctccaaatat gcacatcata tgttacgtgc aaaggtgatt gtcacccccc gaaagaccat 3600
attgtgacac accctcagta tcacgcccaa acatttacag ccgcggtgtc aaaaaccgcg 3660
tggacgtggt taacatccct gctgggagga tcagccgtaa ttattataat tggcttggtg 3720
ctggctacta ttgtggccat gtacgtgctg accaaccaga aacataat 3768

<210> SEQ ID NO 56
<211> LENGTH: 30
<212> TYPE: PRT
<213> ORGANISM: Artificial Sequence
<220> FEATURE:

<223> OTHER INFORMATION: Synthetic malaria antigen with linker

<400> SEQUENCE: 56

Ser Gly Gly Asn Pro Asn Ala Asn Pro Asn Ala Asn Pro Asn Ala Asn
1               5                   10                  15

Pro Asn Ala Asn Pro Asn Ala Asn Pro Asn Ala Gly Gly Ser
            20                  25                  30

<210> SEQ ID NO 57
<211> LENGTH: 8476
<212> TYPE: DNA
<213> ORGANISM: Artificial Sequence
<220> FEATURE:
<223> OTHER INFORMATION: Synthetic Expression vector for CHIKV viral structural protein containing CSP repeat antigen "74" in E3 (74.16)

<400> SEQUENCE: 57
gaattcccat tgcatacgtt gtatccatat cataatatgt acatttatat tggctcatgt 60
ccaacattac cgccatgttg acattgatta ttgactagtt attaatagta atcaattacg 120
gggtcattag ttcatagccc atatatggag ttccgcgtta cataacttac ggtaaatggc 180
ccgcctggct gaccgcccaa cgacccccgc ccattgacgt caataatgac gtatgttccc 240
atagtaacgc caatagggac tttccattga cgtcaatggg tggagtattt acggtaaact 300
gcccacttgg cagtacatca agtgtatcat atgccaagta cgccccctat tgacgtcaat 360
gacggtaaat ggcccgcctg gcattatgcc cagtacatga ccttatggga ctttcctact 420
tggcagtaca tctacgtatt agtcatcgct attaccatgg tgatgcggtt ttggcagtac 480
atcaatgggc gtggatagcg gtttgactca cggggatttc caagtctcca ccccattgac 540
gtcaatggga gtttgttttg gcaccaaaat caacgggact ttccaaaatg tcgtaacaac 600
tccgccccat tgacgcaaat gggcggtagg cgtgtacggt gggaggtcta tataagcaga 660
gctcgtttag tgaaccgtca gatcgcctgg agacgccatc cacgctgttt tgacctccat 720
agaagacacc gggaccgatc cagcctccgt taacggtgga gggcagtgta gtctgagcag 780
tactcgttgc tgccgcgcgc gccaccagac ataatagctg acagactaac agactgttcc 840
tttccatggg tcttttctgc agtcaccgtc gtcgacacgt gtgatcagat atcgcggccg 900
ccaccatgga gttcatcccg acgcaaactt tctataacag aaggtaccaa ccccgaccct 960
gggccccacg ccctacaatt caagtaatta gacctagacc acgtccacag aggcaggctg 1020
ggcaactcgc ccagctgatc tccgcagtca acaaattgac catgcgcgcg gtacctcaac 1080
agaagcctcg cagaaatcgg aaaaacaaga agcaaaggca gaagaagcag gcgccgcaaa 1140
acgacccaaa gcaaaagaag caaccaccac aaaagaagcc ggctcaaaag aagaagaaac 1200
caggccgtag ggagagaatg tgcatgaaaa ttgaaaatga ttgcatcttc gaagtcaagc 1260
atgaaggcaa agtgatgggc tacgcatgcc tggtgggggga taaagtaatg aaaccagcac 1320
atgtgaaggg aactatcgac aatgccgatc tggctaaact ggcctttaag cggtcgtcta 1380
aatacgatct tgaatgtgca cagataccgg tgcacatgaa gtctgatgcc tcgaagttta 1440
cccacgagaa acccgagggg tactataact ggcatcacgg agcagtgcag tattcaggag 1500
gccggttcac tatcccgacg ggtgcaggca agccgggaga cagcggcaga ccgatcttcg 1560
acaacaaagg acgggtggtg gccatcgtcc taggaggggc caacgaaggt gcccgcacgg 1620
ccctctccgt ggtgacgtgg aacaaagaca tcgtcacaaa aattacccct gagggagccg 1680
aagagtggag cctcgccctc ccggtcttgt gcctgttggc aaacactaca ttcccctgct 1740
ctcagccgcc ttgcacaccc tgctgctacg aaaaggaacc ggaaagcacc ttgcgcatgc 1800
ttgaggacaa cgtgatgaga cccggatact accagctact aaaagcatcg ctgacttgct 1860
ctccccactc cggaggaaac ccgaatgcca atcccaacgc gaaccccaat gctaacccaa 1920
atgccaaccc aaacgccaac cccaacgctg gtggatccag tactaaggac aattttaatg 1980
tctataaagc cacaagacca tatctagctc attgtcctga ctgcggagaa gggcattcgt 2040
gccacagccc tatcgcattg gagcgcatca gaaatgaagc aacggacgga acgctgaaaa 2100
tccaggtctc tttgcagatc gggataaaga cagatgacag ccacgattgg accaagctgc 2160
gctatatgga tagccatacg cccgcggacg cggagcgagc cggattgctt gtaaggactt 2220
cagcaccgtg cacgatcacc gggaccatgg gacactttat tctcgcccga tgcccgaaag 2280
gagagacgct gacagtggga tttacggaca gcagaaagat cagccacaca tgcacacacc 2340
cgttccatca tgaaccacct gtgataggta gggagaggtt ccactctcga ccacaacatg 2400
gtaaagagtt accttgcagc acgtacgtgc agagcaccgc tgccactgct gaggagatag 2460
aggtgcatat gcccccagat actcctgacc gcacgctgat gacgcagcag tctggcaacg 2520
tgaagatcac agttaatggg cagacggtgc ggtacaagtg caactgcggt ggctcaaacg 2580
agggactgac aaccacagac aaagtgatca ataactgcaa aattgatcag tgccatgctg 2640
cagtcactaa tcacaagaat tggcaataca actccccttt agtcccgcgc aacgctgaac 2700
tcggggaccg taaaggaaag atccacatcc cattcccatt ggcaaacgtg acttgcagag 2760
tgccaaaagc aagaaaccct acagtaactt acggaaaaaa ccaagtcacc atgctgctgt 2820
atcctgacca tccgacactc ttgtcttacc gtaacatggg acaggaacca aattaccacg 2880
aggagtgggt gacacacaag aaggaggtta ccttgaccgt gcctactgag ggtctggagg 2940
tcacttgggg caacaacgaa ccatacaagt actggccgca gatgtctacg aacggtactg 3000
ctcatggtca cccacatgag ataatcttgt actattatga gctgtacccc actatgactg 3060
tagtcattgt gtcggtggcc tcgttcgtgc ttctgtcgat ggtgggcaca gcagtgggaa 3120
tgtgtgtgtg cgcacggcgc agatgcatta caccatatga attaacacca ggagccactg 3180
ttcccttcct gctcagcctg ctatgctgcg tcagaacgac caaggcggcc acatattacg 3240
aggctgcggc atatctatgg aacgaacagc agcccctgtt ctggttgcag gctcttatcc 3300
cgctggccgc cttgatcgtc ctgtgcaact gtctgaaact cttgccatgc tgctgtaaga 3360
ccctggcttt tttagccgta atgagcatcg gtgcccacac tgtgagcgcg tacgaacacg 3420
taacagtgat cccgaacacg gtgggagtac cgtataagac tcttgtcaac agaccgggtt 3480
acagccccat ggtgttggag atggagctac aatcagtcac cttggaacca acactgtcac 3540
ttgactacat cacgtgcgag tacaaaactg tcatcccctc cccgtacgtg aagtgctgtg 3600
gtacagcaga gtgcaaggac aagagcctac cagactacag ctgcaaggtc tttactggag 3660
tctacccatt tatgtggggc ggcgcctact gcttttgcga cgccgaaaat acgcaattga 3720
gcgaggcaca tgtagagaaa tctgaatctt gcaaaacaga gtttgcatcg gcctacagag 3780
cccacaccgc atcggcgtcg gcgaagctcc gcgtccttta ccaaggaaac aacattaccg 3840
tagctgccta cgctaacggt gaccatgccg tcacagtaaa ggacgccaag tttgtcgtgg 3900
gcccaatgtc ctccgcctgg acaccttttg acaacaaaat cgtggtgtac aaaggcgacg 3960
tctacaacat ggactaccca ccttttggcg caggaagacc aggacaattt ggtgacattc 4020
aaagtcgtac accggaaagt aaagacgttt atgccaacac tcagttggta ctacagaggc 4080

-continued

```
cagcagcagg cacggtacat gtaccatact ctcaggcacc atctggcttc aagtattggc   4140
tgaaggaacg aggagcatcg ctacagcaca cggcaccgtt cggttgccag attgcgacaa   4200
acccggtaag agctgtaaat tgcgctgtgg ggaacatacc aatttccatc gacataccgg   4260
atgcggcctt tactagggtt gtcgatgcac cctctgtaac ggacatgtca tgcgaagtac   4320
cagcctgcac tcactcctcc gactttgggg gcgtcgccat catcaaatac acagctagca   4380
agaaaggtaa atgtgcagta cattcgatga ccaacgccgt taccattcga gaagccgacg   4440
tagaagtaga ggggaactcc cagctgcaaa tatccttctc aacagccctg gcaagcgccg   4500
agtttcgcgt gcaagtgtgc tccacacaag tacactgcgc agccgcatgc caccctccaa   4560
aggaccacat agtcaattac ccagcatcac acaccaccct tggggtccag gatatatcca   4620
caacggcaat gtcttgggtg cagaagatta cgggaggagt aggattaatt gttgctgttg   4680
ctgccttaat tttaattgtg gtgctatgcg tgtcgtttag caggcactaa ggatctagat   4740
ctgctgtgcc ttctagttgc cagccatctg ttgtttgccc ctcccccgtg ccttccttga   4800
ccctggaagg tgccactccc actgtccttt cctaataaaa tgaggaaatt gcatcgcatt   4860
gtctgagtag gtgtcattct attctggggg gtggggtggg gcaggacagc aagggggagg   4920
attgggaaga caatagcagg catgctgggg atgcggtggg ctctatgggt acccaggtgc   4980
tgaagaattg acccggttcc tcctgggcca gaaagaagca ggcacatccc cttctctgtg   5040
acacaccctg tccacgcccc tggttcttag ttccagcccc actcatagga cactcatagc   5100
tcaggagggc tccgccttca atcccacccg ctaaagtact tggagcggtc tctccctccc   5160
tcatcagccc accaaaccaa acctagcctc caagagtggg aagaaattaa agcaagatag   5220
gctattaagt gcagagggag agaaaatgcc tccaacatgt gaggaagtaa tgagagaaat   5280
catagaattt taaggccatg atttaaggcc atcatggcct aagcttgaaa ggagatagga   5340
tcaaagcttg gcgtaatcat ggtcatagct gtttcctgtg tgaaattgtt atccgctcac   5400
aattccacac aacatacgag ccggaagcat aaagtgtaaa gcctggggtg cctaatgagt   5460
gagctaactc acattaattg cgttgcgctc actgcccgct ttccagtcgg gaaacctgtc   5520
gtgccagctg cattaatgaa tcggccaacg cgcggggaga ggcggtttgc gtattgggcg   5580
ctcttccgct tcctcgctca ctgactcgct gcgctcggtc gttcggctgc ggcgagcggt   5640
atcagctcac tcaaaggcgg taatacggtt atccacagaa tcaggggata acgcaggaaa   5700
gaacatgtga gcaaaaggcc agcaaaaggc caggaaccgt aaaaaggccg cgttgctggc   5760
gtttttccat aggctccgcc cccctgacga gcatcacaaa aatcgacgct caagtcagag   5820
gtggcgaaac ccgacaggac tataaagata ccaggcgttt ccccctggaa gctccctcgt   5880
gcgctctcct gttccgaccc tgccgcttac cggatacctg tccgcctttc tcccttcggg   5940
aagcgtggcg ctttctcata gctcacgctg taggtatctc agttcggtgt aggtcgttcg   6000
ctccaagctg ggctgtgtgc acgaaccccc cgttcagccc gaccgctgcg ccttatccgg   6060
taactatcgt cttgagtcca acccggtaag acacgactta tcgccactgg cagcagccac   6120
tggtaacagg attagcagag cgaggtatgt aggcggtgct acagagttct tgaagtggtg   6180
gcctaactac ggctacacta gaagaacagt atttggtatc tgcgctctgc tgaagccagt   6240
taccttcgga aaaagagttg gtagctcttg atccggcaaa caaaccaccg ctggtagcgg   6300
tggttttttt gtttgcaagc agcagattac gcgcagaaaa aaaggatctc aagaagatcc   6360
tttgatcttt tctacggggt ctgacgctca gtggaacgaa aactcacgtt aagggatttt   6420
ggtcatgaga ttatcaaaaa ggatcttcac ctagatcctt ttaaattaaa aatgaagttt   6480
```

taaatcaatc taaagtatat atgagtaaac ttggtctgac agttaccaat gcttaatcag 6540
tgaggcacct atctcagcga tctgtctatt tcgttcatcc atagttgcct gactccccgt 6600
cgtgtagata actacgatac gggagggctt accatctggc cccagtgctg caatgatacc 6660
gcgagaacca cgctcaccgg ctccagattt atcagcaata aaccagccag ccggaagggc 6720
cgagcgcaga agtggtcctg caactttatc cgcctccatc cagtctatta attgttgccg 6780
ggaagctaga gtaagtagtt cgccagttaa tagtttgcgc aacgttgttg ccattgctac 6840
aggcatcgtg gtgtcacgct cgtcgtttgg tatggcttca ttcagctccg gttcccaacg 6900
atcaaggcga gttacatgat cccccatgtt gtgcaaaaaa gcggttagct ccttcggtcc 6960
tccgatcgtt gtcagaagta agttggccgc agtgttatca ctcatggtta tggcagcact 7020
gcataattct cttactgtca tgccatccgt aagatgcttt tctgtgactg gtgagtactc 7080
aaccaagtca ttctgagaat agtgtatgcg gcgaccgagt tgctcttgcc cggcgtcaat 7140
acgggataat accgcgccac atagcagaac tttaaaagtg ctcatcattg gaaaacgttc 7200
ttcggggcga aaactctcaa ggatcttacc gctgttgaga tccagttcga tgtaacccac 7260
tcgtgcaccc aactgatctt cagcatcttt tactttcacc agcgtttctg ggtgagcaaa 7320
aacaggaagg caaaatgccg caaaaaaggg aataagggcg acacggaaat gttgaatact 7380
catactcttc ctttttcaat attattgaag catttatcag ggttattgtc tcatgagcgg 7440
atacatattt gaatgtattt agaaaaataa acaaataggg gttccgcgca catttccccg 7500
aaaagtgcca cctgacgtct aagaaaccat tattatcatg acattaacct ataaaaatag 7560
gcgtatcacg aggccctttc gggtcgcgcg tttcggtgat gacggtgaaa acctctgaca 7620
catgcagctc ccgttgacgg tcacagcttg tctgtaagcg gatgccggga gcagacaagc 7680
ccgtcagggc gcgtcagcgg gtgttggcgg gtgtcggggc tggcttaact atgcggcatc 7740
agagcagatt gtactgagag tgcaccataa aattgtaaac gttaatattt tgttaaaatt 7800
cgcgttaaat ttttgttaaa tcagctcatt ttttaaccaa taggccgaaa tcggcaaaat 7860
cccttataaa tcaaaagaat agcccgagat agggttgagt gttgttccag tttggaacaa 7920
gagtccacta ttaaagaacg tggactccaa cgtcaaaggg cgaaaaaccg tctatcaggg 7980
cgatggccca ctacgtgaac catcacccaa atcaagtttt ttggggtcga ggtgccgtaa 8040
agcactaaat cggaacccta aagggagccc ccgatttaga gcttgacggg gaaagccggc 8100
gaacgtggcg agaaaggaag ggaagaaagc gaaaggagcg ggcgctaggg cgctggcaag 8160
tgtagcggtc acgctgcgcg taaccaccac acccgccgcg cttaatgcgc cgctacaggg 8220
cgcgtactat ggttgctttg acgtatgcgg tgtgaaatac cgcacagatg cgtaaggaga 8280
aaataccgca tcaggcgcca ttcgccattc aggctgcgca actgttggga agggcgatcg 8340
gtgcgggcct cttcgctatt acgccagctg gcgaaagggg gatgtgctgc aaggcgatta 8400
agttgggtaa cgccagggtt ttcccagtca cgacgttgta aaacgacggc cagtgaattc 8460
catggtctca actttc 8476

<210> SEQ ID NO 58
<211> LENGTH: 30
<212> TYPE: PRT
<213> ORGANISM: Artificial Sequence
<220> FEATURE:
<223> OTHER INFORMATION: Synthetic malaria antigen with linker

<400> SEQUENCE: 58

-continued

```
Ser Gly Gly Gln Gly Pro Gly Ala Pro Gln Gly Pro Gly Ala Pro Gln
1               5                   10                  15

Gly Pro Gly Ala Pro Gln Gly Pro Gly Ala Pro Gly Gly Ser
            20                  25                  30


<210> SEQ ID NO 59
<211> LENGTH: 8497
<212> TYPE: DNA
<213> ORGANISM: Artificial Sequence
<220> FEATURE:
<223> OTHER INFORMATION: Synthetic Expression vector for VEEV viral
      structural protein containing an antigen "261" in E3 (261.66)

<400> SEQUENCE: 59

gaattcccat tgcatacgtt gtatccatat cataatatgt acatttatat tggctcatgt     60

ccaacattac cgccatgttg acattgatta ttgactagtt attaatagta atcaattacg    120

gggtcattag ttcatagccc atatatggag ttccgcgtta cataacttac ggtaaatggc    180

ccgcctggct gaccgcccaa cgacccccgc ccattgacgt caataatgac gtatgttccc    240

atagtaacgc caatagggac tttccattga cgtcaatggg tggagtattt acggtaaact    300

gcccacttgg cagtacatca agtgtatcat atgccaagta cgccccctat tgacgtcaat    360

gacggtaaat ggcccgcctg gcattatgcc cagtacatga ccttatggga ctttcctact    420

tggcagtaca tctacgtatt agtcatcgct attaccatgg tgatgcggtt ttggcagtac    480

atcaatgggc gtggatagcg gtttgactca cggggatttc caagtctcca ccccattgac    540

gtcaatggga gtttgttttg gcaccaaaat caacgggact ttccaaaatg tcgtaacaac    600

tccgccccat tgacgcaaat gggcggtagg cgtgtacggt gggaggtcta tataagcaga    660

gctcgtttag tgaaccgtca gatcgcctgg agacgccatc cacgctgttt tgacctccat    720

agaagacacc gggaccgatc cagcctccgt taacggtgga gggcagtgta gtctgagcag    780

tactcgttgc tgccgcgcgc gccaccagac ataatagctg acagactaac agactgttcc    840

tttccatggg tcttttctgc agtcaccgtc gtcgacacgt gtgatcagat atcgcggccg    900

ccaccatgtt cccgttccag ccaatgtatc cgatgcagcc aatgccctat cgcaacccgt    960

tcgcggcccc gcgcaggccc tggttcccca gaaccgaccc ttttctggcg atgcaggtgc   1020

aggaattaac ccgctcgatg gctaacctga cgttcaagca acgccgggac gcgccacctg   1080

aggggccatc cgctaataaa ccgaagaagg aggcctcgca aaaacagaaa gggggaggcc   1140

aagggaagaa gaagaagaac caagggaaga agaaggctaa gacagggccg cctaatccga   1200

aggcacagaa tggaaacaag aagaagacca acaagaaacc aggcaagaga cagcgcatgg   1260

tcatgaaatt ggaatctgac aagacgttcc caatcatgtt ggaagggaag ataaacggct   1320

acgcttgtgt ggtcggaggg aagttattca ggccgatgca tgtggaaggc aagatcgaca   1380

acgacgttct ggccgcgctt aagacgaaga aagcatccaa atacgatctt gagtatgcag   1440

atgtgccaca gaacatgcgg gccgatacat tcaaatacac ccatgagaaa ccccaaggct   1500

attacagctg gcatcatgga gcagtccaat atgaaaatgg gcgtttcacg gtgccgaaag   1560

gagttggggc caagggagac agcggacgac ccattctgga taaccaggga cgggtggtcg   1620

ctattgtgct gggaggtgtg aatgaaggat ctaggacagc cctttcagtc gtcatgtgga   1680

acgagaaggg agttaccgtg aagtatactc cagagaactg cgagcaatgg tcactagtga   1740

ccaccatgtg tctgctcgcc aatgtgacgt tcccatgtgc tcaaccacca atttgctacg   1800

acagaaaacc agcagagact ttggccatgc tcagcgttaa cgttgacaac ccgggctacg   1860
```

atgagctgct ggaagcagct gttaagtgcc ccgggtccgg aggacaggga cctggcgctc 1920
ctcagggacc aggggcacca cagggcccag gcgccccaca ggggcctggg gcccctgggg 1980
gatcctccac cgaggagctg tttaatgagt ataagctaac gcgcccttac atggccagat 2040
gcatcagatg tgcagttggg agctgccata gtccaatagc aatcgaggca gtaaagagcg 2100
acgggcacga cggttatgtt agacttcaga cttcctcgca gtatggcctg gattcctccg 2160
gcaacttaaa gggcaggacc atgcggtatg acatgcacgg gaccattaaa gagataccac 2220
tacatcaagt gtcactctat acatctcgcc cgtgtcacat tgtggatggg cacggttatt 2280
tcctgcttgc caggtgcccg gcaggggact ccatcaccat ggaatttaag aaagattccg 2340
tcagacactc ctgctcggtg ccgtatgaag tgaaatttaa tcctgtaggc agagaactct 2400
atactcatcc cccagaacac ggagtagagc aagcgtgcca agtctacgca catgatgcac 2460
agaacagagg agcttatgtc gagatgcacc tcccgggctc agaagtggac agcagtttgg 2520
tttccttgag cggcagttca gtcaccgtga cacctcctga tgggactagc gccctggtgg 2580
aatgcgagtg tggcggcaca aagatctccg agaccatcaa caagacaaaa cagttcagcc 2640
agtgcacaaa gaaggagcag tgcagagcat atcggctgca gaacgataag tgggtgtata 2700
attctgacaa actgcccaaa gcagcgggag ccaccttaaa aggaaaactg catgtcccat 2760
tcttgctggc agacggcaaa tgcaccgtgc ctctagcacc agaacctatg ataaccttcg 2820
gtttcagatc agtgtcactg aaactgcacc ctaagaatcc cacatatcta atcacccgcc 2880
aacttgctga tgagcctcac tacacgcacg agctcatatc tgaaccagct gttaggaatt 2940
ttaccgtcac cgaaaaaggg tgggagtttg tatggggaaa ccacccgccg aaaaggtttt 3000
gggcacagga aacagcaccc ggaaatccac atgggctacc gcacgaggtg ataactcatt 3060
attaccacag ataccctatg tccaccatcc tgggtttgtc aatttgtgcc gccattgcaa 3120
ccgtttccgt tgcagcgtct acctggctgt tttgcagatc aagagttgcg tgcctaactc 3180
cttaccggct aacacctaac gctaggatac cattttgtct ggctgtgctt tgctgcgccc 3240
gcactgcccg ggccgagacc acctgggagt ccttggatca cctatggaac aataaccaac 3300
agatgttctg gattcaattg ctgatccctc tggccgcctt gatcgtagtg actcgcctgc 3360
tcaggtgcgt gtgctgtgtc gtgccttttt tagtcatggc cggcgccgca ggcgccggcg 3420
cctacgagca cgcgaccacg atgccgagcc aagcgggaat ctcgtataac actatagtca 3480
acagagcagg ctacgcacca ctccctatca gcataacacc aacaaagatc aagctgatac 3540
ctacagtgaa cttggagtac gtcacctgcc actacaaaac aggaatggat tcaccagcca 3600
tcaaatgctg cggatctcag gaatgcactc caacttacag gcctgatgaa cagtgcaaag 3660
tcttcacagg ggtttacccg ttcatgtggg gtggtgcata ttgcttttgc gacactgaga 3720
acacccaagt cagcaaggcc tacgtaatga aatctgacga ctgccttgcg gatcatgctg 3780
aagcatataa agcgcacaca gcctcagtgc aggcgttcct caacatcaca gtgggagaac 3840
actctattgt gactaccgtg tatgtgaatg gagaaactcc tgtgaatttc aatggggtca 3900
aaataactgc aggtccgctt tccacagctt ggacaccctt tgatcgcaaa atcgtgcagt 3960
atgccgggga gatctataat tatgattttc ctgagtatgg ggcaggacaa ccaggagcat 4020
ttggagatat acaatccaga acagtctcaa gctctgatct gtatgccaat accaacctag 4080
tgctgcagag acccaaagca ggagcgatcc acgtgccata cactcaggca ccttcgggtt 4140
ttgagcaatg gaagaaagat aaagctccat cattgaaatt taccgcccct ttcggatgcg 4200
aaatatatac aaaccccatt cgcgccgaaa actgtgctgt agggtcaatt ccattagcct 4260

-continued

```
ttgacattcc cgacgccttg ttcaccaggg tgtcagaaac accgacactt tcagcggccg   4320
aatgcactct taacgagtgc gtgtattctt ccgactttgg tgggatcgcc acggtcaagt   4380
actcggccag caagtcaggc aagtgcgcag tccatgtgcc atcagggact gctaccctaa   4440
aagaagcagc agtcgagcta accgagcaag ggtcggcgac tatccatttc tcgaccgcaa   4500
atatccaccc ggagttcagg ctccaaatat gcacatcata tgttacgtgc aaaggtgatt   4560
gtcacccccc gaaagaccat attgtgacac accctcagta tcacgcccaa acatttacag   4620
ccgcggtgtc aaaaaccgcg tggacgtggt taacatccct gctgggagga tcagccgtaa   4680
ttattataat tggcttggtg ctggctacta ttgtggccat gtacgtgctg accaaccaga   4740
aacataatta aggatctaga tctgctgtgc cttctagttg ccagccatct gttgtttgcc   4800
cctcccccgt gccttccttg accctggaag gtgccactcc cactgtcctt tcctaataaa   4860
atgaggaaat tgcatcgcat tgtctgagta ggtgtcattc tattctgggg ggtggggtgg   4920
ggcaggacag caagggggag gattgggaag acaatagcag gcatgctggg gatgcggtgg   4980
gctctatggg tacccaggtg ctgaagaatt gacccggttc ctcctgggcc agaaagaagc   5040
aggcacatcc ccttctctgt gacacaccct gtccacgccc ctggttctta gttccagccc   5100
cactcatagg acactcatag ctcaggaggg ctccgccttc aatcccaccc gctaaagtac   5160
ttggagcggt ctctccctcc ctcatcagcc caccaaacca aacctagcct ccaagagtgg   5220
gaagaaatta aagcaagata ggctattaag tgcagaggga gagaaaatgc ctccaacatg   5280
tgaggaagta atgagagaaa tcatagaatt ttaaggccat gatttaaggc catcatggcc   5340
taagcttgaa aggagatagg atcaaagctt ggcgtaatca tggtcatagc tgtttcctgt   5400
gtgaaattgt tatccgctca caattccaca caacatacga gccggaagca taaagtgtaa   5460
agcctggggt gcctaatgag tgagctaact cacattaatt gcgttgcgct cactgcccgc   5520
tttccagtcg ggaaacctgt cgtgccagct gcattaatga atcggccaac gcgcggggag   5580
aggcggtttg cgtattgggc gctcttccgc ttcctcgctc actgactcgc tgcgctcggt   5640
cgttcggctg cggcgagcgg tatcagctca ctcaaaggcg gtaatacggt tatccacaga   5700
atcaggggat aacgcaggaa agaacatgtg agcaaaaggc cagcaaaagg ccaggaaccg   5760
taaaaaggcc gcgttgctgg cgtttttcca taggctccgc ccccctgacg agcatcacaa   5820
aaatcgacgc tcaagtcaga ggtggcgaaa cccgacagga ctataaagat accaggcgtt   5880
tccccctgga agctccctcg tgcgctctcc tgttccgacc ctgccgctta ccggatacct   5940
gtccgccttt ctcccttcgg gaagcgtggc gctttctcat agctcacgct gtaggtatct   6000
cagttcggtg taggtcgttc gctccaagct gggctgtgtg cacgaacccc ccgttcagcc   6060
cgaccgctgc gccttatccg gtaactatcg tcttgagtcc aacccggtaa gacacgactt   6120
atcgccactg gcagcagcca ctggtaacag gattagcaga gcgaggtatg taggcggtgc   6180
tacagagttc ttgaagtggt ggcctaacta cggctacact agaagaacag tatttggtat   6240
ctgcgctctg ctgaagccag ttaccttcgg aaaaagagtt ggtagctctt gatccggcaa   6300
acaaaccacc gctggtagcg gtggtttttt tgtttgcaag cagcagatta cgcgcagaaa   6360
aaaaggatct caagaagatc ctttgatctt ttctacgggg tctgacgctc agtggaacga   6420
aaactcacgt taagggattt tggtcatgag attatcaaaa aggatcttca cctagatcct   6480
tttaaattaa aaatgaagtt ttaaatcaat ctaaagtata tatgagtaaa cttggtctga   6540
cagttaccaa tgcttaatca gtgaggcacc tatctcagcg atctgtctat ttcgttcatc   6600
```

-continued

```
catagttgcc tgactccccg tcgtgtagat aactacgata cgggagggct taccatctgg   6660

ccccagtgct gcaatgatac cgcgagaacc acgctcaccg gctccagatt tatcagcaat   6720

aaaccagcca gccggaaggg ccgagcgcag aagtggtcct gcaactttat ccgcctccat   6780

ccagtctatt aattgttgcc gggaagctag agtaagtagt tcgccagtta atagtttgcg   6840

caacgttgtt gccattgcta caggcatcgt ggtgtcacgc tcgtcgtttg gtatggcttc   6900

attcagctcc ggttcccaac gatcaaggcg agttacatga tcccccatgt tgtgcaaaaa   6960

agcggttagc tccttcggtc ctccgatcgt tgtcagaagt aagttggccg cagtgttatc   7020

actcatggtt atggcagcac tgcataattc tcttactgtc atgccatccg taagatgctt   7080

ttctgtgact ggtgagtact caaccaagtc attctgagaa tagtgtatgc ggcgaccgag   7140

ttgctcttgc ccggcgtcaa tacgggataa taccgcgcca catagcagaa ctttaaaagt   7200

gctcatcatt ggaaaacgtt cttcggggcg aaaactctca aggatcttac cgctgttgag   7260

atccagttcg atgtaaccca ctcgtgcacc caactgatct tcagcatctt ttactttcac   7320

cagcgtttct gggtgagcaa aaacaggaag gcaaaatgcc gcaaaaaagg gaataagggc   7380

gacacggaaa tgttgaatac tcatactctt cctttttcaa tattattgaa gcatttatca   7440

gggttattgt ctcatgagcg gatacatatt tgaatgtatt tagaaaaata aacaaatagg   7500

ggttccgcgc acatttcccc gaaaagtgcc acctgacgtc taagaaacca ttattatcat   7560

gacattaacc tataaaaata ggcgtatcac gaggcccttt cgggtcgcgc gtttcggtga   7620

tgacggtgaa aacctctgac acatgcagct cccgttgacg gtcacagctt gtctgtaagc   7680

ggatgccggg agcagacaag cccgtcaggg cgcgtcagcg ggtgttggcg ggtgtcgggg   7740

ctggcttaac tatgcggcat cagagcagat tgtactgaga gtgcaccata aaattgtaaa   7800

cgttaatatt ttgttaaaat tcgcgttaaa tttttgttaa atcagctcat tttttaacca   7860

ataggccgaa atcggcaaaa tcccttataa atcaaaagaa tagcccgaga tagggttgag   7920

tgttgttcca gtttggaaca agagtccact attaaagaac gtggactcca acgtcaaagg   7980

gcgaaaaacc gtctatcagg gcgatggccc actacgtgaa ccatcaccca aatcaagttt   8040

tttggggtcg aggtgccgta aagcactaaa tcggaaccct aaagggagcc cccgatttag   8100

agcttgacgg ggaaagccgg cgaacgtggc gagaaaggaa gggaagaaag cgaaaggagc   8160

gggcgctagg gcgctggcaa gtgtagcggt cacgctgcgc gtaaccacca cacccgccgc   8220

gcttaatgcg ccgctacagg gcgcgtacta tggttgcttt gacgtatgcg gtgtgaaata   8280

ccgcacagat gcgtaaggag aaaataccgc atcaggcgcc attcgccatt caggctgcgc   8340

aactgttggg aagggcgatc ggtgcgggcc tcttcgctat tacgccagct ggcgaaaggg   8400

ggatgtgctg caaggcgatt aagttgggta acgccagggt tttcccagtc acgacgttgt   8460

aaaacgacgg ccagtgaatt ccatggtctc aactttc                            8497
```

<210> SEQ ID NO 60
<211> LENGTH: 90
<212> TYPE: DNA
<213> ORGANISM: Artificial Sequence
<220> FEATURE:
<223> OTHER INFORMATION: Synthetic CSP repeat antigen “74” (6 repeat of NPNA) with linker

<400> SEQUENCE: 60

```
tccggaggaa acccgaatgc caatcccaac gcgaacccca atgctaaccc aaatgccaac     60

ccaaacgcca accccaacgc tggtggatcc                                      90
```

<210> SEQ ID NO 61
<211> LENGTH: 62
<212> TYPE: PRT
<213> ORGANISM: Artificial Sequence
<220> FEATURE:
<223> OTHER INFORMATION: Synthetic CSP repeat antigen “76” (14 repeat of NPNA) with linker

<400> SEQUENCE: 61

```
Ser Gly Gly Asn Pro Asn Ala Asn Pro Asn Ala Asn Pro Asn Ala Asn
1               5                   10                  15

Pro Asn Ala Asn Pro Asn Ala Asn Pro Asn Ala Asn Pro Asn Ala Asn
            20                  25                  30

Pro Asn Ala Asn Pro Asn Ala Asn Pro Asn Ala Asn Pro Asn Ala Asn
        35                  40                  45

Pro Asn Ala Asn Pro Asn Ala Asn Pro Asn Ala Gly Gly Ser
    50                  55                  60
```

<210> SEQ ID NO 62
<211> LENGTH: 186
<212> TYPE: DNA
<213> ORGANISM: Artificial Sequence
<220> FEATURE:
<223> OTHER INFORMATION: Synthetic CSP repeat antigen “76” (14 repeat of NPNA) with linker

<400> SEQUENCE: 62

```
tccggaggca accccaacgc caaccctaat gccaatccca acgctaatcc caatgctaac      60

cctaacgcaa atccaaatgc aaaccccaat gccaacccaa acgctaaccc taacgccaac     120

cctaacgcaa acccaaacgc caatcctaat gctaacccaa atgcaaaccc taatgctggc     180

ggatcc                                                                186
```

<210> SEQ ID NO 63
<211> LENGTH: 106
<212> TYPE: PRT
<213> ORGANISM: Artificial Sequence
<220> FEATURE:
<223> OTHER INFORMATION: Synthetic CSP repeat antigen “78” (25 repeat of NPNA) with linker

<400> SEQUENCE: 63

```
Ser Gly Gly Asn Pro Asn Ala Asn Pro Asn Ala Asn Pro Asn Ala Asn
1               5                   10                  15

Pro Asn Ala Asn Pro Asn Ala Asn Pro Asn Val Asp Pro Asn Ala Asn
            20                  25                  30

Pro Asn Ala Asn Pro Asn Ala Asn Pro Asn Ala Asn Pro Asn Ala Asn
        35                  40                  45

Pro Asn Ala Asn Pro Asn Ala Asn Pro Asn Ala Asn Pro Asn Ala Asn
    50                  55                  60

Pro Asn Ala Asn Pro Asn Ala Asn Pro Asn Ala Asn Pro Asn Ala Asn
65                  70                  75                  80

Pro Asn Ala Asn Pro Asn Ala Asn Pro Asn Ala Asn Pro Asn Ala Asn
                85                  90                  95

Pro Asn Ala Asn Pro Asn Ala Gly Gly Ser
            100                 105
```

<210> SEQ ID NO 64
<211> LENGTH: 318
<212> TYPE: DNA
<213> ORGANISM: Artificial Sequence
<220> FEATURE:
<223> OTHER INFORMATION: Synthetic CSP repeat antigen "78" (25 repeat of NPNA) with linker

<400> SEQUENCE: 64
tccggaggaa acccgaatgc caatcccaac gcgaacccca acgctaaccc caacgccaat 60
ccgaatgcaa acccgaacgt tgacccaaac gccaacccga atgccaatcc caacgcgaac 120
cccaatgcta acccaaatgc caacccaaac gccaacccca acgctaatcc aaacgccaac 180
cctaacgcca atcccaacgc gaatcctaac gctaatccca acgcaaatcc caatgctaat 240
ccgaacgcga accctaatgc aaaccccaac gccaacccga acgctaaccc gaacgctaat 300
cccaacgccg gtggatcc 318

<210> SEQ ID NO 65
<211> LENGTH: 90
<212> TYPE: DNA
<213> ORGANISM: Artificial Sequence
<220> FEATURE:
<223> OTHER INFORMATION: Synthetic CSP repeat antigen "261" (repeat of qgpgap)

<400> SEQUENCE: 65
tccggaggac agggacctgg cgctcctcag ggaccagggg caccacaggg cccaggcgcc 60
ccacaggggc ctggggcccc tgggggatcc 90

<210> SEQ ID NO 66
<211> LENGTH: 19
<212> TYPE: PRT
<213> ORGANISM: Artificial Sequence
<220> FEATURE:
<223> OTHER INFORMATION: 302R (Synthetic antigen derived from pfs25 with liner)

<400> SEQUENCE: 66

Ser Gly Gly Cys Ile Lys Ile Asp Gly Asn Pro Val Ser Tyr Ala Cys
1               5                   10                  15

Gly Gly Ser

<210> SEQ ID NO 67
<211> LENGTH: 57
<212> TYPE: DNA
<213> ORGANISM: Artificial Sequence
<220> FEATURE:
<223> OTHER INFORMATION: 302R (Synthetic antigen derived from pfs25 with linker)

<400> SEQUENCE: 67
tccggagggt gcatcaagat cgacggcaac cccgtgtcct acgcctgcgg gggatcc 57

<210> SEQ ID NO 68
<211> LENGTH: 20
<212> TYPE: PRT
<213> ORGANISM: Artificial Sequence
<220> FEATURE:
<223> OTHER INFORMATION: 303R (Synthetic antigen derived from pfs25 with linker)

<400> SEQUENCE: 68

Ser Gly Gly Cys Ile Leu Asp Thr Ser Asn Pro Val Lys Thr Gly Val
1               5                   10                  15

Cys Gly Gly Ser
            20

<210> SEQ ID NO 69
<211> LENGTH: 60
<212> TYPE: DNA
<213> ORGANISM: Artificial Sequence
<220> FEATURE:
<223> OTHER INFORMATION: 303R (Synthetic antigen derived from pfs25 with
      linker)

<400> SEQUENCE: 69
tccggaggct gcatcctgga caccagcaac cccgtgaaaa ccggcgtgtg tggcggatcc     60

<210> SEQ ID NO 70
<211> LENGTH: 48
<212> TYPE: DNA
<213> ORGANISM: Artificial Sequence
<220> FEATURE:
<223> OTHER INFORMATION: 299 (Synthetic mousePD-L1 antigen with linker)

<400> SEQUENCE: 70
tccggaggat gcatcatcag ctacggcgga gccgactacg gaggatcc     48

<210> SEQ ID NO 71
<211> LENGTH: 17
<212> TYPE: PRT
<213> ORGANISM: Artificial Sequence
<220> FEATURE:
<223> OTHER INFORMATION: 299 (Synthetic mousePD-L1 antigen with linker)

<400> SEQUENCE: 71

Ser Gly Gly Cys Ile Ile Ser Tyr Gly Gly Ala Asp Tyr Cys Gly Gly
1               5                   10                  15

Ser

<210> SEQ ID NO 72
<211> LENGTH: 60
<212> TYPE: DNA
<213> ORGANISM: Artificial Sequence
<220> FEATURE:
<223> OTHER INFORMATION: 274 (Synthetic mousePD-1 antigen with linker)

<400> SEQUENCE: 72
tccggaggag gcgccatcag cctgcacccc aaggccaaga tcgaggaatc tggaggatcc     60

<210> SEQ ID NO 73
<211> LENGTH: 19
<212> TYPE: PRT
<213> ORGANISM: Artificial Sequence
<220> FEATURE:
<223> OTHER INFORMATION: 274 (Synthetic mousePD-1 antigen with linker)

<400> SEQUENCE: 73

Ser Gly Gly Gly Ala Ile Ser Leu His Pro Lys Ala Lys Ile Glu Glu
1               5                   10                  15

Ser Gly Ser

<210> SEQ ID NO 74
<211> LENGTH: 24
<212> TYPE: PRT
<213> ORGANISM: Artificial Sequence
<220> FEATURE:
<223> OTHER INFORMATION: Synthetic mCTLA-4 _ver2 antigen with linker

<400> SEQUENCE: 74

Ser Gly Gly Gly Gly Lys Val Glu Leu Met Tyr Pro Pro Pro Tyr Phe
1               5                   10                  15

Val Gly Met Gly Gly Gly Gly Ser
20

<210> SEQ ID NO 75
<211> LENGTH: 261
<212> TYPE: PRT
<213> ORGANISM: Artificial Sequence
<220> FEATURE:
<223> OTHER INFORMATION: Synthetic CHIKV Capsid (OPY-1 strain)

<400> SEQUENCE: 75

Met Glu Phe Ile Pro Thr Gln Thr Phe Tyr Asn Arg Arg Tyr Gln Pro
1 5 10 15

Arg Pro Trp Thr Pro Arg Pro Thr Ile Gln Val Ile Arg Pro Arg Pro
20 25 30

Arg Pro Gln Arg Gln Ala Gly Gln Leu Ala Gln Leu Ile Ser Ala Val
35 40 45

Asn Lys Leu Thr Met Arg Ala Val Pro Gln Gln Lys Pro Arg Arg Asn
50 55 60

Arg Lys Asn Lys Lys Gln Lys Gln Lys Gln Gln Ala Pro Gln Asn Asn
65 70 75 80

Thr Asn Gln Lys Lys Gln Pro Pro Lys Lys Lys Pro Ala Gln Lys Lys
85 90 95

Lys Lys Pro Gly Arg Arg Glu Arg Met Cys Met Lys Ile Glu Asn Asp
100 105 110

Cys Ile Phe Glu Val Lys His Glu Gly Lys Val Thr Gly Tyr Ala Cys
115 120 125

Leu Val Gly Asp Lys Val Met Lys Pro Ala His Val Lys Gly Thr Ile
130 135 140

Asp Asn Ala Asp Leu Ala Lys Leu Ala Phe Lys Arg Ser Ser Lys Tyr
145 150 155 160

Asp Leu Glu Cys Ala Gln Ile Pro Val His Met Lys Ser Asp Ala Ser
165 170 175

Lys Phe Thr His Glu Lys Pro Glu Gly Tyr Tyr Asn Trp His His Gly
180 185 190

Ala Val Gln Tyr Ser Gly Gly Arg Phe Thr Ile Pro Thr Gly Ala Gly
195 200 205

Lys Pro Gly Asp Ser Gly Arg Pro Ile Phe Asp Asn Lys Gly Arg Val
210 215 220

Val Ala Ile Val Leu Gly Gly Ala Asn Glu Gly Ala Arg Thr Ala Leu
225 230 235 240

Ser Val Val Thr Trp Asn Lys Asp Ile Val Thr Lys Ile Thr Pro Glu
245 250 255

Gly Ala Glu Glu Trp
260

<210> SEQ ID NO 76
<211> LENGTH: 439
<212> TYPE: PRT
<213> ORGANISM: Artificial Sequence
<220> FEATURE:
<223> OTHER INFORMATION: Synthetic CHIKV E1 (OPY-1 strain)

<400> SEQUENCE: 76

Tyr Glu His Val Thr Val Ile Pro Asn Thr Val Gly Val Pro Tyr Lys
1 5 10 15

Thr Leu Val Asn Arg Pro Gly Tyr Ser Pro Met Val Leu Glu Met Glu

```
            20                  25                  30

Leu Leu Ser Val Thr Leu Glu Pro Thr Leu Ser Leu Asp Tyr Ile Thr
        35                  40                  45

Cys Glu Tyr Lys Thr Val Ile Pro Ser Pro Tyr Val Lys Cys Cys Gly
    50                  55                  60

Thr Ala Glu Cys Lys Asp Lys Asn Leu Pro Asp Tyr Ser Cys Lys Val
65                  70                  75                  80

Phe Thr Gly Val Tyr Pro Phe Met Trp Gly Gly Ala Tyr Cys Phe Cys
                85                  90                  95

Asp Ala Glu Asn Thr Gln Leu Ser Glu Ala His Val Glu Lys Ser Glu
            100                 105                 110

Ser Cys Lys Thr Glu Phe Ala Ser Ala Tyr Arg Ala His Thr Ala Ser
        115                 120                 125

Ala Ser Ala Lys Leu Arg Val Leu Tyr Gln Gly Asn Asn Ile Thr Val
    130                 135                 140

Thr Ala Tyr Ala Asn Gly Asp His Ala Val Thr Val Lys Asp Ala Lys
145                 150                 155                 160

Phe Ile Val Gly Pro Met Ser Ser Ala Trp Thr Pro Phe Asp Asn Lys
                165                 170                 175

Ile Val Val Tyr Lys Gly Asp Val Tyr Asn Met Asp Tyr Pro Pro Phe
            180                 185                 190

Gly Ala Gly Arg Pro Gly Gln Phe Gly Asp Ile Gln Ser Arg Thr Pro
        195                 200                 205

Glu Ser Lys Asp Val Tyr Ala Asn Thr Gln Leu Val Leu Gln Arg Pro
    210                 215                 220

Ala Val Gly Thr Val His Val Pro Tyr Ser Gln Ala Pro Ser Gly Phe
225                 230                 235                 240

Lys Tyr Trp Leu Lys Glu Arg Gly Ala Ser Leu Gln His Thr Ala Pro
                245                 250                 255

Phe Gly Cys Gln Ile Ala Thr Asn Pro Val Arg Ala Val Asn Cys Ala
            260                 265                 270

Val Gly Asn Met Pro Ile Ser Ile Asp Ile Pro Glu Ala Ala Phe Thr
        275                 280                 285

Arg Val Val Asp Ala Pro Ser Leu Thr Asp Met Ser Cys Glu Val Pro
    290                 295                 300

Ala Cys Thr His Ser Ser Asp Phe Gly Gly Val Ala Ile Ile Lys Tyr
305                 310                 315                 320

Ala Ala Ser Lys Lys Gly Lys Cys Ala Val His Ser Met Thr Asn Ala
                325                 330                 335

Val Thr Ile Arg Glu Ala Glu Ile Glu Val Glu Gly Asn Ser Gln Leu
            340                 345                 350

Gln Ile Ser Phe Ser Thr Ala Leu Ala Ser Ala Glu Phe Arg Val Gln
        355                 360                 365

Val Cys Ser Thr Gln Val His Cys Ala Ala Glu Cys His Pro Pro Lys
    370                 375                 380

Asp His Ile Val Asn Tyr Pro Ala Ser His Thr Thr Leu Gly Val Gln
385                 390                 395                 400

Asp Ile Ser Ala Thr Ala Met Ser Trp Val Gln Lys Ile Thr Gly Gly
                405                 410                 415

Val Gly Leu Val Val Ala Val Ala Ala Leu Ile Leu Ile Val Val Leu
            420                 425                 430

Cys Val Ser Phe Ser Arg His
        435
```

<210> SEQ ID NO 77
<211> LENGTH: 483
<212> TYPE: PRT
<213> ORGANISM: Artificial Sequence
<220> FEATURE:
<223> OTHER INFORMATION: Synthetic CHIKV E3-insert-E2 (OPY-1 strain)
<220> FEATURE:
<221> NAME/KEY: NON_CONS
<222> LOCATION: (60)..(61)
<223> OTHER INFORMATION: antigen will be inserted

<400> SEQUENCE: 77

Ser Leu Ala Ile Pro Val Met Cys Leu Leu Ala Asn Thr Thr Phe Pro
1 5 10 15

Cys Ser Gln Pro Pro Cys Thr Pro Cys Cys Tyr Glu Lys Glu Pro Glu
20 25 30

Glu Thr Leu Arg Met Leu Glu Asp Asn Val Met Arg Pro Gly Tyr Tyr
35 40 45

Gln Leu Leu Gln Ala Ser Leu Thr Cys Ser Pro His Ser Thr Lys Asp
50 55 60

Asn Phe Asn Val Tyr Lys Ala Thr Arg Pro Tyr Leu Ala His Cys Pro
65 70 75 80

Asp Cys Gly Glu Gly His Ser Cys His Ser Pro Val Ala Leu Glu Arg
85 90 95

Ile Arg Asn Glu Ala Thr Asp Gly Thr Leu Lys Ile Gln Val Ser Leu
100 105 110

Gln Ile Gly Ile Lys Thr Asp Asp Ser His Asp Trp Thr Lys Leu Arg
115 120 125

Tyr Met Asp Asn His Met Pro Ala Asp Ala Glu Arg Ala Gly Leu Phe
130 135 140

Val Arg Thr Ser Ala Pro Cys Thr Ile Thr Gly Thr Met Gly His Phe
145 150 155 160

Ile Leu Ala Arg Cys Pro Lys Gly Glu Thr Leu Thr Val Gly Phe Thr
165 170 175

Asp Ser Arg Lys Ile Ser His Ser Cys Thr His Pro Phe His His Asp
180 185 190

Pro Pro Val Ile Gly Arg Glu Lys Phe His Ser Arg Pro Gln His Gly
195 200 205

Lys Glu Leu Pro Cys Ser Thr Tyr Val Gln Ser Thr Ala Ala Thr Thr
210 215 220

Glu Glu Ile Glu Val His Met Pro Pro Asp Thr Pro Asp Arg Thr Leu
225 230 235 240

Met Ser Gln Gln Ser Gly Asn Val Lys Ile Thr Val Asn Gly Gln Thr
245 250 255

Val Arg Tyr Lys Cys Asn Cys Gly Gly Ser Asn Glu Gly Leu Thr Thr
260 265 270

Thr Asp Lys Val Ile Asn Asn Cys Lys Val Asp Gln Cys His Ala Ala
275 280 285

Val Thr Asn His Lys Lys Trp Gln Tyr Asn Ser Pro Leu Val Pro Arg
290 295 300

Asn Ala Glu Leu Gly Asp Arg Lys Gly Lys Ile His Ile Pro Phe Pro
305 310 315 320

Leu Ala Asn Val Thr Cys Arg Val Pro Lys Ala Arg Asn Pro Thr Val
325 330 335

Thr Tyr Gly Lys Asn Gln Val Ile Met Leu Leu Tyr Pro Asp His Pro 340 345 350

Thr Leu Leu Ser Tyr Arg Asn Met Gly Glu Glu Pro Asn Tyr Gln Glu
355 360 365

Glu Trp Val Met His Lys Lys Glu Val Val Leu Thr Val Pro Thr Glu
370 375 380

Gly Leu Glu Val Thr Trp Gly Asn Asn Glu Pro Tyr Lys Tyr Trp Pro
385 390 395 400

Gln Leu Ser Thr Asn Gly Thr Ala His Gly His Pro His Glu Ile Ile
405 410 415

Leu Tyr Tyr Tyr Glu Leu Tyr Pro Thr Met Thr Val Val Val Val Ser
420 425 430

Val Ala Thr Phe Ile Leu Leu Ser Met Val Gly Met Ala Ala Gly Met
435 440 445

Cys Met Cys Ala Arg Arg Arg Cys Ile Thr Pro Tyr Glu Leu Thr Pro
450 455 460

Gly Ala Thr Val Pro Phe Leu Leu Ser Leu Ile Cys Cys Ile Arg Thr
465 470 475 480

Ala Lys Ala

<210> SEQ ID NO 78
<211> LENGTH: 72
<212> TYPE: DNA
<213> ORGANISM: Artificial Sequence
<220> FEATURE:
<223> OTHER INFORMATION: Synthetic mCTLA-4 _ver2 with linker

<400> SEQUENCE: 78
tccggaggcg gcggcaaggt ggaactcatg tacccaccgc catactttgt gggcatgggc 60
ggcggcggat cc 72

<210> SEQ ID NO 79
<211> LENGTH: 25
<212> TYPE: PRT
<213> ORGANISM: Artificial Sequence
<220> FEATURE:
<223> OTHER INFORMATION: Synthetic mCTLA-4 _ver4 with linker

<400> SEQUENCE: 79

Ser Gly Gly Cys Ala Thr Thr Phe Thr Glu Lys Asn Thr Val Gly Phe
1 5 10 15

Leu Asp Tyr Pro Phe Cys Gly Gly Ser
20 25

<210> SEQ ID NO 80
<211> LENGTH: 75
<212> TYPE: DNA
<213> ORGANISM: Artificial Sequence
<220> FEATURE:
<223> OTHER INFORMATION: Synthetic mCTLA-4 _ver4 with linker

<400> SEQUENCE: 80
tccggaggct gtgccacgac attcacagag aagaatacag tgggcttcct agattacccc 60
ttctgcggcg gatcc 75

<210> SEQ ID NO 81
<211> LENGTH: 23
<212> TYPE: PRT
<213> ORGANISM: Artificial Sequence
<220> FEATURE:
<223> OTHER INFORMATION: Synthetic mCTLA-4 _ver5 with linker

<400> SEQUENCE: 81

Ser Gly Gly Ala Thr Thr Phe Thr Glu Lys Asn Thr Val Gly Phe Leu
1 5 10 15

Asp Tyr Pro Phe Gly Gly Ser
20

<210> SEQ ID NO 82
<211> LENGTH: 69
<212> TYPE: DNA
<213> ORGANISM: Artificial Sequence
<220> FEATURE:
<223> OTHER INFORMATION: Synthetic mCTLA-4 _ver5 with linker

<400> SEQUENCE: 82
tccggaggcg ccacgacatt cacagagaag aatacagtgg gcttcctaga ttaccccttc 60
ggcggatcc 69

<210> SEQ ID NO 83
<211> LENGTH: 9257
<212> TYPE: DNA
<213> ORGANISM: Artificial Sequence
<220> FEATURE:
<223> OTHER INFORMATION: Synthetic Expression vector for CHIKV containing Mouse IL2(wt) antigen in E3

<400> SEQUENCE: 83
gaattcccat tgcatacgtt gtatccatat cataatatgt acatttatat tggctcatgt 60
ccaacattac cgccatgttg acattgatta ttgactagtt attaatagta atcaattacg 120
gggtcattag ttcatagccc atatatggag ttccgcgtta cataacttac ggtaaatggc 180
ccgcctggct gaccgcccaa cgacccccgc ccattgacgt caataatgac gtatgttccc 240
atagtaacgc caatagggac tttccattga cgtcaatggg tggagtattt acggtaaact 300
gcccacttgg cagtacatca agtgtatcat atgccaagta cgccccctat tgacgtcaat 360
gacggtaaat ggcccgcctg gcattatgcc cagtacatga ccttatggga ctttcctact 420
tggcagtaca tctacgtatt agtcatcgct attaccatgg tgatgcggtt ttggcagtac 480
atcaatgggc gtggatagcg gtttgactca cggggatttc caagtctcca ccccattgac 540
gtcaatggga gtttgttttg gcaccaaaat caacgggact ttccaaaatg tcgtaacaac 600
tccgccccat tgacgcaaat gggcggtagg cgtgtacggt gggaggtcta tataagcaga 660
gctcgtttag tgaaccgtca gatcgcctgg agacgccatc cacgctgttt tgacctccat 720
agaagacacc gggaccgatc cagcctccgt taacggtgga gggcagtgta gtctgagcag 780
tactcgttgc tgccgcgcgc gccaccagac ataatagctg acagactaac agactgttcc 840
tttgcggccg ctctagacac catggagttc atcccgacgc aaactttcta taacagaagg 900
taccaacccc gaccctgggc cccacgccct acaattcaag taattagacc tagaccacgt 960
ccacagaggc aggctgggca actcgcccag ctgatctccg cagtcaacaa attgaccatg 1020
cgcgcggtac ctcaacagaa gcctcgcaga aatcggaaaa acaagaagca aaggcagaag 1080
aagcaggcgc cgcaaaacga cccaaagcaa aagaagcaac caccacaaaa gaagccggct 1140
caaaagaaga agaaaccagg ccgtagggag agaatgtgca tgaaaattga aaatgattgc 1200
atcttcgaag tcaagcatga aggcaaagtg atgggctacg catgcctggt gggggataaa 1260
gtaatgaaac cagcacatgt gaagggaact atcgacaatg ccgatctggc taaactggcc 1320
tttaagcggt cgtctaaata cgatcttgaa tgtgcacaga taccggtgca catgaagtct 1380
gatgcctcga agtttaccca cgagaaaccc gaggggtact ataactggca tcacggagca 1440
gtgcagtatt caggaggccg gttcactatc ccgacgggtg caggcaagcc gggagacagc 1500
ggcagaccga tcttcgacaa caaaggacgg gtggtggcca tcgtcctagg aggggccaac 1560
gaaggtgccc gcacggccct ctccgtggtg acgtggaaca aagacatcgt cacaaaaatt 1620
acccctgagg gagccgaaga gtggagcctc gccctcccgg tcttgtgcct gttggcaaac 1680
actacattcc cctgctctca gccgccttgc acaccctgct gctacgaaaa ggaaccggaa 1740
agcaccttgc gcatgcttga ggacaacgtg atgagacccg gatactacca gctactaaaa 1800
gcatcgctga cttgctctcc ccactccgga ggggcaccca cttcaagctc cacttcaagc 1860
tctacagcgg aagcacagca gcagcagcag cagcagcagc agcagcagca cctggagcag 1920
ctgttgatgg acctacagga gctcctgagc aggatggaga attacaggaa cctgaaactc 1980
cccaggatgc tcaccttcaa attttacttg cccaagcagg ccacagaatt gaaagatctt 2040
cagtgcctag aagatgaact tggacctctg cggcatgttc tggatttgac tcaaagcaaa 2100
agctttcaat tggaagatgc tgagaatttc atcagcaata tcagagtaac tgttgtaaaa 2160
ctaaagggct ctgacaacac atttgagtgc caattcgatg atgagtcagc aactgtggtg 2220
gactttctga ggagatggat agccttctgt caaagcatca tctcaacaag ccctcaaggg 2280
ggatccagta ctaaggacaa ttttaatgtc tataaagcca caagaccata tctagctcat 2340
tgtcctgact gcggagaagg gcattcgtgc cacagcccta tcgcattgga gcgcatcaga 2400
aatgaagcaa cggacggaac gctgaaaatc caggtctctt tgcagatcgg gataaagaca 2460
gatgacagcc acgattggac caagctgcgc tatatggata gccatacgcc cgcggacgcg 2520
gagcgagccg gattgcttgt aaggacttca gcaccgtgca cgatcaccgg gaccatggga 2580
cactttattc tcgcccgatg cccgaaagga gagacgctga cagtgggatt tacggacagc 2640
agaaagatca gccacacatg cacacacccg ttccatcatg aaccacctgt gataggtagg 2700
gagaggttcc actctcgacc acaacatggt aaagagttac cttgcagcac gtacgtgcag 2760
agcaccgctg ccactgctga ggagatagag gtgcatatgc cccagatac tcctgaccgc 2820
acgctgatga cgcagcagtc tggcaacgtg aagatcacag ttaatgggca gacggtgcgg 2880
tacaagtgca actgcggtgg ctcaaacgag ggactgacaa ccacagacaa agtgatcaat 2940
aactgcaaaa ttgatcagtg ccatgctgca gtcactaatc acaagaattg gcaatacaac 3000
tcccctttag tcccgcgcaa cgctgaactc ggggaccgta aaggaaagat ccacatccca 3060
ttcccattgg caaacgtgac ttgcagagtg ccaaaagcaa gaaaccctac agtaacttac 3120
ggaaaaaacc aagtcaccat gctgctgtat cctgaccatc cgacactctt gtcttaccgt 3180
aacatgggac aggaaccaaa ttaccacgag gagtgggtga cacacaagaa ggaggttacc 3240
ttgaccgtgc ctactgaggg tctggaggtc acttggggca acaacgaacc atacaagtac 3300
tggccgcaga tgtctacgaa cggtactgct catggtcacc cacatgagat aatcttgtac 3360
tattatgagc tgtaccccac tatgactgta gtcattgtgt cggtggcctc gttcgtgctt 3420
ctgtcgatgg tgggcacagc agtgggaatg tgtgtgtgcg cacggcgcag atgcattaca 3480
ccatatgaat taacaccagg agccactgtt cccttcctgc tcagcctgct atgctgcgtc 3540
agaacgacca aggcggccac atattacgag gctgcggcat atctatggaa cgaacagcag 3600
cccctgttct ggttgcaggc tcttatcccg ctggccgcct tgatcgtcct gtgcaactgt 3660
ctgaaactct tgccatgctg ctgtaagacc ctggcttttt tagccgtaat gagcatcggt 3720

```
gcccacactg tgagcgcgta cgaacacgta acagtgatcc cgaacacggt gggagtaccg   3780
tataagactc ttgtcaacag accgggttac agccccatgg tgttggagat ggagctacaa   3840
tcagtcacct tggaaccaac actgtcactt gactacatca cgtgcgagta caaaactgtc   3900
atcccctccc cgtacgtgaa gtgctgtggt acagcagagt gcaaggacaa gagcctacca   3960
gactacagct gcaaggtctt tactggagtc tacccattta tgtggggcgg cgcctactgc   4020
ttttgcgacg ccgaaaatac gcaattgagc gaggcacatg tagagaaatc tgaatcttgc   4080
aaaacagagt ttgcatcggc ctacagagcc cacaccgcat cggcgtcggc gaagctccgc   4140
gtcctttacc aaggaaacaa cattaccgta gctgcctacg ctaacggtga ccatgccgtc   4200
acagtaaagg acgccaagtt tgtcgtgggc ccaatgtcct ccgcctggac accttttgac   4260
aacaaaatcg tggtgtacaa aggcgacgtc tacaacatgg actacccacc ttttggcgca   4320
ggaagaccag gacaatttgg tgacattcaa agtcgtacac cggaaagtaa agacgtttat   4380
gccaacactc agttggtact acagaggcca gcagcaggca cggtacatgt accatactct   4440
caggcaccat ctggcttcaa gtattggctg aaggaacgag gagcatcgct acagcacacg   4500
gcaccgttcg gttgccagat tgcgacaaac ccggtaagag ctgtaaattg cgctgtgggg   4560
aacataccaa tttccatcga cataccggat gcggccttta ctagggttgt cgatgcaccc   4620
tctgtaacgg acatgtcatg cgaagtacca gcctgcactc actcctccga ctttgggggc   4680
gtcgccatca tcaaatacac agctagcaag aaaggtaaat gtgcagtaca ttcgatgacc   4740
aacgccgtta ccattcgaga agccgacgta gaagtagagg ggaactccca gctgcaaata   4800
tccttctcaa cagccctggc aagcgccgag tttcgcgtgc aagtgtgctc cacacaagta   4860
cactgcgcag ccgcatgcca ccctccaaag gaccacatag tcaattaccc agcatcacac   4920
accacccttg ggtccaggat tatatccaca acggcaatgt cttgggtgca gaagattacg   4980
ggaggagtag gattaattgt tgctgttgct gccttaattt taattgtggt gctatgcgtg   5040
tcgtttagca ggcactaatg atccggaggg gcacccactt caagctccac ttcaagctct   5100
acagcggaag cacagcagca gcagcagcag cagcagcagc agcagcacct ggagcagctg   5160
ttgatggacc tacaggagct cctgagcagg atggagaatt acaggaacct gaaactcccc   5220
aggatgctca ccttcaaatt ttacttgccc aagcaggcca cagaattgaa agatcttcag   5280
tgcctagaag atgaacttgg acctctgcgg catgttctgg atttgactca aagcaaaagc   5340
tttcaattgg aagatgctga gaatttcatc agcaatatca gagtaactgt tgtaaaacta   5400
aagggctctg acaacacatt tgagtgccaa ttcgatgatg agtcagcaac tgtggtggac   5460
tttctgagga gatggatagc cttctgtcaa agcatcatct caacaagccc tcaaggggga   5520
tccgctgtgc cttctagttg ccagccatct gttgtttgcc cctcccccgt gccttccttg   5580
accctggaag gtgccactcc cactgtcctt tcctaataaa atgaggaaat tgcatcgcat   5640
tgtctgagta ggtgtcattc tattctgggg ggtggggtgg ggcaggacag caagggggag   5700
gattgggaag acaatagcag gcatgctggg gatgcggtgg gctctatggg tacccaggtg   5760
ctgaagaatt gacccggttc ctcctgggcc agaaagaagc aggcacatcc ccttctctgt   5820
gacacaccct gtccacgccc ctggttctta gttccagccc cactcatagg acactcatag   5880
ctcaggaggg ctccgccttc aatcccaccc gctaaagtac ttggagcggt ctctccctcc   5940
ctcatcagcc caccaaacca aacctagcct ccaagagtgg gaagaaatta aagcaagata   6000
ggctattaag tgcagaggga gagaaaatgc ctccaacatg tgaggaagta atgagagaaa   6060
tcatagaatt ttaaggccat gatttaaggc catcatggcc taagcttgaa aggagatagg   6120
```

atcaaagctt ggcgtaatca tggtcatagc tgtttcctgt gtgaaattgt tatccgctca 6180
caattccaca caacatacga gccggaagca taaagtgtaa agcctggggt gcctaatgag 6240
tgagctaact cacattaatt gcgttgcgct cactgcccgc tttccagtcg ggaaacctgt 6300
cgtgccagct gcattaatga atcggccaac gcgcggggag aggcggtttg cgtattgggc 6360
gctcttccgc ttcctcgctc actgactcgc tgcgctcggt cgttcggctg cggcgagcgg 6420
tatcagctca ctcaaaggcg gtaatacggt tatccacaga atcaggggat aacgcaggaa 6480
agaacatgtg agcaaaaggc cagcaaaagg ccaggaaccg taaaaaggcc gcgttgctgg 6540
cgtttttcca taggctccgc ccccctgacg agcatcacaa aaatcgacgc tcaagtcaga 6600
ggtggcgaaa cccgacagga ctataaagat accaggcgtt tccccctgga agctccctcg 6660
tgcgctctcc tgttccgacc ctgccgctta ccggatacct gtccgccttt ctcccttcgg 6720
gaagcgtggc gctttctcat agctcacgct gtaggtatct cagttcggtg taggtcgttc 6780
gctccaagct gggctgtgtg cacgaacccc ccgttcagcc cgaccgctgc gccttatccg 6840
gtaactatcg tcttgagtcc aacccggtaa gacacgactt atcgccactg gcagcagcca 6900
ctggtaacag gattagcaga gcgaggtatg taggcggtgc tacagagttc ttgaagtggt 6960
ggcctaacta cggctacact agaagaacag tatttggtat ctgcgctctg ctgaagccag 7020
ttaccttcgg aaaaagagtt ggtagctctt gatccggcaa acaaaccacc gctggtagcg 7080
gtggtttttt tgtttgcaag cagcagatta cgcgcagaaa aaaaggatct caagaagatc 7140
ctttgatctt ttctacgggg tctgacgctc agtggaacga aaactcacgt taagggattt 7200
tggtcatgag attatcaaaa aggatcttca cctagatcct tttaaattaa aaatgaagtt 7260
ttaaatcaat ctaaagtata tatgagtaaa cttggtctga cagttaccaa tgcttaatca 7320
gtgaggcacc tatctcagcg atctgtctat ttcgttcatc catagttgcc tgactccccg 7380
tcgtgtagat aactacgata cgggagggct taccatctgg ccccagtgct gcaatgatac 7440
cgcgagaacc acgctcaccg gctccagatt tatcagcaat aaaccagcca gccggaaggg 7500
ccgagcgcag aagtggtcct gcaactttat ccgcctccat ccagtctatt aattgttgcc 7560
gggaagctag agtaagtagt tcgccagtta atagtttgcg caacgttgtt gccattgcta 7620
caggcatcgt ggtgtcacgc tcgtcgtttg gtatggcttc attcagctcc ggttcccaac 7680
gatcaaggcg agttacatga tcccccatgt tgtgcaaaaa agcggttagc tccttcggtc 7740
ctccgatcgt tgtcagaagt aagttggccg cagtgttatc actcatggtt atggcagcac 7800
tgcataattc tcttactgtc atgccatccg taagatgctt ttctgtgact ggtgagtact 7860
caaccaagtc attctgagaa tagtgtatgc ggcgaccgag ttgctcttgc ccggcgtcaa 7920
tacgggataa taccgcgcca catagcagaa ctttaaaagt gctcatcatt ggaaaacgtt 7980
cttcggggcg aaaactctca aggatcttac cgctgttgag atccagttcg atgtaaccca 8040
ctcgtgcacc caactgatct tcagcatctt ttactttcac cagcgtttct gggtgagcaa 8100
aaacaggaag gcaaaatgcc gcaaaaaagg gaataagggc gacacggaaa tgttgaatac 8160
tcatactctt cctttttcaa tattattgaa gcatttatca gggttattgt ctcatgagcg 8220
gatacatatt tgaatgtatt tagaaaaata aacaaatagg ggttccgcgc acatttcccc 8280
gaaaagtgcc acctgacgtc taagaaacca ttattatcat gacattaacc tataaaaata 8340
ggcgtatcac gaggcccttt cgggtcgcgc gtttcggtga tgacggtgaa aacctctgac 8400
acatgcagct cccgttgacg gtcacagctt gtctgtaagc ggatgccggg agcagacaag 8460

```
cccgtcaggg cgcgtcagcg ggtgttggcg ggtgtcgggg ctggcttaac tatgcggcat   8520

cagagcagat tgtactgaga gtgcaccata aaattgtaaa cgttaatatt ttgttaaaat   8580

tcgcgttaaa tttttgttaa atcagctcat tttttaacca ataggccgaa atcggcaaaa   8640

tcccttataa atcaaaagaa tagcccgaga tagggttgag tgttgttcca gtttggaaca   8700

agagtccact attaaagaac gtggactcca acgtcaaagg gcgaaaaacc gtctatcagg   8760

gcgatggccc actacgtgaa ccatcaccca aatcaagttt tttggggtcg aggtgccgta   8820

aagcactaaa tcggaaccct aaagggagcc cccgatttag agcttgacgg ggaaagccgg   8880

cgaacgtggc gagaaaggaa gggaagaaag cgaaaggagc gggcgctagg gcgctggcaa   8940

gtgtagcggt cacgctgcgc gtaaccacca cacccgccgc gcttaatgcg ccgctacagg   9000

gcgcgtacta tggttgcttt gacgtatgcg gtgtgaaata ccgcacagat gcgtaaggag   9060

aaaataccgc atcaggcgcc attcgccatt caggctgcgc aactgttggg aagggcgatc   9120

ggtgcgggcc tcttcgctat tacgccagct ggcgaaaggg ggatgtgctg caaggcgatt   9180

aagttgggta acgccagggt tttcccagtc acgacgttgt aaaacgacgg ccagtgaatt   9240

ccatggtctc aactttc                                                  9257
```

<210> SEQ ID NO 84
<211> LENGTH: 1398
<212> TYPE: PRT
<213> ORGANISM: Artificial Sequence
<220> FEATURE:
<223> OTHER INFORMATION: Synthetic CHIKV containing Mouse IL2(wt) antigen in E3

<400> SEQUENCE: 84

```
Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Arg Gln Lys Lys Gln Ala Pro Gln Asn Asp
65                  70                  75                  80

Pro Lys Gln Lys Lys Gln Pro Pro Gln Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Met Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
```

```
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Leu Pro Val Leu Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Ser Thr Leu Arg Met Leu Glu Asp Asn Val Met
    290                 295                 300

Arg Pro Gly Tyr Tyr Gln Leu Leu Lys Ala Ser Leu Thr Cys Ser Pro
305                 310                 315                 320

His Ser Gly Gly Ala Pro Thr Ser Ser Ser Thr Ser Ser Ser Thr Ala
                325                 330                 335

Glu Ala Gln Gln Gln Gln Gln Gln Gln Gln Gln Gln Gln His Leu Glu
            340                 345                 350

Gln Leu Leu Met Asp Leu Gln Glu Leu Leu Ser Arg Met Glu Asn Tyr
        355                 360                 365

Arg Asn Leu Lys Leu Pro Arg Met Leu Thr Phe Lys Phe Tyr Leu Pro
    370                 375                 380

Lys Gln Ala Thr Glu Leu Lys Asp Leu Gln Cys Leu Glu Asp Glu Leu
385                 390                 395                 400

Gly Pro Leu Arg His Val Leu Asp Leu Thr Gln Ser Lys Ser Phe Gln
                405                 410                 415

Leu Glu Asp Ala Glu Asn Phe Ile Ser Asn Ile Arg Val Thr Val Val
            420                 425                 430

Lys Leu Lys Gly Ser Asp Asn Thr Phe Glu Cys Gln Phe Asp Asp Glu
        435                 440                 445

Ser Ala Thr Val Val Asp Phe Leu Arg Arg Trp Ile Ala Phe Cys Gln
    450                 455                 460

Ser Ile Ile Ser Thr Ser Pro Gln Gly Gly Ser Ser Thr Lys Asp Asn
465                 470                 475                 480

Phe Asn Val Tyr Lys Ala Thr Arg Pro Tyr Leu Ala His Cys Pro Asp
                485                 490                 495

Cys Gly Glu Gly His Ser Cys His Ser Pro Ile Ala Leu Glu Arg Ile
            500                 505                 510

Arg Asn Glu Ala Thr Asp Gly Thr Leu Lys Ile Gln Val Ser Leu Gln
        515                 520                 525

Ile Gly Ile Lys Thr Asp Asp Ser His Asp Trp Thr Lys Leu Arg Tyr
    530                 535                 540

Met Asp Ser His Thr Pro Ala Asp Ala Glu Arg Ala Gly Leu Leu Val
545                 550                 555                 560

Arg Thr Ser Ala Pro Cys Thr Ile Thr Gly Thr Met Gly His Phe Ile
                565                 570                 575

Leu Ala Arg Cys Pro Lys Gly Glu Thr Leu Thr Val Gly Phe Thr Asp
            580                 585                 590

Ser Arg Lys Ile Ser His Thr Cys Thr His Pro Phe His His Glu Pro
        595                 600                 605

Pro Val Ile Gly Arg Glu Arg Phe His Ser Arg Pro Gln His Gly Lys
    610                 615                 620

Glu Leu Pro Cys Ser Thr Tyr Val Gln Ser Thr Ala Ala Thr Ala Glu
625                 630                 635                 640
```

```
Glu Ile Glu Val His Met Pro Pro Asp Thr Pro Asp Arg Thr Leu Met
                645                 650                 655

Thr Gln Gln Ser Gly Asn Val Lys Ile Thr Val Asn Gly Gln Thr Val
            660                 665                 670

Arg Tyr Lys Cys Asn Cys Gly Gly Ser Asn Glu Gly Leu Thr Thr Thr
        675                 680                 685

Asp Lys Val Ile Asn Asn Cys Lys Ile Asp Gln Cys His Ala Ala Val
    690                 695                 700

Thr Asn His Lys Asn Trp Gln Tyr Asn Ser Pro Leu Val Pro Arg Asn
705                 710                 715                 720

Ala Glu Leu Gly Asp Arg Lys Gly Lys Ile His Ile Pro Phe Pro Leu
                725                 730                 735

Ala Asn Val Thr Cys Arg Val Pro Lys Ala Arg Asn Pro Thr Val Thr
            740                 745                 750

Tyr Gly Lys Asn Gln Val Thr Met Leu Leu Tyr Pro Asp His Pro Thr
        755                 760                 765

Leu Leu Ser Tyr Arg Asn Met Gly Gln Glu Pro Asn Tyr His Glu Glu
    770                 775                 780

Trp Val Thr His Lys Lys Glu Val Thr Leu Thr Val Pro Thr Glu Gly
785                 790                 795                 800

Leu Glu Val Thr Trp Gly Asn Asn Glu Pro Tyr Lys Tyr Trp Pro Gln
                805                 810                 815

Met Ser Thr Asn Gly Thr Ala His Gly His Pro His Glu Ile Ile Leu
            820                 825                 830

Tyr Tyr Tyr Glu Leu Tyr Pro Thr Met Thr Val Val Ile Val Ser Val
        835                 840                 845

Ala Ser Phe Val Leu Leu Ser Met Val Gly Thr Ala Val Gly Met Cys
    850                 855                 860

Val Cys Ala Arg Arg Arg Cys Ile Thr Pro Tyr Glu Leu Thr Pro Gly
865                 870                 875                 880

Ala Thr Val Pro Phe Leu Leu Ser Leu Leu Cys Cys Val Arg Thr Thr
                885                 890                 895

Lys Ala Ala Thr Tyr Tyr Glu Ala Ala Ala Tyr Leu Trp Asn Glu Gln
            900                 905                 910

Gln Pro Leu Phe Trp Leu Gln Ala Leu Ile Pro Leu Ala Ala Leu Ile
        915                 920                 925

Val Leu Cys Asn Cys Leu Lys Leu Leu Pro Cys Cys Cys Lys Thr Leu
    930                 935                 940

Ala Phe Leu Ala Val Met Ser Ile Gly Ala His Thr Val Ser Ala Tyr
945                 950                 955                 960

Glu His Val Thr Val Ile Pro Asn Thr Val Gly Val Pro Tyr Lys Thr
                965                 970                 975

Leu Val Asn Arg Pro Gly Tyr Ser Pro Met Val Leu Glu Met Glu Leu
            980                 985                 990

Gln Ser Val Thr Leu Glu Pro Thr  Leu Ser Leu Asp Tyr  Ile Thr Cys
        995                 1000                 1005

Glu Tyr  Lys Thr Val Ile Pro  Ser Pro Tyr Val Lys  Cys Cys Gly
    1010                 1015                 1020

Thr Ala  Glu Cys Lys Asp Lys  Ser Leu Pro Asp Tyr  Ser Cys Lys
    1025                 1030                 1035

Val Phe  Thr Gly Val Tyr Pro  Phe Met Trp Gly Gly  Ala Tyr Cys
    1040                 1045                 1050
```

```
Phe Cys  Asp Ala Glu Asn Thr  Gln Leu Ser Glu Ala  His Val Glu
    1055                 1060                 1065

Lys Ser  Glu Ser Cys Lys Thr  Glu Phe Ala Ser Ala  Tyr Arg Ala
    1070                 1075                 1080

His Thr  Ala Ser Ala Ser Ala  Lys Leu Arg Val Leu  Tyr Gln Gly
    1085                 1090                 1095

Asn Asn  Ile Thr Val Ala Ala  Tyr Ala Asn Gly Asp  His Ala Val
    1100                 1105                 1110

Thr Val  Lys Asp Ala Lys Phe  Val Val Gly Pro Met  Ser Ser Ala
    1115                 1120                 1125

Trp Thr  Pro Phe Asp Asn Lys  Ile Val Val Tyr Lys  Gly Asp Val
    1130                 1135                 1140

Tyr Asn  Met Asp Tyr Pro Pro  Phe Gly Ala Gly Arg  Pro Gly Gln
    1145                 1150                 1155

Phe Gly  Asp Ile Gln Ser Arg  Thr Pro Glu Ser Lys  Asp Val Tyr
    1160                 1165                 1170

Ala Asn  Thr Gln Leu Val Leu  Gln Arg Pro Ala Ala  Gly Thr Val
    1175                 1180                 1185

His Val  Pro Tyr Ser Gln Ala  Pro Ser Gly Phe Lys  Tyr Trp Leu
    1190                 1195                 1200

Lys Glu  Arg Gly Ala Ser Leu  Gln His Thr Ala Pro  Phe Gly Cys
    1205                 1210                 1215

Gln Ile  Ala Thr Asn Pro Val  Arg Ala Val Asn Cys  Ala Val Gly
    1220                 1225                 1230

Asn Ile  Pro Ile Ser Ile Asp  Ile Pro Asp Ala Ala  Phe Thr Arg
    1235                 1240                 1245

Val Val  Asp Ala Pro Ser Val  Thr Asp Met Ser Cys  Glu Val Pro
    1250                 1255                 1260

Ala Cys  Thr His Ser Ser Asp  Phe Gly Gly Val Ala  Ile Ile Lys
    1265                 1270                 1275

Tyr Thr  Ala Ser Lys Lys Gly  Lys Cys Ala Val His  Ser Met Thr
    1280                 1285                 1290

Asn Ala  Val Thr Ile Arg Glu  Ala Asp Val Glu Val  Glu Gly Asn
    1295                 1300                 1305

Ser Gln  Leu Gln Ile Ser Phe  Ser Thr Ala Leu Ala  Ser Ala Glu
    1310                 1315                 1320

Phe Arg  Val Gln Val Cys Ser  Thr Gln Val His Cys  Ala Ala Ala
    1325                 1330                 1335

Cys His  Pro Pro Lys Asp His  Ile Val Asn Tyr Pro  Ala Ser His
    1340                 1345                 1350

Thr Thr  Leu Gly Val Gln Asp  Ile Ser Thr Thr Ala  Met Ser Trp
    1355                 1360                 1365

Val Gln  Lys Ile Thr Gly Gly  Val Gly Leu Ile Val  Ala Val Ala
    1370                 1375                 1380

Ala Leu  Ile Leu Ile Val Val  Leu Cys Val Ser Phe  Ser Arg His
    1385                 1390                 1395
```

<210> SEQ ID NO 85
<211> LENGTH: 9212
<212> TYPE: DNA
<213> ORGANISM: Artificial Sequence
<220> FEATURE:
<223> OTHER INFORMATION: Synthetic Expression vector for CHIKV viral
structural protein containing human IL-2(wt) antigen in E3

<400> SEQUENCE: 85

-continued

```
gaattcccat tgcatacgtt gtatccatat cataatatgt acatttatat tggctcatgt     60
ccaacattac cgccatgttg acattgatta ttgactagtt attaatagta atcaattacg    120
gggtcattag ttcatagccc atatatggag ttccgcgtta cataacttac ggtaaatggc    180
ccgcctggct gaccgcccaa cgacccccgc ccattgacgt caataatgac gtatgttccc    240
atagtaacgc caatagggac tttccattga cgtcaatggg tggagtattt acggtaaact    300
gcccacttgg cagtacatca agtgtatcat atgccaagta cgccccctat tgacgtcaat    360
gacggtaaat ggcccgcctg gcattatgcc cagtacatga ccttatggga ctttcctact    420
tggcagtaca tctacgtatt agtcatcgct attaccatgg tgatgcggtt ttggcagtac    480
atcaatgggc gtggatagcg gtttgactca cggggatttc caagtctcca ccccattgac    540
gtcaatggga gtttgttttg gcaccaaaat caacgggact ttccaaaatg tcgtaacaac    600
tccgccccat tgacgcaaat gggcggtagg cgtgtacggt gggaggtcta tataagcaga    660
gctcgtttag tgaaccgtca gatcgcctgg agacgccatc cacgctgttt tgacctccat    720
agaagacacc gggaccgatc cagcctccgt taacggtgga gggcagtgta gtctgagcag    780
tactcgttgc tgccgcgcgc gccaccagac ataatagctg acagactaac agactgttcc    840
tttgcggccg ctctagacac catggagttc atcccgacgc aaactttcta taacagaagg    900
taccaacccc gaccctgggc cccacgccct acaattcaag taattagacc tagaccacgt    960
ccacagaggc aggctgggca actcgcccag ctgatctccg cagtcaacaa attgaccatg   1020
cgcgcggtac ctcaacagaa gcctcgcaga aatcggaaaa acaagaagca aaggcagaag   1080
aagcaggcgc cgcaaaacga cccaaagcaa aagaagcaac caccacaaaa gaagccggct   1140
caaaagaaga agaaaccagg ccgtagggag agaatgtgca tgaaaattga aaatgattgc   1200
atcttcgaag tcaagcatga aggcaaagtg atgggctacg catgcctggt ggggggataaa   1260
gtaatgaaac cagcacatgt gaagggaact atcgacaatg ccgatctggc taaactggcc   1320
tttaagcggt cgtctaaata cgatcttgaa tgtgcacaga taccggtgca catgaagtct   1380
gatgcctcga agtttaccca cgagaaaccc gaggggtact ataactggca tcacggagca   1440
gtgcagtatt caggaggccg gttcactatc ccgacgggtg caggcaagcc gggagacagc   1500
ggcagaccga tcttcgacaa caaaggacgg gtggtggcca tcgtcctagg aggggccaac   1560
gaaggtgccc gcacggccct ctccgtggtg acgtggaaca aagacatcgt cacaaaaatt   1620
acccctgagg gagccgaaga gtggagcctc gccctcccgg tcttgtgcct gttggcaaac   1680
actacattcc cctgctctca gccgccttgc acaccctgct gctacgaaaa ggaaccggaa   1740
agcaccttgc gcatgcttga ggacaacgtg atgagacccg gatactacca gctactaaaa   1800
gcatcgctga cttgctctcc ccactccgga ggggcaccta cttcaagttc tacaaagaaa   1860
acacagctac aactggagca tttactgctg gatttacaga tgattttgaa tggaattaat   1920
aattacaaga atcccaaact caccaggatg ctcacattta agttttacat gcccaagaag   1980
gccacagaac tgaaacatct tcagtgtcta gaagaagaac tcaaacctct ggaggaagtg   2040
ctaaatttag ctcaaagcaa aaactttcac ttaagaccca gggacttaat cagcaatatc   2100
aacgtaatag ttctggaact aaagggatct gaaacaacat tcatgtgtga atatgctgat   2160
gagacagcaa ccattgtaga atttctgaac agatggatta ccttttgtca aagcatcatc   2220
tcaacactga ctgggggatc cagtactaag gacaatttta atgtctataa agccacaaga   2280
ccatatctag ctcattgtcc tgactgcgga gaagggcatt cgtgccacag ccctatcgca   2340
```

-continued

```
ttggagcgca tcagaaatga agcaacggac ggaacgctga aaatccaggt ctctttgcag   2400

atcgggataa agacagatga cagccacgat tggaccaagc tgcgctatat ggatagccat   2460

acgcccgcgg acgcggagcg agccggattg cttgtaagga cttcagcacc gtgcacgatc   2520

accgggacca tgggacactt tattctcgcc cgatgcccga aaggagagac gctgacagtg   2580

ggatttacgg acagcagaaa gatcagccac acatgcacac acccgttcca tcatgaacca   2640

cctgtgatag gtagggagag gttccactct cgaccacaac atggtaaaga gttaccttgc   2700

agcacgtacg tgcagagcac cgctgccact gctgaggaga tagaggtgca tatgcccccca   2760

gatactcctg accgcacgct gatgacgcag cagtctggca acgtgaagat cacagttaat   2820

gggcagacgg tgcggtacaa gtgcaactgc ggtggctcaa acgagggact gacaaccaca   2880

gacaaagtga tcaataactg caaaattgat cagtgccatg ctgcagtcac taatcacaag   2940

aattggcaat acaactcccc tttagtcccg cgcaacgctg aactcgggga ccgtaaagga   3000

aagatccaca tcccattccc attggcaaac gtgacttgca gagtgccaaa agcaagaaac   3060

cctacagtaa cttacggaaa aaaccaagtc accatgctgc tgtatcctga ccatccgaca   3120

ctcttgtctt accgtaacat gggacaggaa ccaaattacc acgaggagtg ggtgacacac   3180

aagaaggagg ttaccttgac cgtgcctact gagggtctgg aggtcacttg gggcaacaac   3240

gaaccataca agtactggcc gcagatgtct acgaacggta ctgctcatgg tcacccacat   3300

gagataatct tgtactatta tgagctgtac cccactatga ctgtagtcat tgtgtcggtg   3360

gcctcgttcg tgcttctgtc gatggtgggc acagcagtgg gaatgtgtgt gtgcgcacgg   3420

cgcagatgca ttacaccata tgaattaaca ccaggagcca ctgttccctt cctgctcagc   3480

ctgctatgct gcgtcagaac gaccaaggcg gccacatatt acgaggctgc ggcatatcta   3540

tggaacgaac agcagcccct gttctggttg caggctctta tcccgctggc cgccttgatc   3600

gtcctgtgca actgtctgaa actcttgcca tgctgctgta agaccctggc tttttttagcc   3660

gtaatgagca tcggtgccca cactgtgagc gcgtacgaac acgtaacagt gatcccgaac   3720

acggtgggag taccgtataa gactcttgtc aacagaccgg gttacagccc catggtgttg   3780

gagatggagc tacaatcagt caccttggaa ccaacactgt cacttgacta catcacgtgc   3840

gagtacaaaa ctgtcatccc ctccccgtac gtgaagtgct gtggtacagc agagtgcaag   3900

gacaagagcc taccagacta cagctgcaag gtctttactg gagtctaccc atttatgtgg   3960

ggcggcgcct actgcttttg cgacgccgaa aatacgcaat tgagcgaggc acatgtagag   4020

aaatctgaat cttgcaaaac agagtttgca tcggcctaca gagcccacac cgcatcggcg   4080

tcggcgaagc tccgcgtcct ttaccaagga aacaacatta ccgtagctgc ctacgctaac   4140

ggtgaccatg ccgtcacagt aaaggacgcc aagtttgtcg tgggcccaat gtcctccgcc   4200

tggacacctt ttgacaacaa aatcgtggtg tacaaaggcg acgtctacaa catggactac   4260

ccaccttttg gcgcaggaag accaggacaa tttggtgaca ttcaaagtcg tacaccggaa   4320

agtaaagacg tttatgccaa cactcagttg gtactacaga ggccagcagc aggcacggta   4380

catgtaccat actctcaggc accatctggc ttcaagtatt ggctgaagga acgaggagca   4440

tcgctacagc acacggcacc gttcggttgc cagattgcga caaacccggt aagagctgta   4500

aattgcgctg tggggaacat accaatttcc atcgacatac cggatgcggc ctttactagg   4560

gttgtcgatg caccctctgt aacggacatg tcatgcgaag taccagcctg cactcactcc   4620

tccgactttg ggggcgtcgc catcatcaaa tacacagcta gcaagaaagg taaatgtgca   4680

gtacattcga tgaccaacgc cgttaccatt cgagaagccg acgtagaagt agaggggaac   4740
```

-continued

```
tcccagctgc aaatatcctt ctcaacagcc ctggcaagcg ccgagtttcg cgtgcaagtg   4800
tgctccacac aagtacactg cgcagccgca tgccaccctc caaaggacca catagtcaat   4860
tacccagcat cacacaccac ccttggggtc caggatatat ccacaacggc aatgtcttgg   4920
gtgcagaaga ttacgggagg agtaggatta attgttgctg ttgctgcctt aattttaatt   4980
gtggtgctat gcgtgtcgtt tagcaggcac taatgatccg gaggggcacc cacttcaagc   5040
tccacttcaa gctctacagc ggaagcacag cagcagcagc agcagcagca gcagcagcag   5100
cacctggagc agctgttgat ggacctacag gagctcctga gcaggatgga gaattacagg   5160
aacctgaaac tccccaggat gctcaccttc aaattttact tgcccaagca ggccacagaa   5220
ttgaaagatc ttcagtgcct agaagatgaa cttggacctc tgcggcatgt tctggatttg   5280
actcaaagca aaagctttca attggaagat gctgagaatt tcatcagcaa tatcagagta   5340
actgttgtaa aactaaaggg ctctgacaac acatttgagt gccaattcga tgatgagtca   5400
gcaactgtgg tggactttct gaggagatgg atagccttct gtcaaagcat catctcaaca   5460
agccctcaag gggatccgc tgtgccttct agttgccagc catctgttgt ttgcccctcc   5520
cccgtgcctt ccttgaccct ggaaggtgcc actcccactg tcctttccta ataaaatgag   5580
gaaattgcat cgcattgtct gagtaggtgt cattctattc tggggggtgg ggtggggcag   5640
gacagcaagg gggaggattg ggaagacaat agcaggcatg ctggggatgc ggtgggctct   5700
atgggtaccc aggtgctgaa gaattgaccc ggttcctcct gggccagaaa gaagcaggca   5760
catccccttc tctgtgacac accctgtcca cgcccctggt tcttagttcc agccccactc   5820
ataggacact catagctcag gagggctccg ccttcaatcc cacccgctaa agtacttgga   5880
gcggtctctc cctccctcat cagcccacca aaccaaacct agcctccaag agtgggaaga   5940
aattaaagca agataggcta ttaagtgcag agggagagaa aatgcctcca acatgtgagg   6000
aagtaatgag agaaatcata gaattttaag gccatgattt aaggccatca tggcctaagc   6060
ttgaaaggag ataggatcaa agcttggcgt aatcatggtc atagctgttt cctgtgtgaa   6120
attgttatcc gctcacaatt ccacacaaca tacgagccgg aagcataaag tgtaaagcct   6180
ggggtgccta atgagtgagc taactcacat taattgcgtt gcgctcactg cccgctttcc   6240
agtcgggaaa cctgtcgtgc cagctgcatt aatgaatcgg ccaacgcgcg gggagaggcg   6300
gtttgcgtat tgggcgctct tccgcttcct cgctcactga ctcgctgcgc tcggtcgttc   6360
ggctgcggcg agcggtatca gctcactcaa aggcggtaat acggttatcc acagaatcag   6420
gggataacgc aggaaagaac atgtgagcaa aaggccagca aaaggccagg aaccgtaaaa   6480
aggccgcgtt gctggcgttt ttccataggc tccgcccccc tgacgagcat cacaaaaatc   6540
gacgctcaag tcagaggtgg cgaaacccga caggactata aagataccag gcgtttcccc   6600
ctggaagctc cctcgtgcgc tctcctgttc cgaccctgcc gcttaccgga tacctgtccg   6660
cctttctccc ttcgggaagc gtggcgcttt ctcatagctc acgctgtagg tatctcagtt   6720
cggtgtaggt cgttcgctcc aagctgggct gtgtgcacga accccccgtt cagcccgacc   6780
gctgcgcctt atccggtaac tatcgtcttg agtccaaccc ggtaagacac gacttatcgc   6840
cactggcagc agccactggt aacaggatta gcagagcgag gtatgtaggc ggtgctacag   6900
agttcttgaa gtggtggcct aactacggct acactagaag aacagtattt ggtatctgcg   6960
ctctgctgaa gccagttacc ttcggaaaaa gagttggtag ctcttgatcc ggcaaacaaa   7020
ccaccgctgg tagcggtggt ttttttgttt gcaagcagca gattacgcgc agaaaaaaag   7080
```

```
gatctcaaga agatcctttg atcttttcta cggggtctga cgctcagtgg aacgaaaact   7140
cacgttaagg gattttggtc atgagattat caaaaaggat cttcacctag atccttttaa   7200
attaaaaatg aagttttaaa tcaatctaaa gtatatatga gtaaacttgg tctgacagtt   7260
accaatgctt aatcagtgag gcacctatct cagcgatctg tctatttcgt tcatccatag   7320
ttgcctgact ccccgtcgtg tagataacta cgatacggga gggcttacca tctggcccca   7380
gtgctgcaat gataccgcga gaaccacgct caccggctcc agatttatca gcaataaacc   7440
agccagccgg aagggccgag cgcagaagtg gtcctgcaac tttatccgcc tccatccagt   7500
ctattaattg ttgccgggaa gctagagtaa gtagttcgcc agttaatagt ttgcgcaacg   7560
ttgttgccat tgctacaggc atcgtggtgt cacgctcgtc gtttggtatg gcttcattca   7620
gctccggttc ccaacgatca aggcgagtta catgatcccc catgttgtgc aaaaaagcgg   7680
ttagctcctt cggtcctccg atcgttgtca gaagtaagtt ggccgcagtg ttatcactca   7740
tggttatggc agcactgcat aattctctta ctgtcatgcc atccgtaaga tgcttttctg   7800
tgactggtga gtactcaacc aagtcattct gagaatagtg tatgcggcga ccgagttgct   7860
cttgcccggc gtcaatacgg gataataccg cgccacatag cagaacttta aaagtgctca   7920
tcattggaaa acgttcttcg gggcgaaaac tctcaaggat cttaccgctg ttgagatcca   7980
gttcgatgta acccactcgt gcacccaact gatcttcagc atcttttact ttcaccagcg   8040
tttctgggtg agcaaaaaca ggaaggcaaa atgccgcaaa aaagggaata agggcgacac   8100
ggaaatgttg aatactcata ctcttccttt ttcaatatta ttgaagcatt tatcagggtt   8160
attgtctcat gagcggatac atatttgaat gtatttagaa aaataaacaa ataggggttc   8220
cgcgcacatt tccccgaaaa gtgccacctg acgtctaaga aaccattatt atcatgacat   8280
taacctataa aaataggcgt atcacgaggc cctttcgggt cgcgcgtttc ggtgatgacg   8340
gtgaaaacct ctgacacatg cagctcccgt tgacggtcac agcttgtctg taagcggatg   8400
ccgggagcag acaagcccgt cagggcgcgt cagcgggtgt tggcgggtgt cggggctggc   8460
ttaactatgc ggcatcagag cagattgtac tgagagtgca ccataaaatt gtaaacgtta   8520
atattttgtt aaaattcgcg ttaaattttt gttaaatcag ctcatttttt aaccaatagg   8580
ccgaaatcgg caaaatccct tataaatcaa aagaatagcc cgagataggg ttgagtgttg   8640
ttccagtttg gaacaagagt ccactattaa agaacgtgga ctccaacgtc aaagggcgaa   8700
aaaccgtcta tcagggcgat ggcccactac gtgaaccatc acccaaatca agttttttgg   8760
ggtcgaggtg ccgtaaagca ctaaatcgga accctaaagg gagcccccga tttagagctt   8820
gacggggaaa gccggcgaac gtggcgagaa aggaagggaa gaaagcgaaa ggagcgggcg   8880
ctagggcgct ggcaagtgta gcggtcacgc tgcgcgtaac caccacaccc gccgcgctta   8940
atgcgccgct acagggcgcg tactatggtt gctttgacgt atgcggtgtg aaataccgca   9000
cagatgcgta aggagaaaat accgcatcag gcgccattcg ccattcaggc tgcgcaactg   9060
ttgggaaggg cgatcggtgc gggcctcttc gctattacgc cagctggcga aagggggatg   9120
tgctgcaagg cgattaagtt gggtaacgcc agggttttcc cagtcacgac gttgtaaaac   9180
gacggccagt gaattccatg gtctcaactt tc                                  9212
```

<210> SEQ ID NO 86
<211> LENGTH: 1383
<212> TYPE: PRT
<213> ORGANISM: Artificial Sequence
<220> FEATURE:
<223> OTHER INFORMATION: Synthetic CHIKV viral structural protein containing human IL-2(wt) antigen in E3

<400> SEQUENCE: 86

```
Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Arg Gln Lys Lys Gln Ala Pro Gln Asn Asp
65                  70                  75                  80

Pro Lys Gln Lys Lys Gln Pro Pro Gln Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Met Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Leu Pro Val Leu Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Ser Thr Leu Arg Met Leu Glu Asp Asn Val Met
    290                 295                 300

Arg Pro Gly Tyr Tyr Gln Leu Leu Lys Ala Ser Leu Thr Cys Ser Pro
305                 310                 315                 320

His Ser Gly Gly Ala Pro Thr Ser Ser Ser Thr Lys Lys Thr Gln Leu
                325                 330                 335

Gln Leu Glu His Leu Leu Leu Asp Leu Gln Met Ile Leu Asn Gly Ile
            340                 345                 350

Asn Asn Tyr Lys Asn Pro Lys Leu Thr Arg Met Leu Thr Phe Lys Phe
        355                 360                 365

Tyr Met Pro Lys Lys Ala Thr Glu Leu Lys His Leu Gln Cys Leu Glu
    370                 375                 380

Glu Glu Leu Lys Pro Leu Glu Glu Val Leu Asn Leu Ala Gln Ser Lys
385                 390                 395                 400
```

-continued

```
Asn Phe His Leu Arg Pro Arg Asp Leu Ile Ser Asn Ile Asn Val Ile
                405                 410                 415

Val Leu Glu Leu Lys Gly Ser Glu Thr Thr Phe Met Cys Glu Tyr Ala
            420                 425                 430

Asp Glu Thr Ala Thr Ile Val Glu Phe Leu Asn Arg Trp Ile Thr Phe
        435                 440                 445

Cys Gln Ser Ile Ile Ser Thr Leu Thr Gly Gly Ser Ser Thr Lys Asp
    450                 455                 460

Asn Phe Asn Val Tyr Lys Ala Thr Arg Pro Tyr Leu Ala His Cys Pro
465                 470                 475                 480

Asp Cys Gly Glu Gly His Ser Cys His Ser Pro Ile Ala Leu Glu Arg
                485                 490                 495

Ile Arg Asn Glu Ala Thr Asp Gly Thr Leu Lys Ile Gln Val Ser Leu
            500                 505                 510

Gln Ile Gly Ile Lys Thr Asp Asp Ser His Asp Trp Thr Lys Leu Arg
        515                 520                 525

Tyr Met Asp Ser His Thr Pro Ala Asp Ala Glu Arg Ala Gly Leu Leu
    530                 535                 540

Val Arg Thr Ser Ala Pro Cys Thr Ile Thr Gly Thr Met Gly His Phe
545                 550                 555                 560

Ile Leu Ala Arg Cys Pro Lys Gly Glu Thr Leu Thr Val Gly Phe Thr
                565                 570                 575

Asp Ser Arg Lys Ile Ser His Thr Cys Thr His Pro Phe His His Glu
            580                 585                 590

Pro Pro Val Ile Gly Arg Glu Arg Phe His Ser Arg Pro Gln His Gly
        595                 600                 605

Lys Glu Leu Pro Cys Ser Thr Tyr Val Gln Ser Thr Ala Ala Thr Ala
    610                 615                 620

Glu Glu Ile Glu Val His Met Pro Pro Asp Thr Pro Asp Arg Thr Leu
625                 630                 635                 640

Met Thr Gln Gln Ser Gly Asn Val Lys Ile Thr Val Asn Gly Gln Thr
                645                 650                 655

Val Arg Tyr Lys Cys Asn Cys Gly Gly Ser Asn Glu Gly Leu Thr Thr
            660                 665                 670

Thr Asp Lys Val Ile Asn Asn Cys Lys Ile Asp Gln Cys His Ala Ala
        675                 680                 685

Val Thr Asn His Lys Asn Trp Gln Tyr Asn Ser Pro Leu Val Pro Arg
    690                 695                 700

Asn Ala Glu Leu Gly Asp Arg Lys Gly Lys Ile His Ile Pro Phe Pro
705                 710                 715                 720

Leu Ala Asn Val Thr Cys Arg Val Pro Lys Ala Arg Asn Pro Thr Val
                725                 730                 735

Thr Tyr Gly Lys Asn Gln Val Thr Met Leu Leu Tyr Pro Asp His Pro
            740                 745                 750

Thr Leu Leu Ser Tyr Arg Asn Met Gly Gln Glu Pro Asn Tyr His Glu
        755                 760                 765

Glu Trp Val Thr His Lys Lys Glu Val Thr Leu Thr Val Pro Thr Glu
    770                 775                 780

Gly Leu Glu Val Thr Trp Gly Asn Asn Glu Pro Tyr Lys Tyr Trp Pro
785                 790                 795                 800

Gln Met Ser Thr Asn Gly Thr Ala His Gly His Pro His Glu Ile Ile
                805                 810                 815

Leu Tyr Tyr Tyr Glu Leu Tyr Pro Thr Met Thr Val Val Ile Val Ser
```

```
            820                 825                 830

Val Ala Ser Phe Val Leu Leu Ser Met Val Gly Thr Ala Val Gly Met
        835                 840                 845

Cys Val Cys Ala Arg Arg Arg Cys Ile Thr Pro Tyr Glu Leu Thr Pro
    850                 855                 860

Gly Ala Thr Val Pro Phe Leu Leu Ser Leu Leu Cys Cys Val Arg Thr
865                 870                 875                 880

Thr Lys Ala Ala Thr Tyr Tyr Glu Ala Ala Ala Tyr Leu Trp Asn Glu
                885                 890                 895

Gln Gln Pro Leu Phe Trp Leu Gln Ala Leu Ile Pro Leu Ala Ala Leu
            900                 905                 910

Ile Val Leu Cys Asn Cys Leu Lys Leu Leu Pro Cys Cys Cys Lys Thr
        915                 920                 925

Leu Ala Phe Leu Ala Val Met Ser Ile Gly Ala His Thr Val Ser Ala
    930                 935                 940

Tyr Glu His Val Thr Val Ile Pro Asn Thr Val Gly Val Pro Tyr Lys
945                 950                 955                 960

Thr Leu Val Asn Arg Pro Gly Tyr Ser Pro Met Val Leu Glu Met Glu
                965                 970                 975

Leu Gln Ser Val Thr Leu Glu Pro Thr Leu Ser Leu Asp Tyr Ile Thr
            980                 985                 990

Cys Glu Tyr Lys Thr Val Ile Pro  Ser Pro Tyr Val Lys  Cys Cys Gly
        995                 1000                1005

Thr Ala  Glu Cys Lys Asp Lys  Ser Leu Pro Asp Tyr  Ser Cys Lys
    1010                 1015                 1020

Val Phe  Thr Gly Val Tyr Pro  Phe Met Trp Gly Gly  Ala Tyr Cys
    1025                 1030                 1035

Phe Cys  Asp Ala Glu Asn Thr  Gln Leu Ser Glu Ala  His Val Glu
    1040                 1045                 1050

Lys Ser  Glu Ser Cys Lys Thr  Glu Phe Ala Ser Ala  Tyr Arg Ala
    1055                 1060                 1065

His Thr  Ala Ser Ala Ser Ala  Lys Leu Arg Val Leu  Tyr Gln Gly
    1070                 1075                 1080

Asn Asn  Ile Thr Val Ala Ala  Tyr Ala Asn Gly Asp  His Ala Val
    1085                 1090                 1095

Thr Val  Lys Asp Ala Lys Phe  Val Val Gly Pro Met  Ser Ser Ala
    1100                 1105                 1110

Trp Thr  Pro Phe Asp Asn Lys  Ile Val Val Tyr Lys  Gly Asp Val
    1115                 1120                 1125

Tyr Asn  Met Asp Tyr Pro Pro  Phe Gly Ala Gly Arg  Pro Gly Gln
    1130                 1135                 1140

Phe Gly  Asp Ile Gln Ser Arg  Thr Pro Glu Ser Lys  Asp Val Tyr
    1145                 1150                 1155

Ala Asn  Thr Gln Leu Val Leu  Gln Arg Pro Ala Ala  Gly Thr Val
    1160                 1165                 1170

His Val  Pro Tyr Ser Gln Ala  Pro Ser Gly Phe Lys  Tyr Trp Leu
    1175                 1180                 1185

Lys Glu  Arg Gly Ala Ser Leu  Gln His Thr Ala Pro  Phe Gly Cys
    1190                 1195                 1200

Gln Ile  Ala Thr Asn Pro Val  Arg Ala Val Asn Cys  Ala Val Gly
    1205                 1210                 1215

Asn Ile  Pro Ile Ser Ile Asp  Ile Pro Asp Ala Ala  Phe Thr Arg
    1220                 1225                 1230
```

Val Val Asp Ala Pro Ser Val Thr Asp Met Ser Cys Glu Val Pro
1235 1240 1245

Ala Cys Thr His Ser Ser Asp Phe Gly Gly Val Ala Ile Ile Lys
1250 1255 1260

Tyr Thr Ala Ser Lys Lys Gly Lys Cys Ala Val His Ser Met Thr
1265 1270 1275

Asn Ala Val Thr Ile Arg Glu Ala Asp Val Glu Val Glu Gly Asn
1280 1285 1290

Ser Gln Leu Gln Ile Ser Phe Ser Thr Ala Leu Ala Ser Ala Glu
1295 1300 1305

Phe Arg Val Gln Val Cys Ser Thr Gln Val His Cys Ala Ala Ala
1310 1315 1320

Cys His Pro Pro Lys Asp His Ile Val Asn Tyr Pro Ala Ser His
1325 1330 1335

Thr Thr Leu Gly Val Gln Asp Ile Ser Thr Thr Ala Met Ser Trp
1340 1345 1350

Val Gln Lys Ile Thr Gly Gly Val Gly Leu Ile Val Ala Val Ala
1355 1360 1365

Ala Leu Ile Leu Ile Val Val Leu Cys Val Ser Phe Ser Arg His
1370 1375 1380

<210> SEQ ID NO 87
<211> LENGTH: 9257
<212> TYPE: DNA
<213> ORGANISM: Artificial Sequence
<220> FEATURE:
<223> OTHER INFORMATION: Synthetic Expression vector for CHIKV viral structural protein containing mouse IL-2 (F54A) antigen in E3

<400> SEQUENCE: 87
gaattcccat tgcatacgtt gtatccatat cataatatgt acatttatat tggctcatgt 60
ccaacattac cgccatgttg acattgatta ttgactagtt attaatagta atcaattacg 120
gggtcattag ttcatagccc atatatggag ttccgcgtta cataacttac ggtaaatggc 180
ccgcctggct gaccgcccaa cgacccccgc ccattgacgt caataatgac gtatgttccc 240
atagtaacgc caatagggac tttccattga cgtcaatggg tggagtattt acggtaaact 300
gcccacttgg cagtacatca agtgtatcat atgccaagta cgccccctat tgacgtcaat 360
gacggtaaat ggcccgcctg gcattatgcc cagtacatga ccttatggga ctttcctact 420
tggcagtaca tctacgtatt agtcatcgct attaccatgg tgatgcggtt ttggcagtac 480
atcaatgggc gtggatagcg gtttgactca cggggatttc caagtctcca ccccattgac 540
gtcaatggga gtttgttttg gcaccaaaat caacgggact ttccaaaatg tcgtaacaac 600
tccgccccat tgacgcaaat gggcggtagg cgtgtacggt gggaggtcta tataagcaga 660
gctcgtttag tgaaccgtca gatcgcctgg agacgccatc cacgctgttt tgacctccat 720
agaagacacc gggaccgatc cagcctccgt taacggtgga gggcagtgta gtctgagcag 780
tactcgttgc tgccgcgcgc gccaccagac ataatagctg acagactaac agactgttcc 840
tttgcggccg ctctagacac catggagttc atcccgacgc aaactttcta taacagaagg 900
taccaacccc gaccctgggc cccacgccct acaattcaag taattagacc tagaccacgt 960
ccacagaggc aggctgggca actcgcccag ctgatctccg cagtcaacaa attgaccatg 1020
cgcgcggtac ctcaacagaa gcctcgcaga aatcggaaaa acaagaagca aaggcagaag 1080
aagcaggcgc cgcaaaacga cccaaagcaa aagaagcaac caccacaaaa gaagccggct 1140

-continued

```
caaaagaaga agaaaccagg ccgtagggag agaatgtgca tgaaaattga aaatgattgc   1200
atcttcgaag tcaagcatga aggcaaagtg atgggctacg catgcctggt gggggataaa   1260
gtaatgaaac cagcacatgt gaagggaact atcgacaatg ccgatctggc taaactggcc   1320
tttaagcggt cgtctaaata cgatcttgaa tgtgcacaga taccggtgca catgaagtct   1380
gatgcctcga agtttaccca cgagaaaccc gaggggtact ataactggca tcacggagca   1440
gtgcagtatt caggaggccg gttcactatc ccgacgggtg caggcaagcc gggagacagc   1500
ggcagaccga tcttcgacaa caaaggacgg gtggtggcca tcgtcctagg aggggccaac   1560
gaaggtgccc gcacggccct ctccgtggtg acgtggaaca aagacatcgt cacaaaaatt   1620
acccctgagg gagccgaaga gtggagcctc gccctcccgg tcttgtgcct gttggcaaac   1680
actacattcc cctgctctca gccgccttgc acaccctgct gctacgaaaa ggaaccggaa   1740
agcaccttgc gcatgcttga ggacaacgtg atgagacccg gatactacca gctactaaaa   1800
gcatcgctga cttgctctcc ccactccgga ggggcaccca cttcaagctc cacttcaagc   1860
tctacagcgg aagcacagca gcagcagcag cagcagcagc agcagcagca cctggagcag   1920
ctgttgatgg acctacagga gctcctgagc aggatggaga attacaggaa cctgaaactc   1980
cccaggatgc tcaccgccaa attttacttg cccaagcagg ccacagaatt gaaagatctt   2040
cagtgcctag aagatgaact tggacctctg cggcatgttc tggatttgac tcaaagcaaa   2100
agctttcaat tggaagatgc tgagaatttc atcagcaata tcagagtaac tgttgtaaaa   2160
ctaaagggct ctgacaacac atttgagtgc caattcgatg atgagtcagc aactgtggtg   2220
gactttctga ggagatggat agccttctgt caaagcatca tctcaacaag ccctcaaggg   2280
ggatccagta ctaaggacaa ttttaatgtc tataaagcca caagaccata tctagctcat   2340
tgtcctgact gcggagaagg gcattcgtgc cacagcccta tcgcattgga gcgcatcaga   2400
aatgaagcaa cggacggaac gctgaaaatc caggtctctt tgcagatcgg gataaagaca   2460
gatgacagcc acgattggac caagctgcgc tatatggata gccatacgcc cgcggacgcg   2520
gagcgagccg gattgcttgt aaggacttca gcaccgtgca cgatcaccgg gaccatggga   2580
cactttattc tcgcccgatg cccgaaagga gagacgctga cagtgggatt tacggacagc   2640
agaaagatca gccacacatg cacacacccg ttccatcatg aaccacctgt gataggtagg   2700
gagaggttcc actctcgacc acaacatggt aaagagttac cttgcagcac gtacgtgcag   2760
agcaccgctg ccactgctga ggagatagag gtgcatatgc ccccagatac tcctgaccgc   2820
acgctgatga cgcagcagtc tggcaacgtg aagatcacag ttaatgggca gacggtgcgg   2880
tacaagtgca actgcggtgg ctcaaacgag ggactgacaa ccacagacaa agtgatcaat   2940
aactgcaaaa ttgatcagtg ccatgctgca gtcactaatc acaagaattg gcaatacaac   3000
tcccctttag tcccgcgcaa cgctgaactc ggggaccgta aaggaaagat ccacatccca   3060
ttcccattgg caaacgtgac ttgcagagtg ccaaaagcaa gaaaccctac agtaacttac   3120
ggaaaaaacc aagtcaccat gctgctgtat cctgaccatc cgacactctt gtcttaccgt   3180
aacatgggac aggaaccaaa ttaccacgag gagtgggtga cacacaagaa ggaggttacc   3240
ttgaccgtgc ctactgaggg tctggaggtc acttggggca acaacgaacc atacaagtac   3300
tggccgcaga tgtctacgaa cggtactgct catggtcacc cacatgagat aatcttgtac   3360
tattatgagc tgtaccccac tatgactgta gtcattgtgt cggtggcctc gttcgtgctt   3420
ctgtcgatgg tgggcacagc agtgggaatg tgtgtgtgcg cacggcgcag atgcattaca   3480
```

```
ccatatgaat taacaccagg agccactgtt cccttcctgc tcagcctgct atgctgcgtc   3540
agaacgacca aggcggccac atattacgag gctgcggcat atctatggaa cgaacagcag   3600
cccctgttct ggttgcaggc tcttatcccg ctggccgcct tgatcgtcct gtgcaactgt   3660
ctgaaactct tgccatgctg ctgtaagacc ctggcttttt tagccgtaat gagcatcggt   3720
gcccacactg tgagcgcgta cgaacacgta acagtgatcc cgaacacggt gggagtaccg   3780
tataagactc ttgtcaacag accgggttac agccccatgg tgttggagat ggagctacaa   3840
tcagtcacct tggaaccaac actgtcactt gactacatca cgtgcgagta caaaactgtc   3900
atcccctccc cgtacgtgaa gtgctgtggt acagcagagt gcaaggacaa gagcctacca   3960
gactacagct gcaaggtctt tactggagtc tacccattta tgtggggcgg cgcctactgc   4020
ttttgcgacg ccgaaaatac gcaattgagc gaggcacatg tagagaaatc tgaatcttgc   4080
aaaacagagt ttgcatcggc ctacagagcc cacaccgcat cggcgtcggc gaagctccgc   4140
gtcctttacc aaggaaacaa cattaccgta gctgcctacg ctaacggtga ccatgccgtc   4200
acagtaaagg acgccaagtt tgtcgtgggc ccaatgtcct ccgcctggac accttttgac   4260
aacaaaatcg tggtgtacaa aggcgacgtc tacaacatgg actacccacc ttttggcgca   4320
ggaagaccag gacaatttgg tgacattcaa agtcgtacac cggaaagtaa agacgtttat   4380
gccaacactc agttggtact acagaggcca gcagcaggca cggtacatgt accatactct   4440
caggcaccat ctggcttcaa gtattggctg aaggaacgag gagcatcgct acagcacacg   4500
gcaccgttcg gttgccagat tgcgacaaac ccggtaagag ctgtaaattg cgctgtgggg   4560
aacataccaa tttccatcga cataccggat gcggccttta ctagggttgt cgatgcaccc   4620
tctgtaacgg acatgtcatg cgaagtacca gcctgcactc actcctccga ctttgggggc   4680
gtcgccatca tcaaatacac agctagcaag aaaggtaaat gtgcagtaca ttcgatgacc   4740
aacgccgtta ccattcgaga agccgacgta gaagtagagg ggaactccca gctgcaaata   4800
tccttctcaa cagccctggc aagcgccgag tttcgcgtgc aagtgtgctc cacacaagta   4860
cactgcgcag ccgcatgcca ccctccaaag gaccacatag tcaattaccc agcatcacac   4920
accacccttg ggtccagga tatatccaca acggcaatgt cttgggtgca gaagattacg   4980
ggaggagtag gattaattgt tgctgttgct gccttaattt taattgtggt gctatgcgtg   5040
tcgtttagca ggcactaatg atccggaggg gcacccactt caagctccac ttcaagctct   5100
acagcggaag cacagcagca gcagcagcag cagcagcagc agcagcacct ggagcagctg   5160
ttgatggacc tacaggagct cctgagcagg atggagaatt acaggaacct gaaactcccc   5220
aggatgctca ccttcaaatt ttacttgccc aagcaggcca cagaattgaa agatcttcag   5280
tgcctagaag atgaacttgg acctctgcgg catgttctgg atttgactca aagcaaaagc   5340
tttcaattgg aagatgctga gaatttcatc agcaatatca gagtaactgt tgtaaaacta   5400
aagggctctg acaacacatt tgagtgccaa ttcgatgatg agtcagcaac tgtggtggac   5460
tttctgagga gatggatagc cttctgtcaa agcatcatct caacaagccc tcaaggggga   5520
tccgctgtgc cttctagttg ccagccatct gttgtttgcc cctcccccgt gccttccttg   5580
accctggaag gtgccactcc cactgtcctt tcctaataaa atgaggaaat tgcatcgcat   5640
tgtctgagta ggtgtcattc tattctgggg ggtggggtgg ggcaggacag caagggggag   5700
gattgggaag acaatagcag gcatgctggg gatgcggtgg gctctatggg tacccaggtg   5760
ctgaagaatt gacccggttc ctcctgggcc agaaagaagc aggcacatcc ccttctctgt   5820
gacacaccct gtccacgccc ctggttctta gttccagccc cactcatagg acactcatag   5880
```

-continued

```
ctcaggaggg ctccgccttc aatcccaccc gctaaagtac ttggagcggt ctctccctcc   5940
ctcatcagcc caccaaacca aacctagcct ccaagagtgg gaagaaatta aagcaagata   6000
ggctattaag tgcagaggga gagaaaatgc ctccaacatg tgaggaagta atgagagaaa   6060
tcatagaatt ttaaggccat gatttaaggc catcatggcc taagcttgaa aggagatagg   6120
atcaaagctt ggcgtaatca tggtcatagc tgtttcctgt gtgaaattgt tatccgctca   6180
caattccaca caacatacga gccggaagca taaagtgtaa agcctggggt gcctaatgag   6240
tgagctaact cacattaatt gcgttgcgct cactgcccgc tttccagtcg ggaaacctgt   6300
cgtgccagct gcattaatga atcggccaac gcgcggggag aggcggtttg cgtattgggc   6360
gctcttccgc ttcctcgctc actgactcgc tgcgctcggt cgttcggctg cggcgagcgg   6420
tatcagctca ctcaaaggcg gtaatacggt tatccacaga atcaggggat aacgcaggaa   6480
agaacatgtg agcaaaaggc cagcaaaagg ccaggaaccg taaaaaggcc gcgttgctgg   6540
cgtttttcca taggctccgc ccccctgacg agcatcacaa aaatcgacgc tcaagtcaga   6600
ggtggcgaaa cccgacagga ctataaagat accaggcgtt tccccctgga agctccctcg   6660
tgcgctctcc tgttccgacc ctgccgctta ccggatacct gtccgccttt ctcccttcgg   6720
gaagcgtggc gctttctcat agctcacgct gtaggtatct cagttcggtg taggtcgttc   6780
gctccaagct gggctgtgtg cacgaacccc ccgttcagcc cgaccgctgc gccttatccg   6840
gtaactatcg tcttgagtcc aacccggtaa gacacgactt atcgccactg gcagcagcca   6900
ctggtaacag gattagcaga gcgaggtatg taggcggtgc tacagagttc ttgaagtggt   6960
ggcctaacta cggctacact agaagaacag tatttggtat ctgcgctctg ctgaagccag   7020
ttaccttcgg aaaaagagtt ggtagctctt gatccggcaa acaaaccacc gctggtagcg   7080
gtggtttttt tgtttgcaag cagcagatta cgcgcagaaa aaaaggatct caagaagatc   7140
ctttgatctt ttctacgggg tctgacgctc agtggaacga aaactcacgt taagggattt   7200
tggtcatgag attatcaaaa aggatcttca cctagatcct tttaaattaa aaatgaagtt   7260
ttaaatcaat ctaaagtata tatgagtaaa cttggtctga cagttaccaa tgcttaatca   7320
gtgaggcacc tatctcagcg atctgtctat ttcgttcatc catagttgcc tgactccccg   7380
tcgtgtagat aactacgata cgggagggct taccatctgg ccccagtgct gcaatgatac   7440
cgcgagaacc acgctcaccg gctccagatt tatcagcaat aaaccagcca gccggaaggg   7500
ccgagcgcag aagtggtcct gcaactttat ccgcctccat ccagtctatt aattgttgcc   7560
gggaagctag agtaagtagt tcgccagtta atagtttgcg caacgttgtt gccattgcta   7620
caggcatcgt ggtgtcacgc tcgtcgtttg gtatggcttc attcagctcc ggttcccaac   7680
gatcaaggcg agttacatga tcccccatgt tgtgcaaaaa agcggttagc tccttcggtc   7740
ctccgatcgt tgtcagaagt aagttggccg cagtgttatc actcatggtt atggcagcac   7800
tgcataattc tcttactgtc atgccatccg taagatgctt ttctgtgact ggtgagtact   7860
caaccaagtc attctgagaa tagtgtatgc ggcgaccgag ttgctcttgc ccggcgtcaa   7920
tacgggataa taccgcgcca catagcagaa ctttaaaagt gctcatcatt ggaaaacgtt   7980
cttcggggcg aaaactctca aggatcttac cgctgttgag atccagttcg atgtaaccca   8040
ctcgtgcacc caactgatct tcagcatctt ttactttcac cagcgtttct gggtgagcaa   8100
aaacaggaag gcaaaatgcc gcaaaaaagg gaataagggc gacacggaaa tgttgaatac   8160
tcatactctt cctttttcaa tattattgaa gcatttatca gggttattgt ctcatgagcg   8220
```

```
gatacatatt tgaatgtatt tagaaaaata aacaaatagg ggttccgcgc acatttcccc   8280

gaaaagtgcc acctgacgtc taagaaacca ttattatcat gacattaacc tataaaaata   8340

ggcgtatcac gaggcccttt cgggtcgcgc gtttcggtga tgacggtgaa aacctctgac   8400

acatgcagct cccgttgacg gtcacagctt gtctgtaagc ggatgccggg agcagacaag   8460

cccgtcaggg cgcgtcagcg ggtgttggcg ggtgtcgggg ctggcttaac tatgcggcat   8520

cagagcagat tgtactgaga gtgcaccata aaattgtaaa cgttaatatt ttgttaaaat   8580

tcgcgttaaa tttttgttaa atcagctcat tttttaacca ataggccgaa atcggcaaaa   8640

tcccttataa atcaaaagaa tagcccgaga tagggttgag tgttgttcca gtttggaaca   8700

agagtccact attaaagaac gtggactcca acgtcaaagg gcgaaaaacc gtctatcagg   8760

gcgatggccc actacgtgaa ccatcaccca aatcaagttt tttggggtcg aggtgccgta   8820

aagcactaaa tcggaaccct aaagggagcc cccgatttag agcttgacgg ggaaagccgg   8880

cgaacgtggc gagaaaggaa gggaagaaag cgaaaggagc gggcgctagg gcgctggcaa   8940

gtgtagcggt cacgctgcgc gtaaccacca cacccgccgc gcttaatgcg ccgctacagg   9000

gcgcgtacta tggttgcttt gacgtatgcg gtgtgaaata ccgcacagat gcgtaaggag   9060

aaaataccgc atcaggcgcc attcgccatt caggctgcgc aactgttggg aagggcgatc   9120

ggtgcgggcc tcttcgctat tacgccagct ggcgaaaggg ggatgtgctg caaggcgatt   9180

aagttgggta acgccagggt tttcccagtc acgacgttgt aaaacgacgg ccagtgaatt   9240

ccatggtctc aactttc                                                  9257
```

<210> SEQ ID NO 88
<211> LENGTH: 1398
<212> TYPE: PRT
<213> ORGANISM: Artificial Sequence
<220> FEATURE:
<223> OTHER INFORMATION: Synthetic CHIKV viral structural protein containing mouse IL-2 (F54A) antigen in E3

<400> SEQUENCE: 88

```
Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Arg Gln Lys Lys Gln Ala Pro Gln Asn Asp
65                  70                  75                  80

Pro Lys Gln Lys Lys Gln Pro Pro Gln Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Met Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175
```

-continued

```
Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Leu Pro Val Leu Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Ser Thr Leu Arg Met Leu Glu Asp Asn Val Met
    290                 295                 300

Arg Pro Gly Tyr Tyr Gln Leu Leu Lys Ala Ser Leu Thr Cys Ser Pro
305                 310                 315                 320

His Ser Gly Gly Ala Pro Thr Ser Ser Ser Thr Ser Ser Ser Thr Ala
                325                 330                 335

Glu Ala Gln Gln Gln Gln Gln Gln Gln Gln Gln Gln Gln His Leu Glu
            340                 345                 350

Gln Leu Leu Met Asp Leu Gln Glu Leu Leu Ser Arg Met Glu Asn Tyr
        355                 360                 365

Arg Asn Leu Lys Leu Pro Arg Met Leu Thr Ala Lys Phe Tyr Leu Pro
    370                 375                 380

Lys Gln Ala Thr Glu Leu Lys Asp Leu Gln Cys Leu Glu Asp Glu Leu
385                 390                 395                 400

Gly Pro Leu Arg His Val Leu Asp Leu Thr Gln Ser Lys Ser Phe Gln
                405                 410                 415

Leu Glu Asp Ala Glu Asn Phe Ile Ser Asn Ile Arg Val Thr Val Val
            420                 425                 430

Lys Leu Lys Gly Ser Asp Asn Thr Phe Glu Cys Gln Phe Asp Asp Glu
        435                 440                 445

Ser Ala Thr Val Val Asp Phe Leu Arg Arg Trp Ile Ala Phe Cys Gln
    450                 455                 460

Ser Ile Ile Ser Thr Ser Pro Gln Gly Gly Ser Ser Thr Lys Asp Asn
465                 470                 475                 480

Phe Asn Val Tyr Lys Ala Thr Arg Pro Tyr Leu Ala His Cys Pro Asp
                485                 490                 495

Cys Gly Glu Gly His Ser Cys His Ser Pro Ile Ala Leu Glu Arg Ile
            500                 505                 510

Arg Asn Glu Ala Thr Asp Gly Thr Leu Lys Ile Gln Val Ser Leu Gln
        515                 520                 525

Ile Gly Ile Lys Thr Asp Asp Ser His Asp Trp Thr Lys Leu Arg Tyr
    530                 535                 540

Met Asp Ser His Thr Pro Ala Asp Ala Glu Arg Ala Gly Leu Leu Val
545                 550                 555                 560

Arg Thr Ser Ala Pro Cys Thr Ile Thr Gly Thr Met Gly His Phe Ile
                565                 570                 575

Leu Ala Arg Cys Pro Lys Gly Glu Thr Leu Thr Val Gly Phe Thr Asp
            580                 585                 590
```

```
Ser Arg Lys Ile Ser His Thr Cys Thr His Pro Phe His His Glu Pro
        595                 600                 605

Pro Val Ile Gly Arg Glu Arg Phe His Ser Arg Pro Gln His Gly Lys
    610                 615                 620

Glu Leu Pro Cys Ser Thr Tyr Val Gln Ser Thr Ala Ala Thr Ala Glu
625                 630                 635                 640

Glu Ile Glu Val His Met Pro Pro Asp Thr Pro Asp Arg Thr Leu Met
                645                 650                 655

Thr Gln Gln Ser Gly Asn Val Lys Ile Thr Val Asn Gly Gln Thr Val
            660                 665                 670

Arg Tyr Lys Cys Asn Cys Gly Gly Ser Asn Glu Gly Leu Thr Thr Thr
        675                 680                 685

Asp Lys Val Ile Asn Asn Cys Lys Ile Asp Gln Cys His Ala Ala Val
    690                 695                 700

Thr Asn His Lys Asn Trp Gln Tyr Asn Ser Pro Leu Val Pro Arg Asn
705                 710                 715                 720

Ala Glu Leu Gly Asp Arg Lys Gly Lys Ile His Ile Pro Phe Pro Leu
                725                 730                 735

Ala Asn Val Thr Cys Arg Val Pro Lys Ala Arg Asn Pro Thr Val Thr
            740                 745                 750

Tyr Gly Lys Asn Gln Val Thr Met Leu Leu Tyr Pro Asp His Pro Thr
        755                 760                 765

Leu Leu Ser Tyr Arg Asn Met Gly Gln Glu Pro Asn Tyr His Glu Glu
    770                 775                 780

Trp Val Thr His Lys Lys Glu Val Thr Leu Thr Val Pro Thr Glu Gly
785                 790                 795                 800

Leu Glu Val Thr Trp Gly Asn Asn Glu Pro Tyr Lys Tyr Trp Pro Gln
                805                 810                 815

Met Ser Thr Asn Gly Thr Ala His Gly His Pro His Glu Ile Ile Leu
            820                 825                 830

Tyr Tyr Tyr Glu Leu Tyr Pro Thr Met Thr Val Val Ile Val Ser Val
        835                 840                 845

Ala Ser Phe Val Leu Leu Ser Met Val Gly Thr Ala Val Gly Met Cys
    850                 855                 860

Val Cys Ala Arg Arg Arg Cys Ile Thr Pro Tyr Glu Leu Thr Pro Gly
865                 870                 875                 880

Ala Thr Val Pro Phe Leu Leu Ser Leu Leu Cys Cys Val Arg Thr Thr
                885                 890                 895

Lys Ala Ala Thr Tyr Tyr Glu Ala Ala Ala Tyr Leu Trp Asn Glu Gln
            900                 905                 910

Gln Pro Leu Phe Trp Leu Gln Ala Leu Ile Pro Leu Ala Ala Leu Ile
        915                 920                 925

Val Leu Cys Asn Cys Leu Lys Leu Leu Pro Cys Cys Cys Lys Thr Leu
    930                 935                 940

Ala Phe Leu Ala Val Met Ser Ile Gly Ala His Thr Val Ser Ala Tyr
945                 950                 955                 960

Glu His Val Thr Val Ile Pro Asn Thr Val Gly Val Pro Tyr Lys Thr
                965                 970                 975

Leu Val Asn Arg Pro Gly Tyr Ser Pro Met Val Leu Glu Met Glu Leu
            980                 985                 990

Gln Ser Val Thr Leu Glu Pro Thr  Leu Ser Leu Asp Tyr  Ile Thr Cys
        995                 1000                1005

Glu Tyr  Lys Thr Val Ile Pro  Ser Pro Tyr Val Lys  Cys Cys Gly
```

-continued

```
    1010                1015                1020

Thr Ala  Glu Cys Lys Asp Lys  Ser Leu Pro Asp Tyr  Ser Cys Lys
    1025                1030                1035

Val Phe  Thr Gly Val Tyr Pro  Phe Met Trp Gly Gly  Ala Tyr Cys
    1040                1045                1050

Phe Cys  Asp Ala Glu Asn Thr  Gln Leu Ser Glu Ala  His Val Glu
    1055                1060                1065

Lys Ser  Glu Ser Cys Lys Thr  Glu Phe Ala Ser Ala  Tyr Arg Ala
    1070                1075                1080

His Thr  Ala Ser Ala Ser Ala  Lys Leu Arg Val Leu  Tyr Gln Gly
    1085                1090                1095

Asn Asn  Ile Thr Val Ala Ala  Tyr Ala Asn Gly Asp  His Ala Val
    1100                1105                1110

Thr Val  Lys Asp Ala Lys Phe  Val Val Gly Pro Met  Ser Ser Ala
    1115                1120                1125

Trp Thr  Pro Phe Asp Asn Lys  Ile Val Val Tyr Lys  Gly Asp Val
    1130                1135                1140

Tyr Asn  Met Asp Tyr Pro Pro  Phe Gly Ala Gly Arg  Pro Gly Gln
    1145                1150                1155

Phe Gly  Asp Ile Gln Ser Arg  Thr Pro Glu Ser Lys  Asp Val Tyr
    1160                1165                1170

Ala Asn  Thr Gln Leu Val Leu  Gln Arg Pro Ala Ala  Gly Thr Val
    1175                1180                1185

His Val  Pro Tyr Ser Gln Ala  Pro Ser Gly Phe Lys  Tyr Trp Leu
    1190                1195                1200

Lys Glu  Arg Gly Ala Ser Leu  Gln His Thr Ala Pro  Phe Gly Cys
    1205                1210                1215

Gln Ile  Ala Thr Asn Pro Val  Arg Ala Val Asn Cys  Ala Val Gly
    1220                1225                1230

Asn Ile  Pro Ile Ser Ile Asp  Ile Pro Asp Ala Ala  Phe Thr Arg
    1235                1240                1245

Val Val  Asp Ala Pro Ser Val  Thr Asp Met Ser Cys  Glu Val Pro
    1250                1255                1260

Ala Cys  Thr His Ser Ser Asp  Phe Gly Gly Val Ala  Ile Ile Lys
    1265                1270                1275

Tyr Thr  Ala Ser Lys Lys Gly  Lys Cys Ala Val His  Ser Met Thr
    1280                1285                1290

Asn Ala  Val Thr Ile Arg Glu  Ala Asp Val Glu Val  Glu Gly Asn
    1295                1300                1305

Ser Gln  Leu Gln Ile Ser Phe  Ser Thr Ala Leu Ala  Ser Ala Glu
    1310                1315                1320

Phe Arg  Val Gln Val Cys Ser  Thr Gln Val His Cys  Ala Ala Ala
    1325                1330                1335

Cys His  Pro Pro Lys Asp His  Ile Val Asn Tyr Pro  Ala Ser His
    1340                1345                1350

Thr Thr  Leu Gly Val Gln Asp  Ile Ser Thr Thr Ala  Met Ser Trp
    1355                1360                1365

Val Gln  Lys Ile Thr Gly Gly  Val Gly Leu Ile Val  Ala Val Ala
    1370                1375                1380

Ala Leu  Ile Leu Ile Val Val  Leu Cys Val Ser Phe  Ser Arg His
    1385                1390                1395
```

<210> SEQ ID NO 89

```
<211> LENGTH: 9257
<212> TYPE: DNA
<213> ORGANISM: Artificial Sequence
<220> FEATURE:
<223> OTHER INFORMATION: Synthetic Expression vector for CHIKV viral
      structural protein containing mouse IL-2 (D34K) antigen in E3

<400> SEQUENCE: 89

gaattcccat tgcatacgtt gtatccatat cataatatgt acatttatat tggctcatgt     60
ccaacattac cgccatgttg acattgatta ttgactagtt attaatagta atcaattacg    120
gggtcattag ttcatagccc atatatggag ttccgcgtta cataacttac ggtaaatggc    180
ccgcctggct gaccgcccaa cgacccccgc ccattgacgt caataatgac gtatgttccc    240
atagtaacgc caatagggac tttccattga cgtcaatggg tggagtattt acggtaaact    300
gcccacttgg cagtacatca agtgtatcat atgccaagta cgccccctat tgacgtcaat    360
gacggtaaat ggcccgcctg gcattatgcc cagtacatga ccttatggga ctttcctact    420
tggcagtaca tctacgtatt agtcatcgct attaccatgg tgatgcggtt ttggcagtac    480
atcaatgggc gtggatagcg gtttgactca cggggatttc caagtctcca ccccattgac    540
gtcaatggga gtttgttttg gcaccaaaat caacgggact ttccaaaatg tcgtaacaac    600
tccgccccat tgacgcaaat gggcggtagg cgtgtacggt gggaggtcta tataagcaga    660
gctcgtttag tgaaccgtca gatcgcctgg agacgccatc cacgctgttt tgacctccat    720
agaagacacc gggaccgatc cagcctccgt taacggtgga gggcagtgta gtctgagcag    780
tactcgttgc tgccgcgcgc gccaccagac ataatagctg acagactaac agactgttcc    840
tttgcggccg ctctagacac catggagttc atcccgacgc aaactttcta taacagaagg    900
taccaacccc gaccctgggc cccacgccct acaattcaag taattagacc tagaccacgt    960
ccacagaggc aggctgggca actcgcccag ctgatctccg cagtcaacaa attgaccatg   1020
cgcgcggtac ctcaacagaa gcctcgcaga aatcggaaaa acaagaagca aaggcagaag   1080
aagcaggcgc cgcaaaacga cccaaagcaa aagaagcaac caccacaaaa gaagccggct   1140
caaaagaaga agaaaccagg ccgtagggag agaatgtgca tgaaaattga aaatgattgc   1200
atcttcgaag tcaagcatga aggcaaagtg atgggctacg catgcctggt gggggataaa   1260
gtaatgaaac cagcacatgt gaagggaact atcgacaatg ccgatctggc taaactggcc   1320
tttaagcggt cgtctaaata cgatcttgaa tgtgcacaga taccggtgca catgaagtct   1380
gatgcctcga agtttaccca cgagaaaccc gaggggtact ataactggca tcacggagca   1440
gtgcagtatt caggaggccg gttcactatc ccgacgggtg caggcaagcc gggagacagc   1500
ggcagaccga tcttcgacaa caaaggacgg gtggtggcca tcgtcctagg aggggccaac   1560
gaaggtgccc gcacggccct ctccgtggtg acgtggaaca aagacatcgt cacaaaaatt   1620
acccctgagg gagccgaaga gtggagcctc gccctcccgg tcttgtgcct gttggcaaac   1680
actacattcc cctgctctca gccgccttgc acaccctgct gctacgaaaa ggaaccggaa   1740
agcaccttgc gcatgcttga ggacaacgtg atgagacccg gatactacca gctactaaaa   1800
gcatcgctga cttgctctcc ccactccgga ggggcaccca cttcaagctc cacttcaagc   1860
tctacagcgg aagcacagca gcagcagcag cagcagcagc agcagcagca cctggagcag   1920
ctgttgatga agctacagga gctcctgagc aggatggaga attacaggaa cctgaaactc   1980
cccaggatgc tcaccttcaa attttacttg cccaagcagg ccacagaatt gaaagatctt   2040
cagtgcctag aagatgaact tggacctctg cggcatgttc tggatttgac tcaaagcaaa   2100
```

-continued

```
agctttcaat tggaagatgc tgagaatttc atcagcaata tcagagtaac tgttgtaaaa   2160
ctaaagggct ctgacaacac atttgagtgc caattcgatg atgagtcagc aactgtggtg   2220
gactttctga ggagatggat agccttctgt caaagcatca tctcaacaag ccctcaaggg   2280
ggatccagta ctaaggacaa ttttaatgtc tataaagcca caagaccata tctagctcat   2340
tgtcctgact gcggagaagg gcattcgtgc cacagcccta tcgcattgga gcgcatcaga   2400
aatgaagcaa cggacggaac gctgaaaatc caggtctctt tgcagatcgg gataaagaca   2460
gatgacagcc acgattggac caagctgcgc tatatggata gccatacgcc cgcggacgcg   2520
gagcgagccg gattgcttgt aaggacttca gcaccgtgca cgatcaccgg gaccatggga   2580
cactttattc tcgcccgatg cccgaaagga gagacgctga cagtgggatt tacggacagc   2640
agaaagatca gccacacatg cacacacccg ttccatcatg aaccacctgt gataggtagg   2700
gagaggttcc actctcgacc acaacatggt aaagagttac cttgcagcac gtacgtgcag   2760
agcaccgctg ccactgctga ggagatagag gtgcatatgc cccagatac tcctgaccgc   2820
acgctgatga cgcagcagtc tggcaacgtg aagatcacag ttaatgggca gacggtgcgg   2880
tacaagtgca actgcggtgg ctcaaacgag ggactgacaa ccacagacaa agtgatcaat   2940
aactgcaaaa ttgatcagtg ccatgctgca gtcactaatc acaagaattg gcaatacaac   3000
tcccctttag tcccgcgcaa cgctgaactc ggggaccgta aaggaaagat ccacatccca   3060
ttcccattgg caaacgtgac ttgcagagtg ccaaaagcaa gaaaccctac agtaacttac   3120
ggaaaaaacc aagtcaccat gctgctgtat cctgaccatc cgacactctt gtcttaccgt   3180
aacatgggac aggaaccaaa ttaccacgag gagtgggtga cacacaagaa ggaggttacc   3240
ttgaccgtgc ctactgaggg tctggaggtc acttggggca acaacgaacc atacaagtac   3300
tggccgcaga tgtctacgaa cggtactgct catggtcacc cacatgagat aatcttgtac   3360
tattatgagc tgtaccccac tatgactgta gtcattgtgt cggtggcctc gttcgtgctt   3420
ctgtcgatgg tgggcacagc agtgggaatg tgtgtgtgcg cacggcgcag atgcattaca   3480
ccatatgaat taacaccagg agccactgtt cccttcctgc tcagcctgct atgctgcgtc   3540
agaacgacca aggcggccac atattacgag gctgcggcat atctatggaa cgaacagcag   3600
cccctgttct ggttgcaggc tcttatcccg ctggccgcct tgatcgtcct gtgcaactgt   3660
ctgaaactct tgccatgctg ctgtaagacc ctggcttttt tagccgtaat gagcatcggt   3720
gcccacactg tgagcgcgta cgaacacgta acagtgatcc cgaacacggt gggagtaccg   3780
tataagactc ttgtcaacag accgggttac agccccatgg tgttggagat ggagctacaa   3840
tcagtcacct tggaaccaac actgtcactt gactacatca cgtgcgagta caaaactgtc   3900
atcccctccc cgtacgtgaa gtgctgtggt acagcagagt gcaaggacaa gagcctacca   3960
gactacagct gcaaggtctt tactggagtc tacccattta tgtggggcgg cgcctactgc   4020
ttttgcgacg ccgaaaatac gcaattgagc gaggcacatg tagagaaatc tgaatcttgc   4080
aaaacagagt ttgcatcggc ctacagagcc cacaccgcat cggcgtcggc gaagctccgc   4140
gtcctttacc aaggaaacaa cattaccgta gctgcctacg ctaacggtga ccatgccgtc   4200
acagtaaagg acgccaagtt tgtcgtgggc ccaatgtcct ccgcctggac accttttgac   4260
aacaaaatcg tggtgtacaa aggcgacgtc tacaacatgg actacccacc ttttggcgca   4320
ggaagaccag gacaatttgg tgacattcaa agtcgtacac cggaaagtaa agacgtttat   4380
gccaacactc agttggtact acagaggcca gcagcaggca cggtacatgt accatactct   4440
caggcaccat ctggcttcaa gtattggctg aaggaacgag gagcatcgct acagcacacg   4500
```

-continued gcaccgttcg gttgccagat tgcgacaaac ccggtaagag ctgtaaattg cgctgtgggg 4560
aacataccaa tttccatcga cataccggat gcggccttta ctagggttgt cgatgcaccc 4620
tctgtaacgg acatgtcatg cgaagtacca gcctgcactc actcctccga ctttgggggc 4680
gtcgccatca tcaaatacac agctagcaag aaaggtaaat gtgcagtaca ttcgatgacc 4740
aacgccgtta ccattcgaga agccgacgta gaagtagagg ggaactccca gctgcaaata 4800
tccttctcaa cagccctggc aagcgccgag tttcgcgtgc aagtgtgctc cacacaagta 4860
cactgcgcag ccgcatgcca ccctccaaag gaccacatag tcaattaccc agcatcacac 4920
accacccttg ggtccagga tatatccaca acggcaatgt cttgggtgca gaagattacg 4980
ggaggagtag gattaattgt tgctgttgct gccttaattt taattgtggt gctatgcgtg 5040
tcgtttagca ggcactaatg atccggaggg gcacccactt caagctccac ttcaagctct 5100
acagcggaag cacagcagca gcagcagcag cagcagcagc agcagcacct ggagcagctg 5160
ttgatggacc tacaggagct cctgagcagg atggagaatt acaggaacct gaaactcccc 5220
aggatgctca ccttcaaatt ttacttgccc aagcaggcca cagaattgaa agatcttcag 5280
tgcctagaag atgaacttgg acctctgcgg catgttctgg atttgactca aagcaaaagc 5340
tttcaattgg aagatgctga gaatttcatc agcaatatca gagtaactgt tgtaaaacta 5400
aagggctctg acaacacatt tgagtgccaa ttcgatgatg agtcagcaac tgtggtggac 5460
tttctgagga gatggatagc cttctgtcaa agcatcatct caacaagccc tcaaggggga 5520
tccgctgtgc cttctagttg ccagccatct gttgtttgcc cctcccccgt gccttccttg 5580
accctggaag gtgccactcc cactgtcctt tcctaataaa atgaggaaat tgcatcgcat 5640
tgtctgagta ggtgtcattc tattctgggg ggtggggtgg ggcaggacag caagggggag 5700
gattgggaag acaatagcag gcatgctggg gatgcggtgg gctctatggg tacccaggtg 5760
ctgaagaatt gacccggttc ctcctgggcc agaaagaagc aggcacatcc ccttctctgt 5820
gacacaccct gtccacgccc ctggttctta gttccagccc cactcatagg acactcatag 5880
ctcaggaggg ctccgccttc aatcccaccc gctaaagtac ttggagcggt ctctccctcc 5940
ctcatcagcc caccaaacca aacctagcct ccaagagtgg gaagaaatta aagcaagata 6000
ggctattaag tgcagaggga gagaaaatgc ctccaacatg tgaggaagta atgagagaaa 6060
tcatagaatt ttaaggccat gatttaaggc catcatggcc taagcttgaa aggagatagg 6120
atcaaagctt ggcgtaatca tggtcatagc tgtttcctgt gtgaaattgt tatccgctca 6180
caattccaca caacatacga gccggaagca taaagtgtaa agcctggggt gcctaatgag 6240
tgagctaact cacattaatt gcgttgcgct cactgcccgc tttccagtcg ggaaacctgt 6300
cgtgccagct gcattaatga atcggccaac gcgcggggag aggcggtttg cgtattgggc 6360
gctcttccgc ttcctcgctc actgactcgc tgcgctcggt cgttcggctg cggcgagcgg 6420
tatcagctca ctcaaaggcg gtaatacggt tatccacaga atcaggggat aacgcaggaa 6480
agaacatgtg agcaaaaggc cagcaaaagg ccaggaaccg taaaaaggcc gcgttgctgg 6540
cgtttttcca taggctccgc ccccctgacg agcatcacaa aaatcgacgc tcaagtcaga 6600
ggtggcgaaa cccgacagga ctataaagat accaggcgtt tccccctgga agctccctcg 6660
tgcgctctcc tgttccgacc ctgccgctta ccggatacct gtccgccttt ctcccttcgg 6720
gaagcgtggc gctttctcat agctcacgct gtaggtatct cagttcggtg taggtcgttc 6780
gctccaagct gggctgtgtg cacgaacccc ccgttcagcc cgaccgctgc gccttatccg 6840
gtaactatcg tcttgagtcc aacccggtaa gacacgactt atcgccactg gcagcagcca 6900
ctggtaacag gattagcaga gcgaggtatg taggcggtgc tacagagttc ttgaagtggt 6960
ggcctaacta cggctacact agaagaacag tatttggtat ctgcgctctg ctgaagccag 7020
ttaccttcgg aaaaagagtt ggtagctctt gatccggcaa acaaaccacc gctggtagcg 7080
gtggtttttt tgtttgcaag cagcagatta cgcgcagaaa aaaaggatct caagaagatc 7140
ctttgatctt ttctacgggg tctgacgctc agtggaacga aaactcacgt taagggattt 7200
tggtcatgag attatcaaaa aggatcttca cctagatcct tttaaattaa aaatgaagtt 7260
ttaaatcaat ctaaagtata tatgagtaaa cttggtctga cagttaccaa tgcttaatca 7320
gtgaggcacc tatctcagcg atctgtctat ttcgttcatc catagttgcc tgactccccg 7380
tcgtgtagat aactacgata cgggagggct taccatctgg ccccagtgct gcaatgatac 7440
cgcgagaacc acgctcaccg gctccagatt tatcagcaat aaaccagcca gccggaaggg 7500
ccgagcgcag aagtggtcct gcaactttat ccgcctccat ccagtctatt aattgttgcc 7560
gggaagctag agtaagtagt tcgccagtta atagtttgcg caacgttgtt gccattgcta 7620
caggcatcgt ggtgtcacgc tcgtcgtttg gtatggcttc attcagctcc ggttcccaac 7680
gatcaaggcg agttacatga tcccccatgt tgtgcaaaaa agcggttagc tccttcggtc 7740
ctccgatcgt tgtcagaagt aagttggccg cagtgttatc actcatggtt atggcagcac 7800
tgcataattc tcttactgtc atgccatccg taagatgctt ttctgtgact ggtgagtact 7860
caaccaagtc attctgagaa tagtgtatgc ggcgaccgag ttgctcttgc ccggcgtcaa 7920
tacgggataa taccgcgcca catagcagaa ctttaaaagt gctcatcatt ggaaaacgtt 7980
cttcggggcg aaaactctca aggatcttac cgctgttgag atccagttcg atgtaaccca 8040
ctcgtgcacc caactgatct tcagcatctt ttactttcac cagcgtttct gggtgagcaa 8100
aaacaggaag gcaaaatgcc gcaaaaaagg gaataagggc gacacggaaa tgttgaatac 8160
tcatactctt cctttttcaa tattattgaa gcatttatca gggttattgt ctcatgagcg 8220
gatacatatt tgaatgtatt tagaaaaata aacaaatagg ggttccgcgc acatttcccc 8280
gaaaagtgcc acctgacgtc taagaaacca ttattatcat gacattaacc tataaaaata 8340
ggcgtatcac gaggcccttt cgggtcgcgc gtttcggtga tgacggtgaa aacctctgac 8400
acatgcagct cccgttgacg gtcacagctt gtctgtaagc ggatgccggg agcagacaag 8460
cccgtcaggg cgcgtcagcg ggtgttggcg ggtgtcgggg ctggcttaac tatgcggcat 8520
cagagcagat tgtactgaga gtgcaccata aaattgtaaa cgttaatatt ttgttaaaat 8580
tcgcgttaaa tttttgttaa atcagctcat tttttaacca ataggccgaa atcggcaaaa 8640
tcccttataa atcaaaagaa tagcccgaga tagggttgag tgttgttcca gtttggaaca 8700
agagtccact attaaagaac gtggactcca acgtcaaagg gcgaaaaacc gtctatcagg 8760
gcgatggccc actacgtgaa ccatcaccca aatcaagttt tttggggtcg aggtgccgta 8820
aagcactaaa tcggaaccct aaagggagcc cccgatttag agcttgacgg ggaaagccgg 8880
cgaacgtggc gagaaaggaa gggaagaaag cgaaaggagc gggcgctagg gcgctggcaa 8940
gtgtagcggt cacgctgcgc gtaaccacca cacccgccgc gcttaatgcg ccgctacagg 9000
gcgcgtacta tggttgcttt gacgtatgcg gtgtgaaata ccgcacagat gcgtaaggag 9060
aaaataccgc atcaggcgcc attcgccatt caggctgcgc aactgttggg aagggcgatc 9120
ggtgcgggcc tcttcgctat tacgccagct ggcgaaaggg ggatgtgctg caaggcgatt 9180
aagttgggta acgccagggt tttcccagtc acgacgttgt aaaacgacgg ccagtgaatt 9240
ccatggtctc aactttc 9257

<210> SEQ ID NO 90
<211> LENGTH: 1398
<212> TYPE: PRT
<213> ORGANISM: Artificial Sequence
<220> FEATURE:
<223> OTHER INFORMATION: Synthetic CHIKV viral structural protein containing mouse IL-2 (D34K) antigen in E3

<400> SEQUENCE: 90

Met Glu Phe Ile Pro Thr Gln Thr Phe Tyr Asn Arg Arg Tyr Gln Pro
1 5 10 15

Arg Pro Trp Ala Pro Arg Pro Thr Ile Gln Val Ile Arg Pro Arg Pro
20 25 30

Arg Pro Gln Arg Gln Ala Gly Gln Leu Ala Gln Leu Ile Ser Ala Val
35 40 45

Asn Lys Leu Thr Met Arg Ala Val Pro Gln Gln Lys Pro Arg Arg Asn
50 55 60

Arg Lys Asn Lys Lys Gln Arg Gln Lys Lys Gln Ala Pro Gln Asn Asp
65 70 75 80

Pro Lys Gln Lys Lys Gln Pro Pro Gln Lys Lys Pro Ala Gln Lys Lys
85 90 95

Lys Lys Pro Gly Arg Arg Glu Arg Met Cys Met Lys Ile Glu Asn Asp
100 105 110

Cys Ile Phe Glu Val Lys His Glu Gly Lys Val Met Gly Tyr Ala Cys
115 120 125

Leu Val Gly Asp Lys Val Met Lys Pro Ala His Val Lys Gly Thr Ile
130 135 140

Asp Asn Ala Asp Leu Ala Lys Leu Ala Phe Lys Arg Ser Ser Lys Tyr
145 150 155 160

Asp Leu Glu Cys Ala Gln Ile Pro Val His Met Lys Ser Asp Ala Ser
165 170 175

Lys Phe Thr His Glu Lys Pro Glu Gly Tyr Tyr Asn Trp His His Gly
180 185 190

Ala Val Gln Tyr Ser Gly Gly Arg Phe Thr Ile Pro Thr Gly Ala Gly
195 200 205

Lys Pro Gly Asp Ser Gly Arg Pro Ile Phe Asp Asn Lys Gly Arg Val
210 215 220

Val Ala Ile Val Leu Gly Gly Ala Asn Glu Gly Ala Arg Thr Ala Leu
225 230 235 240

Ser Val Val Thr Trp Asn Lys Asp Ile Val Thr Lys Ile Thr Pro Glu
245 250 255

Gly Ala Glu Glu Trp Ser Leu Ala Leu Pro Val Leu Cys Leu Leu Ala
260 265 270

Asn Thr Thr Phe Pro Cys Ser Gln Pro Pro Cys Thr Pro Cys Cys Tyr
275 280 285

Glu Lys Glu Pro Glu Ser Thr Leu Arg Met Leu Glu Asp Asn Val Met
290 295 300

Arg Pro Gly Tyr Tyr Gln Leu Leu Lys Ala Ser Leu Thr Cys Ser Pro
305 310 315 320

His Ser Gly Gly Ala Pro Thr Ser Ser Ser Thr Ser Ser Ser Thr Ala
325 330 335

Glu Ala Gln Gln Gln Gln Gln Gln Gln Gln Gln Gln Gln His Leu Glu
340 345 350

-continued

```
Gln Leu Leu Met Lys Leu Gln Glu Leu Leu Ser Arg Met Glu Asn Tyr
        355                 360                 365

Arg Asn Leu Lys Leu Pro Arg Met Leu Thr Phe Lys Phe Tyr Leu Pro
    370                 375                 380

Lys Gln Ala Thr Glu Leu Lys Asp Leu Gln Cys Leu Glu Asp Glu Leu
385                 390                 395                 400

Gly Pro Leu Arg His Val Leu Asp Leu Thr Gln Ser Lys Ser Phe Gln
                405                 410                 415

Leu Glu Asp Ala Glu Asn Phe Ile Ser Asn Ile Arg Val Thr Val Val
            420                 425                 430

Lys Leu Lys Gly Ser Asp Asn Thr Phe Glu Cys Gln Phe Asp Asp Glu
        435                 440                 445

Ser Ala Thr Val Val Asp Phe Leu Arg Arg Trp Ile Ala Phe Cys Gln
    450                 455                 460

Ser Ile Ile Ser Thr Ser Pro Gln Gly Gly Ser Ser Thr Lys Asp Asn
465                 470                 475                 480

Phe Asn Val Tyr Lys Ala Thr Arg Pro Tyr Leu Ala His Cys Pro Asp
                485                 490                 495

Cys Gly Glu Gly His Ser Cys His Ser Pro Ile Ala Leu Glu Arg Ile
            500                 505                 510

Arg Asn Glu Ala Thr Asp Gly Thr Leu Lys Ile Gln Val Ser Leu Gln
        515                 520                 525

Ile Gly Ile Lys Thr Asp Asp Ser His Asp Trp Thr Lys Leu Arg Tyr
    530                 535                 540

Met Asp Ser His Thr Pro Ala Asp Ala Glu Arg Ala Gly Leu Leu Val
545                 550                 555                 560

Arg Thr Ser Ala Pro Cys Thr Ile Thr Gly Thr Met Gly His Phe Ile
                565                 570                 575

Leu Ala Arg Cys Pro Lys Gly Glu Thr Leu Thr Val Gly Phe Thr Asp
            580                 585                 590

Ser Arg Lys Ile Ser His Thr Cys Thr His Pro Phe His His Glu Pro
        595                 600                 605

Pro Val Ile Gly Arg Glu Arg Phe His Ser Arg Pro Gln His Gly Lys
    610                 615                 620

Glu Leu Pro Cys Ser Thr Tyr Val Gln Ser Thr Ala Ala Thr Ala Glu
625                 630                 635                 640

Glu Ile Glu Val His Met Pro Pro Asp Thr Pro Asp Arg Thr Leu Met
                645                 650                 655

Thr Gln Gln Ser Gly Asn Val Lys Ile Thr Val Asn Gly Gln Thr Val
            660                 665                 670

Arg Tyr Lys Cys Asn Cys Gly Gly Ser Asn Glu Gly Leu Thr Thr Thr
        675                 680                 685

Asp Lys Val Ile Asn Asn Cys Lys Ile Asp Gln Cys His Ala Ala Val
    690                 695                 700

Thr Asn His Lys Asn Trp Gln Tyr Asn Ser Pro Leu Val Pro Arg Asn
705                 710                 715                 720

Ala Glu Leu Gly Asp Arg Lys Gly Lys Ile His Ile Pro Phe Pro Leu
                725                 730                 735

Ala Asn Val Thr Cys Arg Val Pro Lys Ala Arg Asn Pro Thr Val Thr
            740                 745                 750

Tyr Gly Lys Asn Gln Val Thr Met Leu Leu Tyr Pro Asp His Pro Thr
        755                 760                 765
```

```
Leu Leu Ser Tyr Arg Asn Met Gly Gln Glu Pro Asn Tyr His Glu Glu
    770                 775                 780

Trp Val Thr His Lys Lys Glu Val Thr Leu Thr Val Pro Thr Glu Gly
785                 790                 795                 800

Leu Glu Val Thr Trp Gly Asn Asn Glu Pro Tyr Lys Tyr Trp Pro Gln
                805                 810                 815

Met Ser Thr Asn Gly Thr Ala His Gly His Pro His Glu Ile Ile Leu
            820                 825                 830

Tyr Tyr Tyr Glu Leu Tyr Pro Thr Met Thr Val Val Ile Val Ser Val
        835                 840                 845

Ala Ser Phe Val Leu Leu Ser Met Val Gly Thr Ala Val Gly Met Cys
    850                 855                 860

Val Cys Ala Arg Arg Arg Cys Ile Thr Pro Tyr Glu Leu Thr Pro Gly
865                 870                 875                 880

Ala Thr Val Pro Phe Leu Leu Ser Leu Leu Cys Cys Val Arg Thr Thr
                885                 890                 895

Lys Ala Ala Thr Tyr Tyr Glu Ala Ala Ala Tyr Leu Trp Asn Glu Gln
            900                 905                 910

Gln Pro Leu Phe Trp Leu Gln Ala Leu Ile Pro Leu Ala Ala Leu Ile
        915                 920                 925

Val Leu Cys Asn Cys Leu Lys Leu Leu Pro Cys Cys Cys Lys Thr Leu
    930                 935                 940

Ala Phe Leu Ala Val Met Ser Ile Gly Ala His Thr Val Ser Ala Tyr
945                 950                 955                 960

Glu His Val Thr Val Ile Pro Asn Thr Val Gly Val Pro Tyr Lys Thr
                965                 970                 975

Leu Val Asn Arg Pro Gly Tyr Ser Pro Met Val Leu Glu Met Glu Leu
            980                 985                 990

Gln Ser Val Thr Leu Glu Pro Thr  Leu Ser Leu Asp Tyr  Ile Thr Cys
        995                 1000                1005

Glu Tyr  Lys Thr Val Ile Pro  Ser Pro Tyr Val Lys  Cys Cys Gly
    1010                1015                1020

Thr Ala  Glu Cys Lys Asp Lys  Ser Leu Pro Asp Tyr  Ser Cys Lys
    1025                1030                1035

Val Phe  Thr Gly Val Tyr Pro  Phe Met Trp Gly Gly  Ala Tyr Cys
    1040                1045                1050

Phe Cys  Asp Ala Glu Asn Thr  Gln Leu Ser Glu Ala  His Val Glu
    1055                1060                1065

Lys Ser  Glu Ser Cys Lys Thr  Glu Phe Ala Ser Ala  Tyr Arg Ala
    1070                1075                1080

His Thr  Ala Ser Ala Ser Ala  Lys Leu Arg Val Leu  Tyr Gln Gly
    1085                1090                1095

Asn Asn  Ile Thr Val Ala Ala  Tyr Ala Asn Gly Asp  His Ala Val
    1100                1105                1110

Thr Val  Lys Asp Ala Lys Phe  Val Val Gly Pro Met  Ser Ser Ala
    1115                1120                1125

Trp Thr  Pro Phe Asp Asn Lys  Ile Val Val Tyr Lys  Gly Asp Val
    1130                1135                1140

Tyr Asn  Met Asp Tyr Pro Pro  Phe Gly Ala Gly Arg  Pro Gly Gln
    1145                1150                1155

Phe Gly  Asp Ile Gln Ser Arg  Thr Pro Glu Ser Lys  Asp Val Tyr
    1160                1165                1170

Ala Asn  Thr Gln Leu Val Leu  Gln Arg Pro Ala Ala  Gly Thr Val
```

```
    1175                1180                1185

His Val  Pro Tyr Ser Gln Ala  Pro Ser Gly Phe Lys  Tyr Trp Leu
    1190                1195                1200

Lys Glu  Arg Gly Ala Ser Leu  Gln His Thr Ala Pro  Phe Gly Cys
    1205                1210                1215

Gln Ile  Ala Thr Asn Pro Val  Arg Ala Val Asn Cys  Ala Val Gly
    1220                1225                1230

Asn Ile  Pro Ile Ser Ile Asp  Ile Pro Asp Ala Ala  Phe Thr Arg
    1235                1240                1245

Val Val  Asp Ala Pro Ser Val  Thr Asp Met Ser Cys  Glu Val Pro
    1250                1255                1260

Ala Cys  Thr His Ser Ser Asp  Phe Gly Gly Val Ala  Ile Ile Lys
    1265                1270                1275

Tyr Thr  Ala Ser Lys Lys Gly  Lys Cys Ala Val His  Ser Met Thr
    1280                1285                1290

Asn Ala  Val Thr Ile Arg Glu  Ala Asp Val Glu Val  Glu Gly Asn
    1295                1300                1305

Ser Gln  Leu Gln Ile Ser Phe  Ser Thr Ala Leu Ala  Ser Ala Glu
    1310                1315                1320

Phe Arg  Val Gln Val Cys Ser  Thr Gln Val His Cys  Ala Ala Ala
    1325                1330                1335

Cys His  Pro Pro Lys Asp His  Ile Val Asn Tyr Pro  Ala Ser His
    1340                1345                1350

Thr Thr  Leu Gly Val Gln Asp  Ile Ser Thr Thr Ala  Met Ser Trp
    1355                1360                1365

Val Gln  Lys Ile Thr Gly Gly  Val Gly Leu Ile Val  Ala Val Ala
    1370                1375                1380

Ala Leu  Ile Leu Ile Val Val  Leu Cys Val Ser Phe  Ser Arg His
    1385                1390                1395
```

```
<210> SEQ ID NO 91
<211> LENGTH: 9212
<212> TYPE: DNA
<213> ORGANISM: Artificial Sequence
<220> FEATURE:
<223> OTHER INFORMATION: Synthetic Expression vector for CHIKV viral
      structural protein containing human IL-2 (FDVVFmutant) antigen in
      E3

<400> SEQUENCE: 91

gaattcccat tgcatacgtt gtatccatat cataatatgt acatttatat tggctcatgt      60

ccaacattac cgccatgttg acattgatta ttgactagtt attaatagta atcaattacg     120

gggtcattag ttcatagccc atatatggag ttccgcgtta cataacttac ggtaaatggc     180

ccgcctggct gaccgcccaa cgacccccgc ccattgacgt caataatgac gtatgttccc     240

atagtaacgc caatagggac tttccattga cgtcaatggg tggagtattt acggtaaact     300

gcccacttgg cagtacatca agtgtatcat atgccaagta cgccccctat tgacgtcaat     360

gacggtaaat ggcccgcctg gcattatgcc cagtacatga ccttatggga ctttcctact     420

tggcagtaca tctacgtatt agtcatcgct attaccatgg tgatgcggtt ttggcagtac     480

atcaatgggc gtggatagcg gtttgactca cggggatttc caagtctcca ccccattgac     540

gtcaatggga gtttgttttg gcaccaaaat caacgggact ttccaaaatg tcgtaacaac     600

tccgccccat tgacgcaaat gggcggtagg cgtgtacggt gggaggtcta tataagcaga     660

gctcgtttag tgaaccgtca gatcgcctgg agacgccatc cacgctgttt tgacctccat     720
```

```
agaagacacc gggaccgatc cagcctccgt taacggtgga gggcagtgta gtctgagcag    780
tactcgttgc tgccgcgcgc gccaccagac ataatagctg acagactaac agactgttcc    840
tttgcggccg ctctagacac catggagttc atcccgacgc aaactttcta taacagaagg    900
taccaacccc gaccctgggc cccacgccct acaattcaag taattagacc tagaccacgt    960
ccacagaggc aggctgggca actcgcccag ctgatctccg cagtcaacaa attgaccatg   1020
cgcgcggtac ctcaacagaa gcctcgcaga aatcggaaaa acaagaagca aaggcagaag   1080
aagcaggcgc cgcaaaacga cccaaagcaa aagaagcaac caccacaaaa gaagccggct   1140
caaaagaaga agaaaccagg ccgtagggag agaatgtgca tgaaaattga aaatgattgc   1200
atcttcgaag tcaagcatga aggcaaagtg atgggctacg catgcctggt gggggataaa   1260
gtaatgaaac cagcacatgt gaagggaact atcgacaatg ccgatctggc taaactggcc   1320
tttaagcggt cgtctaaata cgatcttgaa tgtgcacaga taccggtgca catgaagtct   1380
gatgcctcga agtttaccca cgagaaaccc gaggggtact ataactggca tcacggagca   1440
gtgcagtatt caggaggccg gttcactatc ccgacgggtg caggcaagcc gggagacagc   1500
ggcagaccga tcttcgacaa caaaggacgg gtggtggcca tcgtcctagg aggggccaac   1560
gaaggtgccc gcacggccct ctccgtggtg acgtggaaca aagacatcgt cacaaaaatt   1620
acccctgagg gagccgaaga gtggagcctc gccctcccgg tcttgtgcct gttggcaaac   1680
actacattcc cctgctctca gccgccttgc acaccctgct gctacgaaaa ggaaccggaa   1740
agcaccttgc gcatgcttga ggacaacgtg atgagacccg gatactacca gctactaaaa   1800
gcatcgctga cttgctctcc ccactccgga ggcgccccta caagcagcag caccaagaaa   1860
acccagctgc agctggaaca tctgctgctg gacctgcaga tgatcctgaa cggcatcaac   1920
aactacaaga accccaagct gacccggatg ctgaccttca agttctacat gcccaagaag   1980
gccaccgaac tgaaacatct gcagtgcctg gaagaggaac tgaagcccct ggaagaagtg   2040
ctgaacctgg cccagagcaa gaacttccac ttcgaccccc gggacgtggt gtccaacatc   2100
aacgtgttcg tgctggaact gaaaggcagc gagacaacct tcatgtgcga gtacgccgac   2160
gagacagcta ccatcgtgga atttctgaat cggtggatca ccttctgcca gagcatcatc   2220
agcaccctga ccggcggatc cagtactaag gacaatttta atgtctataa agccacaaga   2280
ccatatctag ctcattgtcc tgactgcgga gaagggcatt cgtgccacag ccctatcgca   2340
ttggagcgca tcagaaatga agcaacggac ggaacgctga aaatccaggt ctctttgcag   2400
atcgggataa agacagatga cagccacgat tggaccaagc tgcgctatat ggatagccat   2460
acgcccgcgg acgcggagcg agccggattg cttgtaagga cttcagcacc gtgcacgatc   2520
accgggacca tgggacactt tattctcgcc cgatgcccga aaggagagac gctgacagtg   2580
ggatttacgg acagcagaaa gatcagccac acatgcacac acccgttcca tcatgaacca   2640
cctgtgatag gtagggagag gttccactct cgaccacaac atggtaaaga gttaccttgc   2700
agcacgtacg tgcagagcac cgctgccact gctgaggaga tagaggtgca tatgcccccca  2760
gatactcctg accgcacgct gatgacgcag cagtctggca acgtgaagat cacagttaat   2820
gggcagacgg tgcggtacaa gtgcaactgc ggtggctcaa acgagggact gacaaccaca   2880
gacaaagtga tcaataactg caaaattgat cagtgccatg ctgcagtcac taatcacaag   2940
aattggcaat acaactcccc tttagtcccg cgcaacgctg aactcgggga ccgtaaagga   3000
aagatccaca tcccattccc attggcaaac gtgacttgca gagtgccaaa agcaagaaac   3060
```

-continued

```
cctacagtaa cttacggaaa aaaccaagtc accatgctgc tgtatcctga ccatccgaca   3120
ctcttgtctt accgtaacat gggacaggaa ccaaattacc acgaggagtg ggtgacacac   3180
aagaaggagg ttaccttgac cgtgcctact gagggtctgg aggtcacttg gggcaacaac   3240
gaaccataca agtactggcc gcagatgtct acgaacggta ctgctcatgg tcacccacat   3300
gagataatct tgtactatta tgagctgtac cccactatga ctgtagtcat tgtgtcggtg   3360
gcctcgttcg tgcttctgtc gatggtgggc acagcagtgg gaatgtgtgt gtgcgcacgg   3420
cgcagatgca ttacaccata tgaattaaca ccaggagcca ctgttccctt cctgctcagc   3480
ctgctatgct gcgtcagaac gaccaaggcg gccacatatt acgaggctgc ggcatatcta   3540
tggaacgaac agcagcccct gttctggttg caggctctta tcccgctggc cgccttgatc   3600
gtcctgtgca actgtctgaa actcttgcca tgctgctgta agaccctggc tttttagcc    3660
gtaatgagca tcggtgccca cactgtgagc gcgtacgaac acgtaacagt gatcccgaac   3720
acggtgggag taccgtataa gactcttgtc aacagaccgg gttacagccc catggtgttg   3780
gagatggagc tacaatcagt caccttggaa ccaacactgt cacttgacta catcacgtgc   3840
gagtacaaaa ctgtcatccc ctccccgtac gtgaagtgct gtggtacagc agagtgcaag   3900
gacaagagcc taccagacta cagctgcaag gtctttactg gagtctaccc atttatgtgg   3960
ggcggcgcct actgcttttg cgacgccgaa aatacgcaat tgagcgaggc acatgtagag   4020
aaatctgaat cttgcaaaac agagtttgca tcggcctaca gagcccacac cgcatcggcg   4080
tcggcgaagc tccgcgtcct ttaccaagga aacaacatta ccgtagctgc ctacgctaac   4140
ggtgaccatg ccgtcacagt aaaggacgcc aagtttgtcg tgggcccaat gtcctccgcc   4200
tggacacctt ttgacaacaa aatcgtggtg tacaaaggcg acgtctacaa catggactac   4260
ccaccttttg gcgcaggaag accaggacaa tttggtgaca ttcaaagtcg tacaccggaa   4320
agtaaagacg tttatgccaa cactcagttg gtactacaga ggccagcagc aggcacggta   4380
catgtaccat actctcaggc accatctggc ttcaagtatt ggctgaagga acgaggagca   4440
tcgctacagc acacggcacc gttcggttgc cagattgcga caaacccggt aagagctgta   4500
aattgcgctg tggggaacat accaatttcc atcgacatac cggatgcggc ctttactagg   4560
gttgtcgatg caccctctgt aacggacatg tcatgcgaag taccagcctg cactcactcc   4620
tccgactttg gggcgtcgc catcatcaaa tacacagcta gcaagaaagg taaatgtgca    4680
gtacattcga tgaccaacgc cgttaccatt cgagaagccg acgtagaagt agaggggaac   4740
tcccagctgc aaatatcctt ctcaacagcc ctggcaagcg ccgagtttcg cgtgcaagtg   4800
tgctccacac aagtacactg cgcagccgca tgccaccctc caaaggacca catagtcaat   4860
tacccagcat cacacaccac ccttggggtc caggatatat ccacaacggc aatgtcttgg   4920
gtgcagaaga ttacgggagg agtaggatta attgttgctg ttgctgcctt aattttaatt   4980
gtggtgctat gcgtgtcgtt tagcaggcac taatgatccg gaggggcacc cacttcaagc   5040
tccacttcaa gctctacagc ggaagcacag cagcagcagc agcagcagca gcagcagcag   5100
cacctggagc agctgttgat ggacctacag gagctcctga gcaggatgga gaattacagg   5160
aacctgaaac tccccaggat gctcaccttc aaattttact tgcccaagca ggccacagaa   5220
ttgaaagatc ttcagtgcct agaagatgaa cttggacctc tgcggcatgt tctggatttg   5280
actcaaagca aaagctttca attggaagat gctgagaatt tcatcagcaa tatcagagta   5340
actgttgtaa aactaaaggg ctctgacaac acatttgagt gccaattcga tgatgagtca   5400
gcaactgtgg tggactttct gaggagatgg atagccttct gtcaaagcat catctcaaca   5460
```

agccctcaag gggatccgc tgtgccttct agttgccagc catctgttgt ttgcccctcc 5520
cccgtgcctt ccttgaccct ggaaggtgcc actcccactg tcctttccta ataaaatgag 5580
gaaattgcat cgcattgtct gagtaggtgt cattctattc tggggggtgg ggtggggcag 5640
gacagcaagg gggaggattg ggaagacaat agcaggcatg ctggggatgc ggtgggctct 5700
atgggtaccc aggtgctgaa gaattgaccc ggttcctcct gggccagaaa gaagcaggca 5760
catccccttc tctgtgacac accctgtcca cgcccctggt tcttagttcc agccccactc 5820
ataggacact catagctcag gagggctccg ccttcaatcc cacccgctaa agtacttgga 5880
gcggtctctc cctccctcat cagcccacca aaccaaacct agcctccaag agtgggaaga 5940
aattaaagca agataggcta ttaagtgcag agggagagaa aatgcctcca acatgtgagg 6000
aagtaatgag agaaatcata gaattttaag gccatgattt aaggccatca tggcctaagc 6060
ttgaaaggag ataggatcaa agcttggcgt aatcatggtc atagctgttt cctgtgtgaa 6120
attgttatcc gctcacaatt ccacacaaca tacgagccgg aagcataaag tgtaaagcct 6180
ggggtgccta atgagtgagc taactcacat taattgcgtt gcgctcactg cccgctttcc 6240
agtcgggaaa cctgtcgtgc cagctgcatt aatgaatcgg ccaacgcgcg gggagaggcg 6300
gtttgcgtat tgggcgctct tccgcttcct cgctcactga ctcgctgcgc tcggtcgttc 6360
ggctgcggcg agcggtatca gctcactcaa aggcggtaat acggttatcc acagaatcag 6420
gggataacgc aggaaagaac atgtgagcaa aaggccagca aaaggccagg aaccgtaaaa 6480
aggccgcgtt gctggcgttt ttccataggc tccgcccccc tgacgagcat cacaaaaatc 6540
gacgctcaag tcagaggtgg cgaaacccga caggactata aagataccag gcgtttcccc 6600
ctggaagctc cctcgtgcgc tctcctgttc cgaccctgcc gcttaccgga tacctgtccg 6660
cctttctccc ttcgggaagc gtggcgcttt ctcatagctc acgctgtagg tatctcagtt 6720
cggtgtaggt cgttcgctcc aagctgggct gtgtgcacga accccccgtt cagcccgacc 6780
gctgcgcctt atccggtaac tatcgtcttg agtccaaccc ggtaagacac gacttatcgc 6840
cactggcagc agccactggt aacaggatta gcagagcgag gtatgtaggc ggtgctacag 6900
agttcttgaa gtggtggcct aactacggct acactagaag aacagtattt ggtatctgcg 6960
ctctgctgaa gccagttacc ttcggaaaaa gagttggtag ctcttgatcc ggcaaacaaa 7020
ccaccgctgg tagcggtggt ttttttgttt gcaagcagca gattacgcgc agaaaaaaag 7080
gatctcaaga agatcctttg atcttttcta cggggtctga cgctcagtgg aacgaaaact 7140
cacgttaagg gattttggtc atgagattat caaaaaggat cttcacctag atccttttaa 7200
attaaaaatg aagttttaaa tcaatctaaa gtatatatga gtaaacttgg tctgacagtt 7260
accaatgctt aatcagtgag gcacctatct cagcgatctg tctatttcgt tcatccatag 7320
ttgcctgact ccccgtcgtg tagataacta cgatacggga gggcttacca tctggcccca 7380
gtgctgcaat gataccgcga gaaccacgct caccggctcc agatttatca gcaataaacc 7440
agccagccgg aagggccgag cgcagaagtg gtcctgcaac tttatccgcc tccatccagt 7500
ctattaattg ttgccgggaa gctagagtaa gtagttcgcc agttaatagt ttgcgcaacg 7560
ttgttgccat tgctacaggc atcgtggtgt cacgctcgtc gtttggtatg gcttcattca 7620
gctccggttc ccaacgatca aggcgagtta catgatcccc catgttgtgc aaaaaagcgg 7680
ttagctcctt cggtcctccg atcgttgtca gaagtaagtt ggccgcagtg ttatcactca 7740
tggttatggc agcactgcat aattctctta ctgtcatgcc atccgtaaga tgcttttctg 7800

-continued

```
tgactggtga gtactcaacc aagtcattct gagaatagtg tatgcggcga ccgagttgct   7860

cttgcccggc gtcaatacgg gataataccg cgccacatag cagaacttta aaagtgctca   7920

tcattggaaa acgttcttcg gggcgaaaac tctcaaggat cttaccgctg ttgagatcca   7980

gttcgatgta acccactcgt gcacccaact gatcttcagc atcttttact ttcaccagcg   8040

tttctgggtg agcaaaaaca ggaaggcaaa atgccgcaaa aaagggaata agggcgacac   8100

ggaaatgttg aatactcata ctcttccttt ttcaatatta ttgaagcatt tatcagggtt   8160

attgtctcat gagcggatac atatttgaat gtatttagaa aaataaacaa ataggggttc   8220

cgcgcacatt tccccgaaaa gtgccacctg acgtctaaga aaccattatt atcatgacat   8280

taacctataa aaataggcgt atcacgaggc cctttcgggt cgcgcgtttc ggtgatgacg   8340

gtgaaaacct ctgacacatg cagctcccgt tgacggtcac agcttgtctg taagcggatg   8400

ccgggagcag acaagcccgt cagggcgcgt cagcgggtgt tggcgggtgt cggggctggc   8460

ttaactatgc ggcatcagag cagattgtac tgagagtgca ccataaaatt gtaaacgtta   8520

atattttgtt aaaattcgcg ttaaattttt gttaaatcag ctcatttttt aaccaatagg   8580

ccgaaatcgg caaaatccct tataaatcaa aagaatagcc cgagataggg ttgagtgttg   8640

ttccagtttg gaacaagagt ccactattaa agaacgtgga ctccaacgtc aaagggcgaa   8700

aaaccgtcta tcagggcgat ggcccactac gtgaaccatc acccaaatca agtttttttgg   8760

ggtcgaggtg ccgtaaagca ctaaatcgga accctaaagg gagcccccga tttagagctt   8820

gacggggaaa gccggcgaac gtggcgagaa aggaagggaa gaaagcgaaa ggagcgggcg   8880

ctagggcgct ggcaagtgta gcggtcacgc tgcgcgtaac caccacaccc gccgcgctta   8940

atgcgccgct acagggcgcg tactatggtt gctttgacgt atgcggtgtg aaataccgca   9000

cagatgcgta aggagaaaat accgcatcag gcgccattcg ccattcaggc tgcgcaactg   9060

ttgggaaggg cgatcggtgc gggcctcttc gctattacgc cagctggcga aagggggatg   9120

tgctgcaagg cgattaagtt gggtaacgcc agggttttcc cagtcacgac gttgtaaaac   9180

gacggccagt gaattccatg gtctcaactt tc                                 9212
```

<210> SEQ ID NO 92
<211> LENGTH: 1383
<212> TYPE: PRT
<213> ORGANISM: Artificial Sequence
<220> FEATURE:
<223> OTHER INFORMATION: Synthetic CHIKV viral structural protein containing human IL-2 (FDVVFmutant) antigen in E3

<400> SEQUENCE: 92

```
Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Arg Gln Lys Lys Gln Ala Pro Gln Asn Asp
65                  70                  75                  80

Pro Lys Gln Lys Lys Gln Pro Pro Gln Lys Lys Pro Ala Gln Lys Lys
                85                  90                  95

Lys Lys Pro Gly Arg Arg Glu Arg Met Cys Met Lys Ile Glu Asn Asp
            100                 105                 110
```

-continued

```
Cys Ile Phe Glu Val Lys His Glu Gly Lys Val Met Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Leu Pro Val Leu Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Ser Thr Leu Arg Met Leu Glu Asp Asn Val Met
    290                 295                 300

Arg Pro Gly Tyr Tyr Gln Leu Leu Lys Ala Ser Leu Thr Cys Ser Pro
305                 310                 315                 320

His Ser Gly Gly Ala Pro Thr Ser Ser Ser Thr Lys Lys Thr Gln Leu
                325                 330                 335

Gln Leu Glu His Leu Leu Leu Asp Leu Gln Met Ile Leu Asn Gly Ile
            340                 345                 350

Asn Asn Tyr Lys Asn Pro Lys Leu Thr Arg Met Leu Thr Phe Lys Phe
        355                 360                 365

Tyr Met Pro Lys Lys Ala Thr Glu Leu Lys His Leu Gln Cys Leu Glu
    370                 375                 380

Glu Glu Leu Lys Pro Leu Glu Glu Val Leu Asn Leu Ala Gln Ser Lys
385                 390                 395                 400

Asn Phe His Phe Asp Pro Arg Asp Val Val Ser Asn Ile Asn Val Phe
                405                 410                 415

Val Leu Glu Leu Lys Gly Ser Glu Thr Thr Phe Met Cys Glu Tyr Ala
            420                 425                 430

Asp Glu Thr Ala Thr Ile Val Glu Phe Leu Asn Arg Trp Ile Thr Phe
        435                 440                 445

Cys Gln Ser Ile Ile Ser Thr Leu Thr Gly Gly Ser Ser Thr Lys Asp
    450                 455                 460

Asn Phe Asn Val Tyr Lys Ala Thr Arg Pro Tyr Leu Ala His Cys Pro
465                 470                 475                 480

Asp Cys Gly Glu Gly His Ser Cys His Ser Pro Ile Ala Leu Glu Arg
                485                 490                 495

Ile Arg Asn Glu Ala Thr Asp Gly Thr Leu Lys Ile Gln Val Ser Leu
            500                 505                 510

Gln Ile Gly Ile Lys Thr Asp Asp Ser His Asp Trp Thr Lys Leu Arg
        515                 520                 525
```

```
Tyr Met Asp Ser His Thr Pro Ala Asp Ala Glu Arg Ala Gly Leu Leu
    530                 535                 540

Val Arg Thr Ser Ala Pro Cys Thr Ile Thr Gly Thr Met Gly His Phe
545                 550                 555                 560

Ile Leu Ala Arg Cys Pro Lys Gly Glu Thr Leu Thr Val Gly Phe Thr
                565                 570                 575

Asp Ser Arg Lys Ile Ser His Thr Cys Thr His Pro Phe His His Glu
            580                 585                 590

Pro Pro Val Ile Gly Arg Glu Arg Phe His Ser Arg Pro Gln His Gly
        595                 600                 605

Lys Glu Leu Pro Cys Ser Thr Tyr Val Gln Ser Thr Ala Ala Thr Ala
    610                 615                 620

Glu Glu Ile Glu Val His Met Pro Pro Asp Thr Pro Asp Arg Thr Leu
625                 630                 635                 640

Met Thr Gln Gln Ser Gly Asn Val Lys Ile Thr Val Asn Gly Gln Thr
                645                 650                 655

Val Arg Tyr Lys Cys Asn Cys Gly Gly Ser Asn Glu Gly Leu Thr Thr
            660                 665                 670

Thr Asp Lys Val Ile Asn Asn Cys Lys Ile Asp Gln Cys His Ala Ala
        675                 680                 685

Val Thr Asn His Lys Asn Trp Gln Tyr Asn Ser Pro Leu Val Pro Arg
    690                 695                 700

Asn Ala Glu Leu Gly Asp Arg Lys Gly Lys Ile His Ile Pro Phe Pro
705                 710                 715                 720

Leu Ala Asn Val Thr Cys Arg Val Pro Lys Ala Arg Asn Pro Thr Val
                725                 730                 735

Thr Tyr Gly Lys Asn Gln Val Thr Met Leu Leu Tyr Pro Asp His Pro
            740                 745                 750

Thr Leu Leu Ser Tyr Arg Asn Met Gly Gln Glu Pro Asn Tyr His Glu
        755                 760                 765

Glu Trp Val Thr His Lys Lys Glu Val Thr Leu Thr Val Pro Thr Glu
    770                 775                 780

Gly Leu Glu Val Thr Trp Gly Asn Asn Glu Pro Tyr Lys Tyr Trp Pro
785                 790                 795                 800

Gln Met Ser Thr Asn Gly Thr Ala His Gly His Pro His Glu Ile Ile
                805                 810                 815

Leu Tyr Tyr Tyr Glu Leu Tyr Pro Thr Met Thr Val Val Ile Val Ser
            820                 825                 830

Val Ala Ser Phe Val Leu Leu Ser Met Val Gly Thr Ala Val Gly Met
        835                 840                 845

Cys Val Cys Ala Arg Arg Arg Cys Ile Thr Pro Tyr Glu Leu Thr Pro
    850                 855                 860

Gly Ala Thr Val Pro Phe Leu Leu Ser Leu Leu Cys Cys Val Arg Thr
865                 870                 875                 880

Thr Lys Ala Ala Thr Tyr Tyr Glu Ala Ala Ala Tyr Leu Trp Asn Glu
                885                 890                 895

Gln Gln Pro Leu Phe Trp Leu Gln Ala Leu Ile Pro Leu Ala Ala Leu
            900                 905                 910

Ile Val Leu Cys Asn Cys Leu Lys Leu Leu Pro Cys Cys Cys Lys Thr
        915                 920                 925

Leu Ala Phe Leu Ala Val Met Ser Ile Gly Ala His Thr Val Ser Ala
    930                 935                 940

Tyr Glu His Val Thr Val Ile Pro Asn Thr Val Gly Val Pro Tyr Lys
```

-continued

```
945                 950                 955                 960

Thr Leu Val Asn Arg Pro Gly Tyr Ser Pro Met Val Leu Glu Met Glu
                965                 970                 975

Leu Gln Ser Val Thr Leu Glu Pro Thr Leu Ser Leu Asp Tyr Ile Thr
            980                 985                 990

Cys Glu Tyr Lys Thr Val Ile Pro  Ser Pro Tyr Val Lys  Cys Cys Gly
        995                 1000                 1005

Thr Ala  Glu Cys Lys Asp Lys  Ser Leu Pro Asp Tyr  Ser Cys Lys
    1010                 1015                 1020

Val Phe  Thr Gly Val Tyr Pro  Phe Met Trp Gly Gly  Ala Tyr Cys
    1025                 1030                 1035

Phe Cys  Asp Ala Glu Asn Thr  Gln Leu Ser Glu Ala  His Val Glu
    1040                 1045                 1050

Lys Ser  Glu Ser Cys Lys Thr  Glu Phe Ala Ser Ala  Tyr Arg Ala
    1055                 1060                 1065

His Thr  Ala Ser Ala Ser Ala  Lys Leu Arg Val Leu  Tyr Gln Gly
    1070                 1075                 1080

Asn Asn  Ile Thr Val Ala Ala  Tyr Ala Asn Gly Asp  His Ala Val
    1085                 1090                 1095

Thr Val  Lys Asp Ala Lys Phe  Val Val Gly Pro Met  Ser Ser Ala
    1100                 1105                 1110

Trp Thr  Pro Phe Asp Asn Lys  Ile Val Val Tyr Lys  Gly Asp Val
    1115                 1120                 1125

Tyr Asn  Met Asp Tyr Pro Pro  Phe Gly Ala Gly Arg  Pro Gly Gln
    1130                 1135                 1140

Phe Gly  Asp Ile Gln Ser Arg  Thr Pro Glu Ser Lys  Asp Val Tyr
    1145                 1150                 1155

Ala Asn  Thr Gln Leu Val Leu  Gln Arg Pro Ala Ala  Gly Thr Val
    1160                 1165                 1170

His Val  Pro Tyr Ser Gln Ala  Pro Ser Gly Phe Lys  Tyr Trp Leu
    1175                 1180                 1185

Lys Glu  Arg Gly Ala Ser Leu  Gln His Thr Ala Pro  Phe Gly Cys
    1190                 1195                 1200

Gln Ile  Ala Thr Asn Pro Val  Arg Ala Val Asn Cys  Ala Val Gly
    1205                 1210                 1215

Asn Ile  Pro Ile Ser Ile Asp  Ile Pro Asp Ala Ala  Phe Thr Arg
    1220                 1225                 1230

Val Val  Asp Ala Pro Ser Val  Thr Asp Met Ser Cys  Glu Val Pro
    1235                 1240                 1245

Ala Cys  Thr His Ser Ser Asp  Phe Gly Gly Val Ala  Ile Ile Lys
    1250                 1255                 1260

Tyr Thr  Ala Ser Lys Lys Gly  Lys Cys Ala Val His  Ser Met Thr
    1265                 1270                 1275

Asn Ala  Val Thr Ile Arg Glu  Ala Asp Val Glu Val  Glu Gly Asn
    1280                 1285                 1290

Ser Gln  Leu Gln Ile Ser Phe  Ser Thr Ala Leu Ala  Ser Ala Glu
    1295                 1300                 1305

Phe Arg  Val Gln Val Cys Ser  Thr Gln Val His Cys  Ala Ala Ala
    1310                 1315                 1320

Cys His  Pro Pro Lys Asp His  Ile Val Asn Tyr Pro  Ala Ser His
    1325                 1330                 1335

Thr Thr  Leu Gly Val Gln Asp  Ile Ser Thr Thr Ala  Met Ser Trp
    1340                 1345                 1350
```

Val Gln Lys Ile Thr Gly Gly Val Gly Leu Ile Val Ala Val Ala
1355 1360 1365

Ala Leu Ile Leu Ile Val Val Leu Cys Val Ser Phe Ser Arg His
1370 1375 1380

<210> SEQ ID NO 93
<211> LENGTH: 30
<212> TYPE: PRT
<213> ORGANISM: Artificial Sequence
<220> FEATURE:
<223> OTHER INFORMATION: Synthetic mouse malaria (Plasmodium yoelii) CSP epitope 4X(261) with linker

<400> SEQUENCE: 93

Ser Gly Gly Gln Gly Pro Gly Ala Pro Gln Gly Pro Gly Ala Pro Gln
1 5 10 15

Gly Pro Gly Ala Pro Gln Gly Pro Gly Ala Pro Gly Gly Ser
20 25 30

<210> SEQ ID NO 94
<211> LENGTH: 90
<212> TYPE: DNA
<213> ORGANISM: Artificial Sequence
<220> FEATURE:
<223> OTHER INFORMATION: Synthetic mouse malaria (Plasmodium yoelii) CSP epitope 4X(261) with linker

<400> SEQUENCE: 94
tccggaggac agggacctgg cgctcctcag ggaccagggg caccacaggg cccaggcgcc 60
ccacaggggc ctggggcccc tgggggatcc 90

<210> SEQ ID NO 95
<211> LENGTH: 90
<212> TYPE: PRT
<213> ORGANISM: Artificial Sequence
<220> FEATURE:
<223> OTHER INFORMATION: Synthetic mouse malaria (Plasmodium yoelii) CSP epitope 14X(264) with linker

<400> SEQUENCE: 95

Ser Gly Gly Gln Gly Pro Gly Ala Pro Gln Gly Pro Gly Ala Pro Gln
1 5 10 15

Gly Pro Gly Ala Pro Gln Gly Pro Gly Ala Pro Gln Gly Pro Gly Ala
20 25 30

Pro Gln Gly Pro Gly Ala Pro Gln Gly Pro Gly Ala Pro Gln Gly Pro
35 40 45

Gly Ala Pro Gln Gly Pro Gly Ala Pro Gln Gly Pro Gly Ala Pro Gln
50 55 60

Gly Pro Gly Ala Pro Gln Gly Pro Gly Ala Pro Gln Gly Pro Gly Ala
65 70 75 80

Pro Gln Gly Pro Gly Ala Pro Gly Gly Ser
85 90

<210> SEQ ID NO 96
<211> LENGTH: 270
<212> TYPE: DNA
<213> ORGANISM: Artificial Sequence
<220> FEATURE:
<223> OTHER INFORMATION: Synthetic mouse malaria (Plasmodium yoelii) CSP epitope 14X(264) with linker

<400> SEQUENCE: 96

-continued

```
tccggaggac agggacctgg cgctcctcag ggaccagggg caccacaggg cccaggcgcc      60

ccacaggggc ctggggcacc ccagggacct ggggctccac aggggcctgg cgcacctcag     120

ggcccaggcg ctcctcaggg acctggcgct ccacagggac ccggcgctcc tcaggggcct     180

ggggcccctc agggacccgg cgcacctcag ggaccaggcg caccccaggg gccaggggct     240

cctcagggcc caggggctcc aggcggatcc                                      270


<210> SEQ ID NO 97
<211> LENGTH: 1303
<212> TYPE: PRT
<213> ORGANISM: Artificial Sequence
<220> FEATURE:
<223> OTHER INFORMATION: Synthetic CHIKV viral structural protein
      containing CSP epitope 4X(261) in E2 and E3 (261 dual)

<400> SEQUENCE: 97

Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Arg Gln Lys Lys Gln Ala Pro Gln Asn Asp
65                  70                  75                  80

Pro Lys Gln Lys Lys Gln Pro Pro Gln Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Met Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Leu Pro Val Leu Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Ser Thr Leu Arg Met Leu Glu Asp Asn Val Met
    290                 295                 300

Arg Pro Gly Tyr Tyr Gln Leu Leu Lys Ala Ser Leu Thr Cys Ser Pro
```

-continued

```
305                 310                 315                 320

His Ser Gly Gly Gln Gly Pro Gly Ala Pro Gln Gly Pro Gly Ala Pro
                325                 330                 335

Gln Gly Pro Gly Ala Pro Gln Gly Pro Gly Ala Pro Gly Gly Ser Ser
            340                 345                 350

Thr Lys Asp Asn Phe Asn Val Tyr Lys Ala Thr Arg Pro Tyr Leu Ala
        355                 360                 365

His Cys Pro Asp Cys Gly Glu Gly His Ser Cys His Ser Pro Ile Ala
    370                 375                 380

Leu Glu Arg Ile Arg Asn Glu Ala Thr Asp Gly Thr Leu Lys Ile Gln
385                 390                 395                 400

Val Ser Leu Gln Ile Gly Ile Lys Thr Asp Asp Ser His Asp Trp Thr
                405                 410                 415

Lys Leu Arg Tyr Met Asp Ser His Thr Pro Ala Asp Ala Glu Arg Ala
            420                 425                 430

Gly Leu Leu Val Arg Thr Ser Ala Pro Cys Thr Ile Thr Gly Thr Met
        435                 440                 445

Gly His Phe Ile Leu Ala Arg Cys Pro Lys Gly Glu Thr Leu Thr Val
    450                 455                 460

Gly Phe Thr Asp Ser Arg Lys Ile Ser His Thr Cys Thr His Pro Phe
465                 470                 475                 480

His His Glu Pro Pro Val Ile Gly Arg Glu Arg Phe His Ser Arg Pro
                485                 490                 495

Gln His Gly Lys Glu Leu Pro Cys Ser Thr Tyr Val Gln Ser Thr Ala
            500                 505                 510

Ala Thr Ala Glu Glu Ile Glu Val His Met Pro Pro Asp Thr Pro Asp
        515                 520                 525

Arg Thr Leu Met Thr Gln Gln Ser Gly Asn Val Lys Ile Thr Val Asn
    530                 535                 540

Gly Gln Thr Val Arg Tyr Lys Cys Asn Cys Gly Gly Ser Gly Gly Gln
545                 550                 555                 560

Gly Pro Gly Ala Pro Gln Gly Pro Gly Ala Pro Gln Gly Pro Gly Ala
                565                 570                 575

Pro Gln Gly Pro Gly Ala Pro Gly Gly Ser Asn Glu Gly Leu Thr Thr
            580                 585                 590

Thr Asp Lys Val Ile Asn Asn Cys Lys Ile Asp Gln Cys His Ala Ala
        595                 600                 605

Val Thr Asn His Lys Asn Trp Gln Tyr Asn Ser Pro Leu Val Pro Arg
    610                 615                 620

Asn Ala Glu Leu Gly Asp Arg Lys Gly Lys Ile His Ile Pro Phe Pro
625                 630                 635                 640

Leu Ala Asn Val Thr Cys Arg Val Pro Lys Ala Arg Asn Pro Thr Val
                645                 650                 655

Thr Tyr Gly Lys Asn Gln Val Thr Met Leu Leu Tyr Pro Asp His Pro
            660                 665                 670

Thr Leu Leu Ser Tyr Arg Asn Met Gly Gln Glu Pro Asn Tyr His Glu
        675                 680                 685

Glu Trp Val Thr His Lys Lys Glu Val Thr Leu Thr Val Pro Thr Glu
    690                 695                 700

Gly Leu Glu Val Thr Trp Gly Asn Asn Glu Pro Tyr Lys Tyr Trp Pro
705                 710                 715                 720

Gln Met Ser Thr Asn Gly Thr Ala His Gly His Pro His Glu Ile Ile
                725                 730                 735
```

```
Leu Tyr Tyr Tyr Glu Leu Tyr Pro Thr Met Thr Val Val Ile Val Ser
            740                 745                 750

Val Ala Ser Phe Val Leu Leu Ser Met Val Gly Thr Ala Val Gly Met
        755                 760                 765

Cys Val Cys Ala Arg Arg Arg Cys Ile Thr Pro Tyr Glu Leu Thr Pro
    770                 775                 780

Gly Ala Thr Val Pro Phe Leu Leu Ser Leu Leu Cys Cys Val Arg Thr
785                 790                 795                 800

Thr Lys Ala Ala Thr Tyr Tyr Glu Ala Ala Ala Tyr Leu Trp Asn Glu
                805                 810                 815

Gln Gln Pro Leu Phe Trp Leu Gln Ala Leu Ile Pro Leu Ala Ala Leu
            820                 825                 830

Ile Val Leu Cys Asn Cys Leu Lys Leu Leu Pro Cys Cys Cys Lys Thr
        835                 840                 845

Leu Ala Phe Leu Ala Val Met Ser Ile Gly Ala His Thr Val Ser Ala
    850                 855                 860

Tyr Glu His Val Thr Val Ile Pro Asn Thr Val Gly Val Pro Tyr Lys
865                 870                 875                 880

Thr Leu Val Asn Arg Pro Gly Tyr Ser Pro Met Val Leu Glu Met Glu
                885                 890                 895

Leu Gln Ser Val Thr Leu Glu Pro Thr Leu Ser Leu Asp Tyr Ile Thr
            900                 905                 910

Cys Glu Tyr Lys Thr Val Ile Pro Ser Pro Tyr Val Lys Cys Cys Gly
        915                 920                 925

Thr Ala Glu Cys Lys Asp Lys Ser Leu Pro Asp Tyr Ser Cys Lys Val
    930                 935                 940

Phe Thr Gly Val Tyr Pro Phe Met Trp Gly Gly Ala Tyr Cys Phe Cys
945                 950                 955                 960

Asp Ala Glu Asn Thr Gln Leu Ser Glu Ala His Val Glu Lys Ser Glu
                965                 970                 975

Ser Cys Lys Thr Glu Phe Ala Ser Ala Tyr Arg Ala His Thr Ala Ser
            980                 985                 990

Ala Ser Ala Lys Leu Arg Val Leu  Tyr Gln Gly Asn Asn  Ile Thr Val
        995                 1000                 1005

Ala Ala  Tyr Ala Asn Gly Asp  His Ala Val Thr Val  Lys Asp Ala
    1010                 1015                 1020

Lys Phe  Val Val Gly Pro Met  Ser Ser Ala Trp Thr  Pro Phe Asp
    1025                 1030                 1035

Asn Lys  Ile Val Val Tyr Lys  Gly Asp Val Tyr Asn  Met Asp Tyr
    1040                 1045                 1050

Pro Pro  Phe Gly Ala Gly Arg  Pro Gly Gln Phe Gly  Asp Ile Gln
    1055                 1060                 1065

Ser Arg  Thr Pro Glu Ser Lys  Asp Val Tyr Ala Asn  Thr Gln Leu
    1070                 1075                 1080

Val Leu  Gln Arg Pro Ala Ala  Gly Thr Val His Val  Pro Tyr Ser
    1085                 1090                 1095

Gln Ala  Pro Ser Gly Phe Lys  Tyr Trp Leu Lys Glu  Arg Gly Ala
    1100                 1105                 1110

Ser Leu  Gln His Thr Ala Pro  Phe Gly Cys Gln Ile  Ala Thr Asn
    1115                 1120                 1125

Pro Val  Arg Ala Val Asn Cys  Ala Val Gly Asn Ile  Pro Ile Ser
    1130                 1135                 1140
```

-continued

```
Ile Asp  Ile Pro Asp Ala Ala  Phe Thr Arg Val Val  Asp Ala Pro
    1145                 1150                 1155

Ser Val  Thr Asp Met Ser Cys  Glu Val Pro Ala Cys  Thr His Ser
    1160                 1165                 1170

Ser Asp  Phe Gly Gly Val Ala  Ile Ile Lys Tyr Thr  Ala Ser Lys
    1175                 1180                 1185

Lys Gly  Lys Cys Ala Val His  Ser Met Thr Asn Ala  Val Thr Ile
    1190                 1195                 1200

Arg Glu  Ala Asp Val Glu Val  Glu Gly Asn Ser Gln  Leu Gln Ile
    1205                 1210                 1215

Ser Phe  Ser Thr Ala Leu Ala  Ser Ala Glu Phe Arg  Val Gln Val
    1220                 1225                 1230

Cys Ser  Thr Gln Val His Cys  Ala Ala Ala Cys His  Pro Pro Lys
    1235                 1240                 1245

Asp His  Ile Val Asn Tyr Pro  Ala Ser His Thr Thr  Leu Gly Val
    1250                 1255                 1260

Gln Asp  Ile Ser Thr Thr Ala  Met Ser Trp Val Gln  Lys Ile Thr
    1265                 1270                 1275

Gly Gly  Val Gly Leu Ile Val  Ala Val Ala Ala Leu  Ile Leu Ile
    1280                 1285                 1290

Val Val  Leu Cys Val Ser Phe  Ser Arg His
    1295                 1300
```

<210> SEQ ID NO 98
<211> LENGTH: 8972
<212> TYPE: DNA
<213> ORGANISM: Artificial Sequence
<220> FEATURE:
<223> OTHER INFORMATION: Synthetic Expression Vector for CHIKV viral structural protein containing CSP epitope 4X(261) in E2 and E3 (261.261.58)

<400> SEQUENCE: 98

```
gaattcccat tgcatacgtt gtatccatat cataatatgt acatttatat tggctcatgt     60

ccaacattac cgccatgttg acattgatta ttgactagtt attaatagta atcaattacg    120

gggtcattag ttcatagccc atatatggag ttccgcgtta cataacttac ggtaaatggc    180

ccgcctggct gaccgcccaa cgacccccgc ccattgacgt caataatgac gtatgttccc    240

atagtaacgc caatagggac tttccattga cgtcaatggg tggagtattt acggtaaact    300

gcccacttgg cagtacatca agtgtatcat atgccaagta cgccccctat tgacgtcaat    360

gacggtaaat ggcccgcctg gcattatgcc cagtacatga ccttatggga ctttcctact    420

tggcagtaca tctacgtatt agtcatcgct attaccatgg tgatgcggtt ttggcagtac    480

atcaatgggc gtggatagcg gtttgactca cggggatttc caagtctcca ccccattgac    540

gtcaatggga gtttgttttg gcaccaaaat caacgggact ttccaaaatg tcgtaacaac    600

tccgccccat tgacgcaaat gggcggtagg cgtgtacggt gggaggtcta tataagcaga    660

gctcgtttag tgaaccgtca gatcgcctgg agacgccatc cacgctgttt tgacctccat    720

agaagacacc gggaccgatc cagcctccgt taacggtgga gggcagtgta gtctgagcag    780

tactcgttgc tgccgcgcgc gccaccagac ataatagctg acagactaac agactgttcc    840

tttgcggccg ctctagacac catggagttc atcccgacgc aaactttcta taacagaagg    900

taccaacccc gaccctgggc cccacgccct acaattcaag taattagacc tagaccacgt    960

ccacagaggc aggctgggca actcgcccag ctgatctccg cagtcaacaa attgaccatg   1020
```

cgcgcggtac ctcaacagaa gcctcgcaga aatcggaaaa acaagaagca aaggcagaag 1080
aagcaggcgc cgcaaaacga cccaaagcaa aagaagcaac caccacaaaa gaagccggct 1140
caaaagaaga agaaaccagg ccgtagggag agaatgtgca tgaaaattga aaatgattgc 1200
atcttcgaag tcaagcatga aggcaaagtg atgggctacg catgcctggt gggggataaa 1260
gtaatgaaac cagcacatgt gaagggaact atcgacaatg ccgatctggc taaactggcc 1320
tttaagcggt cgtctaaata cgatcttgaa tgtgcacaga taccggtgca catgaagtct 1380
gatgcctcga agtttaccca cgagaaaccc gaggggtact ataactggca tcacggagca 1440
gtgcagtatt caggaggccg gttcactatc ccgacgggtg caggcaagcc gggagacagc 1500
ggcagaccga tcttcgacaa caaaggacgg gtggtggcca tcgtcctagg aggggccaac 1560
gaaggtgccc gcacggccct ctccgtggtg acgtggaaca aagacatcgt cacaaaaatt 1620
acccctgagg gagccgaaga gtggagcctc gccctcccgg tcttgtgcct gttggcaaac 1680
actacattcc cctgctctca gccgccttgc acaccctgct gctacgaaaa ggaaccggaa 1740
agcaccttgc gcatgcttga ggacaacgtg atgagacccg gatactacca gctactaaaa 1800
gcatcgctga cttgctctcc ccactccgga ggacagggac ctggcgctcc tcagggacca 1860
ggggcaccac agggcccagg cgccccacag gggcctgggg cccctggggg atccagtact 1920
aaggacaatt ttaatgtcta taaagccaca agaccatatc tagctcattg tcctgactgc 1980
ggagaagggc attcgtgcca cagccctatc gcattggagc gcatcagaaa tgaagcaacg 2040
gacggaacgc tgaaaatcca ggtctctttg cagatcggga taaagacaga tgacagccac 2100
gattggacca agctgcgcta tatggatagc catacgcccg cggacgcgga gcgagccgga 2160
ttgcttgtaa ggacttcagc accgtgcacg atcaccggga ccatgggaca ctttattctc 2220
gcccgatgcc cgaaaggaga gacgctgaca gtgggattta cggacagcag aaagatcagc 2280
cacacatgca cacacccgtt ccatcatgaa ccacctgtga taggtaggga gaggttccac 2340
tctcgaccac aacatggtaa agagttacct tgcagcacgt acgtgcagag caccgctgcc 2400
actgctgagg agatagaggt gcatatgccc ccagatactc ctgaccgcac gctgatgacg 2460
cagcagtctg gcaacgtgaa gatcacagtt aatgggcaga cggtgcggta caagtgcaac 2520
tgcggtggct ccggaggaca gggacctggc gctcctcagg gaccaggggc accacagggc 2580
ccaggcgccc cacaggggcc tggggcccct gggggatcca acgagggact gacaaccaca 2640
gacaaagtga tcaataactg caaaattgat cagtgccatg ctgcagtcac taatcacaag 2700
aattggcaat acaactcccc tttagtcccg cgcaacgctg aactcgggga ccgtaaagga 2760
aagatccaca tcccattccc attggcaaac gtgacttgca gagtgccaaa agcaagaaac 2820
cctacagtaa cttacggaaa aaaccaagtc accatgctgc tgtatcctga ccatccgaca 2880
ctcttgtctt accgtaacat gggacaggaa ccaaattacc acgaggagtg ggtgacacac 2940
aagaaggagg ttaccttgac cgtgcctact gagggtctgg aggtcacttg gggcaacaac 3000
gaaccataca agtactggcc gcagatgtct acgaacggta ctgctcatgg tcacccacat 3060
gagataatct tgtactatta tgagctgtac cccactatga ctgtagtcat tgtgtcggtg 3120
gcctcgttcg tgcttctgtc gatggtgggc acagcagtgg gaatgtgtgt gtgcgcacgg 3180
cgcagatgca ttacaccata tgaattaaca ccaggagcca ctgttccctt cctgctcagc 3240
ctgctatgct gcgtcagaac gaccaaggcg gccacatatt acgaggctgc ggcatatcta 3300
tggaacgaac agcagcccct gttctggttg caggctctta tcccgctggc cgccttgatc 3360
gtcctgtgca actgtctgaa actcttgcca tgctgctgta agaccctggc ttttttagcc 3420
gtaatgagca tcggtgccca cactgtgagc gcgtacgaac acgtaacagt gatcccgaac 3480
acggtgggag taccgtataa gactcttgtc aacagaccgg gttacagccc catggtgttg 3540
gagatggagc tacaatcagt caccttggaa ccaacactgt cacttgacta catcacgtgc 3600
gagtacaaaa ctgtcatccc ctccccgtac gtgaagtgct gtggtacagc agagtgcaag 3660
gacaagagcc taccagacta cagctgcaag gtctttactg gagtctaccc atttatgtgg 3720
ggcggcgcct actgcttttg cgacgccgaa aatacgcaat tgagcgaggc acatgtagag 3780
aaatctgaat cttgcaaaac agagtttgca tcggcctaca gagcccacac cgcatcggcg 3840
tcggcgaagc tccgcgtcct ttaccaagga aacaacatta ccgtagctgc ctacgctaac 3900
ggtgaccatg ccgtcacagt aaaggacgcc aagtttgtcg tgggcccaat gtcctccgcc 3960
tggacacctt ttgacaacaa aatcgtggtg tacaaaggcg acgtctacaa catggactac 4020
ccaccttttg gcgcaggaag accaggacaa tttggtgaca ttcaaagtcg tacaccggaa 4080
agtaaagacg tttatgccaa cactcagttg gtactacaga ggccagcagc aggcacggta 4140
catgtaccat actctcaggc accatctggc ttcaagtatt ggctgaagga acgaggagca 4200
tcgctacagc acacggcacc gttcggttgc cagattgcga caaacccggt aagagctgta 4260
aattgcgctg tggggaacat accaatttcc atcgacatac cggatgcggc ctttactagg 4320
gttgtcgatg caccctctgt aacggacatg tcatgcgaag taccagcctg cactcactcc 4380
tccgactttg gggcgtcgc catcatcaaa tacacagcta gcaagaaagg taaatgtgca 4440
gtacattcga tgaccaacgc cgttaccatt cgagaagccg acgtagaagt agaggggaac 4500
tcccagctgc aaatatcctt ctcaacagcc ctggcaagcg ccgagtttcg cgtgcaagtg 4560
tgctccacac aagtacactg cgcagccgca tgccaccctc caaaggacca catagtcaat 4620
tacccagcat cacacaccac ccttggggtc caggatatat ccacaacggc aatgtcttgg 4680
gtgcagaaga ttacgggagg agtaggatta attgttgctg ttgctgcctt aattttaatt 4740
gtggtgctat gcgtgtcgtt tagcaggcac taatgatccg gaggggcacc cacttcaagc 4800
tccacttcaa gctctacagc ggaagcacag cagcagcagc agcagcagca gcagcagcag 4860
cacctggagc agctgttgat ggacctacag gagctcctga gcaggatgga gaattacagg 4920
aacctgaaac tccccaggat gctcaccttc aaattttact tgcccaagca ggccacagaa 4980
ttgaaagatc ttcagtgcct agaagatgaa cttggacctc tgcggcatgt tctggatttg 5040
actcaaagca aaagctttca attggaagat gctgagaatt tcatcagcaa tatcagagta 5100
actgttgtaa aactaaaggg ctctgacaac acatttgagt gccaattcga tgatgagtca 5160
gcaactgtgg tggactttct gaggagatgg atagccttct gtcaaagcat catctcaaca 5220
agccctcaag gggatccgc tgtgccttct agttgccagc catctgttgt ttgcccctcc 5280
cccgtgcctt ccttgaccct ggaaggtgcc actcccactg tcctttccta ataaaatgag 5340
gaaattgcat cgcattgtct gagtaggtgt cattctattc tggggggtgg ggtggggcag 5400
gacagcaagg gggaggattg ggaagacaat agcaggcatg ctggggatgc ggtgggctct 5460
atgggtaccc aggtgctgaa gaattgaccc ggttcctcct gggccagaaa gaagcaggca 5520
catccccttc tctgtgacac accctgtcca cgcccctggt tcttagttcc agccccactc 5580
ataggacact catagctcag gagggctccg ccttcaatcc cacccgctaa agtacttgga 5640
gcggtctctc cctccctcat cagcccacca aaccaaacct agcctccaag agtgggaaga 5700
aattaaagca agataggcta ttaagtgcag agggagagaa aatgcctcca acatgtgagg 5760

-continued

```
aagtaatgag agaaatcata gaattttaag gccatgattt aaggccatca tggcctaagc   5820
ttgaaaggag ataggatcaa agcttggcgt aatcatggtc atagctgttt cctgtgtgaa   5880
attgttatcc gctcacaatt ccacacaaca tacgagccgg aagcataaag tgtaaagcct   5940
ggggtgccta atgagtgagc taactcacat taattgcgtt gcgctcactg cccgctttcc   6000
agtcgggaaa cctgtcgtgc cagctgcatt aatgaatcgg ccaacgcgcg gggagaggcg   6060
gtttgcgtat tgggcgctct tccgcttcct cgctcactga ctcgctgcgc tcggtcgttc   6120
ggctgcggcg agcggtatca gctcactcaa aggcggtaat acggttatcc acagaatcag   6180
gggataacgc aggaaagaac atgtgagcaa aaggccagca aaaggccagg aaccgtaaaa   6240
aggccgcgtt gctggcgttt ttccataggc tccgcccccc tgacgagcat cacaaaaatc   6300
gacgctcaag tcagaggtgg cgaaacccga caggactata aagataccag gcgtttcccc   6360
ctggaagctc cctcgtgcgc tctcctgttc cgaccctgcc gcttaccgga tacctgtccg   6420
cctttctccc ttcgggaagc gtggcgcttt ctcatagctc acgctgtagg tatctcagtt   6480
cggtgtaggt cgttcgctcc aagctgggct gtgtgcacga accccccgtt cagcccgacc   6540
gctgcgcctt atccggtaac tatcgtcttg agtccaaccc ggtaagacac gacttatcgc   6600
cactggcagc agccactggt aacaggatta gcagagcgag gtatgtaggc ggtgctacag   6660
agttcttgaa gtggtggcct aactacggct acactagaag aacagtattt ggtatctgcg   6720
ctctgctgaa gccagttacc ttcggaaaaa gagttggtag ctcttgatcc ggcaaacaaa   6780
ccaccgctgg tagcggtggt ttttttgttt gcaagcagca gattacgcgc agaaaaaaag   6840
gatctcaaga agatcctttg atcttttcta cggggtctga cgctcagtgg aacgaaaact   6900
cacgttaagg gattttggtc atgagattat caaaaaggat cttcacctag atccttttaa   6960
attaaaaatg aagttttaaa tcaatctaaa gtatatatga gtaaacttgg tctgacagtt   7020
accaatgctt aatcagtgag gcacctatct cagcgatctg tctatttcgt tcatccatag   7080
ttgcctgact ccccgtcgtg tagataacta cgatacggga gggcttacca tctggcccca   7140
gtgctgcaat gataccgcga gaaccacgct caccggctcc agatttatca gcaataaacc   7200
agccagccgg aagggccgag cgcagaagtg gtcctgcaac tttatccgcc tccatccagt   7260
ctattaattg ttgccgggaa gctagagtaa gtagttcgcc agttaatagt ttgcgcaacg   7320
ttgttgccat tgctacaggc atcgtggtgt cacgctcgtc gtttggtatg gcttcattca   7380
gctccggttc ccaacgatca aggcgagtta catgatcccc catgttgtgc aaaaaagcgg   7440
ttagctcctt cggtcctccg atcgttgtca gaagtaagtt ggccgcagtg ttatcactca   7500
tggttatggc agcactgcat aattctctta ctgtcatgcc atccgtaaga tgcttttctg   7560
tgactggtga gtactcaacc aagtcattct gagaatagtg tatgcggcga ccgagttgct   7620
cttgcccggc gtcaatacgg gataataccg cgccacatag cagaacttta aaagtgctca   7680
tcattggaaa acgttcttcg gggcgaaaac tctcaaggat cttaccgctg ttgagatcca   7740
gttcgatgta acccactcgt gcacccaact gatcttcagc atcttttact ttcaccagcg   7800
tttctgggtg agcaaaaaca ggaaggcaaa atgccgcaaa aaagggaata agggcgacac   7860
ggaaatgttg aatactcata ctcttccttt ttcaatatta ttgaagcatt tatcagggtt   7920
attgtctcat gagcggatac atatttgaat gtatttagaa aaataaacaa ataggggttc   7980
cgcgcacatt tccccgaaaa gtgccacctg acgtctaaga aaccattatt atcatgacat   8040
taacctataa aaataggcgt atcacgaggc cctttcgggt cgcgcgtttc ggtgatgacg   8100
gtgaaaacct ctgacacatg cagctcccgt tgacggtcac agcttgtctg taagcggatg   8160
```

-continued

```
ccgggagcag acaagcccgt cagggcgcgt cagcgggtgt tggcgggtgt cggggctggc   8220

ttaactatgc ggcatcagag cagattgtac tgagagtgca ccataaaatt gtaaacgtta   8280

atattttgtt aaaattcgcg ttaaattttt gttaaatcag ctcatttttt aaccaatagg   8340

ccgaaatcgg caaaatccct tataaatcaa aagaatagcc cgagataggg ttgagtgttg   8400

ttccagtttg gaacaagagt ccactattaa agaacgtgga ctccaacgtc aaagggcgaa   8460

aaaccgtcta tcagggcgat ggcccactac gtgaaccatc acccaaatca agttttttgg   8520

ggtcgaggtg ccgtaaagca ctaaatcgga accctaaagg gagcccccga tttagagctt   8580

gacggggaaa gccggcgaac gtggcgagaa aggaagggaa gaaagcgaaa ggagcgggcg   8640

ctagggcgct ggcaagtgta gcggtcacgc tgcgcgtaac caccacaccc gccgcgctta   8700

atgcgccgct acagggcgcg tactatggtt gctttgacgt atgcggtgtg aaataccgca   8760

cagatgcgta aggagaaaat accgcatcag gcgccattcg ccattcaggc tgcgcaactg   8820

ttgggaaggg cgatcggtgc gggcctcttc gctattacgc cagctggcga aagggggatg   8880

tgctgcaagg cgattaagtt gggtaacgcc agggttttcc cagtcacgac gttgtaaaac   8940

gacggccagt gaattccatg gtctcaactt tc                                 8972


<210> SEQ ID NO 99
<211> LENGTH: 1423
<212> TYPE: PRT
<213> ORGANISM: Artificial Sequence
<220> FEATURE:
<223> OTHER INFORMATION: Synthetic CHIKV  264.264.58 ( 264 dual)

<400> SEQUENCE: 99

Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Arg Gln Lys Lys Gln Ala Pro Gln Asn Asp
65                  70                  75                  80

Pro Lys Gln Lys Lys Gln Pro Pro Gln Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Met Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
```

-continued

```
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Leu Pro Val Leu Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Ser Thr Leu Arg Met Leu Glu Asp Asn Val Met
    290                 295                 300

Arg Pro Gly Tyr Tyr Gln Leu Leu Lys Ala Ser Leu Thr Cys Ser Pro
305                 310                 315                 320

His Ser Gly Gly Gln Gly Pro Gly Ala Pro Gln Gly Pro Gly Ala Pro
                325                 330                 335

Gln Gly Pro Gly Ala Pro Gln Gly Pro Gly Ala Pro Gln Gly Pro Gly
            340                 345                 350

Ala Pro Gln Gly Pro Gly Ala Pro Gln Gly Pro Gly Ala Pro Gln Gly
        355                 360                 365

Pro Gly Ala Pro Gln Gly Pro Gly Ala Pro Gln Gly Pro Gly Ala Pro
    370                 375                 380

Gln Gly Pro Gly Ala Pro Gln Gly Pro Gly Ala Pro Gln Gly Pro Gly
385                 390                 395                 400

Ala Pro Gln Gly Pro Gly Ala Pro Gly Gly Ser Ser Thr Lys Asp Asn
                405                 410                 415

Phe Asn Val Tyr Lys Ala Thr Arg Pro Tyr Leu Ala His Cys Pro Asp
            420                 425                 430

Cys Gly Glu Gly His Ser Cys His Ser Pro Ile Ala Leu Glu Arg Ile
        435                 440                 445

Arg Asn Glu Ala Thr Asp Gly Thr Leu Lys Ile Gln Val Ser Leu Gln
    450                 455                 460

Ile Gly Ile Lys Thr Asp Asp Ser His Asp Trp Thr Lys Leu Arg Tyr
465                 470                 475                 480

Met Asp Ser His Thr Pro Ala Asp Ala Glu Arg Ala Gly Leu Leu Val
                485                 490                 495

Arg Thr Ser Ala Pro Cys Thr Ile Thr Gly Thr Met Gly His Phe Ile
            500                 505                 510

Leu Ala Arg Cys Pro Lys Gly Glu Thr Leu Thr Val Gly Phe Thr Asp
        515                 520                 525

Ser Arg Lys Ile Ser His Thr Cys Thr His Pro Phe His His Glu Pro
    530                 535                 540

Pro Val Ile Gly Arg Glu Arg Phe His Ser Arg Pro Gln His Gly Lys
545                 550                 555                 560

Glu Leu Pro Cys Ser Thr Tyr Val Gln Ser Thr Ala Ala Thr Ala Glu
                565                 570                 575

Glu Ile Glu Val His Met Pro Pro Asp Thr Pro Asp Arg Thr Leu Met
            580                 585                 590

Thr Gln Gln Ser Gly Asn Val Lys Ile Thr Val Asn Gly Gln Thr Val
        595                 600                 605

Arg Tyr Lys Cys Asn Cys Gly Gly Ser Gly Gly Gln Gly Pro Gly Ala
    610                 615                 620

Pro Gln Gly Pro Gly Ala Pro Gln Gly Pro Gly Ala Pro Gln Gly Pro
625                 630                 635                 640
```

-continued

```
Gly Ala Pro Gln Gly Pro Gly Ala Pro Gln Gly Pro Gly Ala Pro Gln
                645                 650                 655

Gly Pro Gly Ala Pro Gln Gly Pro Gly Ala Pro Gln Gly Pro Gly Ala
            660                 665                 670

Pro Gln Gly Pro Gly Ala Pro Gln Gly Pro Gly Ala Pro Gln Gly Pro
        675                 680                 685

Gly Ala Pro Gln Gly Pro Gly Ala Pro Gln Gly Pro Gly Ala Pro Gly
    690                 695                 700

Gly Ser Asn Glu Gly Leu Thr Thr Thr Asp Lys Val Ile Asn Asn Cys
705                 710                 715                 720

Lys Ile Asp Gln Cys His Ala Ala Val Thr Asn His Lys Asn Trp Gln
                725                 730                 735

Tyr Asn Ser Pro Leu Val Pro Arg Asn Ala Glu Leu Gly Asp Arg Lys
            740                 745                 750

Gly Lys Ile His Ile Pro Phe Pro Leu Ala Asn Val Thr Cys Arg Val
        755                 760                 765

Pro Lys Ala Arg Asn Pro Thr Val Thr Tyr Gly Lys Asn Gln Val Thr
    770                 775                 780

Met Leu Leu Tyr Pro Asp His Pro Thr Leu Leu Ser Tyr Arg Asn Met
785                 790                 795                 800

Gly Gln Glu Pro Asn Tyr His Glu Glu Trp Val Thr His Lys Lys Glu
                805                 810                 815

Val Thr Leu Thr Val Pro Thr Glu Gly Leu Glu Val Thr Trp Gly Asn
            820                 825                 830

Asn Glu Pro Tyr Lys Tyr Trp Pro Gln Met Ser Thr Asn Gly Thr Ala
        835                 840                 845

His Gly His Pro His Glu Ile Ile Leu Tyr Tyr Tyr Glu Leu Tyr Pro
    850                 855                 860

Thr Met Thr Val Val Ile Val Ser Val Ala Ser Phe Val Leu Leu Ser
865                 870                 875                 880

Met Val Gly Thr Ala Val Gly Met Cys Val Cys Ala Arg Arg Arg Cys
                885                 890                 895

Ile Thr Pro Tyr Glu Leu Thr Pro Gly Ala Thr Val Pro Phe Leu Leu
            900                 905                 910

Ser Leu Leu Cys Cys Val Arg Thr Thr Lys Ala Ala Thr Tyr Tyr Glu
        915                 920                 925

Ala Ala Ala Tyr Leu Trp Asn Glu Gln Gln Pro Leu Phe Trp Leu Gln
    930                 935                 940

Ala Leu Ile Pro Leu Ala Ala Leu Ile Val Leu Cys Asn Cys Leu Lys
945                 950                 955                 960

Leu Leu Pro Cys Cys Cys Lys Thr Leu Ala Phe Leu Ala Val Met Ser
                965                 970                 975

Ile Gly Ala His Thr Val Ser Ala Tyr Glu His Val Thr Val Ile Pro
            980                 985                 990

Asn Thr Val Gly Val Pro Tyr Lys  Thr Leu Val Asn Arg  Pro Gly Tyr
        995                 1000                1005

Ser Pro  Met Val Leu Glu Met  Glu Leu Gln Ser Val  Thr Leu Glu
    1010                1015                1020

Pro Thr  Leu Ser Leu Asp Tyr  Ile Thr Cys Glu Tyr  Lys Thr Val
    1025                1030                1035

Ile Pro  Ser Pro Tyr Val Lys  Cys Cys Gly Thr Ala  Glu Cys Lys
    1040                1045                1050
```

```
Asp Lys  Ser Leu Pro Asp Tyr  Ser Cys Lys Val Phe  Thr Gly Val
    1055                 1060                 1065

Tyr Pro  Phe Met Trp Gly Gly  Ala Tyr Cys Phe Cys  Asp Ala Glu
    1070                 1075                 1080

Asn Thr  Gln Leu Ser Glu Ala  His Val Glu Lys Ser  Glu Ser Cys
    1085                 1090                 1095

Lys Thr  Glu Phe Ala Ser Ala  Tyr Arg Ala His Thr  Ala Ser Ala
    1100                 1105                 1110

Ser Ala  Lys Leu Arg Val Leu  Tyr Gln Gly Asn Asn  Ile Thr Val
    1115                 1120                 1125

Ala Ala  Tyr Ala Asn Gly Asp  His Ala Val Thr Val  Lys Asp Ala
    1130                 1135                 1140

Lys Phe  Val Val Gly Pro Met  Ser Ser Ala Trp Thr  Pro Phe Asp
    1145                 1150                 1155

Asn Lys  Ile Val Val Tyr Lys  Gly Asp Val Tyr Asn  Met Asp Tyr
    1160                 1165                 1170

Pro Pro  Phe Gly Ala Gly Arg  Pro Gly Gln Phe Gly  Asp Ile Gln
    1175                 1180                 1185

Ser Arg  Thr Pro Glu Ser Lys  Asp Val Tyr Ala Asn  Thr Gln Leu
    1190                 1195                 1200

Val Leu  Gln Arg Pro Ala Ala  Gly Thr Val His Val  Pro Tyr Ser
    1205                 1210                 1215

Gln Ala  Pro Ser Gly Phe Lys  Tyr Trp Leu Lys Glu  Arg Gly Ala
    1220                 1225                 1230

Ser Leu  Gln His Thr Ala Pro  Phe Gly Cys Gln Ile  Ala Thr Asn
    1235                 1240                 1245

Pro Val  Arg Ala Val Asn Cys  Ala Val Gly Asn Ile  Pro Ile Ser
    1250                 1255                 1260

Ile Asp  Ile Pro Asp Ala Ala  Phe Thr Arg Val Val  Asp Ala Pro
    1265                 1270                 1275

Ser Val  Thr Asp Met Ser Cys  Glu Val Pro Ala Cys  Thr His Ser
    1280                 1285                 1290

Ser Asp  Phe Gly Gly Val Ala  Ile Ile Lys Tyr Thr  Ala Ser Lys
    1295                 1300                 1305

Lys Gly  Lys Cys Ala Val His  Ser Met Thr Asn Ala  Val Thr Ile
    1310                 1315                 1320

Arg Glu  Ala Asp Val Glu Val  Glu Gly Asn Ser Gln  Leu Gln Ile
    1325                 1330                 1335

Ser Phe  Ser Thr Ala Leu Ala  Ser Ala Glu Phe Arg  Val Gln Val
    1340                 1345                 1350

Cys Ser  Thr Gln Val His Cys  Ala Ala Ala Cys His  Pro Pro Lys
    1355                 1360                 1365

Asp His  Ile Val Asn Tyr Pro  Ala Ser His Thr Thr  Leu Gly Val
    1370                 1375                 1380

Gln Asp  Ile Ser Thr Thr Ala  Met Ser Trp Val Gln  Lys Ile Thr
    1385                 1390                 1395

Gly Gly  Val Gly Leu Ile Val  Ala Val Ala Ala Leu  Ile Leu Ile
    1400                 1405                 1410

Val Val  Leu Cys Val Ser Phe  Ser Arg His
    1415                 1420
```

<210> SEQ ID NO 100
<211> LENGTH: 9332
<212> TYPE: DNA

<213> ORGANISM: Artificial Sequence
<220> FEATURE:
<223> OTHER INFORMATION: Synthetic Expression Vector for CHIKV viral
      structural protein containing CSP epitope 14X(264) in E2 and E3
      (264 dual)

<400> SEQUENCE: 100

```
gaattcccat tgcatacgtt gtatccatat cataatatgt acatttatat tggctcatgt     60

ccaacattac cgccatgttg acattgatta ttgactagtt attaatagta atcaattacg    120

gggtcattag ttcatagccc atatatggag ttccgcgtta cataacttac ggtaaatggc    180

ccgcctggct gaccgcccaa cgacccccgc ccattgacgt caataatgac gtatgttccc    240

atagtaacgc caatagggac tttccattga cgtcaatggg tggagtattt acggtaaact    300

gcccacttgg cagtacatca agtgtatcat atgccaagta cgccccctat tgacgtcaat    360

gacggtaaat ggcccgcctg gcattatgcc cagtacatga ccttatggga ctttcctact    420

tggcagtaca tctacgtatt agtcatcgct attaccatgg tgatgcggtt ttggcagtac    480

atcaatgggc gtggatagcg gtttgactca cggggatttc caagtctcca ccccattgac    540

gtcaatggga gtttgttttg gcaccaaaat caacgggact ttccaaaatg tcgtaacaac    600

tccgccccat tgacgcaaat gggcggtagg cgtgtacggt gggaggtcta tataagcaga    660

gctcgtttag tgaaccgtca gatcgcctgg agacgccatc cacgctgttt tgacctccat    720

agaagacacc gggaccgatc cagcctccgt taacggtgga gggcagtgta gtctgagcag    780

tactcgttgc tgccgcgcgc gccaccagac ataatagctg acagactaac agactgttcc    840

tttgcggccg ctctagacac catggagttc atcccgacgc aaactttcta taacagaagg    900

taccaacccc gaccctgggc cccacgccct acaattcaag taattagacc tagaccacgt    960

ccacagaggc aggctgggca actcgcccag ctgatctccg cagtcaacaa attgaccatg   1020

cgcgcggtac ctcaacagaa gcctcgcaga aatcggaaaa acaagaagca aaggcagaag   1080

aagcaggcgc cgcaaaacga cccaaagcaa aagaagcaac caccacaaaa gaagccggct   1140

caaaagaaga agaaaccagg ccgtagggag agaatgtgca tgaaaattga aaatgattgc   1200

atcttcgaag tcaagcatga aggcaaagtg atgggctacg catgcctggt gggggataaa   1260

gtaatgaaac cagcacatgt gaagggaact atcgacaatg ccgatctggc taaactggcc   1320

tttaagcggt cgtctaaata cgatcttgaa tgtgcacaga taccggtgca catgaagtct   1380

gatgcctcga agtttaccca cgagaaaccc gaggggtact ataactggca tcacggagca   1440

gtgcagtatt caggaggccg gttcactatc ccgacgggtg caggcaagcc gggagacagc   1500

ggcagaccga tcttcgacaa caaaggacgg gtggtggcca tcgtcctagg aggggccaac   1560

gaaggtgccc gcacggccct ctccgtggtg acgtggaaca aagacatcgt cacaaaaatt   1620

acccctgagg gagccgaaga gtggagcctc gccctcccgg tcttgtgcct gttggcaaac   1680

actacattcc cctgctctca gccgccttgc acaccctgct gctacgaaaa ggaaccggaa   1740

agcaccttgc gcatgcttga ggacaacgtg atgagacccg gatactacca gctactaaaa   1800

gcatcgctga cttgctctcc ccactccgga ggacagggac ctggcgctcc tcagggacca   1860

ggggcaccac agggcccagg cgccccacag gggcctgggg caccccaggg acctggggct   1920

ccacaggggc ctggcgcacc tcagggccca ggcgctcctc agggacctgg cgctccacag   1980

ggacccggcg ctcctcaggg gcctggggcc cctcagggac ccggcgcacc tcagggacca   2040

ggcgcacccc aggggccagg ggctcctcag ggcccagggg ctccaggcgg atccagtact   2100

aaggacaatt ttaatgtcta taaagccaca agaccatatc tagctcattg tcctgactgc   2160
```

-continued ggagaagggc attcgtgcca cagccctatc gcattggagc gcatcagaaa tgaagcaacg 2220
gacggaacgc tgaaaatcca ggtctctttg cagatcggga taaagacaga tgacagccac 2280
gattggacca agctgcgcta tatggatagc catacgcccg cggacgcgga gcgagccgga 2340
ttgcttgtaa ggacttcagc accgtgcacg atcaccggga ccatgggaca ctttattctc 2400
gcccgatgcc cgaaaggaga gacgctgaca gtgggattta cggacagcag aaagatcagc 2460
cacacatgca cacacccgtt ccatcatgaa ccacctgtga taggtaggga gaggttccac 2520
tctcgaccac aacatggtaa agagttacct tgcagcacgt acgtgcagag caccgctgcc 2580
actgctgagg agatagaggt gcatatgccc ccagatactc ctgaccgcac gctgatgacg 2640
cagcagtctg gcaacgtgaa gatcacagtt aatgggcaga cggtgcggta caagtgcaac 2700
tgcggtggct ccggaggaca gggacctggc gctcctcagg gaccaggggc accacagggc 2760
ccaggcgccc cacaggggcc tggggcaccc cagggacctg ggctccaca ggggcctggc 2820
gcacctcagg gcccaggcgc tcctcaggga cctggcgctc cacagggacc cggcgctcct 2880
caggggcctg ggcccctca gggacccggc gcacctcagg gaccaggcgc accccagggg 2940
ccaggggctc ctcagggccc aggggctcca ggcggatcca acgagggact gacaaccaca 3000
gacaaagtga tcaataactg caaaattgat cagtgccatg ctgcagtcac taatcacaag 3060
aattggcaat acaactcccc tttagtcccg cgcaacgctg aactcgggga ccgtaaagga 3120
aagatccaca tcccattccc attggcaaac gtgacttgca gagtgccaaa agcaagaaac 3180
cctacagtaa cttacggaaa aaaccaagtc accatgctgc tgtatcctga ccatccgaca 3240
ctcttgtctt accgtaacat gggacaggaa ccaaattacc acgaggagtg ggtgacacac 3300
aagaaggagg ttaccttgac cgtgcctact gagggtctgg aggtcacttg gggcaacaac 3360
gaaccataca agtactggcc gcagatgtct acgaacggta ctgctcatgg tcacccacat 3420
gagataatct tgtactatta tgagctgtac cccactatga ctgtagtcat tgtgtcggtg 3480
gcctcgttcg tgcttctgtc gatggtgggc acagcagtgg gaatgtgtgt gtgcgcacgg 3540
cgcagatgca ttacaccata tgaattaaca ccaggagcca ctgttccctt cctgctcagc 3600
ctgctatgct gcgtcagaac gaccaaggcg gccacatatt acgaggctgc ggcatatcta 3660
tggaacgaac agcagcccct gttctggttg caggctctta tcccgctggc cgccttgatc 3720
gtcctgtgca actgtctgaa actcttgcca tgctgctgta agaccctggc tttttagcc 3780
gtaatgagca tcggtgccca cactgtgagc gcgtacgaac acgtaacagt gatcccgaac 3840
acggtgggag taccgtataa gactcttgtc aacagaccgg gttacagccc catggtgttg 3900
gagatggagc tacaatcagt caccttggaa ccaacactgt cacttgacta catcacgtgc 3960
gagtacaaaa ctgtcatccc ctccccgtac gtgaagtgct gtggtacagc agagtgcaag 4020
gacaagagcc taccagacta cagctgcaag gtctttactg gagtctaccc atttatgtgg 4080
ggcggcgcct actgcttttg cgacgccgaa aatacgcaat tgagcgaggc acatgtagag 4140
aaatctgaat cttgcaaaac agagtttgca tcggcctaca gagcccacac cgcatcggcg 4200
tcggcgaagc tccgcgtcct ttaccaagga aacaacatta ccgtagctgc ctacgctaac 4260
ggtgaccatg ccgtcacagt aaaggacgcc aagtttgtcg tgggcccaat gtcctccgcc 4320
tggacacctt ttgacaacaa aatcgtggtg tacaaaggcg acgtctacaa catggactac 4380
ccaccttttg gcgcaggaag accaggacaa tttggtgaca ttcaaagtcg tacaccggaa 4440
agtaaagacg tttatgccaa cactcagttg gtactacaga ggccagcagc aggcacggta 4500

-continued

```
catgtaccat actctcaggc accatctggc ttcaagtatt ggctgaagga acgaggagca   4560
tcgctacagc acacggcacc gttcggttgc cagattgcga caaacccggt aagagctgta   4620
aattgcgctg tggggaacat accaatttcc atcgacatac cggatgcggc ctttactagg   4680
gttgtcgatg caccctctgt aacggacatg tcatgcgaag taccagcctg cactcactcc   4740
tccgactttg gggcgtcgc catcatcaaa tacacagcta gcaagaaagg taaatgtgca   4800
gtacattcga tgaccaacgc cgttaccatt cgagaagccg acgtagaagt agaggggaac   4860
tcccagctgc aaatatcctt ctcaacagcc ctggcaagcg ccgagtttcg cgtgcaagtg   4920
tgctccacac aagtacactg cgcagccgca tgccaccctc caaaggacca catagtcaat   4980
tacccagcat cacacaccac ccttggggtc caggatatat ccacaacggc aatgtcttgg   5040
gtgcagaaga ttacgggagg agtaggatta attgttgctg ttgctgcctt aattttaatt   5100
gtggtgctat gcgtgtcgtt tagcaggcac taatgatccg gaggggcacc cacttcaagc   5160
tccacttcaa gctctacagc ggaagcacag cagcagcagc agcagcagca gcagcagcag   5220
cacctggagc agctgttgat ggacctacag gagctcctga gcaggatgga gaattacagg   5280
aacctgaaac tccccaggat gctcaccttc aaattttact tgcccaagca ggccacagaa   5340
ttgaaagatc ttcagtgcct agaagatgaa cttggacctc tgcggcatgt tctggatttg   5400
actcaaagca aaagctttca attggaagat gctgagaatt tcatcagcaa tatcagagta   5460
actgttgtaa aactaaaggg ctctgacaac acatttgagt gccaattcga tgatgagtca   5520
gcaactgtgg tggactttct gaggagatgg atagccttct gtcaaagcat catctcaaca   5580
agccctcaag gggatccgc tgtgccttct agttgccagc catctgttgt ttgcccctcc   5640
cccgtgcctt ccttgaccct ggaaggtgcc actcccactg tcctttccta ataaaatgag   5700
gaaattgcat cgcattgtct gagtaggtgt cattctattc tggggggtgg ggtggggcag   5760
gacagcaagg gggaggattg ggaagacaat agcaggcatg ctggggatgc ggtgggctct   5820
atgggtaccc aggtgctgaa gaattgaccc ggttcctcct gggccagaaa gaagcaggca   5880
catccccttc tctgtgacac accctgtcca cgcccctggt tcttagttcc agccccactc   5940
ataggacact catagctcag gagggctccg ccttcaatcc cacccgctaa agtacttgga   6000
gcggtctctc cctccctcat cagcccacca aaccaaacct agcctccaag agtgggaaga   6060
aattaaagca agataggcta ttaagtgcag agggagagaa aatgcctcca acatgtgagg   6120
aagtaatgag agaaatcata gaattttaag gccatgattt aaggccatca tggcctaagc   6180
ttgaaaggag ataggatcaa agcttggcgt aatcatggtc atagctgttt cctgtgtgaa   6240
attgttatcc gctcacaatt ccacacaaca tacgagccgg aagcataaag tgtaaagcct   6300
ggggtgccta atgagtgagc taactcacat taattgcgtt gcgctcactg cccgctttcc   6360
agtcgggaaa cctgtcgtgc cagctgcatt aatgaatcgg ccaacgcgcg gggagaggcg   6420
gtttgcgtat tgggcgctct tccgcttcct cgctcactga ctcgctgcgc tcggtcgttc   6480
ggctgcggcg agcggtatca gctcactcaa aggcggtaat acggttatcc acagaatcag   6540
gggataacgc aggaaagaac atgtgagcaa aaggccagca aaaggccagg aaccgtaaaa   6600
aggccgcgtt gctggcgttt ttccataggc tccgcccccc tgacgagcat cacaaaaatc   6660
gacgctcaag tcagaggtgg cgaaacccga caggactata aagataccag gcgtttcccc   6720
ctggaagctc cctcgtgcgc tctcctgttc cgaccctgcc gcttaccgga tacctgtccg   6780
cctttctccc ttcgggaagc gtggcgcttt ctcatagctc acgctgtagg tatctcagtt   6840
cggtgtaggt cgttcgctcc aagctgggct gtgtgcacga accccccgtt cagcccgacc   6900
```

```
gctgcgcctt atccggtaac tatcgtcttg agtccaaccc ggtaagacac gacttatcgc   6960
cactggcagc agccactggt aacaggatta gcagagcgag gtatgtaggc ggtgctacag   7020
agttcttgaa gtggtggcct aactacggct acactagaag aacagtattt ggtatctgcg   7080
ctctgctgaa gccagttacc ttcggaaaaa gagttggtag ctcttgatcc ggcaaacaaa   7140
ccaccgctgg tagcggtggt ttttttgttt gcaagcagca gattacgcgc agaaaaaaag   7200
gatctcaaga agatcctttg atcttttcta cggggtctga cgctcagtgg aacgaaaact   7260
cacgttaagg gattttggtc atgagattat caaaaaggat cttcacctag atccttttaa   7320
attaaaaatg aagttttaaa tcaatctaaa gtatatatga gtaaacttgg tctgacagtt   7380
accaatgctt aatcagtgag gcacctatct cagcgatctg tctatttcgt tcatccatag   7440
ttgcctgact ccccgtcgtg tagataacta cgatacggga gggcttacca tctggcccca   7500
gtgctgcaat gataccgcga gaaccacgct caccggctcc agatttatca gcaataaacc   7560
agccagccgg aagggccgag cgcagaagtg gtcctgcaac tttatccgcc tccatccagt   7620
ctattaattg ttgccgggaa gctagagtaa gtagttcgcc agttaatagt ttgcgcaacg   7680
ttgttgccat tgctacaggc atcgtggtgt cacgctcgtc gtttggtatg gcttcattca   7740
gctccggttc ccaacgatca aggcgagtta catgatcccc catgttgtgc aaaaaagcgg   7800
ttagctcctt cggtcctccg atcgttgtca gaagtaagtt ggccgcagtg ttatcactca   7860
tggttatggc agcactgcat aattctctta ctgtcatgcc atccgtaaga tgcttttctg   7920
tgactggtga gtactcaacc aagtcattct gagaatagtg tatgcggcga ccgagttgct   7980
cttgcccggc gtcaatacgg gataataccg cgccacatag cagaacttta aaagtgctca   8040
tcattggaaa acgttcttcg gggcgaaaac tctcaaggat cttaccgctg ttgagatcca   8100
gttcgatgta acccactcgt gcacccaact gatcttcagc atcttttact ttcaccagcg   8160
tttctgggtg agcaaaaaca ggaaggcaaa atgccgcaaa aaagggaata agggcgacac   8220
ggaaatgttg aatactcata ctcttccttt ttcaatatta ttgaagcatt tatcagggtt   8280
attgtctcat gagcggatac atatttgaat gtatttagaa aaataaacaa ataggggttc   8340
cgcgcacatt tccccgaaaa gtgccacctg acgtctaaga aaccattatt atcatgacat   8400
taacctataa aaataggcgt atcacgaggc cctttcgggt cgcgcgtttc ggtgatgacg   8460
gtgaaaacct ctgacacatg cagctcccgt tgacggtcac agcttgtctg taagcggatg   8520
ccgggagcag acaagcccgt cagggcgcgt cagcgggtgt tggcgggtgt cggggctggc   8580
ttaactatgc ggcatcagag cagattgtac tgagagtgca ccataaaatt gtaaacgtta   8640
atattttgtt aaaattcgcg ttaaattttt gttaaatcag ctcatttttt aaccaatagg   8700
ccgaaatcgg caaaatccct tataaatcaa aagaatagcc cgagataggg ttgagtgttg   8760
ttccagtttg gaacaagagt ccactattaa agaacgtgga ctccaacgtc aaagggcgaa   8820
aaaccgtcta tcagggcgat ggcccactac gtgaaccatc acccaaatca agttttttgg   8880
ggtcgaggtg ccgtaaagca ctaaatcgga accctaaagg gagcccccga tttagagctt   8940
gacggggaaa gccggcgaac gtggcgagaa aggaagggaa gaaagcgaaa ggagcgggcg   9000
ctagggcgct ggcaagtgta gcggtcacgc tgcgcgtaac caccacaccc gccgcgctta   9060
atgcgccgct acagggcgcg tactatggtt gctttgacgt atgcggtgtg aaataccgca   9120
cagatgcgta aggagaaaat accgcatcag gcgccattcg ccattcaggc tgcgcaactg   9180
ttgggaaggg cgatcggtgc gggcctcttc gctattacgc cagctggcga aagggggatg   9240
```

```
tgctgcaagg cgattaagtt gggtaacgcc agggttttcc cagtcacgac gttgtaaaac   9300

gacggccagt gaattccatg gtctcaactt tc                                 9332


<210> SEQ ID NO 101
<211> LENGTH: 1303
<212> TYPE: PRT
<213> ORGANISM: Artificial Sequence
<220> FEATURE:
<223> OTHER INFORMATION: Synthetic CHIKV viral structural protein
      containing CSP antigen 74 in E2 and E3 (74 dual)

<400> SEQUENCE: 101

Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Arg Gln Lys Lys Gln Ala Pro Gln Asn Asp
65                  70                  75                  80

Pro Lys Gln Lys Lys Gln Pro Pro Gln Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Met Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Leu Pro Val Leu Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Ser Thr Leu Arg Met Leu Glu Asp Asn Val Met
    290                 295                 300

Arg Pro Gly Tyr Tyr Gln Leu Leu Lys Ala Ser Leu Thr Cys Ser Pro
305                 310                 315                 320

His Ser Gly Gly Asn Pro Asn Ala Asn Pro Asn Ala Asn Pro Asn Ala
                325                 330                 335

Asn Pro Asn Ala Asn Pro Asn Ala Asn Pro Asn Ala Gly Gly Ser Ser
```

```
            340                 345                 350

Thr Lys Asp Asn Phe Asn Val Tyr Lys Ala Thr Arg Pro Tyr Leu Ala
        355                 360                 365

His Cys Pro Asp Cys Gly Glu Gly His Ser Cys His Ser Pro Ile Ala
    370                 375                 380

Leu Glu Arg Ile Arg Asn Glu Ala Thr Asp Gly Thr Leu Lys Ile Gln
385                 390                 395                 400

Val Ser Leu Gln Ile Gly Ile Lys Thr Asp Asp Ser His Asp Trp Thr
                405                 410                 415

Lys Leu Arg Tyr Met Asp Ser His Thr Pro Ala Asp Ala Glu Arg Ala
            420                 425                 430

Gly Leu Leu Val Arg Thr Ser Ala Pro Cys Thr Ile Thr Gly Thr Met
        435                 440                 445

Gly His Phe Ile Leu Ala Arg Cys Pro Lys Gly Glu Thr Leu Thr Val
    450                 455                 460

Gly Phe Thr Asp Ser Arg Lys Ile Ser His Thr Cys Thr His Pro Phe
465                 470                 475                 480

His His Glu Pro Pro Val Ile Gly Arg Glu Arg Phe His Ser Arg Pro
                485                 490                 495

Gln His Gly Lys Glu Leu Pro Cys Ser Thr Tyr Val Gln Ser Thr Ala
            500                 505                 510

Ala Thr Ala Glu Glu Ile Glu Val His Met Pro Pro Asp Thr Pro Asp
        515                 520                 525

Arg Thr Leu Met Thr Gln Gln Ser Gly Asn Val Lys Ile Thr Val Asn
    530                 535                 540

Gly Gln Thr Val Arg Tyr Lys Cys Asn Cys Gly Gly Ser Gly Gly Asn
545                 550                 555                 560

Pro Asn Ala Asn Pro Asn Ala Asn Pro Asn Ala Asn Pro Asn Ala Asn
                565                 570                 575

Pro Asn Ala Asn Pro Asn Ala Gly Gly Ser Asn Glu Gly Leu Thr Thr
            580                 585                 590

Thr Asp Lys Val Ile Asn Asn Cys Lys Ile Asp Gln Cys His Ala Ala
        595                 600                 605

Val Thr Asn His Lys Asn Trp Gln Tyr Asn Ser Pro Leu Val Pro Arg
    610                 615                 620

Asn Ala Glu Leu Gly Asp Arg Lys Gly Lys Ile His Ile Pro Phe Pro
625                 630                 635                 640

Leu Ala Asn Val Thr Cys Arg Val Pro Lys Ala Arg Asn Pro Thr Val
                645                 650                 655

Thr Tyr Gly Lys Asn Gln Val Thr Met Leu Leu Tyr Pro Asp His Pro
            660                 665                 670

Thr Leu Leu Ser Tyr Arg Asn Met Gly Gln Glu Pro Asn Tyr His Glu
        675                 680                 685

Glu Trp Val Thr His Lys Lys Glu Val Thr Leu Thr Val Pro Thr Glu
    690                 695                 700

Gly Leu Glu Val Thr Trp Gly Asn Asn Glu Pro Tyr Lys Tyr Trp Pro
705                 710                 715                 720

Gln Met Ser Thr Asn Gly Thr Ala His Gly His Pro His Glu Ile Ile
                725                 730                 735

Leu Tyr Tyr Tyr Glu Leu Tyr Pro Thr Met Thr Val Val Ile Val Ser
            740                 745                 750

Val Ala Ser Phe Val Leu Leu Ser Met Val Gly Thr Ala Val Gly Met
        755                 760                 765
```

-continued

```
Cys Val Cys Ala Arg Arg Arg Cys Ile Thr Pro Tyr Glu Leu Thr Pro
    770                 775                 780

Gly Ala Thr Val Pro Phe Leu Leu Ser Leu Leu Cys Cys Val Arg Thr
785                 790                 795                 800

Thr Lys Ala Ala Thr Tyr Tyr Glu Ala Ala Tyr Leu Trp Asn Glu
                805                 810                 815

Gln Gln Pro Leu Phe Trp Leu Gln Ala Leu Ile Pro Leu Ala Ala Leu
            820                 825                 830

Ile Val Leu Cys Asn Cys Leu Lys Leu Leu Pro Cys Cys Cys Lys Thr
        835                 840                 845

Leu Ala Phe Leu Ala Val Met Ser Ile Gly Ala His Thr Val Ser Ala
    850                 855                 860

Tyr Glu His Val Thr Val Ile Pro Asn Thr Val Gly Val Pro Tyr Lys
865                 870                 875                 880

Thr Leu Val Asn Arg Pro Gly Tyr Ser Pro Met Val Leu Glu Met Glu
                885                 890                 895

Leu Gln Ser Val Thr Leu Glu Pro Thr Leu Ser Leu Asp Tyr Ile Thr
            900                 905                 910

Cys Glu Tyr Lys Thr Val Ile Pro Ser Pro Tyr Val Lys Cys Cys Gly
        915                 920                 925

Thr Ala Glu Cys Lys Asp Lys Ser Leu Pro Asp Tyr Ser Cys Lys Val
    930                 935                 940

Phe Thr Gly Val Tyr Pro Phe Met Trp Gly Gly Ala Tyr Cys Phe Cys
945                 950                 955                 960

Asp Ala Glu Asn Thr Gln Leu Ser Glu Ala His Val Glu Lys Ser Glu
                965                 970                 975

Ser Cys Lys Thr Glu Phe Ala Ser Ala Tyr Arg Ala His Thr Ala Ser
            980                 985                 990

Ala Ser Ala Lys Leu Arg Val Leu  Tyr Gln Gly Asn Asn  Ile Thr Val
        995                 1000                 1005

Ala Ala  Tyr Ala Asn Gly Asp  His Ala Val Thr Val  Lys Asp Ala
    1010                 1015                 1020

Lys Phe  Val Val Gly Pro Met  Ser Ser Ala Trp Thr  Pro Phe Asp
    1025                 1030                 1035

Asn Lys  Ile Val Val Tyr Lys  Gly Asp Val Tyr Asn  Met Asp Tyr
    1040                 1045                 1050

Pro Pro  Phe Gly Ala Gly Arg  Pro Gly Gln Phe Gly  Asp Ile Gln
    1055                 1060                 1065

Ser Arg  Thr Pro Glu Ser Lys  Asp Val Tyr Ala Asn  Thr Gln Leu
    1070                 1075                 1080

Val Leu  Gln Arg Pro Ala Ala  Gly Thr Val His Val  Pro Tyr Ser
    1085                 1090                 1095

Gln Ala  Pro Ser Gly Phe Lys  Tyr Trp Leu Lys Glu  Arg Gly Ala
    1100                 1105                 1110

Ser Leu  Gln His Thr Ala Pro  Phe Gly Cys Gln Ile  Ala Thr Asn
    1115                 1120                 1125

Pro Val  Arg Ala Val Asn Cys  Ala Val Gly Asn Ile  Pro Ile Ser
    1130                 1135                 1140

Ile Asp  Ile Pro Asp Ala Ala  Phe Thr Arg Val Val  Asp Ala Pro
    1145                 1150                 1155

Ser Val  Thr Asp Met Ser Cys  Glu Val Pro Ala Cys  Thr His Ser
    1160                 1165                 1170
```

```
Ser Asp  Phe Gly Gly Val Ala  Ile Ile Lys Tyr Thr  Ala Ser Lys
    1175                 1180                 1185

Lys Gly  Lys Cys Ala Val His  Ser Met Thr Asn Ala  Val Thr Ile
    1190                 1195                 1200

Arg Glu  Ala Asp Val Glu Val  Glu Gly Asn Ser Gln  Leu Gln Ile
    1205                 1210                 1215

Ser Phe  Ser Thr Ala Leu Ala  Ser Ala Glu Phe Arg  Val Gln Val
    1220                 1225                 1230

Cys Ser  Thr Gln Val His Cys  Ala Ala Ala Cys His  Pro Pro Lys
    1235                 1240                 1245

Asp His  Ile Val Asn Tyr Pro  Ala Ser His Thr Thr  Leu Gly Val
    1250                 1255                 1260

Gln Asp  Ile Ser Thr Thr Ala  Met Ser Trp Val Gln  Lys Ile Thr
    1265                 1270                 1275

Gly Gly  Val Gly Leu Ile Val  Ala Val Ala Ala Leu  Ile Leu Ile
    1280                 1285                 1290

Val Val  Leu Cys Val Ser Phe  Ser Arg His
    1295                 1300
```

<210> SEQ ID NO 102
<211> LENGTH: 8972
<212> TYPE: DNA
<213> ORGANISM: Artificial Sequence
<220> FEATURE:
<223> OTHER INFORMATION: Synthetic Expression vector for CHIKV viral structural protein containing CSP antigen 74 in E2 and E3 (74 dual) (CHIKV 74.74.58)

<400> SEQUENCE: 102

```
gaattcccat tgcatacgtt gtatccatat cataatatgt acatttatat tggctcatgt     60

ccaacattac cgccatgttg acattgatta ttgactagtt attaatagta atcaattacg    120

gggtcattag ttcatagccc atatatggag ttccgcgtta cataacttac ggtaaatggc    180

ccgcctggct gaccgcccaa cgacccccgc ccattgacgt caataatgac gtatgttccc    240

atagtaacgc caatagggac tttccattga cgtcaatggg tggagtattt acggtaaact    300

gcccacttgg cagtacatca agtgtatcat atgccaagta cgccccctat tgacgtcaat    360

gacggtaaat ggcccgcctg gcattatgcc cagtacatga ccttatggga ctttcctact    420

tggcagtaca tctacgtatt agtcatcgct attaccatgg tgatgcggtt ttggcagtac    480

atcaatgggc gtggatagcg gtttgactca cggggatttc caagtctcca ccccattgac    540

gtcaatggga gtttgttttg gcaccaaaat caacgggact ttccaaaatg tcgtaacaac    600

tccgccccat tgacgcaaat gggcggtagg cgtgtacggt gggaggtcta tataagcaga    660

gctcgtttag tgaaccgtca gatcgcctgg agacgccatc cacgctgttt tgacctccat    720

agaagacacc gggaccgatc cagcctccgt taacggtgga gggcagtgta gtctgagcag    780

tactcgttgc tgccgcgcgc gccaccagac ataatagctg acagactaac agactgttcc    840

tttgcggccg ctctagacac catggagttc atcccgacgc aaactttcta taacagaagg    900

taccaacccc gaccctgggc cccacgccct acaattcaag taattagacc tagaccacgt    960

ccacagaggc aggctgggca actcgcccag ctgatctccg cagtcaacaa attgaccatg   1020

cgcgcggtac ctcaacagaa gcctcgcaga aatcggaaaa acaagaagca aaggcagaag   1080

aagcaggcgc cgcaaaacga cccaaagcaa aagaagcaac caccacaaaa gaagccggct   1140

caaaagaaga agaaaccagg ccgtagggag agaatgtgca tgaaaattga aaatgattgc   1200
```

-continued

```
atcttcgaag tcaagcatga aggcaaagtg atgggctacg catgcctggt gggggataaa   1260
gtaatgaaac cagcacatgt gaagggaact atcgacaatg ccgatctggc taaactggcc   1320
tttaagcggt cgtctaaata cgatcttgaa tgtgcacaga taccggtgca catgaagtct   1380
gatgcctcga agtttaccca cgagaaaccc gaggggtact ataactggca tcacggagca   1440
gtgcagtatt caggaggccg gttcactatc ccgacgggtg caggcaagcc gggagacagc   1500
ggcagaccga tcttcgacaa caaaggacgg gtggtggcca tcgtcctagg aggggccaac   1560
gaaggtgccc gcacggccct ctccgtggtg acgtggaaca aagacatcgt cacaaaaatt   1620
acccctgagg gagccgaaga gtggagcctc gccctcccgg tcttgtgcct gttggcaaac   1680
actacattcc cctgctctca gccgccttgc acaccctgct gctacgaaaa ggaaccggaa   1740
agcaccttgc gcatgcttga ggacaacgtg atgagacccg gatactacca gctactaaaa   1800
gcatcgctga cttgctctcc ccactccgga ggaaacccga atgccaatcc caacgcgaac   1860
cccaatgcta acccaaatgc caacccaaac gccaacccca acgctggtgg atccagtact   1920
aaggacaatt ttaatgtcta taaagccaca agaccatatc tagctcattg tcctgactgc   1980
ggagaagggc attcgtgcca cagccctatc gcattggagc gcatcagaaa tgaagcaacg   2040
gacggaacgc tgaaaatcca ggtctctttg cagatcggga taaagacaga tgacagccac   2100
gattggacca agctgcgcta tatggatagc catacgcccg cggacgcgga gcgagccgga   2160
ttgcttgtaa ggacttcagc accgtgcacg atcaccggga ccatgggaca ctttattctc   2220
gcccgatgcc cgaaaggaga gacgctgaca gtgggattta cggacagcag aaagatcagc   2280
cacacatgca cacacccgtt ccatcatgaa ccacctgtga taggtaggga gaggttccac   2340
tctcgaccac aacatggtaa agagttacct tgcagcacgt acgtgcagag caccgctgcc   2400
actgctgagg agatagaggt gcatatgccc ccagatactc ctgaccgcac gctgatgacg   2460
cagcagtctg gcaacgtgaa gatcacagtt aatgggcaga cggtgcggta caagtgcaac   2520
tgcggtggct ccggaggaaa cccgaatgcc aatcccaacg cgaaccccaa tgctaaccca   2580
aatgccaacc caaacgccaa ccccaacgct ggtggatcca acgagggact gacaaccaca   2640
gacaaagtga tcaataactg caaaattgat cagtgccatg ctgcagtcac taatcacaag   2700
aattggcaat acaactcccc tttagtcccg cgcaacgctg aactcgggga ccgtaaagga   2760
aagatccaca tcccattccc attggcaaac gtgacttgca gagtgccaaa agcaagaaac   2820
cctacagtaa cttacggaaa aaaccaagtc accatgctgc tgtatcctga ccatccgaca   2880
ctcttgtctt accgtaacat gggacaggaa ccaaattacc acgaggagtg ggtgacacac   2940
aagaaggagg ttaccttgac cgtgcctact gagggtctgg aggtcacttg gggcaacaac   3000
gaaccataca agtactggcc gcagatgtct acgaacggta ctgctcatgg tcacccacat   3060
gagataatct tgtactatta tgagctgtac cccactatga ctgtagtcat tgtgtcggtg   3120
gcctcgttcg tgcttctgtc gatggtgggc acagcagtgg gaatgtgtgt gtgcgcacgg   3180
cgcagatgca ttacaccata tgaattaaca ccaggagcca ctgttccctt cctgctcagc   3240
ctgctatgct gcgtcagaac gaccaaggcg gccacatatt acgaggctgc ggcatatcta   3300
tggaacgaac agcagcccct gttctggttg caggctctta tcccgctggc cgccttgatc   3360
gtcctgtgca actgtctgaa actcttgcca tgctgctgta agaccctggc tttttttagcc   3420
gtaatgagca tcggtgccca cactgtgagc gcgtacgaac acgtaacagt gatcccgaac   3480
acggtgggag taccgtataa gactcttgtc aacagaccgg gttacagccc catggtgttg   3540
gagatggagc tacaatcagt caccttggaa ccaacactgt cacttgacta catcacgtgc   3600
```

-continued

```
gagtacaaaa ctgtcatccc ctccccgtac gtgaagtgct gtggtacagc agagtgcaag   3660
gacaagagcc taccagacta cagctgcaag gtctttactg gagtctaccc atttatgtgg   3720
ggcggcgcct actgcttttg cgacgccgaa aatacgcaat tgagcgaggc acatgtagag   3780
aaatctgaat cttgcaaaac agagtttgca tcggcctaca gagcccacac cgcatcggcg   3840
tcggcgaagc tccgcgtcct ttaccaagga aacaacatta ccgtagctgc ctacgctaac   3900
ggtgaccatg ccgtcacagt aaaggacgcc aagtttgtcg tgggcccaat gtcctccgcc   3960
tggacacctt ttgacaacaa aatcgtggtg tacaaaggcg acgtctacaa catggactac   4020
ccaccttttg gcgcaggaag accaggacaa tttggtgaca ttcaaagtcg tacaccggaa   4080
agtaaagacg tttatgccaa cactcagttg gtactacaga ggccagcagc aggcacggta   4140
catgtaccat actctcaggc accatctggc ttcaagtatt ggctgaagga acgaggagca   4200
tcgctacagc acacggcacc gttcggttgc cagattgcga caaacccggt aagagctgta   4260
aattgcgctg tggggaacat accaatttcc atcgacatac cggatgcggc ctttactagg   4320
gttgtcgatg caccctctgt aacggacatg tcatgcgaag taccagcctg cactcactcc   4380
tccgactttg ggggcgtcgc catcatcaaa tacacagcta gcaagaaagg taaatgtgca   4440
gtacattcga tgaccaacgc cgttaccatt cgagaagccg acgtagaagt agaggggaac   4500
tcccagctgc aaatatcctt ctcaacagcc ctggcaagcg ccgagtttcg cgtgcaagtg   4560
tgctccacac aagtacactg cgcagccgca tgccaccctc caaaggacca catagtcaat   4620
tacccagcat cacacaccac ccttggggtc caggatatat ccacaacggc aatgtcttgg   4680
gtgcagaaga ttacgggagg agtaggatta attgttgctg ttgctgcctt aattttaatt   4740
gtggtgctat gcgtgtcgtt tagcaggcac taatgatccg gaggggcacc cacttcaagc   4800
tccacttcaa gctctacagc ggaagcacag cagcagcagc agcagcagca gcagcagcag   4860
cacctggagc agctgttgat ggacctacag gagctcctga gcaggatgga gaattacagg   4920
aacctgaaac tccccaggat gctcaccttc aaattttact tgcccaagca ggccacagaa   4980
ttgaaagatc ttcagtgcct agaagatgaa cttggacctc tgcggcatgt tctggatttg   5040
actcaaagca aaagctttca attggaagat gctgagaatt tcatcagcaa tatcagagta   5100
actgttgtaa aactaaaggg ctctgacaac acatttgagt gccaattcga tgatgagtca   5160
gcaactgtgg tggactttct gaggagatgg atagccttct gtcaaagcat catctcaaca   5220
agccctcaag gggatccgc tgtgccttct agttgccagc catctgttgt ttgcccctcc   5280
cccgtgcctt ccttgaccct ggaaggtgcc actcccactg tcctttccta ataaaatgag   5340
gaaattgcat cgcattgtct gagtaggtgt cattctattc tggggggtgg ggtggggcag   5400
gacagcaagg gggaggattg ggaagacaat agcaggcatg ctggggatgc ggtgggctct   5460
atgggtaccc aggtgctgaa gaattgaccc ggttcctcct gggccagaaa gaagcaggca   5520
catccccttc tctgtgacac accctgtcca cgcccctggt tcttagttcc agccccactc   5580
ataggacact catagctcag gagggctccg ccttcaatcc cacccgctaa agtacttgga   5640
gcggtctctc cctccctcat cagcccacca aaccaaacct agcctccaag agtgggaaga   5700
aattaaagca agataggcta ttaagtgcag agggagagaa aatgcctcca acatgtgagg   5760
aagtaatgag agaaatcata gaattttaag gccatgattt aaggccatca tggcctaagc   5820
ttgaaaggag ataggatcaa agcttggcgt aatcatggtc atagctgttt cctgtgtgaa   5880
attgttatcc gctcacaatt ccacacaaca tacgagccgg aagcataaag tgtaaagcct   5940
```

-continued

```
ggggtgccta atgagtgagc taactcacat taattgcgtt gcgctcactg cccgctttcc   6000
agtcgggaaa cctgtcgtgc cagctgcatt aatgaatcgg ccaacgcgcg gggagaggcg   6060
gtttgcgtat tgggcgctct tccgcttcct cgctcactga ctcgctgcgc tcggtcgttc   6120
ggctgcggcg agcggtatca gctcactcaa aggcggtaat acggttatcc acagaatcag   6180
gggataacgc aggaaagaac atgtgagcaa aaggccagca aaaggccagg aaccgtaaaa   6240
aggccgcgtt gctggcgttt ttccataggc tccgcccccc tgacgagcat cacaaaaatc   6300
gacgctcaag tcagaggtgg cgaaacccga caggactata aagataccag gcgtttcccc   6360
ctggaagctc cctcgtgcgc tctcctgttc cgaccctgcc gcttaccgga tacctgtccg   6420
cctttctccc ttcgggaagc gtggcgcttt ctcatagctc acgctgtagg tatctcagtt   6480
cggtgtaggt cgttcgctcc aagctgggct gtgtgcacga accccccgtt cagcccgacc   6540
gctgcgcctt atccggtaac tatcgtcttg agtccaaccc ggtaagacac gacttatcgc   6600
cactggcagc agccactggt aacaggatta gcagagcgag gtatgtaggc ggtgctacag   6660
agttcttgaa gtggtggcct aactacggct acactagaag aacagtattt ggtatctgcg   6720
ctctgctgaa gccagttacc ttcggaaaaa gagttggtag ctcttgatcc ggcaaacaaa   6780
ccaccgctgg tagcggtggt ttttttgttt gcaagcagca gattacgcgc agaaaaaaag   6840
gatctcaaga agatcctttg atcttttcta cggggtctga cgctcagtgg aacgaaaact   6900
cacgttaagg gattttggtc atgagattat caaaaaggat cttcacctag atccttttaa   6960
attaaaaatg aagttttaaa tcaatctaaa gtatatatga gtaaacttgg tctgacagtt   7020
accaatgctt aatcagtgag gcacctatct cagcgatctg tctatttcgt tcatccatag   7080
ttgcctgact ccccgtcgtg tagataacta cgatacggga gggcttacca tctggcccca   7140
gtgctgcaat gataccgcga gaaccacgct caccggctcc agatttatca gcaataaacc   7200
agccagccgg aagggccgag cgcagaagtg gtcctgcaac tttatccgcc tccatccagt   7260
ctattaattg ttgccgggaa gctagagtaa gtagttcgcc agttaatagt ttgcgcaacg   7320
ttgttgccat tgctacaggc atcgtggtgt cacgctcgtc gtttggtatg gcttcattca   7380
gctccggttc ccaacgatca aggcgagtta catgatcccc catgttgtgc aaaaaagcgg   7440
ttagctcctt cggtcctccg atcgttgtca gaagtaagtt ggccgcagtg ttatcactca   7500
tggttatggc agcactgcat aattctctta ctgtcatgcc atccgtaaga tgcttttctg   7560
tgactggtga gtactcaacc aagtcattct gagaatagtg tatgcggcga ccgagttgct   7620
cttgcccggc gtcaatacgg gataataccg cgccacatag cagaacttta aaagtgctca   7680
tcattggaaa acgttcttcg gggcgaaaac tctcaaggat cttaccgctg ttgagatcca   7740
gttcgatgta acccactcgt gcacccaact gatcttcagc atcttttact ttcaccagcg   7800
tttctgggtg agcaaaaaca ggaaggcaaa atgccgcaaa aaagggaata agggcgacac   7860
ggaaatgttg aatactcata ctcttccttt ttcaatatta ttgaagcatt tatcagggtt   7920
attgtctcat gagcggatac atatttgaat gtatttagaa aaataaacaa ataggggttc   7980
cgcgcacatt tccccgaaaa gtgccacctg acgtctaaga aaccattatt atcatgacat   8040
taacctataa aaataggcgt atcacgaggc cctttcgggt cgcgcgtttc ggtgatgacg   8100
gtgaaaacct ctgacacatg cagctcccgt tgacggtcac agcttgtctg taagcggatg   8160
ccgggagcag acaagcccgt cagggcgcgt cagcgggtgt tggcgggtgt cggggctggc   8220
ttaactatgc ggcatcagag cagattgtac tgagagtgca ccataaaatt gtaaacgtta   8280
atattttgtt aaaattcgcg ttaaattttt gttaaatcag ctcatttttt aaccaatagg   8340
```

```
ccgaaatcgg caaaatccct tataaatcaa aagaatagcc cgagataggg ttgagtgttg   8400

ttccagtttg gaacaagagt ccactattaa agaacgtgga ctccaacgtc aaagggcgaa   8460

aaaccgtcta tcagggcgat ggcccactac gtgaaccatc acccaaatca agttttttgg   8520

ggtcgaggtg ccgtaaagca ctaaatcgga accctaaagg gagcccccga tttagagctt   8580

gacggggaaa gccggcgaac gtggcgagaa aggaagggaa gaaagcgaaa ggagcgggcg   8640

ctagggcgct ggcaagtgta gcggtcacgc tgcgcgtaac caccacaccc gccgcgctta   8700

atgcgccgct acagggcgcg tactatggtt gctttgacgt atgcggtgtg aaataccgca   8760

cagatgcgta aggagaaaat accgcatcag gcgccattcg ccattcaggc tgcgcaactg   8820

ttgggaaggg cgatcggtgc gggcctcttc gctattacgc cagctggcga aagggggatg   8880

tgctgcaagg cgattaagtt gggtaacgcc agggttttcc cagtcacgac gttgtaaaac   8940

gacggccagt gaattccatg gtctcaactt tc                                 8972
```

<210> SEQ ID NO 103
<211> LENGTH: 1367
<212> TYPE: PRT
<213> ORGANISM: Artificial Sequence
<220> FEATURE:
<223> OTHER INFORMATION: Synthetic CHIKV viral structural protein containing CSP antigen 76 in E2 and E3 (76 Dual)

<400> SEQUENCE: 103

```
Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Arg Gln Lys Lys Gln Ala Pro Gln Asn Asp
65                  70                  75                  80

Pro Lys Gln Lys Lys Gln Pro Pro Gln Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Met Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240
```

-continued

```
Ser Val Val Thr Trp Asn Lys Asp Ile Val Thr Lys Ile Thr Pro Glu
                245                 250                 255

Gly Ala Glu Glu Trp Ser Leu Ala Leu Pro Val Leu Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Ser Thr Leu Arg Met Leu Glu Asp Asn Val Met
    290                 295                 300

Arg Pro Gly Tyr Tyr Gln Leu Leu Lys Ala Ser Leu Thr Cys Ser Pro
305                 310                 315                 320

His Ser Gly Gly Asn Pro Asn Ala Asn Pro Asn Ala Asn Pro Asn Ala
                325                 330                 335

Asn Pro Asn Ala Asn Pro Asn Ala Asn Pro Asn Ala Asn Pro Asn Ala
            340                 345                 350

Asn Pro Asn Ala Asn Pro Asn Ala Asn Pro Asn Ala Asn Pro Asn Ala
        355                 360                 365

Asn Pro Asn Ala Asn Pro Asn Ala Asn Pro Asn Ala Gly Gly Ser Ser
    370                 375                 380

Thr Lys Asp Asn Phe Asn Val Tyr Lys Ala Thr Arg Pro Tyr Leu Ala
385                 390                 395                 400

His Cys Pro Asp Cys Gly Glu Gly His Ser Cys His Ser Pro Ile Ala
                405                 410                 415

Leu Glu Arg Ile Arg Asn Glu Ala Thr Asp Gly Thr Leu Lys Ile Gln
            420                 425                 430

Val Ser Leu Gln Ile Gly Ile Lys Thr Asp Asp Ser His Asp Trp Thr
        435                 440                 445

Lys Leu Arg Tyr Met Asp Ser His Thr Pro Ala Asp Ala Glu Arg Ala
    450                 455                 460

Gly Leu Leu Val Arg Thr Ser Ala Pro Cys Thr Ile Thr Gly Thr Met
465                 470                 475                 480

Gly His Phe Ile Leu Ala Arg Cys Pro Lys Gly Glu Thr Leu Thr Val
                485                 490                 495

Gly Phe Thr Asp Ser Arg Lys Ile Ser His Thr Cys Thr His Pro Phe
            500                 505                 510

His His Glu Pro Pro Val Ile Gly Arg Glu Arg Phe His Ser Arg Pro
        515                 520                 525

Gln His Gly Lys Glu Leu Pro Cys Ser Thr Tyr Val Gln Ser Thr Ala
    530                 535                 540

Ala Thr Ala Glu Glu Ile Glu Val His Met Pro Pro Asp Thr Pro Asp
545                 550                 555                 560

Arg Thr Leu Met Thr Gln Gln Ser Gly Asn Val Lys Ile Thr Val Asn
                565                 570                 575

Gly Gln Thr Val Arg Tyr Lys Cys Asn Cys Gly Gly Ser Gly Gly Asn
            580                 585                 590

Pro Asn Ala Asn Pro Asn Ala Asn Pro Asn Ala Asn Pro Asn Ala Asn
        595                 600                 605

Pro Asn Ala Asn Pro Asn Ala Asn Pro Asn Ala Asn Pro Asn Ala Asn
    610                 615                 620

Pro Asn Ala Asn Pro Asn Ala Asn Pro Asn Ala Asn Pro Asn Ala Asn
625                 630                 635                 640

Pro Asn Ala Asn Pro Asn Ala Gly Gly Ser Asn Glu Gly Leu Thr Thr
                645                 650                 655

Thr Asp Lys Val Ile Asn Asn Cys Lys Ile Asp Gln Cys His Ala Ala
```

-continued 660 665 670

Val Thr Asn His Lys Asn Trp Gln Tyr Asn Ser Pro Leu Val Pro Arg
675 680 685

Asn Ala Glu Leu Gly Asp Arg Lys Gly Lys Ile His Ile Pro Phe Pro
690 695 700

Leu Ala Asn Val Thr Cys Arg Val Pro Lys Ala Arg Asn Pro Thr Val
705 710 715 720

Thr Tyr Gly Lys Asn Gln Val Thr Met Leu Leu Tyr Pro Asp His Pro
725 730 735

Thr Leu Leu Ser Tyr Arg Asn Met Gly Gln Glu Pro Asn Tyr His Glu
740 745 750

Glu Trp Val Thr His Lys Lys Glu Val Thr Leu Thr Val Pro Thr Glu
755 760 765

Gly Leu Glu Val Thr Trp Gly Asn Asn Glu Pro Tyr Lys Tyr Trp Pro
770 775 780

Gln Met Ser Thr Asn Gly Thr Ala His Gly His Pro His Glu Ile Ile
785 790 795 800

Leu Tyr Tyr Tyr Glu Leu Tyr Pro Thr Met Thr Val Val Ile Val Ser
805 810 815

Val Ala Ser Phe Val Leu Leu Ser Met Val Gly Thr Ala Val Gly Met
820 825 830

Cys Val Cys Ala Arg Arg Arg Cys Ile Thr Pro Tyr Glu Leu Thr Pro
835 840 845

Gly Ala Thr Val Pro Phe Leu Leu Ser Leu Leu Cys Cys Val Arg Thr
850 855 860

Thr Lys Ala Ala Thr Tyr Tyr Glu Ala Ala Ala Tyr Leu Trp Asn Glu
865 870 875 880

Gln Gln Pro Leu Phe Trp Leu Gln Ala Leu Ile Pro Leu Ala Ala Leu
885 890 895

Ile Val Leu Cys Asn Cys Leu Lys Leu Leu Pro Cys Cys Cys Lys Thr
900 905 910

Leu Ala Phe Leu Ala Val Met Ser Ile Gly Ala His Thr Val Ser Ala
915 920 925

Tyr Glu His Val Thr Val Ile Pro Asn Thr Val Gly Val Pro Tyr Lys
930 935 940

Thr Leu Val Asn Arg Pro Gly Tyr Ser Pro Met Val Leu Glu Met Glu
945 950 955 960

Leu Gln Ser Val Thr Leu Glu Pro Thr Leu Ser Leu Asp Tyr Ile Thr
965 970 975

Cys Glu Tyr Lys Thr Val Ile Pro Ser Pro Tyr Val Lys Cys Cys Gly
980 985 990

Thr Ala Glu Cys Lys Asp Lys Ser Leu Pro Asp Tyr Ser Cys Lys Val
995 1000 1005

Phe Thr Gly Val Tyr Pro Phe Met Trp Gly Gly Ala Tyr Cys Phe
1010 1015 1020

Cys Asp Ala Glu Asn Thr Gln Leu Ser Glu Ala His Val Glu Lys
1025 1030 1035

Ser Glu Ser Cys Lys Thr Glu Phe Ala Ser Ala Tyr Arg Ala His
1040 1045 1050

Thr Ala Ser Ala Ser Ala Lys Leu Arg Val Leu Tyr Gln Gly Asn
1055 1060 1065

Asn Ile Thr Val Ala Ala Tyr Ala Asn Gly Asp His Ala Val Thr
1070 1075 1080

```
Val Lys Asp Ala Lys Phe Val Val Gly Pro Met Ser Ser Ala Trp
    1085                1090                1095

Thr Pro Phe Asp Asn Lys Ile Val Val Tyr Lys Gly Asp Val Tyr
    1100                1105                1110

Asn Met Asp Tyr Pro Pro Phe Gly Ala Gly Arg Pro Gly Gln Phe
    1115                1120                1125

Gly Asp Ile Gln Ser Arg Thr Pro Glu Ser Lys Asp Val Tyr Ala
    1130                1135                1140

Asn Thr Gln Leu Val Leu Gln Arg Pro Ala Ala Gly Thr Val His
    1145                1150                1155

Val Pro Tyr Ser Gln Ala Pro Ser Gly Phe Lys Tyr Trp Leu Lys
    1160                1165                1170

Glu Arg Gly Ala Ser Leu Gln His Thr Ala Pro Phe Gly Cys Gln
    1175                1180                1185

Ile Ala Thr Asn Pro Val Arg Ala Val Asn Cys Ala Val Gly Asn
    1190                1195                1200

Ile Pro Ile Ser Ile Asp Ile Pro Asp Ala Ala Phe Thr Arg Val
    1205                1210                1215

Val Asp Ala Pro Ser Val Thr Asp Met Ser Cys Glu Val Pro Ala
    1220                1225                1230

Cys Thr His Ser Ser Asp Phe Gly Gly Val Ala Ile Ile Lys Tyr
    1235                1240                1245

Thr Ala Ser Lys Lys Gly Lys Cys Ala Val His Ser Met Thr Asn
    1250                1255                1260

Ala Val Thr Ile Arg Glu Ala Asp Val Glu Val Glu Gly Asn Ser
    1265                1270                1275

Gln Leu Gln Ile Ser Phe Ser Thr Ala Leu Ala Ser Ala Glu Phe
    1280                1285                1290

Arg Val Gln Val Cys Ser Thr Gln Val His Cys Ala Ala Ala Cys
    1295                1300                1305

His Pro Pro Lys Asp His Ile Val Asn Tyr Pro Ala Ser His Thr
    1310                1315                1320

Thr Leu Gly Val Gln Asp Ile Ser Thr Thr Ala Met Ser Trp Val
    1325                1330                1335

Gln Lys Ile Thr Gly Gly Val Gly Leu Ile Val Ala Val Ala Ala
    1340                1345                1350

Leu Ile Leu Ile Val Val Leu Cys Val Ser Phe Ser Arg His
    1355                1360                1365
```

<210> SEQ ID NO 104
<211> LENGTH: 9164
<212> TYPE: DNA
<213> ORGANISM: Artificial Sequence
<220> FEATURE:
<223> OTHER INFORMATION: Synthetic Expression vector for CHIKV viral structural protein containing CSP antigen 76 in E2 and E3 (76.76.58)

<400> SEQUENCE: 104

```
gaattcccat tgcatacgtt gtatccatat cataatatgt acatttatat tggctcatgt      60

ccaacattac cgccatgttg acattgatta ttgactagtt attaatagta atcaattacg     120

gggtcattag ttcatagccc atatatggag ttccgcgtta cataacttac ggtaaatggc     180

ccgcctggct gaccgcccaa cgacccccgc ccattgacgt caataatgac gtatgttccc     240

atagtaacgc caatagggac tttccattga cgtcaatggg tggagtattt acggtaaact     300
```

-continued

```
gcccacttgg cagtacatca agtgtatcat atgccaagta cgccccctat tgacgtcaat    360
gacggtaaat ggcccgcctg gcattatgcc cagtacatga ccttatggga ctttcctact    420
tggcagtaca tctacgtatt agtcatcgct attaccatgg tgatgcggtt ttggcagtac    480
atcaatgggc gtggatagcg gtttgactca cggggatttc caagtctcca ccccattgac    540
gtcaatggga gtttgttttg gcaccaaaat caacgggact ttccaaaatg tcgtaacaac    600
tccgccccat tgacgcaaat gggcggtagg cgtgtacggt gggaggtcta tataagcaga    660
gctcgtttag tgaaccgtca gatcgcctgg agacgccatc cacgctgttt tgacctccat    720
agaagacacc gggaccgatc cagcctccgt taacggtgga gggcagtgta gtctgagcag    780
tactcgttgc tgccgcgcgc gccaccagac ataatagctg acagactaac agactgttcc    840
tttgcggccg ctctagacac catggagttc atcccgacgc aaactttcta taacagaagg    900
taccaacccc gaccctgggc cccacgccct acaattcaag taattagacc tagaccacgt    960
ccacagaggc aggctgggca actcgcccag ctgatctccg cagtcaacaa attgaccatg   1020
cgcgcggtac ctcaacagaa gcctcgcaga aatcggaaaa acaagaagca aaggcagaag   1080
aagcaggcgc cgcaaaacga cccaaagcaa aagaagcaac caccacaaaa gaagccggct   1140
caaaagaaga agaaaccagg ccgtagggag agaatgtgca tgaaaattga aaatgattgc   1200
atcttcgaag tcaagcatga aggcaaagtg atgggctacg catgcctggt gggggataaa   1260
gtaatgaaac cagcacatgt gaagggaact atcgacaatg ccgatctggc taaactggcc   1320
tttaagcggt cgtctaaata cgatcttgaa tgtgcacaga taccggtgca catgaagtct   1380
gatgcctcga agtttaccca cgagaaaccc gaggggtact ataactggca tcacggagca   1440
gtgcagtatt caggaggccg gttcactatc ccgacgggtg caggcaagcc gggagacagc   1500
ggcagaccga tcttcgacaa caaaggacgg gtggtggcca tcgtcctagg aggggccaac   1560
gaaggtgccc gcacggccct ctccgtggtg acgtggaaca aagacatcgt cacaaaaatt   1620
acccctgagg gagccgaaga gtggagcctc gccctcccgg tcttgtgcct gttggcaaac   1680
actacattcc cctgctctca gccgccttgc acaccctgct gctacgaaaa ggaaccggaa   1740
agcaccttgc gcatgcttga ggacaacgtg atgagacccg gatactacca gctactaaaa   1800
gcatcgctga cttgctctcc ccactccgga ggcaacccca acgccaaccc taatgccaat   1860
cccaacgcta atcccaatgc taaccctaac gcaaatccaa atgcaaaccc caatgccaac   1920
ccaaacgcta accctaacgc caaccctaac gcaaacccaa acgccaatcc taatgctaac   1980
ccaaatgcaa accctaatgc tggcggatcc agtactaagg acaattttaa tgtctataaa   2040
gccacaagac catatctagc tcattgtcct gactgcggag aagggcattc gtgccacagc   2100
cctatcgcat tggagcgcat cagaaatgaa gcaacggacg gaacgctgaa aatccaggtc   2160
tctttgcaga tcgggataaa gacagatgac agccacgatt ggaccaagct gcgctatatg   2220
gatagccata cgcccgcgga cgcggagcga gccggattgc ttgtaaggac ttcagcaccg   2280
tgcacgatca ccgggaccat gggacacttt attctcgccc gatgcccgaa aggagagacg   2340
ctgacagtgg gatttacgga cagcagaaag atcagccaca catgcacaca cccgttccat   2400
catgaaccac ctgtgatagg tagggagagg ttccactctc gaccacaaca tggtaaagag   2460
ttaccttgca gcacgtacgt gcagagcacc gctgccactg ctgaggagat agaggtgcat   2520
atgcccccag atactcctga ccgcacgctg atgacgcagc agtctggcaa cgtgaagatc   2580
acagttaatg ggcagacggt gcggtacaag tgcaactgcg gtggctccgg aggcaacccc   2640
```

-continued

```
aacgccaacc ctaatgccaa tcccaacgct aatcccaatg ctaaccctaa cgcaaatcca   2700

aatgcaaacc ccaatgccaa cccaaacgct aaccctaacg ccaaccctaa cgcaaaccca   2760

aacgccaatc ctaatgctaa cccaaatgca aaccctaatg ctggcggatc caacgaggga   2820

ctgacaacca cagacaaagt gatcaataac tgcaaaattg atcagtgcca tgctgcagtc   2880

actaatcaca agaattggca atacaactcc cctttagtcc cgcgcaacgc tgaactcggg   2940

gaccgtaaag gaaagatcca catcccattc ccattggcaa acgtgacttg cagagtgcca   3000

aaagcaagaa accctacagt aacttacgga aaaaaccaag tcaccatgct gctgtatcct   3060

gaccatccga cactcttgtc ttaccgtaac atgggacagg aaccaaatta ccacgaggag   3120

tgggtgacac acaagaagga ggttaccttg accgtgccta ctgagggtct ggaggtcact   3180

tggggcaaca acgaaccata caagtactgg ccgcagatgt ctacgaacgg tactgctcat   3240

ggtcacccac atgagataat cttgtactat tatgagctgt accccactat gactgtagtc   3300

attgtgtcgg tggcctcgtt cgtgcttctg tcgatggtgg gcacagcagt gggaatgtgt   3360

gtgtgcgcac ggcgcagatg cattacacca tatgaattaa caccaggagc cactgttccc   3420

ttcctgctca gcctgctatg ctgcgtcaga acgaccaagg cggccacata ttacgaggct   3480

gcggcatatc tatggaacga acagcagccc ctgttctggt tgcaggctct tatcccgctg   3540

gccgccttga tcgtcctgtg caactgtctg aaactcttgc catgctgctg taagaccctg   3600

gctttttag ccgtaatgag catcggtgcc cacactgtga gcgcgtacga acacgtaaca   3660

gtgatcccga acacggtggg agtaccgtat aagactcttg tcaacagacc gggttacagc   3720

cccatggtgt tggagatgga gctacaatca gtcaccttgg aaccaacact gtcacttgac   3780

tacatcacgt gcgagtacaa aactgtcatc ccctccccgt acgtgaagtg ctgtggtaca   3840

gcagagtgca aggacaagag cctaccagac tacagctgca aggtctttac tggagtctac   3900

ccatttatgt ggggcggcgc ctactgcttt tgcgacgccg aaaatacgca attgagcgag   3960

gcacatgtag agaaatctga atcttgcaaa acagagtttg catcggccta cagagcccac   4020

accgcatcgg cgtcggcgaa gctccgcgtc ctttaccaag gaaacaacat taccgtagct   4080

gcctacgcta acggtgacca tgccgtcaca gtaaaggacg ccaagtttgt cgtgggccca   4140

atgtcctccg cctggacacc ttttgacaac aaaatcgtgg tgtacaaagg cgacgtctac   4200

aacatggact acccaccttt tggcgcagga agaccaggac aatttggtga cattcaaagt   4260

cgtacaccgg aaagtaaaga cgtttatgcc aacactcagt tggtactaca gaggccagca   4320

gcaggcacgg tacatgtacc atactctcag gcaccatctg gcttcaagta ttggctgaag   4380

gaacgaggag catcgctaca gcacacggca ccgttcggtt gccagattgc gacaaacccg   4440

gtaagagctg taaattgcgc tgtggggaac ataccaattt ccatcgacat accggatgcg   4500

gcctttacta gggttgtcga tgcaccctct gtaacggaca tgtcatgcga agtaccagcc   4560

tgcactcact cctccgactt tgggggcgtc gccatcatca aatacacagc tagcaagaaa   4620

ggtaaatgtg cagtacattc gatgaccaac gccgttacca ttcgagaagc cgacgtagaa   4680

gtagagggga actcccagct gcaaatatcc ttctcaacag ccctggcaag cgccgagttt   4740

cgcgtgcaag tgtgctccac acaagtacac tgcgcagccg catgccaccc tccaaaggac   4800

cacatagtca attacccagc atcacacacc acccttgggg tccaggatat atccacaacg   4860

gcaatgtctt gggtgcagaa gattacggga ggagtaggat taattgttgc tgttgctgcc   4920

ttaattttaa ttgtggtgct atgcgtgtcg tttagcaggc actaatgatc cggaggggca   4980

cccacttcaa gctccacttc aagctctaca gcggaagcac agcagcagca gcagcagcag   5040
```

cagcagcagc agcacctgga gcagctgttg atggacctac aggagctcct gagcaggatg 5100
gagaattaca ggaacctgaa actccccagg atgctcacct tcaaatttta cttgcccaag 5160
caggccacag aattgaaaga tcttcagtgc ctagaagatg aacttggacc tctgcggcat 5220
gttctggatt tgactcaaag caaaagcttt caattggaag atgctgagaa tttcatcagc 5280
aatatcagag taactgttgt aaaactaaag ggctctgaca acacatttga gtgccaattc 5340
gatgatgagt cagcaactgt ggtggacttt ctgaggagat ggatagcctt ctgtcaaagc 5400
atcatctcaa caagccctca agggggatcc gctgtgcctt ctagttgcca gccatctgtt 5460
gtttgcccct cccccgtgcc ttccttgacc ctggaaggtg ccactcccac tgtcctttcc 5520
taataaaatg aggaaattgc atcgcattgt ctgagtaggt gtcattctat tctggggggt 5580
ggggtggggc aggacagcaa gggggaggat tgggaagaca atagcaggca tgctggggat 5640
gcggtgggct ctatgggtac ccaggtgctg aagaattgac ccggttcctc ctgggccaga 5700
aagaagcagg cacatcccct tctctgtgac acaccctgtc cacgcccctg gttcttagtt 5760
ccagccccac tcataggaca ctcatagctc aggagggctc cgccttcaat cccacccgct 5820
aaagtacttg gagcggtctc tccctccctc atcagcccac caaaccaaac ctagcctcca 5880
agagtgggaa gaaattaaag caagataggc tattaagtgc agagggagag aaaatgcctc 5940
caacatgtga ggaagtaatg agagaaatca tagaatttta aggccatgat ttaaggccat 6000
catggcctaa gcttgaaagg agataggatc aaagcttggc gtaatcatgg tcatagctgt 6060
ttcctgtgtg aaattgttat ccgctcacaa ttccacacaa catacgagcc ggaagcataa 6120
agtgtaaagc ctggggtgcc taatgagtga gctaactcac attaattgcg ttgcgctcac 6180
tgcccgcttt ccagtcggga aacctgtcgt gccagctgca ttaatgaatc ggccaacgcg 6240
cggggagagg cggtttgcgt attgggcgct cttccgcttc ctcgctcact gactcgctgc 6300
gctcggtcgt tcggctgcgg cgagcggtat cagctcactc aaaggcggta atacggttat 6360
ccacagaatc aggggataac gcaggaaaga acatgtgagc aaaaggccag caaaaggcca 6420
ggaaccgtaa aaaggccgcg ttgctggcgt ttttccatag gctccgcccc cctgacgagc 6480
atcacaaaaa tcgacgctca agtcagaggt ggcgaaaccc gacaggacta taaagatacc 6540
aggcgtttcc ccctggaagc tccctcgtgc gctctcctgt tccgaccctg ccgcttaccg 6600
gatacctgtc cgcctttctc ccttcgggaa gcgtggcgct ttctcatagc tcacgctgta 6660
ggtatctcag ttcggtgtag gtcgttcgct ccaagctggg ctgtgtgcac gaaccccccg 6720
ttcagcccga ccgctgcgcc ttatccggta actatcgtct tgagtccaac ccggtaagac 6780
acgacttatc gccactggca gcagccactg gtaacaggat tagcagagcg aggtatgtag 6840
gcggtgctac agagttcttg aagtggtggc ctaactacgg ctacactaga agaacagtat 6900
ttggtatctg cgctctgctg aagccagtta ccttcggaaa aagagttggt agctcttgat 6960
ccggcaaaca aaccaccgct ggtagcggtg gtttttttgt ttgcaagcag cagattacgc 7020
gcagaaaaaa aggatctcaa gaagatcctt tgatcttttc tacggggtct gacgctcagt 7080
ggaacgaaaa ctcacgttaa gggattttgg tcatgagatt atcaaaaagg atcttcacct 7140
agatcctttt aaattaaaaa tgaagtttta aatcaatcta aagtatatat gagtaaactt 7200
ggtctgacag ttaccaatgc ttaatcagtg aggcacctat ctcagcgatc tgtctatttc 7260
gttcatccat agttgcctga ctccccgtcg tgtagataac tacgatacgg gagggcttac 7320
catctggccc cagtgctgca atgataccgc gagaaccacg ctcaccggct ccagatttat 7380

-continued

```
cagcaataaa ccagccagcc ggaagggccg agcgcagaag tggtcctgca actttatccg   7440

cctccatcca gtctattaat tgttgccggg aagctagagt aagtagttcg ccagttaata   7500

gtttgcgcaa cgttgttgcc attgctacag gcatcgtggt gtcacgctcg tcgtttggta   7560

tggcttcatt cagctccggt tcccaacgat caaggcgagt tacatgatcc cccatgttgt   7620

gcaaaaaagc ggttagctcc ttcggtcctc cgatcgttgt cagaagtaag ttggccgcag   7680

tgttatcact catggttatg gcagcactgc ataattctct tactgtcatg ccatccgtaa   7740

gatgcttttc tgtgactggt gagtactcaa ccaagtcatt ctgagaatag tgtatgcggc   7800

gaccgagttg ctcttgcccg gcgtcaatac gggataatac cgcgccacat agcagaactt   7860

taaaagtgct catcattgga aaacgttctt cggggcgaaa actctcaagg atcttaccgc   7920

tgttgagatc cagttcgatg taacccactc gtgcacccaa ctgatcttca gcatctttta   7980

ctttcaccag cgtttctggg tgagcaaaaa caggaaggca aaatgccgca aaaaagggaa   8040

taagggcgac acggaaatgt tgaatactca tactcttcct ttttcaatat tattgaagca   8100

tttatcaggg ttattgtctc atgagcggat acatatttga atgtatttag aaaaataaac   8160

aaataggggt tccgcgcaca tttccccgaa aagtgccacc tgacgtctaa gaaaccatta   8220

ttatcatgac attaacctat aaaaataggc gtatcacgag gccctttcgg gtcgcgcgtt   8280

tcggtgatga cggtgaaaac ctctgacaca tgcagctccc gttgacggtc acagcttgtc   8340

tgtaagcgga tgccgggagc agacaagccc gtcagggcgc gtcagcgggt gttggcgggt   8400

gtcggggctg gcttaactat gcggcatcag agcagattgt actgagagtg caccataaaa   8460

ttgtaaacgt taatattttg ttaaaattcg cgttaaattt ttgttaaatc agctcatttt   8520

ttaaccaata ggccgaaatc ggcaaaatcc cttataaatc aaaagaatag cccgagatag   8580

ggttgagtgt tgttccagtt tggaacaaga gtccactatt aaagaacgtg gactccaacg   8640

tcaaagggcg aaaaaccgtc tatcagggcg atggcccact acgtgaacca tcacccaaat   8700

caagtttttt ggggtcgagg tgccgtaaag cactaaatcg gaaccctaaa gggagccccc   8760

gatttagagc ttgacgggga aagccggcga acgtggcgag aaaggaaggg aagaaagcga   8820

aaggagcggg cgctagggcg ctggcaagtg tagcggtcac gctgcgcgta accaccacac   8880

ccgccgcgct taatgcgccg ctacagggcg cgtactatgg ttgctttgac gtatgcggtg   8940

tgaaataccg cacagatgcg taaggagaaa ataccgcatc aggcgccatt cgccattcag   9000

gctgcgcaac tgttgggaag ggcgatcggt gcgggcctct tcgctattac gccagctggc   9060

gaaaggggga tgtgctgcaa ggcgattaag ttgggtaacg ccagggtttt cccagtcacg   9120

acgttgtaaa acgacggcca gtgaattcca tggtctcaac tttc                    9164
```

```
<210> SEQ ID NO 105
<211> LENGTH: 33
<212> TYPE: PRT
<213> ORGANISM: Artificial Sequence
<220> FEATURE:
<223> OTHER INFORMATION: Synthetic DISC1_451 antigen with linker

<400> SEQUENCE: 105

Ser Gly Gly Leu Leu Ile Gln Ser Leu Gln Leu Gln Glu Ala Arg Gly
1               5                   10                  15

Glu Leu Ser Val Glu Asp Glu Arg Gln Met Asp Asp Leu Glu Gly Gly
            20                  25                  30

Ser
```

<210> SEQ ID NO 106
<211> LENGTH: 24
<212> TYPE: PRT
<213> ORGANISM: Artificial Sequence
<220> FEATURE:
<223> OTHER INFORMATION: Synthetic DISC1_452 antigen with linker

<400> SEQUENCE: 106

Ser Gly Gly Glu Ala Arg Gly Glu Leu Ser Val Glu Asp Glu Arg Gln
1 5 10 15

Met Asp Asp Leu Glu Gly Gly Ser
20

<210> SEQ ID NO 107
<211> LENGTH: 15
<212> TYPE: PRT
<213> ORGANISM: Artificial Sequence
<220> FEATURE:
<223> OTHER INFORMATION: Synthetic DISC1_454 antigen with linker

<400> SEQUENCE: 107

Ser Gly Gly Glu Ala Arg Gly Glu Leu Ser Val Glu Gly Gly Ser
1 5 10 15

<210> SEQ ID NO 108
<211> LENGTH: 18
<212> TYPE: PRT
<213> ORGANISM: Artificial Sequence
<220> FEATURE:
<223> OTHER INFORMATION: Synthetic HER2 antigen with linker

<400> SEQUENCE: 108

Ser Gly Gly Val Thr Tyr Asn Thr Asp Thr Phe Glu Ser Met Pro Gly
1 5 10 15

Gly Ser

<210> SEQ ID NO 109
<211> LENGTH: 16
<212> TYPE: PRT
<213> ORGANISM: Artificial Sequence
<220> FEATURE:
<223> OTHER INFORMATION: Synthetic HER2 antigen with linker

<400> SEQUENCE: 109

Ser Gly Gly Glu Tyr Val Asn Ala Arg His Cys Leu Pro Gly Gly Ser
1 5 10 15

<210> SEQ ID NO 110
<211> LENGTH: 14
<212> TYPE: PRT
<213> ORGANISM: Artificial Sequence
<220> FEATURE:
<223> OTHER INFORMATION: Synthetic HER2 antigen with linker

<400> SEQUENCE: 110

Ser Gly Gly Tyr Val Asn Ala Arg His Cys Leu Gly Gly Ser
1 5 10

<210> SEQ ID NO 111
<211> LENGTH: 14
<212> TYPE: PRT
<213> ORGANISM: Artificial Sequence
<220> FEATURE:
<223> OTHER INFORMATION: Synthetic HER2 antigen with linker

<400> SEQUENCE: 111

Ser Gly Gly Tyr Val Asn Ala Arg His Gly Leu Gly Gly Ser
1 5 10

<210> SEQ ID NO 112
<211> LENGTH: 20
<212> TYPE: PRT
<213> ORGANISM: Artificial Sequence
<220> FEATURE:
<223> OTHER INFORMATION: Synthetic HER2 antigen with linker

<400> SEQUENCE: 112

Ser Gly Gly Lys Phe Pro Asp Glu Glu Gly Ala Cys Gln Pro Cys Pro
1 5 10 15

Ile Gly Gly Ser
20

<210> SEQ ID NO 113
<211> LENGTH: 17
<212> TYPE: PRT
<213> ORGANISM: Artificial Sequence
<220> FEATURE:
<223> OTHER INFORMATION: Synthetic HER2 antigen with linker

<400> SEQUENCE: 113

Ser Gly Gly Lys Phe Pro Asp Glu Glu Gly Ala Cys Gln Pro Gly Gly
1 5 10 15

Ser

<210> SEQ ID NO 114
<211> LENGTH: 13
<212> TYPE: PRT
<213> ORGANISM: Artificial Sequence
<220> FEATURE:
<223> OTHER INFORMATION: Synthetic HER2 antigen with linker

<400> SEQUENCE: 114

Ser Gly Gly Lys Asp Pro Pro Phe Cys Val Gly Gly Ser
1 5 10

<210> SEQ ID NO 115
<211> LENGTH: 15
<212> TYPE: PRT
<213> ORGANISM: Artificial Sequence
<220> FEATURE:
<223> OTHER INFORMATION: Synthetic HER2 antigen with linker

<400> SEQUENCE: 115

Ser Gly Gly Tyr Lys Asp Pro Pro Phe Cys Val Ala Gly Gly Ser
1 5 10 15

<210> SEQ ID NO 116
<211> LENGTH: 14
<212> TYPE: PRT
<213> ORGANISM: Artificial Sequence
<220> FEATURE:
<223> OTHER INFORMATION: Synthetic HER2 antigen with linker

<400> SEQUENCE: 116

Ser Gly Gly Tyr Lys Asp Pro Pro Phe Cys Val Gly Gly Ser
1 5 10

<210> SEQ ID NO 117
<211> LENGTH: 99
<212> TYPE: DNA
<213> ORGANISM: Artificial Sequence
<220> FEATURE:

<223> OTHER INFORMATION: Synthetic DISC1_451 with linker

<400> SEQUENCE: 117
tccggagggc tgctgatcca gtctctgcag ctgcaggaag ccagaggcga gctgagcgtg 60
gaagatgagc ggcagatgga cgacctggaa gggggatcc 99

<210> SEQ ID NO 118
<211> LENGTH: 72
<212> TYPE: DNA
<213> ORGANISM: Artificial Sequence
<220> FEATURE:
<223> OTHER INFORMATION: Synthetic DISC1_452 with linker

<400> SEQUENCE: 118
tccggagggg aagccagagg cgagctgagc gtggaagatg agcggcagat ggacgacctg 60
gaagggggat cc 72

<210> SEQ ID NO 119
<211> LENGTH: 45
<212> TYPE: DNA
<213> ORGANISM: Artificial Sequence
<220> FEATURE:
<223> OTHER INFORMATION: Synthetic DISC1_454 with linker

<400> SEQUENCE: 119
tccggagggg aagccagagg cgagctgagc gtggaagggg gatcc 45

<210> SEQ ID NO 120
<211> LENGTH: 63
<212> TYPE: DNA
<213> ORGANISM: Artificial Sequence
<220> FEATURE:
<223> OTHER INFORMATION: Synthetic hHER2 antigen with linker

<400> SEQUENCE: 120
aaaaaatccg gaggcgtcac ctacaacaca gacacgtttg agtccatgcc cggcggatcc 60
aaa 63

<210> SEQ ID NO 121
<211> LENGTH: 51
<212> TYPE: DNA
<213> ORGANISM: Artificial Sequence
<220> FEATURE:
<223> OTHER INFORMATION: Synthetic hHER2 antigen with linker

<400> SEQUENCE: 121
aaaaaatccg gaggctatgt gaatgccagg cactgtttgg gcggatccaa a 51

<210> SEQ ID NO 122
<211> LENGTH: 51
<212> TYPE: DNA
<213> ORGANISM: Artificial Sequence
<220> FEATURE:
<223> OTHER INFORMATION: Synthetic HER2 antigen with linker

<400> SEQUENCE: 122
aaaaaatccg gaggctatgt gaatgccagg cacggtttgg gcggatccaa a 51

<210> SEQ ID NO 123
<211> LENGTH: 69
<212> TYPE: DNA
<213> ORGANISM: artificial sequence
<220> FEATURE:
<223> OTHER INFORMATION: Synthetic HER2 antigen with linker

<400> SEQUENCE: 123
aaaaaatccg gaggcaagtt tccagatgag gagggcgcat gccagccttg ccccatcggc 60
ggatccaaa 69

<210> SEQ ID NO 124
<211> LENGTH: 60
<212> TYPE: DNA
<213> ORGANISM: Artificial Sequence
<220> FEATURE:
<223> OTHER INFORMATION: Synthetic HER2 antigen

<400> SEQUENCE: 124
aaaaaatccg gaggcaagtt tccagatgag gagggcgcat gccagcctgg cggatccaaa 60

<210> SEQ ID NO 125
<211> LENGTH: 48
<212> TYPE: DNA
<213> ORGANISM: Artificial Sequence
<220> FEATURE:
<223> OTHER INFORMATION: Synthetic HER2 antigen with linker

<400> SEQUENCE: 125
aaaaaatccg gaggcaagga ccctcccttc tgcgtgggcg gatccaaa 48

<210> SEQ ID NO 126
<211> LENGTH: 54
<212> TYPE: DNA
<213> ORGANISM: Artificial Sequence
<220> FEATURE:
<223> OTHER INFORMATION: Synthetic HER2 antigen with linker

<400> SEQUENCE: 126
aaaaaatccg gaggctataa ggaccctccc ttctgcgtgg cgggcggatc caaa 54

<210> SEQ ID NO 127
<211> LENGTH: 51
<212> TYPE: DNA
<213> ORGANISM: Artificial Sequence
<220> FEATURE:
<223> OTHER INFORMATION: Synthetic HER2 antigen with linker

<400> SEQUENCE: 127
aaaaaatccg gaggctataa ggaccctccc ttctgcgtgg gcggatccaa a 51

<210> SEQ ID NO 128
<211> LENGTH: 14
<212> TYPE: PRT
<213> ORGANISM: Artificial Sequence
<220> FEATURE:
<223> OTHER INFORMATION: Synthetic HER2 antigen with linker

<400> SEQUENCE: 128

Ser Gly Gly Tyr Val Asn Ala Arg His Gly Leu Gly Gly Ser
1 5 10

<210> SEQ ID NO 129
<211> LENGTH: 18
<212> TYPE: PRT
<213> ORGANISM: Artificial Sequence
<220> FEATURE:
<223> OTHER INFORMATION: Synthetic HER2 antigen with linker

<400> SEQUENCE: 129

Ser Gly Gly Cys Gly Tyr Val Asn Ala Arg His Gly Leu Gly Cys Gly 1 5 10 15

Gly Ser

<210> SEQ ID NO 130
<211> LENGTH: 14
<212> TYPE: PRT
<213> ORGANISM: Artificial Sequence
<220> FEATURE:
<223> OTHER INFORMATION: Synthetic HER2 antigen with linker

<400> SEQUENCE: 130

Ser Gly Gly Tyr Lys Asp Pro Pro Phe Cys Val Gly Gly Ser
1 5 10

<210> SEQ ID NO 131
<211> LENGTH: 14
<212> TYPE: PRT
<213> ORGANISM: Artificial Sequence
<220> FEATURE:
<223> OTHER INFORMATION: Synthetic HER2 antigen with linker

<400> SEQUENCE: 131

Ser Gly Gly Tyr Lys Asp Pro Pro Phe Gly Val Gly Gly Ser
1 5 10

<210> SEQ ID NO 132
<211> LENGTH: 14
<212> TYPE: PRT
<213> ORGANISM: Artificial Sequence
<220> FEATURE:
<223> OTHER INFORMATION: Synthetic hBTLA antigen with linker

<400> SEQUENCE: 132

Ser Gly Gly Cys Lys Leu Asn Gly Thr Thr Cys Gly Gly Ser
1 5 10

<210> SEQ ID NO 133
<211> LENGTH: 20
<212> TYPE: PRT
<213> ORGANISM: Artificial Sequence
<220> FEATURE:
<223> OTHER INFORMATION: Synthetic hHVEM antigen

<400> SEQUENCE: 133

Ser Gly Gly Cys Val Lys Glu Ala Ser Gly Glu Leu Thr Gly Thr Val
1 5 10 15

Cys Gly Gly Ser
20

<210> SEQ ID NO 134
<211> LENGTH: 25
<212> TYPE: PRT
<213> ORGANISM: Artificial Sequence
<220> FEATURE:
<223> OTHER INFORMATION: Synthetic hHVEM antigen with linker

<400> SEQUENCE: 134

Ser Gly Gly Cys Tyr Arg Val Lys Glu Ala Ser Gly Glu Leu Thr Gly
1 5 10 15

Thr Val Ser Glu Pro Cys Gly Gly Ser
20 25

<210> SEQ ID NO 135
<211> LENGTH: 19
<212> TYPE: PRT

<213> ORGANISM: Artificial Sequence
<220> FEATURE:
<223> OTHER INFORMATION: Synthetic hHVEM antigen with linker

<400> SEQUENCE: 135

Ser Gly Gly Cys Ser Arg Asn Ser Ser Arg Thr Glu Asn Ala Val Cys
1 5 10 15

Gly Gly Ser

<210> SEQ ID NO 136
<211> LENGTH: 21
<212> TYPE: PRT
<213> ORGANISM: Artificial Sequence
<220> FEATURE:
<223> OTHER INFORMATION: Synthetic hHVEM antigen with linker

<400> SEQUENCE: 136

Ser Gly Gly Cys Gln Met Ser Asp Pro Ala Met Gly Leu Arg Ser Arg
1 5 10 15

Asn Cys Gly Gly Ser
20

<210> SEQ ID NO 137
<211> LENGTH: 61
<212> TYPE: PRT
<213> ORGANISM: Artificial Sequence
<220> FEATURE:
<223> OTHER INFORMATION: Synthetic CHIKV OPY-1 strain 6K sequence

<400> SEQUENCE: 137

Ala Thr Tyr Gln Glu Ala Ala Ile Tyr Leu Trp Asn Glu Gln Gln Pro
1 5 10 15

Leu Phe Trp Leu Gln Ala Leu Ile Pro Leu Ala Ala Leu Ile Val Leu
20 25 30

Cys Asn Cys Leu Arg Leu Leu Pro Cys Cys Cys Lys Thr Leu Ala Phe
35 40 45

Leu Ala Val Met Ser Val Gly Ala His Thr Val Ser Ala
50 55 60

<210> SEQ ID NO 138
<211> LENGTH: 61
<212> TYPE: PRT
<213> ORGANISM: Artificial Sequence
<220> FEATURE:
<223> OTHER INFORMATION: Synthetic CHIKV 37997 strain 6K sequence

<400> SEQUENCE: 138

Ala Thr Tyr Tyr Glu Ala Ala Ala Tyr Leu Trp Asn Glu Gln Gln Pro
1 5 10 15

Leu Phe Trp Leu Gln Ala Leu Ile Pro Leu Ala Ala Leu Ile Val Leu
20 25 30

Cys Asn Cys Leu Lys Leu Leu Pro Cys Cys Cys Lys Thr Leu Ala Phe
35 40 45

Leu Ala Val Met Ser Ile Gly Ala His Thr Val Ser Ala
50 55 60

<210> SEQ ID NO 139
<211> LENGTH: 56
<212> TYPE: PRT
<213> ORGANISM: Artificial Sequence
<220> FEATURE:
<223> OTHER INFORMATION: Synthetic VEEV TC-83 strain 6K sequence -continued

```
<400> SEQUENCE: 139

Glu Thr Thr Trp Glu Ser Leu Asp His Leu Trp Asn Asn Asn Gln Gln
1               5                   10                  15

Met Phe Trp Ile Gln Leu Leu Ile Pro Leu Ala Ala Leu Ile Val Val
            20                  25                  30

Thr Arg Leu Leu Arg Cys Val Cys Cys Val Val Pro Phe Leu Val Met
        35                  40                  45

Ala Gly Ala Ala Gly Ala Gly Ala
    50                  55


<210> SEQ ID NO 140
<211> LENGTH: 4
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (1)..(4)
<223> OTHER INFORMATION: amino acid residues 1 to 4 may repeat 4 to 30
      times

<400> SEQUENCE: 140

Asn Pro Asn Ala
1
```

VIRUS LIKE PARTICLE COMPRISING MODIFIED ENVELOPE PROTEIN E3

CROSS REFERENCE TO RELATED APPLICATIONS

This application claims the benefit of U.S. Provisional Applications No. 62/035,037 filed Aug. 8, 2014, No. 62/079,128 filed Nov. 13, 2014, No. 62/101,514 filed Jan. 9, 2015, No. 62/120,569 filed Feb. 25, 2015 and 62/198,949 filed Jul. 30, 2015. The contents of those 5 provisional applications are herein incorporated by reference.

TECHNICAL FIELD

The present application relates to a virus like particle comprising a modified envelope protein E3, and use thereof.

BACKGROUND ART

Virus-like particles (VLPs) are multiprotein structures that mimic the organization and conformation of authentic native viruses but lack the viral genome, potentially yielding safer and cheaper vaccine candidates. A handful of prophylactic VLP-based vaccines is currently commercialized worldwide: GlaxoSmithKline's Engerix® (hepatitis B virus) and Cervarix® (human papillomavirus), and Merck and Co., Inc.'s Recombivax HB® (hepatitis B virus) and Gardasil® (human papillomavirus) are some examples. Other VLP-based vaccine candidates are in clinical trials or undergoing preclinical evaluation, such as, influenza virus, parvovirus, Norwalk and various chimeric VLPs. Many others are still restricted to small-scale fundamental research, despite their success in preclinical tests. The implications of large-scale VLP production are discussed in the context of process control, monitorization and optimization. The main up- and down-stream technical challenges are identified and discussed accordingly. Successful VLP-based vaccine blockbusters are briefly presented concomitantly with the latest results from clinical trials and the recent developments in chimeric VLP-based technology for either therapeutic or prophylactic vaccination.

Up to now, VLP-based vaccines have been produced for more than 30 different viruses that infect human and other animals. The examples include AAV (Adeno-associated virus), H5N3 (Avian influenza), BFDV (Budgerigar fledgling disease virus), BTV (Bluetongue virus), Ebola, Enterovirus 71, GHPV (Goose hemorrhagic polyoma virus), HBV (Hepatitis B virus), HCV (Hepatitis C virus), HDV (Hepatitis δ virus), HEV (Hepatitis E virus), HIV, HPV (Human papillomavirus), IBDV (Infectious bursal disease virus), Influenza A, Influenza A H1N1, Influenza A H3N2, JC polymavirus, Margurg, MS2, IPCV (Indian peanut clump virus), NDV (Newcastle disease virus), No (Norovirus) Nv (Norwalk virus), PhMV (Physalis mottle virus), Polymavirus, PPV (Porcine parvovirus), RHDV (Rabbit hemorrhagic disease virus), Rotavirus, SARS, SIV (Simian immunodeficiency virus), SV40 (Simian virus 40), SVDV (Swine vesicular disease virus) and so on. (Expert Rev. Vaccines 9(10), 1149-1176, 2010).

To quickly generate large quantity of VLPs or vaccines for both pre-clinical and clinical trials, almost all drug development will face the same challenging obstacle of rapidly generating a high stable producer. Developing and identifying a stable cell line is a critical part of the development. However, to generate a stable cell line with high titer and good product quality is not so easily accomplished until now.

Chikungunya virus (CHIKV) has infected millions of people in Africa, Europe and Asia since this alphavirus reemerged from Kenya in 2004. The severity of the disease and the spread of this epidemic virus present a serious public health threat in the absence of vaccines or antiviral therapies. It is reported that a VLP vaccine for epidemic Chikungunya virus protects non-human primates against infection (Nat Med. 2010 March; 16(3): 334-338). US patent publication No. 2012/0003266 discloses a virus-like particle (VLP) comprising one or more Chikungunya viral structural proteins which is useful for formulating a vaccine or antigenic composition for Chikungunya that induces immunity to an infection or at least one symptom thereof. WO2012/106356 discloses modified alphavirus or flavivirus virus-like particles (VLPs) and methods for enhancing production of modified VLPs for use in the prevention or treatment of alphavirus and flavivirus-mediated diseases. (these cited references are herein incorporated by reference).

SUMMARY OF INVENTION

According to the present application, followings are provided:

(1) A virus like particle comprising a viral structural protein which comprises modified envelope protein E3.

(2) The virus like particle according to (1), wherein the viral structural protein is derived from alphavirus or flavivirus.

(3) The virus like particle according to (2), wherein the viral structural protein is derived from Chikungunya virus or Venezuelan equine encephalitis virus.

(4) The virus like particle according to (3), wherein the virus like particle is derived from Chikungunya virus strain 37997 or strain OPY-1, or Venezuelan equine encephalitis virus strain TC-83.

(5) The virus like particle according to any one of (1)-(4), wherein one or more amino acid residues in the envelope protein E3 are replaced, added and/or deleted in amino acid sequence of the viral structural protein.

(6) The virus like particle according to (5), wherein one or more amino acid residues are replaced, added and/or deleted in amino acid sequence at furin site in the envelope protein E3.

(7) The virus like particle according to any one of (1)-(6), wherein the viral structural protein comprises capsid, envelope protein E1, envelope protein E2 and envelope protein E3.

(8) The virus like particle according to any one of (1)-(7), wherein an at least one antigen is inserted into the envelope protein E3.

(9) The virus like particle according to (8), wherein the at least one antigen is further inserted into the envelope protein E2.

(10) The virus like particle according to (8) or (9), wherein the at least one antigen is inserted between residues corresponding to 321 and 326 of SEQ ID NO: 1, residues 321 and 326 of SEQ ID NO: 2 or residues 330 and 335 of SEQ ID NO: 3.

(11) The virus like particle according to any one of (8)-(10), wherein the at least one antigen is derived from *Plasmodium falciparum* circumsporozoite protein, PD-1, PD-L1, CTLA-4, DISC1, IL-2, HER2, BTLA or HVEM.

(12) The virus like particle according to (11), wherein a peptide selected from (NPNA)n (n=4-30), amino acid sequence represented by SEQ ID Nos.6-9 and 15-29 is inserted into the envelope E3 protein.

(13) The virus like particle according to any one of (8)-(12), wherein the virus like particle is Chikungunya virus like particle comprises the following amino acid sequences or an amino acid sequence having 90% or more identity to the following sequences:

a capsid which consists of an amino acid sequence represented by SEQ ID NO: 31 or SEQ ID NO: 75;

an E1 which consists of an amino acid sequence represented by SEQ ID NO: 32 or SEQ ID NO: 76; and a complex of E2 and E3 which consists of an amino acid sequence represented by SEQ ID NO: 33 or SEQ ID NO: 77, wherein an amino acid sequence of the at least one antigen is inserted between residues corresponding to residues 321 and 326 of SEQ ID NO: 2.

(14) The virus like particle according to any one of (8)-(12), wherein the virus like particle is Venezuelan equine encephalitis virus like particle comprises the following amino acid sequences or an amino acid sequence having 90% or more identity to the following sequences:

a capsid which consists of an amino acid sequence represented by SEQ ID NO: 35;

an E1 which consists of an amino acid sequence represented by SEQ ID NO: 36; and a complex of E2 and E3 which consists of an amino acid sequence represented by SEQ ID NO: 37, wherein an amino acid sequence of the at least one antigen is inserted between residues corresponding to the residues 330 and 335 of SEQ ID NO: 3.

(15) The virus like particle according to any one of (8)-(12), wherein the virus like particle is Chikungunya virus like particle and the structure of the virus like particle comprises any one of the following sequences (1)-(4) or an amino acid sequence having 90% or more identity to any one of the following sequences (1)-(4):

(1)

an E1 which consists of an amino acid sequence represented by SEQ ID NO: 32;

a complex of E2 and E3 into which a malaria antigen is inserted, which consists of an amino acid sequence represented by SEQ ID NO: 46; and and a capsid which consists of an amino acid sequence represented by SEQ ID NO: 31;

(2)

an E1 which consists of an amino acid sequence represented by SEQ ID NO: 32;

a complex of E2 and E3 into which a PD-1 antigen is inserted, which consists of an amino acid sequence represented by SEQ ID NO: 47; and a capsid which consists of an amino acid sequence represented by SEQ ID NO: 31;

(3)

an E1 which consists of an amino acid sequence represented by SEQ ID NO: 32;

a complex of E2 and E3 into which a PD-L1 ligand antigen is inserted, which consists of an amino acid sequence represented by SEQ ID NO: 48; and a capsid which consists of an amino acid sequence represented by SEQ ID NO: 31; or (4)

an E1 which consists of an amino acid sequence represented by SEQ ID NO: 32;

a complex of E2 and E3 into which a CTLA-4 antigen is inserted, which consists of an amino acid sequence represented by SEQ ID NO: 49; and a capsid which consists of an amino acid sequence represented by SEQ ID NO: 31.

(16) The virus like particle according to any one of (8)-(12), wherein the virus like particle is Venezuelan equine encephalitis virus like particle and the structure of the virus like particle comprises any one of the following sequences (1)-(4) or an amino acid sequence having 90% or more identity to any one of the following sequences (1)-(4):

(1)

an E1 which consists of an amino acid sequence represented by SEQ ID NO: 36;

a complex of E2 and E3 into which a malaria antigen is inserted, which consists of an amino acid sequence represented by SEQ ID NO: 50; and a capsid which consists of an amino acid sequence represented by SEQ ID NO: 35;

(2)

an E1 which consists of an amino acid sequence represented by SEQ ID NO: 36;

a complex of E2 and E3 into which a PD-1 antigen is inserted, which consists of an amino acid sequence represented by SEQ ID NO: 51; and a capsid which consists of an amino acid sequence represented by SEQ ID NO: 35;

(3)

an E1 which consists of an amino acid sequence represented by SEQ ID NO: 36;

a complex of E2 and E3 into which a PD-L1 antigen is inserted, which consists of an amino acid sequence represented by SEQ ID NO: 52; and a capsid which consists of an amino acid sequence represented by SEQ ID NO: 35; or (4)

an E1 which consists of an amino acid sequence represented by SEQ ID NO: 36;

a complex of E2 and E3 into which a CTLA-4 antigen is inserted, which consists of an amino acid sequence represented by SEQ ID NO: 53; and a capsid which consists of an amino acid sequence represented by SEQ ID NO: 35.

(17) The virus like particle according to any one of (1)-(5), wherein furin cleavage site located in envelope protein E3 is altered or mutated to prevent the furin site from cleaving.

(18). An isolated nucleic acid molecule comprising a nucleotide sequence encoding the virus like particle according to any one of (1-17).

(19) An isolated nucleic acid molecule consisting of a nucleotide sequence which has a sequence identity of 90% or more with a nucleotide sequence represented by any one of SEQ ID Nos.38-45.

(20) The nucleic acid molecule according to (19), wherein the nucleic acid molecule consists of a nucleotide sequence represented by any one of SEQ ID Nos.:38-45.

(21) A vector comprising the nucleic acid molecule according to any one of (18)-(20), wherein the vector optionally comprises an expression control sequence operably linked to the nucleic acid molecule.

(22) A vector comprising a nucleic acid molecule which comprises:

a nucleotide sequence represented by SEQ ID NO: 54 or SEQ ID NO: 55, wherein a nucleotide sequence encoding at least one antigen is inserted between residues 963 and 969 of SEQ ID NO: 54 or between residues 990 and 1006 of SEQ ID NO: 55; and an expression control sequence operably linked to the nucleic acid molecule.

(23) A pharmaceutical composition comprising (a) the virus like particle according to any one of (1)-(17), the nucleic acid molecule according to any one of (18)-(20) and/or the vector according to (21) or (22); and (b) a pharmaceutically acceptable carrier.

(24) A vaccine composition comprising the virus like particle according to any one of (1)-(17) and a pharmaceutically acceptable carrier.

(25) A method of producing the virus like particle according to any one of (1)-(17), comprising the steps of:

culturing a cell which is transfected with the vector according to (21)-22) to express the virus like particle; and purifying the generated particle.

(26) A method of enhancing the production of a virus like particle comprising a viral structural protein and at least one antigen, comprising (1) inserting the at least one antigen into an envelope protein E3 of the viral structural protein, and (2) isolating the virus like particle wherein at least one antigen is inserted into the envelope protein E3 of the viral structural protein.

(27) The method according to (26), wherein the step (1) is achieved by a method comprising preparing a nucleic acid molecule comprising a nucleotide sequence encoding the virus like particle wherein at least one antigen is inserted into the envelope protein E3 of the viral structural protein; and allow the nucleic acid molecule to be expressed using cells.

(28) The method according to (26) or (27), wherein the virus like particle is the virus like particle according to any one of (1)-(17).

(29) A method of treating or preventing cancer, neurological disease, infectious disease or malaria; producing an antibody against the at least one antigen in a mammal; modulating an immune response; immunostimulation; inhibiting function of the at least one antigen; or presenting an antigen on macrophage, comprising administering the virus like particle according to any one of (1)-(17), the nucleic acid molecule according to any one of (18)-(20), the vector according to (21) or (22) and/or the composition according to (23) or (24) to a subject in need thereof.

(30) Use of the virus like particle according to any one of (1)-(17), the nucleic acid molecule according to any one of (18)-(20) or the vector according to (21) or (22) for the manufacture of a pharmaceutical composition or a kit for treating or preventing cancer, infectious disease or malaria; producing an antibody against the at least one antigen in a mammal; modulating an immune response; immunostimulation; inhibiting function of the at least one antigen; or presenting an antigen on macrophage.

(31) A cell line expressing a virus like particle, wherein the virus like particle comprises a viral structural protein which comprises an alternation/mutation to the amino acid sequence at the furin site in the envelope protein E3.

(32) The cell line of (31), the alternation to the amino acid sequence at furin site is an alternation to Ile-Glu/Asp-Gly-Arg or Asp-Asp-Asp-Asp-Lys.

(33) The cell line of (31) or (32), wherein the cell line is a stable cell line.

(34) A method for producing a cell line expressing a virus like particle, which comprising the step of:

transfecting a cell line with an expression vector comprising a nucleic acid molecule encoding a viral structural protein whose furin site in an envelope protein E3 is altered to a specific protease recognition site.

(35) The method of (34), wherein the furin site is altered to Factor Xa or Enterokinase recognition site.

(36) The method of (34) or (35), wherein the method provides a stable cell line.

(37) A method for producing a mature virus like particle, which comprises the steps of:

i) generating an immature virus like particle produced by the cell line according to any one of (31)-(33); and ii) removing the E3 from the immature virus like particle.

(38) The method of (37), wherein the E3 is removed by a protease.

(39) The method of (38), wherein the protease is Factor Xa or Enterokinase.

(40) The cell line of (31), wherein the virus like particle is the virus like particle according to any one of (1)-(17).

In a first aspect, the present application provides a virus like particle comprising a modified envelope protein E3.

In a second aspect, the present application provides a nucleic acid molecule comprising or consisting of a nucleotide sequence encoding a virus like particle comprising a modified envelope protein E3.

In a third aspect, the present application provides a pharmaceutical composition and a kit comprising the pharmaceutical composition, wherein the pharmaceutical composition comprises (i) a virus like particle comprising a modified envelope protein E3 and/or (ii) a nucleic acid molecule comprising or consisting of a nucleotide sequence encoding a virus like particle comprising a modified envelope protein E3.

In a fourth aspect, the present application provides a method of producing a virus like particle comprising a modified envelope protein E3, comprising culturing a cell which is transfected with a vector to express the virus like particle; and purifying the particle generated by the cell.

In a fifth aspect, the present application provides a method of enhancing the production of a virus like particle comprising a viral structural protein with a modified envelop protein E3. In one embodiment, the virus like particle comprises a viral structural protein and at least one foreign antigen, comprising:

(1) inserting the at least one foreign antigen into an envelope protein E3 of the viral structural protein, and (2) isolating the virus like particle wherein at least one antigen is inserted into the envelope protein E3 of the viral structural protein.

In a sixth aspect, the present application provides use of (i) a virus like particle comprising a modified envelope protein E3 and/or (ii) a nucleic acid molecule consisting of a nucleotide sequence encoding a virus like particle comprising a modified envelope protein E3 for the manufacture of a pharmaceutical composition or a kit for treating or preventing cancer, neurological disease, infectious disease or malaria; producing an antibody against at least one antigen in a mammal; modulating an immune response; immunostimulation; inhibiting function of at least one antigen; or presenting an antigen on macrophage.

In all aspect, the envelope protein E3 may be modified to comprise at least one antigen or an alternation/mutation to the amino acid sequence at the furin site.

In a seventh aspect, the present application provides a cell line that expresses a viral structural protein and can generate virus like particle, wherein the viral structural protein comprises an alternation/mutation to the amino acid sequence at the furin site, and the method for producing thereof.

In an eighth aspect, the present application provides a method for producing a mature virus like particle, which comprises the steps of:

i) generating an immature virus like particle produced by the cell line described above;
ii) removing the E3 from the immature virus like particle.

DESCRIPTION OF EMBODIMENTS

Figure 1:
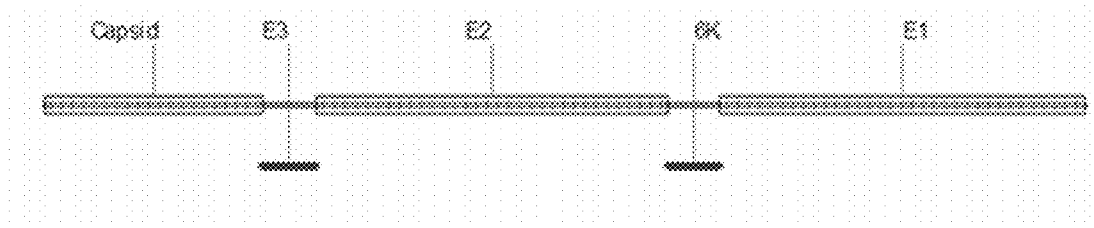
FIG. 1 shows structure of CHIKV or VEEV viral structural protein.

(1) Virus Like Particle Comprising a Modified Envelope Protein E3

In a first aspect, the present application provides a virus like particle comprising a modified envelope protein E3.

In this aspect, the envelope protein E3 may be modified to comprise at least one antigen or an alternation/mutation to the amino acid sequence at the furin site (Arg-X-X-Arg).

The term "Arg-X-X-Arg" indicates the minimal cleavage site of furin and "X-X" includes any two amino acids.

A virus like particle is composed of one or more viral structural proteins that spontaneously assemble into a particulate structure.

A viral structural protein used for the present application may be any viral structural protein as long as it expresses a furin site.

In a seventh aspect, the present application provides a cell line, especially stable cell line expressing a virus like particle, wherein the virus like particle comprises an alternation/mutation to the amino acid sequence at the furin site (Arg-X-X-Arg), and the method for producing thereof. Example of the alternation to the amino acid sequence at furin site includes the alternation to Ile-Glu/Asp-Gly-Arg or Asp-Asp-Asp-Asp-Lys.

In one embodiment, the present application provides a method for producing a cell line expressing a virus like particle, wherein the furin site of the virus like particle is altered to a protease recognition site. In this embodiment, the cell line generated by this method could be a stable cell line. For example, the stable cell line obtained by this embodiment may maintain the ability to express and generate the VLP for relatively long time, such as more than three months.

In one embodiment, the present application provides an immature virus like particle produced by the cell line described above.

In an eighth aspect, the present application provides a method for producing a mature virus like particle, which comprises the steps of:

i) providing an immature virus like particle produced by the cell line described above;

ii) removing the E3 from the immature virus particle.

In one embodiment, the E3 in the immature virus like particle is removed by digestion of the protease recognition site. In one embodiment, the E3 in the immature virus like particle is removed by a protease. Examples of proteases include, but not limited to, Arg-C proteinase, Asp-N endopeptidase, Asp-N endopeptidase+N-terminal Glu, BNPS-Skatole, Caspase1 to Caspase10, Chymotrypsin, Clostripain (Clostridiopeptidase B), CNBr, Enterokinase, Factor Xa, Formic acid, Glutamyl endopeptidase, GranzymeB, Hydroxylamine, Iodosobenzoic acid, LysC, LysN, NTCB (2-nitro-5-thiocyanobenzoic acid), Neutrophil elastase, Pepsin, Proline-endopeptidase, PreScission Protease (PSP), Proteinase K, Staphylococcal peptidase I, Tobacco etch virus protease, Thermolysin, Thrombin and Trypsin. Preferred examples of the protease include Factor Xa, Enterokinase and PreScission Protease (PSP), expecially, Factor Xa and Enterokinase (e.g. Enterokinase (enteropeptidase), light chain).

In another aspect, the present application provides a virus like particle comprising an envelope protein E3, wherein the envelope protein E3 is modified to comprise at least one antigen. The at least one antigen may be a peptide that is not derived from the virus from which the viral structural protein is derived or a peptide that is derived from the same virus that provides the viral structural protein.

A derivative of the above-described virus like particle which can be prepared by modifying the above-described particle is also provided by the present application. Examples of the modification include, but are not limited to, addition, deletion or replacement of one or more amino acid residues.

The particle provided by the present application may be a particle which consists of or comprises i) at least one viral structural protein and ii) at least one antigen, wherein the at least one antigen is inserted into the envelope protein E3 of the viral structural protein. The at least one viral structural protein may consist of one or more kinds of protein or peptide and spontaneously assembles to form a particle. In one embodiment, the particle provided by the present application has a diameter of at least 10 nm, for example, at least 20 nm, preferably at least 50 nm. In one embodiment, molecular weight of the particle is from 100 kDa to 100,000 kDa, preferably from 400 kDa to 30,000 kDa.

One or more amino acid residues can be replaced, added and/or deleted in amino acid sequence of the viral structural protein to allow expression of a virus like particle comprising an envelope protein E3 where at least one antigen is inserted.

In one preferred embodiment, the virus like particle provided by the present application comprising at least one antigen in an envelope protein E3 can be expressed more efficiently in a eukaryotic cell (e.g. 293F cells) than a virus like particle comprising said at least one antigen in an envelope protein E2.

A viral structural protein used for the present application may be a viral structural protein derived from Alphavirus or Flavivirus. Thus, the particle provided by the present application may be a virus like particle including a virus like particle derived from Alphavirus or Flavivirus.

Examples of Alphavirus and Flavivirus include, but not limited to, Aura virus, Babanki virus, Barmah Forest virus (BFV), Bebaru virus, Cabassou virus, Chikungunya virus (CHIKV), Eastern equine encephalitis virus (EEEV), Eilat virus, Everglades virus, Fort Morgan virus, Getah virus, Highlands J virus, Kyzylagach virus, Mayaro virus, Me Tri virus, Middelburg virus, Mosso das Pedras virus, Mucambo virus, Ndumu virus, O'nyong-nyong virus, Pixuna virus, Rio Negro virus, Ross River virus (RRV), Salmon pancreas disease virus, Semliki Forest virus, Sindbis virus, Southern elephant seal virus, Tonate virus, Trocara virus, Una virus, Venezuelan equine encephalitis virus (VEEV), Western equine encephalitis virus (WEEV), Whataroa virus, West Nile virus, dengue virus, tick-borne encephalitis virus and yellow fever virus.

The particle provided by the present application may be a virus like particle derived from Chikungunya virus or Venezuelan equine encephalitis virus. Chikungunya virus may be Chikungunya virus 37997 strain or OPY-1 strain. Venezuelan equine encephalitis virus may be Venezuelan equine encephalitis virus TC-83 strain.

Viral structural protein may be a capsid protein, an envelope protein, a fragment thereof or a complex thereof. Thus, viral structural protein used for the present application may consist of or comprise a capsid protein and/or an envelope protein and/or a fragment or derivative thereof. In one embodiment, the virus like particle provided by the present application consists of or comprises capsid, E3, E2 and E1 proteins, and an antigen is inserted into E3. For example, the virus like particle provided by the present application may be formed by assembling 240 capsids, 240 E1 proteins, 240 E2 proteins and 240 E3 proteins where an antigen is inserted into each of E3 proteins.

Under physiological conditions, E3 can be dissociated from E2 after furin cleavage. In one embodiment, the furin cleavage site located in E3 may be mutated to prevent furin site from cleaving. For example, an antigen can be inserted into the furin cleavage site to introduce a mutation in the furin cleavage site. In this embodiment, the virus like particle provided may consist of or comprises capsid, E3, E2 and E1 proteins, where E3 is bound to E2 to forma single protein and an antigen is inserted into E3 region. For example, the virus like particle provided by the present application may be formed by assembling 240 capsids, 240 E1 proteins, 240 proteins in each of which E2 is bound to E3 and an antigen is inserted into each of E3 regions.

Antigen may be a molecule capable of being bound by an antibody or a T cell receptor (TCR) if it is presented with MHC molecules. Antigen can encompass B-cell epitopes and T-cell epitopes. Antigen disclosed in U.S. patent publication No.: US 2013/0251744 filed Feb. 15, 2013, the entire contents of which are incorporated herein by reference, may be used for the present application. Examples of antigen used for the present application include, but are not limited to, allergens, self-antigens, haptens, cancer antigens, infectious disease antigens and small organic molecules, and fragments and derivatives thereof.

Antigen may be a naturally occurring and/or modified protein, a fragment thereof or derivative of the naturally occurring protein or its fragment. A fragment of a naturally occurring and/or modified protein for use as an antigen contained in the particle provided by the present application may be selected based on the amino acid sequence of the naturally occurring and/or modified protein and/or tertiary structure thereof. For example, a fragment for use as an antigen may consist of or comprise a fragment located in the surface of a naturally occurring protein. Preferably, an antibody against an antigen contained in the particle provided by the present application may inhibit function of the antigen. An antigen (e.g. a fragment of a naturally occurring protein) may be 10-300 amino acid residues (e.g. 10-120, 10-30 or 15-30 amino acid residues) in length. A derivative of a naturally occurring protein or its fragment may be prepared by addition, deletion or replacement of one or several amino acid residues in the naturally occurring protein or its fragment. In one embodiment, a derivative of a naturally occurring protein or its fragment has at least 70%, 75%, 80%, 85%, 90%, 95% or 98% amino acid sequence identity to the corresponding naturally occurring protein or its fragment. In one embodiment, a derivative of a naturally occurring protein or its fragment is a mutant where at most 10% of the amino acids are deleted, substituted, and/or added based on the corresponding naturally occurring protein or its fragment.

In one embodiment, an antigen or epitope (e.g. a fragment of a naturally occurring protein) may be selected so that spatial distance between the N-terminal residue and C-terminal residue of the antigen is 30 Å or less when the distance is determined in a crystal of the antigen or a naturally occurring protein containing the antigen or modified peptide therefrom. For example, an antigen used for the particle provided by the present application can be designed using a free software including PyMOL (e.g. PyMOL v0.99: http:/www.pymol.org). In one embodiment, a spatial distance between N-terminal residue and C-terminal residue of the antigen is 30 Å (angstrom) or less, 20 Å or less, or 10 Å or less (e.g. from 5 Å to 15 Å, from 5 Å to 12 Å, from 5 Å to 11 Å, from 5 Å to 10 Å, from 5 Å to 8 Å, from 8 Å to 15 Å, from 8 Å to 13 Å, from 8 Å to 12 Å, from 8 Å to 11 Å, from 9 Å to 12 Å, from 9 Å to 11 Å, from 9 Å to 10 Å or from 10 Å to 11 Å).

In one embodiment, an antigen or epitope which may be used for the present application may be malaria antigen, PD-1 antigen, PD-1 ligand antigen, CTLA-4 antigen, IL-2 antigen DISC1 antigen, HER2 antigen, BTLA antigen, HVEM antigen, PCSK-9 antigen or DPP-4 antigen.

As used herein, "malaria antigen" refers to an antigen or epitope derived from *Plasmodium* parasite. The *plasmodium* parasite may be selected from any of the known *Plasmodium* (P.) species, for example, *P. falciparum, P. malariae, P. ovale, P. vivax, P. knowlesi, P. berghei, P. chabaudi* and *P. yoelii.*

In one embodiment, malaria antigen is a *Plasmodium falciparum* circumsporozoite protein B cell epitope (hereinafter, referred as CSP protein, Malaria CSP protein, or CSP). Example of *Plasmodium falciparum* circumsporozoite protein B cell epitope may be a repeat sequence of NPNA, including (NPNA) 4-30 (i.e. 4×NPNA, 5×NPNA, 6×NPNA, 7×NPNA, 8×NPNA, 9×NPNA, 10×NPNA, 11×NPNA, 12×NPNA, 13×NPNA 14×NPNA, 15×NPNA, 16×NPNA, 17×NPNA, 18×NPNA, 19×NPNA, 20×NPNA, 21×NPNA, 22×NPNA, 23×NPNA, 24×NPNA, 25×NPNA, 26×NPNA, 27×NPNA, 28×NPNA, 29×NPNA or 30×NPNA).

In one embodiment, malaria antigen is a *Plasmodium yoelii* circumsporozoite protein B cell epitope including (QGPGAP)3-12.

In one embodiment, malaria antigen is a *Plasmodium vivax* circumsporozoite protein B cell epitope including (ANGAGNQPG)1-12.

In one embodiment, malaria antigen is a *Plasmodium malariae* circumsporozoite protein B cell epitope including (NAAG)4-30.

In one embodiment, malaria antigen is a *Plasmodium falciparum* circumsporozoite protein T cell epitope. Example of *Plasmodium falciparum* circumsporozoite protein T cell epitope may be EYLNKIQNSLSTEWSPCSVT (SEQ ID NO: 4). (EYLNKIQNSLSTEWSPCSVT)1-6 may be also used as a malaria antigen.

In one embodiment, malaria antigen is a *Plasmodium yoelii* circumsporozoite protein T cell epitope which is YNRNIVNRLLGDALNGPEEK (SEQ ID NO: 5). (YNRNIVNRLLGDALNGPEEK)1-6 may be also used as a malaria antigen.

As used herein, the term "PD-1 antigen" refers to an antigen or epitope derived from PD-1. Preferably, PD-1 is a human PD-1. An antigen derived from PD-1 may be a fragment of PD-1 or a derivative of a fragment of PD-1.

As used herein, the term "PD-1 ligand antigen" refers to an antigen or epitope derived from a ligand of PD-1. Examples of a ligand of PD-1 include, but are not limited to, PD-L1 and PD-L2. Preferably, a ligand of PD-1 is human PD-L1 or human PD-L2. An antigen derived from PD-L1 may be a fragment of PD-L1 or PD-L2; or a derivative of a fragment of PD-L1 or PD-L2.

Examples of PD-1 antigen for use as an antigen include, but are not limited to, lnwyrmspsnqtdklaaf (SEQ ID NO: 6), mlnwyrmspsnqtdklaafs (SEQ ID NO: 7), vinwyrmspsnqtdklaafp (SEQ ID NO: 8), gaislhpkakiees (SEQ ID NO: 9), cgaislhpkakieec (SEQ IDNO: 10), VLNWYRMSPSNQTDKLAAF (SEQ ID NO: 11), GAISLAPKAQIKES (SEQ ID NO: 12), RNDSGTYLCGAISLAPKAQIKESLRAELRVT (SEQ ID NO: 13) and RNDSGIYLCGAISLHPKAKIEESPGAELVVT (SEQ ID NO: 14). Examples of PD-1 ligand antigen for use as an antigen include, but are not limited to, ciisyggadyc (SEQ ID NO: 15), CMISYGGADYC (SEQ ID NO: 16), LQDAGVYRCMISYGGADYKRITVKVN (SEQ ID NO: 17), LQDAGVYRAMISYGGADYKRITVKVN (SEQ ID NO: 18), DLAALIVYWEMEDKNIIQFVH (SEQ ID NO: 19), DLAALIVYWEMEDKNIIQFVHGG (SEQ ID NO: 20), FTVTVPKDLYVVEYGSNMTIECKFPVE (SEQ ID NO: 21), Lqdagvycciisyggadykritlkvn (SEQ ID NO: 22), lqdagvyaaiisyggadykritlkvn (SEQ ID NO: 23), dllalvvywekedeqviqfva (SEQ ID NO: 24), dllalvvywekedeqviqfvagg (SEQ ID NO: 25) and ftitapkdlyvveygsnvtmecrfpve (SEQ ID NO: 26).

As used herein, the term "CTLA-4 antigen" refers to an antigen or epitope derived from CTLA-4 (cytotoxic T-lymphocyte-associated antigen 4). Preferably, CTLA-4 is a human CTLA-4. An antigen derived from CTLA-4 may be a fragment of CTLA-4 or a derivative of a fragment of CTLA-4. Examples of CTLA-4 antigen for use as an antigen include, but are not limited to, ggkvelmypppyfvgmgg (SEQ ID NO: 27), cattftekntvgfldypfc (SEQ ID NO: 28) and attftekntvgfldypf (SEQ ID NO: 29).

As used herein, the term "DISC1 antigen" refers to an antigen or epitope derived from DISC1. Examples of DISC1 antigen for use as an antigen include, but are not limited to, SGGLLIQSLQLQEARGELSVEDERQMDDLEGGS (DISC1_451) (SEQ ID NO: 105), SGGEARGELSVEDERQMDDLEGGS (DISC1_452) (SEQ ID NO: 106) and SGGEARGELSVEGGS (DISC1_454) (SEQ ID NO: 107).

As used herein, the term "HER2 antigen" refers to an antigen or epitope derived from HER2. Examples of HER2 antigen for use as an antigen include, but are not limited to, SGGVTYNTDTFESMPGGS (SEQ ID NO: 108), SGGEYVNARHCLPGGS(SEQ ID NO: 109), SGGYVNARHCLGGS(SEQ ID NO: 110), SGGYVNARHGLGGS(SEQ ID NO: 111), SGGKFPDEEGACQPCPIGGS(SEQ ID NO: 112), SGGKFPDEEGACQPGGS (SEQ ID NO: 113), SGGKDPPFCVGGS(SEQ ID NO:114), SGGYKDPPFCVAGGS(SEQ ID NO: 115), and SGGYKDPPFCVGGS(SEQ ID NO: 116).

As used herein, the term "BTLA antigen" refers to an antigen or epitope derived from BTLA. Examples of BTLA antigen for use as an antigen include, are not limited to, SGGCKLNGTTCGGS (SEQ ID NO: 132).

As used herein, the term "HVEM antigen" refers to an antigen or epitope derived from HVEM. Examples of HVEM antigen for use as an antigen include, are not limited to, SGGCVKEASGELTGTVCGGS (SEQ ID NO: 133), SGGCYRVKEASGELTGTVSEPCGGS (SEQ ID NO: 134), SGGCSRNSSRTENAVCGGS (SEQ ID NO: 135), and SGGCQMSDPAMGLRSRNCGGS (SEQ ID NO: 136).

In the particle as provided by the present application, a viral structural protein and an antigen may be linked through at least one first attachment site which is present in the viral structural protein and at least one second attachment site which is present in the antigen.

As used herein, each of "a first attachment site" and "a second attachment site" refers to a site where more than one substance is linked each other.

A viral structural protein and an antigen may be directly or indirectly fused. In one embodiment, one or two linkers may intervene between N-terminal residue of an antigen and a viral structural protein and/or between C-terminal residue of an antigen and a viral structural protein.

An antigen or a viral structural protein can be truncated and replaced by short linkers. In some embodiments, an antigen or a viral structural protein include one or more peptide linkers. Typically, a linker consists of from 2 to 25 amino acids (e.g. 2, 3, 4, 5 or 6 amino acids). Usually, it is from 2 to 15 amino acids in length, although in certain circumstances, it can be only one, such as a single glycine residue.

In one embodiment, a nucleic acid molecule, in which polynucleotide encoding the viral structural protein is genetically fused with polynucleotide encoding the antigen, is expressed in a host cell (e.g. mammalian cells (e.g. 293F cells)) so that the first attachment site and the second attachment site are linked through a peptide bond. In this case, the viral structural protein and the antigen are linked through a peptide bond. Relating to this embodiment, the first attachment site and/or the second attachment site may be genetically modified from the original protein or antigen. For example, the first attachment site is modified from the viral structural protein so that through a linker peptide including SG, GS, SGG, GGS and SGSG, the protein is conjugated with the antigen. When the viral structural protein are chemically conjugated with the antigen, the first attachment site and the second attachment site may be linked through a chemical cross-linker which is a chemical compound. Examples of the cross-linker include, but are not limited to, SMPH, Sulfo-MBS, Sulfo-EMCS, Sulfo-GMBS, Sulfo-SIAB, Sulfo-SMPB, Sulfo-SMCC, SVSB, SIA and other cross-linkers available from the Pierce Chemical Company.

Preferably, an antigen may be linked to the Chikungunya viral structural protein or Venezuelan equine encephalitis viral structural protein as a fusion protein produced by way of genetic engineering.

A Chikungunya viral structural protein or Venezuelan equine encephalitis viral structural protein used in the present application may be a Chikungunya or Venezuelan equine encephalitis virus envelope protein or a capsid or a complex of one or more envelope proteins and/or a capsid protein.

Examples of Chikungunya virus include, but are not limited to, strains 37997 and strain LR2006 OPY-1. Examples of Venezuelan equine encephalitis virus include, but are not limited to, strain TC-83.

Chikungunya viral structural protein or Venezuelan equine encephalitis viral structural protein used in the present application may be a naturally occurring viral structural protein or modified protein thereof. The modified protein may be a fragment of the naturally occurring viral structural protein. In one embodiment, the modified protein has at least 70%, 75%, 80%, 85%, 90%, 95% or 98% amino acid sequence identity to a naturally occurring viral capsid and/or envelope protein. In one embodiment, the modified protein is a mutant where at most 10% of the amino acids are deleted, substituted, and/or added based on a naturally occurring viral capsid and/or envelope protein. For example, K64A or K64N mutation may be introduced into a capsid of Venezuelan equine encephalitis viral structural protein used in the present application.

Chikungunya or Venezuelan equine encephalitis viral structural protein may consist of or comprise a capsid, E3, E2 and E1 proteins. E3 and E2 proteins may be expressed together so that E2 and E3 can form one protein.

Examples of Chikungunya viral structural protein include, but are not limited to, Capsid-E3-E2-E1 of Chikungunya virus Strain 37997, and Capsid-E3-E2-E1 of Chikungunya virus LR2006 OPY-1.

Examples of Venezuelan equine encephalitis viral structural protein include, but are not limited to, Capsid-E3-E2-E1 of Venezuelan equine encephalitis virus Strain TC-83.

An exemplary Chikungunya viral structural protein sequence is provided at Genbank Accession No. ABX40006.1, which is described below (SEQ ID NO: 1):

```
mefiptqtfynrryqprpwtprptiqvirprprpqrqagglaqlisavn

kltmravpggkprrnrknkkqkqkqqapqnntnqkkqppkkkpaqkkkk

pgrrermcmkiendcifevkhegkvtgyaclvgdkvmkpahvkgtidna

dlaklafkrsskydlecaqipvhmksdaskfthekpegyynwhhgavqy

sggrftiptgagkpgdsgrpifdnkgrvvaivlgganegartalsvvtw

nkdivtkitpegaeewslaipvmcllanttfpcsqppetpccyekepee

tlrmlednvmrpgyyqllqasltcsphrqrrstkdnfnvykatrpylah
```

-continued

```
cpgcgeghschspvalerirneatdgtlikqvslqigiktddshdwtkl
rymdnhmpadaeraglfvrtsapctitgtmghfilarcpkgecttvgft
dsrkishscthpfhhdppvigrekfhsrpqhgkelpcstyvqstaatte
eievhmppdtpdrtlmsqqsgnvkitvngqtvrykcncggsneglttd
kvinnckvdqchaavtnhkkwqynaplvprnaelgdrkgkihipfplan
vtcrvpkarnptvtygkvqvimllypdphtllsyrnmgeepnyqeewvm
hkkevvltvptcglevtwgnnepykyspqlstngtahghpheiilyyye
lpptmtvvvvsvatfillsmvgmaagmcmcarrrcicpyelcpgatvpf
llsliccircakaatyqeaaiylwneqqplfwlqaliplaalivlcncl
rllpccccktlaflavmsvgahtvsayehvtvipntvgvpyktlvnrpgy
spmvlemellsvtleptlsldyitceyktvipspyvkccgtaeckdknl
pdysckvftgvypfmwggaycfcdaentqlseahveksesecktefasay
rahtasasaklrvlyqgnnitvtayangdhavtvkdakfivgpnssawt
pfdnkivvykgdvynmdyppfgagrpgqfgdiqsrtpeskdvyantqlv
lqrpavgtvhvpysqapsgfkywlkergaslqhtapfgcqiatnpvrav
ncavgnmpisidipeaaftrvvdapsltdmscevpacthssdfggvali
kyaaskkgkcavhsmtnavtireaeievegnsqlqisfstalasaefrv
qvcstqvhcaaechppkdhivnypashttlgvqdisatamswvqkitgg
vglvvavaalilivvlcvsfsrh
```

Another exemplary Chikungunya viral structural protein sequence is provided at Genbank Accession No. ABX40011.1, which is described below (SEQ ID NO: 2):

```
mefiptqtfynrryqprpwaprptiqvirprprpqrqagqlaqlisavnk
ltmravpqqkprrnrknkkqrqkkqapqndpkqkkqppqkkpaqkkkkpg
rrermcmkiendcifevkhegkvmgyaclvgdkvmkpahvkgtidnadla
klafkrsskydlecaqipvhmksdaskfthekpegyynwhhgavqysggr
ftiptgagkpgdsgrpifdnkgrvvaivlgganegartalsvvtwnkdiv
tkitpegaeewslalpvlcllanttfpcsqppctpccyekepestlrmle
dnvmrpgyyqllkasltcsphrqrrstkdnfnvykatrpylahcpdcgeg
hschspialerirneatdgtlkiqvslqigiktddshdwtklrymdshtp
adaeraglllvrtsapctitgtmghfilarcpkgecltvgftdsrkishtc
chpfhheppvigrerfhsrpqhgkelpcstyvqstaataeeievhmppdt
pdrtlmtqqsgnvkitvngqtvrykcncggsnegltttdkvinnckidqc
haavtnhknwqynsplvprnaelgdrkgkihipfplanvtcrvpkarnpt
vtygknqvtmllypdhptllsyrnmgqepnyheewvthkkevtltvpteg
levtwgnnepykywpqmstngtahghpheiilyyyelyptmtvvivsvas
fvllsmvgtavgmcvcarrrcitpyeltpgatvpfllsllccvrttkaat
yyeaaaylvmeqqplfwlqaliplaalivlcnclkllpcecktlaflavm
sigahtvsayehvtvipntvgvpyktlvnrpgyspmvlemelqsvtlept
lsldyitceyktvipspyvkccgtaeckdkslpdysckvftgvypfmwgg
aycfcdaentqlseahveksesscktefasayrahtasasaklrvlyqgnn
itvaayangdhavtvkdakfvvgpmssawtpfdnkivvykgdvynmdypp
fgagrpgqfgdiqsrtpeskdvyantqlvlqrpaagcvhvpysqapsgfk
ywlkergaslqhtapfgcqiatnpvravncavgnipisidipdaaftrvv
dapsvtdmscevpacthssdfggvaiikytaskkgkcavhsmtnavcire
advevegnsqlqisfstalasaefrvqvcstqvhcaaachppkdhivnyp
ashttlgvqdisttamswvqkitggvglivavaalilivvlcvsfsrh.
```

An exemplary Venezuelan equine encephalitis viral structural protein is described below (SEQ ID NO: 3):

```
mfpfqpmypmqpmpyrnpfaaprrpwfprtdpflamqvqeltrsmanlt
fkqrrdappegpsaakpkkeasqkqkgggqgkkkknqgkkkaktgppnp
kaqngnkkktnkkpgkrqrmvmklesdktfpimlegkingyacvvggkl
frpmhvegkidndvlaalktkkaskydleyadvpqnmradtfkythekp
qgyyswhhgavqyengrftvpkgvgakgdsgrpildnqgrvvaivlggv
negsrtalsvvmwnekgvtvkytpenceqwslvttmcllanvtfpcaqp
picydrkpaetlamlsvnvdnpgydelleaavkcpgrkrrsteelfney
kltrpymarcircavgschspiaieavksdghdgyvrlqtssqygldss
gnlkgrtmrydmhgtikeiplhqvslytsrpchivdghgyfllarcpag
dsitmefkkdsvrhscsvpyevkfnpvgrelythppehgveqacqvyah
daqnrgayvemhlpgsevdsslvslsgssvyvtppdgtsalvececggt
kisetinktkqfsqctkkeqcrayrlqndkwvynsdklpkaagatlkgk
lhvpflladgkctvplapepmitfgfrsvslklhpknptylitrqlade
phythelisepavrnftvtekgwefvwgnhppkrfwaqetapgnphglp
hevithyyhrypmstilglsicaaiatvsvaastwlfcrsrvacltpyr
ltpnaripfclavlccartaraettwesldhlwnnnqqmfwiqllipla
alivvtrllrcvccvvpflvmagaagagayehattmpsqagisyntivn
ragyaplpisitptkiklipnvnleyvtchyktgmdspaikccgsqect
ptyrpdeqckvftgvypfmwggaycfcdtentqvskayvmksddcladh
aeaykahcasvqaflnitvgehsivtcvyvngetpvnfngvkitagpls
tawtpfdrkivqyageiynydfpeygagqpgafgdiqsrcvsssdlyan
cnlvlqrpkagaihvpytqapagfeqwkkdkapslkftapfgceiytnp
iraencavgsiplafdipdalftrvsetptlsaaectlnecvyssdfgg
iatvkysasksgkcavhvpsgtatlkeaavelteqgsatihfstanihp
efrlqictsyvtckgdchppkdhivthpqyhaqtftaavsktawtwlts
llggsaviiiiglvlativamyvltnqkhn.
```

In one embodiment, a first attachment site comprises an amino group, preferably an amino group of a lysine residue. In one embodiment, the second attachment site comprises sulfhydryl group, preferably, a sulfhydryl group of a cysteine.

According to the present application, a Chikungunya virus like particle or Venezuelan equine encephalitis virus like particle comprising a Chikungunya or Venezuelan equine encephalitis viral structural protein and at least one antigen, wherein the at least one antigen is inserted in E3 of the viral structural protein, and the Chikungunya viral structural protein or Venezuelan equine encephalitis viral structural protein and the antigen are expressed as a fusion protein can be provided. The antigen may be inserted directly or indirectly in E3 of the viral structural protein.

The viral structural protein of Chikungunya virus as well as Venezuelan equine encephalitis consist of E1, E2, 6k and E3. 6K is naturally cleaved during the process of assemble and removed from the VLPs. The mature VLPs consists of capsid, E1 and E2 (See FIG. 1). In the present specification and claims, "viral structural protein" refers not only those having 6k but also after 6K is removed.

6K sequences of the CHIKV and VEEV strains used in the working examples are as follows:

```
CHIKV OPY-1 Strain, 6K: 749-809aa of SEQ ID NO: 1
                                    (SEQ ID NO: 137)
atyqeaaiylwneqqplfwlqaliplaalivlcnclrllpcccktla
flavmsvgahtvsa

CHIKV 37997 strain, 6K: 749-809aa of SEQ ID NO: 2
                                    (SEQ ID NO: 138)
atyyeaaaylwneqqplfwlqaliplaalivlcnclkllpcccktla
flavmsigahtvsa

VEEV TC-83strain, 6K: 758-813aa of SEQ ID NO: 3
                                    (SEQ ID NO: 139)
ettwesldhlwnnnqqmfwiqlliplaalivvtrllrcvccvvpflv
magaagaga
```

Regarding Chikungunya viral structural protein, at least one antigen may be inserted instead of furin site (RKRR) from 322R to 325R of SEQ ID NO: 1 or 2. For example, regarding Chikungunya viral structural protein, at least one antigen is inserted between residues H at 321-position and S at 326-position of SEQ ID NO: 1 or 2; between P at 320-position and S at 326-position of SEQ ID NO: 1 or 2; or between S at 319-position and S at 326-position of SEQ ID NO: 1 or 2. VLP_CHI 0.56 vector (SEQ ID NO: 30) may be used for preparing Chikungunya virus like particle where the antigen is inserted between residues 321 and 326 of SEQ ID Nos.1 or 2. When an antigen is inserted between residues 321 and 326 of SEQ ID Nos.1 or 2, the virus like particle provided by the present application may be Chikungunya virus like particle consisting of a complex of E2 and E3, capsid and E1, and wherein the at least one antigen is inserted into E3 region, and wherein the capsid consists of an amino acid sequence represented by SEQ ID NO: 31 (or SEQ ID NO: 75); the E1 consists of an amino acid sequence represented by SEQ ID NO: 32 or SEQ ID NO: 76; and the complex of E2 and E3 consists of an amino acid sequence represented by SEQ ID NO: 33 or SEQ ID NO: 77 provided that an amino acid sequence of the at least one antigen is inserted between residues corresponding to 321 and 326 of SEQ ID NO: 1 or 2.

Venezuelan equine encephalitis viral structural protein, at least one antigen may be inserted instead of furin site (RKRR) from 331R to 334R of SEQ ID NO: 3. For example, regarding Venezuelan equine encephalitis viral structural protein, at least one antigen is inserted between G at 330-position and S at 335-position of SEQ ID NO: 3; between P at 329-position and S at 335-position of SEQ ID NO: 3; or between C at 328-position and S at 335-position of SEQ ID NO: 3. VLP_VEEV 0.66 vector (SEQ ID No: 34) may be used for preparing Venezuelan equine encephalitis virus like particle where the antigen is inserted between residues 330 and 335 of SEQ ID NO: 3. When an antigen is inserted between residues 330 and 335 of SEQ ID NO: 3, the virus like particle provided by the present application may be Venezuelan equine encephalitis virus like particle consisting of a complex of E2 and E3, capsid and E1, and wherein the at least one antigen is inserted into E3 region, and wherein the capsid consists of an amino acid sequence represented by SEQ ID NO: 35; the E1 consists of an amino acid sequence represented by SEQ ID NO: 36; and the complex of E2 and E3 consists of an amino acid sequence represented by SEQ ID NO: 37 provided that an amino acid sequence of the at least one antigen is inserted between residues 330 and 335 of SEQ ID NO: 3.

In one embodiment, at least one antigen selected from an antigen derived from *Plasmodium falciparum* circumsporozoite protein, an antigen derived from PD-1, an antigen derived from PD-L1, an antigen derived from CTLA-4, an antigen derived from IL-2, an antigen derived from DISC1 or an antigen derived from HER2 is inserted into E3, an antigen derived from BTLA, an antigen derived from HVEM, an antigen derived from PCSK-9 or an antigen derived from DPP-4 of Chikungunya viral structural protein or Venezuelan equine encephalitis viral structural protein.

The fusion protein may be expressed using a conventional technique in the art. A variety of expression systems can be used for the expression of the fusion protein. For example, the fusion protein can be expressed in 293F cells, Sf9 cells, *E. coli*, insect cell or Baculovirus.

A protein derived from Chikungunya virus (CHIKV) or Venezuelan equine encephalitis virus (VEEV) may be a naturally occurring viral protein or modified protein thereof.

When a protein derived from a virus is conjugated with a protein derived from an antigen, a linker peptide including SG, GS, SGG, GGS SGSG and TRGGS may be used. Examples of conjugation of the protein derived from a virus (referred to as "PFV" below) with the protein derived from the antigen (referred to as "PFA" below) include, but not limited to:

```
PFV-SG-PFA-GS-PFV; PFV-SG-PFA-GGS-PFV;

PFV-SSG-PFA-GS-PFV; PFV-SGG-PFA-GGS-PFV;

PFV-SGSG-PFA-GS-PFV;
and

PFA-SGG-PFA-TRGGS-PFV.
```

In one embodiment, the present application provides a virus like particle comprising a fusion protein of a protein derived from Chikungunya virus (CHIKV) or Venezuelan equine encephalitis virus (VEEV) and a protein derived from *Plasmodium falciparum* circumsporozoite protein, PD-1, PD-L1, CTLA-4, an antigen derived from IL-2, an antigen derived from DISC1, an antigen derived from HER2, an antigen derived from BTLA, an antigen derived from HVEM, an antigen derived from PCSK-9 and an antigen derived from DPP-4, wherein the virus like particle is prepared by transfecting an expression vector comprising a nucleic acid molecule comprising a nucleotide sequence represented by SEQ ID Nos.:38-45 into a mammalian cell (e.g. 293F cell). Regarding this embodiment, modified fusion protein can be prepared by transfecting an expression vector comprising a nucleic acid molecule comprising a nucleotide sequence having at least 70%, 75%, 80%, 85%, 90%, 95% or 98% amino acid sequence identity to SEQ ID Nos.: 38-45 into a mammalian cell (e.g. 293F cell).

In one embodiment, the present application provides a virus like particle comprising or consisting of:

one or more capsid of Chikungunya virus (CHIKV) or Venezuelan equine encephalitis virus (VEEV);

one or more E1 of Chikungunya virus (CHIKV) or Venezuelan equine encephalitis virus (VEEV);

one or more E2 of Chikungunya virus (CHIKV) or Venezuelan equine encephalitis virus (VEEV); and one or more E3 of Chikungunya virus (CHIKV) or Venezuelan equine encephalitis virus (VEEV), wherein each of E2 is bound to each of E3, and an antigen selected from the group consisting of an antigen derived from *Plasmodium falciparum* circumsporozoite protein, an antigen derived from PD-1, an antigen derived from a ligand of PD-1 (e.g. PD-L1, PD-L2), an antigen derived from CTLA-4, an antigen derived from IL-2, an antigen derived from DISC1, an antigen derived from HER2, an antigen derived from BTLA, an antigen derived from HVEM, an antigen derived from PCSK-9, and an antigen derived from DPP-4 is inserted into E3 of Chikungunya virus (CHIKV) or Venezuelan equine encephalitis virus (VEEV). For example, present application provides a virus like particle comprising or consisting of:

240 capsids of Chikungunya virus (CHIKV) or Venezuelan equine encephalitis virus (VEEV);

240 E1s of Chikungunya virus (CHIKV) or Venezuelan equine encephalitis virus (VEEV); and 240 E2s of Chikungunya virus (CHIKV) or Venezuelan equine encephalitis virus (VEEV);

240s E3s of Chikungunya virus (CHIKV) or Venezuelan equine encephalitis virus (VEEV), wherein each of E2 is bound to each of E3, and an antigen selected from the group consisting of an antigen derived from *Plasmodium falciparum* circumsporozoite protein, PD-1, an antigen derived from a ligand of PD-1 (e.g. PD-L1, PD-L2), an antigen derived from CTLA-4, an antigen derived from IL-2, an antigen derived from DISC1, an antigen derived from HER2, an antigen derived from BTLA an antigen derived from HVEM, an antigen derived from PCSK-9 and antigen derived from DPP-4 is inserted into each of E3s of Chikungunya virus (CHIKV) or Venezuelan equine encephalitis virus (VEEV).

Virus like particle may work as a carrier of an antigen, which can be administered to human body. Examples of CHIKV VLP, which can work as a carrier of an antigen, include, but are not limited to, Chikungunya virus like particle comprising or consisting of a complex of E2 and E3, capsid and E1, wherein the capsid consists of an amino acid sequence represented by SEQ ID NO: 31 (or SEQ ID NO: 75); the E1 consists of an amino acid sequence represented by SEQ ID NO: 32 (or SEQ ID NO: 76); and the complex of E2 and E3 consists of an amino acid sequence represented by SEQ ID NO: 33 (or SEQ ID NO: 77) provided that an amino acid sequence of the at least one antigen is inserted between residues corresponding to 321 and 326 of SEQ ID NO: 1 or SEQ ID NO: 2. Examples of VEEV VLP, which can work as a carrier of an antigen, include, but are not limited to, Venezuelan equine encephalitis virus like particle comprising or consisting of a complex of E2 and E3, capsid and E1, wherein the capsid consists of an amino acid sequence represented by SEQ ID NO: 35; the E1 consists of an amino acid sequence represented by SEQ ID NO: 36; and the complex of E2 and E3 consists of an amino acid sequence represented by SEQ ID NO: 37 provided that an amino acid sequence of the at least one antigen is inserted between residues corresponding to 330 and 335 of SEQ ID NO: 3.

Examples of a virus like particle comprising Chikungunya viral structural protein and an antigen derived from *Plasmodium falciparum* circumsporozoite protein, an antigen derived from PD-1, an antigen derived from PD-L1, an antigen derived from CTLA-4, an antigen derived from IL-2, an antigen derived from DISC1, an antigen derived from HER2, an antigen derived from BTLA an antigen derived from HVEM, an antigen derived from PCSK-9 and an antigen derived from DPP-4 include, but are not limited to, Chikungunya virus like particle consisting of a complex of E2 and E3 into which the at least one antigen is inserted, capsid and E1, and wherein the at least one antigen is inserted into E3 region, and wherein amino acid sequence of each of the capsid, E1, complex of E2 and E3 into which the at least one antigen is inserted is described below:

(1)

amino acid sequence of E1 is represented by SEQ ID NO: 32;

amino acid sequence of the complex of E2 and E3 into which the malaria antigen is inserted is represented by SEQ ID NO: 46; and amino acid sequence of capsid is represented by SEQ ID NO: 31;

(2)

amino acid sequence of E1 is represented by SEQ ID NO: 32;

amino acid sequence of the complex of E2 and E3 into which the PD-1 antigen is inserted is represented by SEQ ID NO: 47; and amino acid sequence of capsid is represented by SEQ ID NO: 31;

(3)

amino acid sequence of E1 is represented by SEQ ID NO: 32;

amino acid sequence of the complex of E2 and E3 into which the PD-L1 antigen is inserted is represented by SEQ ID NO: 48; and amino acid sequence of capsid is represented by SEQ ID NO: 31; or (4)

amino acid sequence of E1 is represented by SEQ ID NO: 32;

amino acid sequence of the complex of E2 and E3 into which the CTLA-4 antigen is inserted is represented by SEQ ID NO: 49; and amino acid sequence of capsid is represented by SEQ ID NO: 31.

Examples of a virus like particle comprising Venezuelan equine encephalitis viral structural protein and an antigen derived from *Plasmodium falciparum* circumsporozoite protein, an antigen derived from PD-1, an antigen derived from PD-L1, an antigen derived from CTLA-4, an antigen derived from IL-2, an antigen derived from DISC1, an antigen derived from HER2, an antigen derived from BTLA, an antigen derived from HVEM an antigen derived from PCSK-9 or an antigen derived from DPP-4 include, but are not limited to, Venezuelan equine encephalitis virus like particle consisting of a complex of E2 and E3 into which the at least one antigen is inserted, capsid and E1, and wherein amino acid sequence of each of the capsid, E1, the complex of E2 and E3 into which the at least one antigen is inserted is described below:

(1)

amino acid sequence of E1 is represented by SEQ ID NO: 36;

amino acid sequence of the complex of E2 and E3 into which the malaria antigen is inserted is represented by SEQ ID NO: 50; and amino acid sequence of capsid is represented by SEQ ID NO: 35;

(2)

amino acid sequence of E1 is represented by SEQ ID NO: 36;

amino acid sequence of the complex of E2 and E3 into which the PD-1 antigen is inserted is represented by SEQ ID NO: 51; and amino acid sequence of capsid is represented by SEQ ID NO: 35;

(3)

amino acid sequence of E1 is represented by SEQ ID NO: 36;

amino acid sequence of the complex of E2 and E3 into which the PD-L1 antigen is inserted is represented by SEQ ID NO: 52; and amino acid sequence of capsid is represented by SEQ ID NO: 35; or (4)

amino acid sequence of E1 is represented by SEQ ID NO: 36;

amino acid sequence of the complex of E2 and E3 into which the CTLA-4 antigen is inserted is represented by SEQ ID NO: 53; and amino acid sequence of capsid is represented by SEQ ID NO: 35.

Further, regarding these embodiments, modified capsid of Chikungunya virus (CHIKV) or Venezuelan equine encephalitis virus (VEEV), modified E1 of Chikungunya virus (CHIKV) or Venezuelan equine encephalitis virus (VEEV) and/or modified complex of E2 and E3 of Chikungunya virus (CHIKV) or Venezuelan equine encephalitis virus (VEEV) may be used for the virus like particle. For example, the modified capsid of Chikungunya virus (CHIKV) or Venezuelan equine encephalitis virus (VEEV) may have at least 70%, 75%, 80%, 85%, 90%, 95% or 98% amino acid sequence identity to the amino acid sequence represented by SEQ ID NO: 31 (or SEQ ID NO: 75) or SEQ ID NO: 35; the modified E1 of Chikungunya virus (CHIKV) or Venezuelan equine encephalitis virus (VEEV) may have at least 70%, 75%, 80%, 85%, 90%, 95% or 98% amino acid sequence identity to the amino acid sequence represented by SEQ ID NO: 32 (or SEQ ID NO: 76) or SEQ ID NO: 36; and/or the modified complex of E2 and E3 of Chikungunya virus (CHIKV) or Venezuelan equine encephalitis virus (VEEV) may have at least 70%, 75%, 80%, 85%, 90%, 95% or 98% amino acid sequence identity to the amino acid sequence represented by SEQ ID Nos.: 33 (or SEQ ID NO: 77) or SEQ ID Nos.: 37. Also, the modified capsid, E1 and/or a complex of E2 and E3 may be a mutant where at most 10% of the amino acids are deleted, substituted, and/or added based on the capsid consisting of an amino acid sequence represented by SEQ ID NO: 31 (or SEQ ID NO: 75) or SEQ ID NO: 35; E1 consisting of an amino acid sequence represented by SEQ ID NO: 32 (or SEQ ID NO: 76) or SEQ ID NO: 36; and/or a complex of E2 and E3 consisting of consisting of an amino acid sequence represented by SEQ ID NO: 33 (or SEQ ID NO: 77) or SEQ ID NO: 37.

Virus like particle may be prepared by introducing an expression vector comprising a DNA molecule having a nucleotide sequence encoding the virus like particle into a cell (e.g. 293F cell), culturing the cell and recovering the virus like particle from the conditioned medium using ultracentrifugal method.

(2) Nucleotide, Vector

In a second aspect, the present application provides a nucleic acid molecule comprising or consisting of a nucleotide sequence encoding a virus like particle comprising a modified envelope protein E3.

A derivative of the above-described nucleic acid molecule which can be prepared by modifying the above-described nucleic acid molecule is also provided by the present application. The derivative may consist of a nucleotide sequence which has a sequence identity of 70%, 80%, 90%, 95% or 98% or more with the nucleotide sequence of the above-described nucleic acid molecule.

The nucleic acid molecule provided by the present application may be an isolated nucleic acid molecule encoding a virus like particle (e.g. a Chikungunya virus like particle, Venezuelan equine encephalitis virus like particle) which comprises a viral structural protein with a modified envelope protein E3. One embodiment, the virus like particle comprises a viral structural protein and at least one antigen wherein the at least one antigen is inserted into the envelope protein E3 of the viral structural protein.

One skilled in the art may prepare the nucleic acid molecule provided by the present application described above based on an exemplary nucleotide sequences of Chikungunya or Venezuelan equine viral structural protein that encode capsid and/or envelope represented by SEQ ID Nos.:54-55.

In one embodiment, a nucleotide sequence encoding an antigen can be inserted into nucleotide sequence encoding E3 of Chikungunya or Venezuelan equine viral structural protein. For example, nucleotide sequence encoding an antigen is inserted between residues 963 and 969 of SEQ ID NO: 54 (for CHIKV) or between residues 990 and 1006 of SEQ ID NO: 55 (for VEEV) to prepare a nucleic acid molecule consisting of a nucleotide sequence encoding a virus like particle comprising an envelope protein E3, wherein the envelope protein E3 is modified to comprise at least one antigen. Examples of the nucleic acid molecule provided by the present application include, but are not limited to, a nucleic acid molecule consisting of a nucleotide sequence represented by any one of SEQ ID NOs.:38-45. A nucleic acid molecule consisting of a nucleotide sequence which has a sequence identity of 70%, 80%, 90%, 95% or 98% or more with the nucleotide sequence represented by any one of SEQ IDs.:38-45 is also provided.

In one embodiment, the present application provides a vector comprising the nucleic acid molecule as described above, wherein the vector optionally comprises an expression control sequence operably linked to the nucleic acid molecule. A vector used herein may alter a promoter including enhancer sequence, polyadenylation signal, and antibiotic resistance genes. For example, a vector comprising a nucleic acid molecule which consists of a nucleotide sequence represented by SEQ ID NO: 54 or SEQ ID NO: 55, wherein a nucleotide sequence encoding at least one antigen is inserted between residues 963 and 969 of SEQ ID NO: 54

(for CHIKV VLP) or between residues 990 and 1006 of SEQ ID NO: 55 (for VEEV-VLP); and an expression control sequence operably linked to the nucleic acid molecule is provided.

Examples of an expression control sequence include, but are not limited to, promoter such as CMV promoter, phage lambda PL promoter, the *E. coli* lac, phoA and tac promoters, the SV40 early and late promoters, and promoters of retroviral LTRs.

In this embodiment, the vector comprising an expression control sequence operably linked to the nucleic acid molecule as described above can be used as an expression vector for preparing the particle provided by the present application.

The expression vectors can be prepared by a person skilled in the art based on WO2012/006180, the entire contents of which are incorporated by reference herein.

Examples of vectors which can be used for expressing a virus like particle comprising a fusion protein of a protein derived from Chikungunya virus (CHIKV) and an antigen include a vector shown in VLP_CHI 0.56 vector (SEQ ID NO: 30).

Based on the VLP_CHI 0.56 vector (SEQ ID NO: 30), a skilled person can prepare vectors which can be used for expressing a virus like particle comprising a fusion protein of a protein derived from Chikungunya virus (CHIKV) and a desired antigen. For example, when a skilled person prepares CHIKV VLP comprising a malaria antigen (Sggnpnanpnanpnanpnanpnanpnaggs (SEQ ID NO: 56))-inserted E3, based on the VLP_CHI 0.56 vector, a skilled person can prepare a vector as described below (SEQ ID NO: 57) where nucleotide encoding the antigen is underlined.

```
gaattcccattgcatacgttgtatccatatcataatatgtacatttata
ttggctcatgtccaacattaccgccatgttgacattgattattgactag
ttattaatagtaatcaattacggggtcattagttcatagcccatatatg
gagttccgcgttacataacttacggtaaatggcccgcctggctgaccgc
ccaacgacccccgcccattgacgtcaataatgacgtatgttcccatagt
aacgccaatagggactttccattgacgtcaatgggtggagtatttacgg
taaactgcccacttggcagtacatcaagtgtatcatatgccaagtacgc
cccctattgacgtcaatgacggtaaatggcccgcctggcattatgccca
gtacatgaccttatgggactttcctacttggcagtacatctacgtatta
gtcatcgctattaccatggtgatgcggttttggcagtacatcaatgggc
gtggatagcggtttgactcacggggatttccaagtctccaccccattga
cgtcaatgggagtttgttttggcaccaaaatcaacgggactttccaaaa
tgtcgtaacaactccgccccattgacgcaaatgggcggtaggcgtgtac
ggtgggaggtctatataagcagagctcgtttagtgaaccgtcagatcgc
ctggagacgccatccacgctgttttgacctccatagaagacaccgggac
cgatccagcctccgttaacggtggagggcagtgtagtctgagcagtact
cgttgctgccgcgcgcgccaccagacataatagctgacagactaacaga
ctgttcctttccatgggtcttttctgcagtcaccgtcgtcgacacgtgt
gatcagatatcgcggccgccaccatggagttcatcccgacgcaaacttt
ctataacagaaggtaccaaccccgaccctgggccccacgccctacaatt
```

-continued

```
caagtaattagacctagaccacgtccacagaggcaggctgggcaactcg
cccagctgatctccgcagtcaacaaattgaccatgcgcgcggtacctca
acagaagcctcgcagaaatcggaaaaacaagaagcaaaggcagaagaag
caggcgccgcaaaacgacccaaagcaaaagaagcaaccaccacaaaaga
agccggctcaaaagaagaagaaaccaggccgtagggagagaatgtgcat
gaaaattgaaaatgattgcatcttcgaagtcaagcatgaaggcaaagtg
atgggctacgcatgcctggtgggggataaagtaatgaaaccagcacatg
tgaagggaactatcgacaatgccgatctggctaaactggcctttaagcg
gtcgtctaaatacgatcttgaatgtgcacagataccggtgcacatgaag
tctgatgcctcgaagtttacccacgagaaacccgaggggtactataact
ggcatcacggagcagtgcagtattcaggaggccggttcactatcccgac
gggtgcaggcaagccgggagacagcggcagaccgatcttcgacaacaaa
ggacgggtggtggccatcgtcctaggaggggccaacgaaggtgcccgca
cggccctctccgtggtgacgtggaacaaagacatcgtcacaaaaattac
ccctgagggagccgaagagtggagcctcgccctcccggtcttgtgcctg
ttggcaaacactacattcccctgctctcagccgccttgcacaccctgct
gctacgaaaaggaaccggaaagcaccttgcgcatgcttgaggacaacgt
gatgagacccggatactaccagctactaaaagcatcgctgacttgctct
ccccactccggaggaaacccgaatgccaatcccaacgcgaaccccaatg
ctaacccaaatgccaacccaaacgccaaccccaacgctggtggatccag
tactaaggacaattttaatgtctataaagccacaagaccatatctagct
cattgtcctgactgcggagaagggcattcgtgccacagccctatcgcat
tggagcgcatcagaaatgaagcaacggacggaacgctgaaaatccaggt
ctctttgcagatcgggataaagacagatgacagccacgattggaccaag
ctgcgctatatggatagccatacgcccgcggacgcggagcgagccggat
tgcttgtaaggacttcagcaccgtgcacgatcaccgggaccatgggaca
ctttattctcgcccgatgcccgaaaggagagacgctgacagtgggattt
acggacagcagaaagaccagccacacatgcacacacccgttccatcatg
aaccacctgtgataggtagggagaggttccactctcgaccacaacatgg
taaagagttaccttgcagcacgtacgtgcagagcaccgctgccactgct
gaggagatagaggtgcatatgcccccagatactcctgaccgcacgctga
tgacgcagcagtctggcaacgtgaagatcacagttaatgggcagacggt
gcggtacaagtgcaactgcggtggctcaaacgagggactgacaaccaca
gacaaagtgatcaataactgcaaaattgatcagtgccatgctgcagtca
ctaatcacaagaattggcaatacaactcccctttagtcccgcgcaacgc
cgaactcggggaccgtaaaggaaagatccacatcccattcccattggca
aacgtgacttgcagagtgccaaaagcaagaaaccctacagtaacttacg
gaaaaaaccaagtcaccatgctgctgtatcctgaccatccgacactctt
gtcttaccgtaacatgggacaggaaccaaattaccacgaggagtgggtg
acacacaagaaggaggttaccttgaccgtgcctactgagggtctggagg
```

-continued

```
tcacttggggcaacaacgaaccatacaagtactggccgcagatgtctac
gaacggtactgctcatggtcacccacatgagataatcttgtactattat
gagctgtaccccactatgactgtagtcattgtgtcggtggcctcgttcg
tgcttctgtcgatggtgggcacagcagtgggaatgtgtgtgtgcgcacg
gcgcagatgcattacaccatatgaattaacaccaggagccactgttccc
ttcctgctcagcctgctatgctgcgtcagaacgaccaaggcggccacat
attacgaggctgcggcatatctatggaacgaacagcagcccctgttctg
gttgcaggctcttatcccgctggccgccttgatcgtcctgcgcaactgt
ctgaaactcttgccatgctgctgtaagaccctggctttttagccgtaa
tgagcatcggtgcccacactgtgagcgcgtacgaacacgtaacagtgat
cccgaacacggtgggagtaccgtataagactcttgtcaacagaccgggt
tacagccccatggtgttggagatggagctacaatcagtcaccttggaac
caacactgtcacttgactacatcacgtgcgagtacaaaactgtcatccc
ctccccgtacgtgaagtgctgtggtacagcagagtgcaaggacaagagc
ctaccagactacagctgcaaggtctttactggagtctacccatttatgt
ggggcggcgcctactgcttttgcgacgccgaaaatacgcaattgagcga
ggcacatgtagagaaatctgaatcttgcaaaacagagtttgcatcggcc
tacagagcccacaccgcatcggcgtcggcgaagctccgcgtcctttacc
aaggaaacaacattaccgtagctgcctacgctaacggtgaccatgccgt
cacagtaaaggacgccaagtttgtcgtgggcccaatgtcctccgcctgg
acaccttttgacaacaaaatcgtggtgtacaaaggcgacgtctacaaca
tggactacccaccttttggcgcaggaagaccaggacaatttggtgacat
tcaaagtcgtacaccggaaagtaaagacgtttatgccaacactcagttg
gtactacagaggccagcagcaggcacggtacatgtaccatactctcagg
caccatctggcttcaagtattggctgaaggaacgaggagcatcgctaca
gcacacggcaccgttcggttgccagattgcgacaaacccggtaagagct
gtaaattgcgctgtggggaacataccaatttccatcgacataccggatg
cggcctttactagggttgtcgatgcaccctctgtaacggacatgtcatg
cgaagtaccagcctgcactcactcctccgactttgggggcgtcgccatc
atcaaatacacagctagcaagaaaggtaaatgtgcagtacattcgatga
ccaacgccgttaccattcgagaagccgacgtagaagtagaggggaactc
ccagctgcaaatatccttctcaacagccctggcaagcgccgagtttcgc
gtgcaagtgtgctccacacaagtacactgcgcagccgcatgccaccctc
caaaggaccacatagtcaattacccagcatcacacaccacccttggggt
ccaggatatatccacaacggcaatgtcttgggtgcagaagattacggga
ggagtaggattaattgttgctgctgctgccttaattttaattgtggtgc
tatgcgtgtcgtttagcaggcactaaggatctagatctgctgtgccttc
tagttgccagccatctgttgtttgcccctcccccgtgccttccttgacc
ctggaaggtgccactcccactgtcctttcctaataaaatgaggaaattg
catcgcattgtctgagtaggtgtcattctattctggggggtggggtggg
```

-continued

```
gcaggacagcaagggggaggattgggaagacaatagcaggcatgctggg
gatgcggtgggctctatgggtacccaggtgctgaagaattgacccggtt
cctcctgggccagaaagaagcaggcacatccccttctctgtgacacacc
ctgtccacgcccctggttcttagttccagccccactcataggacactca
tagctcaggagggctccgccttcaatcccacccgctaaagtacttggag
cggtctctccctccctcatcagcccaccaaaccaaacctagcctccaag
agtgggaagaaattaaagcaagataggctattaagtgcagagggagaga
aaatgcctccaacatgtgaggaagtaatgagagaaatcatagaatttta
aggccatgatttaaggccatcatggcctaagcttgaaaggagataggat
caaagcttggcgtaatcatggtcatagctgtttcctgtgtgaaattgtt
atccgctcacaattccacacaacatacgagccggaagcataaagtgtaa
agcctggggtgcctaatgagtgagctaactcacattaattgcgttgcgc
tcactgcccgctttccagtcgggaaacctgtcgtgccagctgcattaat
gaatcggccaacgcgcggggagaggcggtttgcgtattgggcgctcttc
cgcttcctcgctcactgactcgctgcgctcggtcgttcggctgcggcga
gcggtatcagctcactcaaaggcggtaatacggttatccacagaatcag
gggataacgcaggaaagaacatgtgagcaaaaggccagcaaaaggccag
gaaccgtaaaaaggccgcgttgctggcgtttttccataggctccgcccc
cctgacgagcatcacaaaaatcgacgctcaagtcagaggtggcgaaacc
cgacaggactataaagataccaggcgtttccccctggaagctccctcgt
gcgctctcctgttccgaccctgccgcttaccggatacctgtccgccttt
ctcccttcgggaagcgtggcgctttctcatagctcacgctgtaggtatc
tcagttcggtgtaggtcgttcgctccaagctgggctgtgtgcacgaacc
ccccgttcagcccgaccgctgcgccttatccggtaactatcgtcttgag
tccaacccggtaagacacgacttatcgccactggcagcagccactggta
acaggattagcagagcgaggtatgtaggcggtgctacagagttcttgaa
gtggtggcctaactacggctacactagaagaacagtatttggtatctgc
gctctgctgaagccagttaccttcggaaaaagagttggtagctcttgat
ccggcaaacaaaccaccgctggtagcggtggtttttttgtttgcaagca
gcagattacgcgcagaaaaaaaggatctcaagaagatcctttgatcttt
tctacggggtctgacgctcagtggaacgaaaactcacgttaagggattt
tggtcatgagattatcaaaaaggatcttcacctagatccttttaaatta
aaaatgaagttttaaatcaatctaaagtatatatgagtaaacttggtct
gacagttaccaatgcttaatcagtgaggcacctatctcagcgatctgtc
tatttcgttcatccatagttgcctgactccccgtcgtgtagataactac
gatacgggagggcttaccatctggccccagtgctgcaatgataccgcga
gaaccacgctcaccggctccagatttatcagcaataaaccagccagccg
gaagggccgagcgcagaagtggtcctgcaactttatccgcctccatcca
gtctattaattgttgccgggaagctagagtaagtagttcgccagttaat
agtttgcgcaacgttgttgccattgctacaggcatcgtggtgtcacgct
```

-continued

```
cgtcgtttggtatggcttcattcagctccggttcccaacgatcaaggcg

agttacatgatcccccatgttgtgcaaaaaagcggttagctccttcggt

cctccgatcgttgtcagaagtaagttggccgcagtgttatcactcatgg

ttatggcagcactgcataattctcttactgtcatgccatccgtaagatg

cttttctgtgactggtgagtactcaaccaagtcattctgagaatagtgt

atgcggcgaccgagttgctcttgcccggcgtcaatacgggataataccg

cgccacatagcagaactttaaaagtgctcatcattggaaaacgttcttc

ggggcgaaaactctcaaggatcttaccgctgttgagatccagttcgatg

taacccactcgtgcacccaactgatcttcagcatcttttactttcacca

gcgtttctgggtgagcaaaaacaggaaggcaaaatgccgcaaaaaaggg

aataagggcgacacggaaatgttgaatactcatactcttcctttttcaa

tattattgaagcatttatcagggttattgtctcatgagcggatacatat

ttgaatgtatttagaaaaataaacaaataggggttccgcgcacatttcc

ccgaaaagtgccacctgacgtctaagaaaccattattaccatgacatta

acctataaaaataggcgtatcacgaggccctttcgggtcgcgcgtttcg

gtgatgacggtgaaaacctctgacacatgcagctcccgttgacggtcac

agcttgtctgtaagcggatgccgggagcagacaagcccgtcagggcgcg

tcagcgggtgttggcgggtgtcggggctggcttaactatgcggcatcag

agcagattgtactgagagtgcaccataaaattgtaaacgttaatatttt

gttaaaattcgcgttaaatttttgttaaatcagctcattttttaaccaa

taggccgaaatcggcaaaatcccttataaatcaaaagaatagcccgaga

tagggttgagtgttgttccagtttggaacaagagtccactattaaagaa

cgtggactccaacgtcaaagggcgaaaaaccgtctatcagggcgatggc

ccactacgtgaaccatcacccaaatcaagttttttggggtcgaggtgcc

gtaaagcactaaatcggaaccctaaagggagcccccgatttagagcttg

acggggaaagccggcgaacgtggcgagaaaggaagggaagaaagcgaaa

ggagcgggcgctagggcgctggcaagtgtagcggtcacgctgcgcgtaa

ccaccacacccgccgcgcttaatgcgccgctacagggcgcgtactatgg

ttgctttgacgtatgcggtgtgaaataccgcacagatgcgtaaggagaa

aataccgcatcaggcgccattccccattcaggctgcgcaactgttggga

agggcgatcggtgcgggcctcttcgctattacgccagctggcgaaaggg

ggatgtgctgcaaggcgattaagttgggtaacgccagggttttcccagt

cacgacgttgtaaaacgacggccagtgaattccatggtctcaactttc
```

Examples of vectors which can be used for expressing a virus like particle comprising a fusion protein of a protein derived from Venezuelan equine encephalitis virus (VEEV) and an antigen include a vector shown in VLP_VEEV 0.66 vector (SEQ ID NO: 34).

Based on the VLP_VEEV 0.66 vector (SEQ ID NO: 34), a skilled person can prepare vectors which can be used for expressing a virus like particle comprising a fusion protein of a protein derived from Venezuelan equine encephalitis virus (VEEV) and a desired antigen. For example, when a skilled person prepares VEEV VLP comprising a malaria antigen (SGG-qgpgapqgpgapqgpgapqgpgap-GGS (SEQ ID NO: 58))-inserted E3, based on the VLP_VEEV 0.66 vector, a skilled person can prepare a vector as described below (SEQ ID NO: 59) where nucleotide encoding the antigen is underlined.

```
gaattcccattgcatacgttgtacccatatcataatatgtacatttata

ttggctcatgtccaacattaccgccatgttgacattgattattgactag

ttattaatagtaatcaattacggggtcattagttcatagcccatatatg

gagttccgcgttacataacttacggtaaatggcccgcctggctgaccgc

ccaacgacccccgcccattgacgtcaataatgacgtatgttcccatagt

aacgccaatagggactttccattgacgtcaatgggtggagtatttacgg

taaactgcccacttggcagtacatcaagtgtatcatatgccaagtacgc

cccctattgacgtcaatgacggtaaatggcccgcctggcattatgccca

gtacatgaccttatgggactttcctacttggcagtacatctacgtatta

gtcatcgctattaccatggtgatgcggttttggcagtacatcaatgggc

gtggatagcggtttgactcacggggacctccaagcctccaccccattga

cgtcaatgggagtccgttccggcaccaaaaccaacgggactctccaaaa

tgccgtaacaactccgccccattgacgcaaacgggcggtaggcgtgtac

ggtgggaggtccacacaagcagagctcgtttagtgaaccgtcagatcgc

ctggagacgccatccacgctgttttgacctccatagaagacaccgggac

cgatccagcctccgttaacggtggagggcagtgtagtctgagcagtact

cgttgctgccgcgcgcgccaccagacataatagctgacagactaacaga

ctgttcctttccatgggtcttttctgcagtcaccgtcgtcgacacgtgt

gatcagatatcgcggccgccaccatgttcccgttccagccaacgcatcc

gatgcagccaatgccctatcgcaacccgttcgcggccccgcgcaggccc

tggttccccagaaccgacccttttctggcgatgcaggtgcaggaattaa

cccgctcgatggctaacctgacgttcaagcaacgccgggacgcgccacc

tgaggggccacccgctaataaaccgaagaaggaggcctcgcaaaaacag

aaagggggaggccaagggaagaagaagaagaaccaagggaagaagaagg

ccaagacagggccgcctaatccgaaggcacagaatggaaacaagaagaa

gaccaacaagaaaccaggcaagagacagcgcatggtcatgaaattggaa

tctgacaagacgttcccaatcatgttggaagggaagataaacggctacg

cttgtgtggtcggagggaagttattcaggccgatgcatgtggaaggcaa

gatcgacaacgacgctctggccgcgcctaagacgaagaaagcatccaaa

tacgatcttgagtatgcagatgtgccacagaacatgcgggccgatacat

tcaaatacacccatgagaaaccccaaggctattacagctggcatcatgg

agcagtccaatatgaaaatgggcgtctcacggtgccgaaaggagctggg

gccaagggagacagcggacgacccattctggataaccagggacgggtgg

tcgctattgtgctgggaggtgtgaatgaaggatctaggacagccctttc

agtcgtcatgtggaacgagaagggagttaccgtgaagtatactccagag

aactgcgagcaatggtcactagtgaccaccatgtgtccgctcgccaatg

cgacgttcccatgtgctcaaccaccaatttgctacgacagaaaaccagc

agagactttggccatgctcagcgttaacgttgacaacccgggctacgat
```

gagctgccggaagcagctgttaagtgccccgggtccggaggacagggac ctggcgctcctcagggaccaggggcaccacagggcccaggcgccccaca ggggcctggggcccctgggggatcctccaccgaggagctgtttaatgag tataagctaacgcgcccttacatggccagatgcatcagatgtgcagtcg ggagccgccacagtccaatagcaatcgaggcagtaaagagcgacgggca cgacggttatgttagacttcagacccccccgcagcacggcctggacccc cccggcaacccaaagggcaggaccatgcggtatgacatgcacgggacca ttaaagagataccactacatcaagtgtcactctatacatctcgcccgtg tcacattgtggacgggcacggttatttcctgcttgccaggtgcccggca ggggactccatcaccatggaatttaagaaagattccgtcagacactcct gctcggtgccgtatgaagtgaaatttaatcctgtaggcagagaactcta tactcatcccccagaacacggagtagagcaagcgtgccaagtctacgca catgatgcacagaacagaggagcttatgtcgagatgcacctcccgggct cagaagtggacagcagtttggtccccttgagcggcagttcagtcaccgt gacacctcctgatgggactagcgccctggtggaatgcgagtgcggcggc acaaagatctccgagaccatcaacaagacaaaacagttcagccagtgca caaagaaggagcagtgcagagcacaccggccgcagaacgataagtgggt gtataattctgacaaactgcccaaagcagcgggagccaccttaaaagga aaactgcatgtcccctttcttgctggcagacggcaaatgcaccgtgcctc tagcaccagcacctatgataaccttcggtttcagatcagtgtcactgaa actgcaccctaagaatcccacatatctaatcacccgccaacttgctgat gagcctcactacacgcacgagctcatatctgaaccagctgttaggaatt ttaccgtcaccgaaaaagggtgggagtttgtatggggaaaccacccgcc gaaaaggttttgggcacaggaaacagcacccggaaatccacatgggcta ccgcacgaggtgataactcattattaccacagataccctatgtccacca tcctgggtttgtcaatttgtgccgccattgcaaccgtttccgttgcagc gtctacctggctgttttgcagatcaagagttgcgtgcctaactccttac cggctaacacctaacgctaggataccattttgtctggctgtgctttgct gcgcccgcactccccgggccgagaccacctgggagtccttggatcacct atggaacaataaccaacagatgttctggattcaattgctgatccctctg gccgccttgaccgcagtgactcgcctgctcaggtgcgtgtgctgtgtcg tgcctttttttagtcatggccggcgccgcaggcgccggcccctacgagca cgcgaccacgatgccgagccaagcgggaatctcgtataacactatagtc aacagagcaggctacgcaccactccctatcagcataacaccaacaaaga tcaagctgatacctacagtgaacttggagtacgtcacctgccactacaa aacaggaatggattcaccagccatcaaatgctgcggatctcaggaatgc actccaacttacaggcctgatgaacagtgcaaagtcttcacaggggttt acccgttcatgtggggtggtgcatattgcttttgcgacactgagaacac ccaagtcagcaaggcctacgtaatgaaatctgacgactgccttgcggat catgctgaagcatataaagcgcacacagcctcagtgcaggcgttcctca acatcacagtgggagaacactctattgtgactaccgtgtatgtgaatgg agaaactcctgtgaatttcaatggggtcaaaataactgcaggtccgctt tccacagcttggacaccctttgatcgcaaaatcgtgcagtatgccgggg agatctataattatgattttcctgagtatggggcaggacaaccaggagc atttggagatatacaatccagaacagtctcaagctctgatctgtatgcc aataccaacctagtgctgcagagacccaaagcaggagcgatccacgtgc catacactcaggcaccttcgggttttgagcaatggaagaaagataaagc tccatcattgaaatttaccgcccctttcggacgcgaaatatatacaaac cccattcgcgccgaaaactgtgctgtagggtcaattccatcagcctttg acattcccgacgccttgttcaccagggtgtcagaaacaccgacactttc agcggccgaatgcactcttaacgagtgcgtgtattcttccgactttggt gggatcgccacggtcaagtactcggccagcaagtcaggcaagtgcgcag tccaccrgccatcagggactgctaccctaaaagaagcagcagtcgagct aaccgagcaagggtcggcgactatccatttctcgaccgcaaatatccac ccggagttcaggctccaaatatgcacatcatatgttacgtgcaaaggtg attgtcacccccccgaaagaccatattgtgacacaccctcagtatcacgc ccaaacatttacagccgcggtgtcaaaaaccgcgtggacgtggttaaca tccctgctgggaggatcagccgtaattattataattggcttggtgctgg ctactattgtggccatgtacgtgctgaccaaccagaaacataattaagg atctagatctgctgtgccttctagttgccagccatctgttgtttgcccc tcccccgtgccttccttgaccctggaaggtgccactcccactgtccttt cctaataaaatgaggaaattgcatcgcattgtctgagtaggtgtcattc tattctggggggtggggtggggcaggacagcaagggggaggattgggaa gacaatagcaggcatgctggggatgcggtgggctctatgggtacccagg tgctgaagaattgacccggttcctcctgggccagaaagaagcaggcaca tccccttctctgtgacacaccctgtccacgcccctcgttcttagttcca gccccactcataggacactcatagctcaggagggctccgccttcaatcc cacccgctaaagtacttggagcggtctctccctccctcatcagcccacc aaaccaaacctagcctccaagagtgggaagaaattaaagcaagataggc tattaagtgcagagggagagaaaatgcctccaacatgtgaggaagtaat gagagaaatcatagaattttaaggccatgatttaaggccatcatggcct aagcttgaaaggagataggatcaaagcttggcgtaatcatggtcatagc tgtttcctgtgtgaaattgttatccgctcacaattccacacaacatacg agccggaagcataaagtgtaaagcctggggtgcctaatgagtgagctaa ctcacattaattgcgttgcgctcactgcccgctctccagtcgggaaacc ctgtcgtgccagctgcattaatgaatcggccaacgcgcggggagaggcg gtttgcgtattgggcgctcttccgcttcctcgctcactgactcgctgcg ctcggtcgttcggctgcggcgagcggtatcagctcactcaaaggcggta atacggttatcacagaatcaggcgataacgcaggaaagaacatgtgagc aaaaggccagcaaaaggccaggaaccgtaaaaaggccgcgttgctggcg -continued

```
tttttccataggctccgcccccctgacgagcatcacaaaaatcgacgct
caagtcagaggtggcgaaacccgacaggactataaagataccaggcgtt
tcccctggaagctccctcgtgcgctctcctgttccgaccctgccgctt
accggatacctgtccgcctttctcccttcgggaagcgtggcgctttctc
atagctcacgctgtaggtatctcagttcggtgtaggtcgttcgctccaa
gctgggctgtgtgcacgaaccccccgttcagcccgaccgctgcgcctta
tccggtaactatcgtcttgagtccaacccggtaagacacgacttatcgc
cactggcagcagccactggtaacaggattagcagagcgaggtatgtagg
cggtgctacagagttcttgaagtggtggcctaactacggctacactaga
agaacaguatttggtatctgcgctctgctgaagccagttaccttcggaa
aaagagttggtagctcttgatccggcaaacaaaccaccgctggtagcgg
tggtttttttgtttgcaagcagcagattacgcgcagaaaaaaaggatct
caagaagatcctttgatcttttctacggggtctgacgctcagtggaacg
aaaactcacgttaagggattttggtcatgagattatcaaaaaggatctt
cacctagatccttttaaattaaaaatgaagttttaaatcaatctaaagt
acatargagtaaacttggtctgacagttaccaatgcttaatcagtgagg
cacctacctcagcgatctgtctatttcgttcatccatagttgcctgacc
ccccgtcgtgtagataactacgatacgggagggcttaccatctggcccc
agtgctgcaatgataccgcgagaaccacgctcaccggctccagatttat
cagcaataaaccagccagccggaagggccgagcgcagaagtggtcctgc
aactttatccgcctccatccagtctattaattgttgccgggaagctaga
gtaagtagttcgccagttaatagtttgcgcaacgttgttgccattgcta
caggcatcgtggtgtcacgctcgtcgtttggtatggcttcattcagctc
cggttcccaacgatcaacccgagttacatgatcccccatgttgtgcaaa
aaagcggttagctccttcggtcctccgatcgttgtcagaagtaagttgg
ccgcagtgttatcactcatggctatggcagcactgcataattctcttac
tgtcatgccatccgtaagatgcttttctgtgactggtgagtactcaacc
aagtcattctgagaatagtgtatgcggcgaccgagttgctcttgcccgg
cgtcaatacgggataataccgcgccacatagcagaactttaaaagtgct
catcattggaaaacgttcttcggggcgaaaactctcaaggatcttaccg
ctgttgagatccagttcgatgtaacccactcgtgcacccaactgatctt
cagcatcttttactttcaccagcgtttctgggtgagcaaaaacaggaag
gcaaaatgccgcaaaaaagggaataagggcgacacggaaatgttgaata
ctcatactcttcctttttcaatattattgaagcatttatcagggttatt
gtcccacgagcggatacatatttgaatgtatttagaaaaataaacaaat
aggggttccgcgcacatttccccgaaaagtgccacctgacgtctaagaa
accattactatcatgacattaacctataaaaataggcgtatcacgaggc
cctttcgggtcgcgcgtttcggtgatgacggtgaaaacctctgacacat
gcagctcccgttgacggtcacagcttgtctgtaagcggatgccgggagc
agacaagcccgtcagggcgcgtcagcgggtgttggcgggtgtcggggct
```

-continued

```
ggcttaactatgcggcatcagagcagattgtactgagagtgcaccataa
aattgtaaacgttaatattttgttaaaattcgcgttaaatttttgttaa
atcagctcattttttaaccaataggccgaaatcggcaaaatcccttata
aatcaaaagaatagcccgagatagggttgagtgttgttccagtttggaa
caagagtccactattaaagaacgtggactccaacgtcaaagggcgaaaa
accgtctatcagggcgatggcccactacgtgaaccatcacccaaatcaa
gttttttggggtcgaggtgccgtaaagcactaaatcggaaccctaaagg
gagcccccgatttagagcttgacggggaaagccggcgaacgtggcgaga
aaggaagggaagaaagcgaaaggagcgggcgctagggcgctggcaagtg
tagcggtcacgctgcgcgtaaccaccacacccgccgcgcttaatgcgcc
gctacagggcgcgtactatggttgctttgacgtatgcggtgtgaaatac
cgcacagatgcgtaaggagaaaataccgcatcaggcgccattcgccatt
caggctgcgcaactgttgggaagggcgatcggtgcgggcctcttcgcta
ttacgccagctggcgaaagggggatgtgctgcaaggcgattaagttggg
taacgccagggttttcccagtcacgacgttgtaaaacgacggccagtga
attccatggtctcaactttc
```

Figure 2:
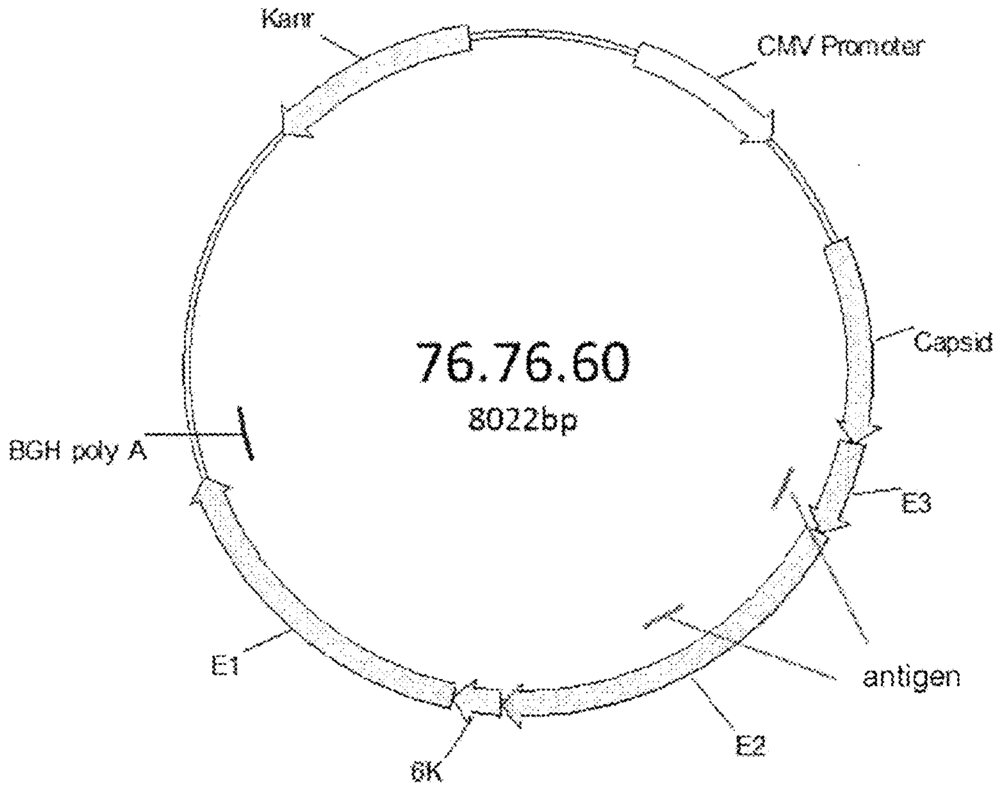
FIG. 2 shows representative structure of expression vector for a viral structural protein with modified E3 and E2 envelope proteins.

Representative structure of plasmid vector that is used to express viral structural protein wherein a nucleotide sequence encoding at least one antigen is inserted in its E2 and E3 regions is shown in FIG. 2.

A nucleic acid molecule having at least 70%, 75%, 80%, 85%, 90%, 95% or 98% nucleotide sequence identity to the nucleic acid molecule having a nucleotide sequence represented by any one of SEQ ID Nos:57 and 59 and a nucleic acid molecule which may be a mutant where at most 10% of the amino acids are deleted, substituted, and/or added based on the nucleic acid molecule having a nucleotide sequence represented by any one of SEQ ID Nos.:57 and 59 are also provided by the present application.

The VLPs described as above may be prepared by stable cell line. The stable cell line can be prepared by using the above-described vectors and according to conventional procedures. For example, the following procedures may be employed to generate a stable cell line:

1. Transfect cells such as 293F cells are transfected with a VLP expression plasmid containing selection marker such as hygromycin B.
2. Incubate the transfected cells for one day
3. Culture the transfected cells in a selection medium containing such as Hygromycin at 150-200 ug/ml for 1-2 weeks.
4. Choose the cells that can grow and be split at least once in the selection medium.
5. Isolate a single cell and confirm the expression of the VLP in the supernatants by western blotting.

(3) Pharmaceutical Composition, Kit

In a third aspect, the present application provides a pharmaceutical composition and a kit comprising a pharmaceutical composition, wherein the pharmaceutical composition comprises (i) a virus like particle comprising a modified envelope protein E3 and/or (ii) a nucleic acid molecule consisting of a nucleotide sequence encoding a virus like particle comprising a modified envelope protein E3.

In one embodiment, the present application provides a pharmaceutical composition or a kit comprising a pharmaceutical composition, wherein the pharmaceutical composition comprises the Alphavirus or Flavivirus virus like particle (e.g. Chikungunya virus like particle or Venezuelan equine encephalitis virus like particle) as described above or the nucleic acid molecule as described above; and a pharmaceutically acceptable carrier. The amount of the Alphavirus or Flavivirus virus like particle and the amount of the nucleic acid molecule in the composition may be 0.00001-1 w/w % of the pharmaceutical composition.

Dosage amount of the particle provided by the present application (e.g. CHIKV VLP or VEEV VLP) may be 1-500 µg/day.

As described above, in one embodiment, the antigen contained in the virus like particle used for the pharmaceutical composition provided by the present application may be derived from *Plasmodium falciparum* circumsporozoite protein, PD-1, PD-L1, CTLA-4, IL-2, DISC1, HER2, BTLA, HVEM, PCSK-9 or DPP-4.

The pharmaceutical composition may further comprise an adjuvant. Examples of adjuvants include, but are not limited to, Ribi solution (Sigma Adjuvant system, Sigma-Aldrich). The pharmaceutical composition provided by the present application may contain a buffering agent such as dibasic sodium phosphate hydrate, sodium dihydrogen phosphate and sodium chloride; and a preserving agent such as thimerosal. In one embodiment, the pharmaceutical composition is an aqueous solution containing 0.001-1 w/w % of a particle (e.g. CHIKV VLP or VEEV VLP) comprising a viral structural protein and an antigen (e.g. antigen derived from *Plasmodium falciparum* circumsporozoite protein, PD-1 or PD-L1), 1-10 w/w % of buffering agent, 0.01-1 w/w % of adjuvant and 0.00001-0.001 w/w % of preserving agent.

A skilled person can prepare the pharmaceutical composition using a conventional technique. For example, a particle (e.g. CHIKV VLP or VEEV VLP) comprising a viral structural protein and an antigen (e.g. antigen derived from *Plasmodium falciparum* circumsporozoite protein, PD-1, PD-L1, CTLA-4, IL-2, DISC1, HER2, BTLA, HVEM, PCSK-9 or DPP-4) is mixed with a buffer solution having physiological pH (e.g. pH 5-9, such as pH7) to prepare the pharmaceutical composition.

In one embodiment, the pharmaceutical composition is a vaccine or an immunostimulant comprising a particle comprising a viral structural protein with a modified envelope protein E3. In one embodiment, the virus like particle comprises a viral structural protein and an antigen (e.g. antigen derived from *Plasmodium falciparum* circumsporozoite protein, PD-1, PD-L1, CTLA-4, IL-2, DISC1, HER2, BTLA, HVEM, PCSK-9 or DPP-4). For example, the vaccine composition provided by the present application can be used for immunotherapy; treating or preventing cancer; treating or preventing infectious disease; or treating or preventing malaria.

In one embodiment, the pharmaceutical composition is a DNA vaccine comprising a nucleic acid molecule comprising a nucleotide sequence for expressing a particle which comprises a viral structural protein with a modified envelope protein E3. One embodiment, the virus like particle comprises a viral structural protein and an exogenous antigen (e.g. antigen derived from *Plasmodium falciparum* circumsporozoite protein, PD-1, PD-L1, CTLA-4, IL-2, DISC1, HER2, BTLA, HVEM, PCSK-9 or DPP-4). In one embodiment, the DNA vaccine provided by the present application comprises CpG containing oligonucleotide.

The pharmaceutical composition provided in the third aspect of the present application can be administered one or more times. When the pharmaceutical composition provided in the third aspect of the present application is administered more than one time, different particles provided in the first aspect of the present application (e.g. CHIKV VLP or VEEV VLP) may be used for each of the administration. In one embodiment, combination of immunization using CHIKV VLP provided in the first aspect of the application and immunization using VEEV VLP provided in the first aspect of the application is employed. For example, CHIKV VLP provided in the first aspect of the present application may be used for the 1st immunization and VEEV VLP provided in the first aspect of the present application may be used for the 2nd immunization, or VEEV VLP provided in the first aspect of the present application may be used for the 1st immunization and CHIKV VLP provided in the first aspect of the present application may be used for the 2nd immunization.

A skilled person can determine timing of immunization using the composition or vaccine provided by the present application. For example, a 2nd immunization is performed 1, 2, 3, 4, 5, 6, 7, 8, 9 or 10 weeks after a 1st immunization.

In one embodiment, the present application provides a kit comprising (a) a pharmaceutical composition comprising a particle provided in the first aspect of the present application; and (b) another pharmaceutical composition comprising a particle provided in the first aspect of the present application, wherein the particle contained in (a) is a virus like particle which is different from the particle contained in (b). In this embodiment, the particle contained in (a) may be Chikungunya virus like particle and the particle contained in (b) may be Venezuelan equine encephalitis virus like particle.

In one embodiment, the present application provides a kit comprising (a) a pharmaceutical composition comprising a particle provided in the first aspect of the present application; and (b) another pharmaceutical composition comprising a particle provided in the first aspect of the present application, (c) one or more pharmaceutical composition, each of which comprises a particle provided in the first aspect of the present application, wherein (a) is used for priming immunization and (b) and (c) are used for boosting immunization; and the particle contained in (a) is a virus like particle which is different from the particle contained in (b); and the particle contained in (c) is different from the particle contained in (a) and (b), or the same as the particle contained in (a) or (b).

The respective pharmaceutical compositions contained in the above-described kit may be administered simultaneously, separately or sequentially.

The Alphavirus or Flavivirus virus like particle (e.g. Chikungunya virus or Venezuelan equine encephalitis virus) provided in the first aspect of the present application or the nucleic acid molecule provided by the second aspect of the application can be used for the pharmaceutical composition provided in the third aspect of the present application.

For example, Chikungunya or Venezuelan equine encephalitis virus like particle comprising or consisting of:

one or more (e.g. 240) capsid of Chikungunya virus (CHIKV) or Venezuelan equine encephalitis virus (VEEV);

one or more (e.g. 240) E1 of Chikungunya virus (CHIKV) or Venezuelan equine encephalitis virus (VEEV);

one or more (e.g. 240) E2 of Chikungunya virus (CHIKV) or Venezuelan equine encephalitis virus (VEEV); and one or more (e.g. 240) E3 of Chikungunya virus (CHIKV) or Venezuelan equine encephalitis virus (VEEV), wherein each of E2 is bound to each of E3, and an antigen is inserted into E3 of Chikungunya virus (CHIKV) or Venezuelan equine encephalitis virus (VEEV) may be used for preparing the composition or vaccine provided in the third aspect of the present application. The complex of E2 and E3 into which the antigen is inserted may consist of an amino acid sequence represented by any one of SEQ ID Nos.:46-49; the E1 may consist of an amino acid sequence represented by SEQ ID NO: 32 (or SEQ ID NO: 76); and the capsid may consist of an amino acid sequence represented by SEQ ID NO: 31 (or SEQ ID NO: 75); or the complex of E2 and E3 into which the antigen is inserted may consist of an amino acid sequence represented by any one of SEQ ID Nos.:50-53; the E1 may consist of an amino acid sequence represented by SEQ ID NO: 35; and the capsid may consist of an amino acid sequence represented by SEQ ID NO: 36.

(4) Method of Producing a Virus Like Particle

In a fourth aspect, the present application provides a method of producing a virus like particle comprising a modified envelope protein E3 comprising:

culturing a cell which is transfected with a vector to express the virus like particle; and purifying the particle.

The virus like particle provided by the first aspect of the present application can be produced by the method provided by a fourth aspect of the present application.

In one embodiment, antigen may be an antigen derived from *Plasmodium falciparum* circumsporozoite protein, an antigen derived from PD-1, an antigen derived from PD-L1 or an antigen derived from CTLA-4, an antigen derived from IL-2, an antigen derived from DISC1, an antigen derived from HER2, an antigen derived from BTLA, an antigen derived from HVEM, an antigen derived from PCSK-9 or an antigen derived from DPP-4.

Various host-vector systems may be used for expression of the virus like particle. Eukaryotic cells can be used for the method provided by the fourth aspect of the present application. Examples of eukaryotic cells include, but are not limited to, insect cells (e.g. sf9 cells, H5 cells), yeast cells (e.g. *S. cerevisiae*) and mammalian cells (e.g. CHO cells, human embryonic kidney (HEK) 293F cells). Vector used for the method provided by the fourth aspect of the present application comprises a nucleic acid molecule encoding the virus like particle to be expressed. Cells may be transfected with the vector using conventional methods (e.g. lipofection, electroporation). A skilled person can select culture medium or with DNA methyl transferase inhibitors and histone deacetylase inhibitors such as sodium butyrate, depending on cells used for the method provided by the fourth aspect of the present application. After the transfection, virus like particle can be produced in the cells and/or culture supernatant. Virus like particle may be recovered from the culture supernatant and purified using ultracentrifugation.

For example, cells are transfected with a vector contains the genes coding for CHIKV structural proteins capsid, 6K, E1, E2 and E3 wherein E3 is modified to contain a desired antigen. The cells transfected with the expression vector produce the proteins and the proteins spontaneously assembled to form the VLPs that can be recovered from the culture medium. The 6K protein acts as a signal sequence for transporting E1 protein to the endoplasmic reticulum, where it is processed by host signal peptidase and it is not assembled into virus particles.

(5) Method of Enhancing the Production of a Virus Like Particle

In a fifth aspect, the present application provides a method of enhancing the production of a virus like particle comprising a modified envelop protein E3. In one embodiment, the virus like particle comprises viral structural protein and at least one antigen, comprising (1) inserting the at least one antigen into an envelope protein E3 of the viral structural protein, and (2) isolating the virus like particle wherein at least one antigen is inserted into the envelope protein E3 of the viral structural protein.

At least one antigen may be inserted into a suitable position of E3. In one preferred embodiment, at least one antigen is inserted into furin cleavage site which is present in E3 of viral structural protein (e.g. CHIKV structural protein, VEEV structural protein) so that the virus like particle comprising antigen-inserted E3 can be expressed more efficiently when compared to expression of virus like particle comprising E2 into which at least one antigen is inserted.

For example, regarding Chikungunya viral structural protein, at least one antigen is inserted between residues H at 321-position and S at 326-position of SEQ ID NO: 1 or 2; between P at 320-position and S at 326-position of SEQ ID NO: 1 or 2; or between S at 319-position and S at 326-position of SEQ ID NO: 1 or 2.

For example, regarding Venezuelan equine encephalitis viral structural protein, at least one antigen is inserted between G at 330-position and S at 335-position of SEQ ID NO: 3; between P at 329-position and S at 335-position of SEQ ID NO: 3; or between C at 328-position and S at 335-position of SEQ ID NO: 3.

The step of inserting the at least one antigen into envelope protein E3 of the viral structural protein may be achieved by preparing a nucleic acid molecule comprising a nucleotide sequence encoding the virus like particle wherein at least one antigen is inserted into the envelope protein E3 of the viral structural protein; and allow the nucleic acid molecule to be expressed using cells such as insect cells (e.g. sf9 cells, H5 cells), yeast cells (e.g. *S. cerevisiae*) and mammalian cells (e.g. CHO cells, 293F cells).

The step of isolating the virus like particle wherein at least one antigen is inserted into the envelope protein E3 of the viral structural protein may be achieved by purifying the virus like particle using ultracentrifugation.

(6) Use of the Disclosed Virus Like Particle

In a sixth aspect, the present application provides use of (i) a virus like particle comprising a modified envelope protein E3 and/or (ii) a nucleic acid molecule consisting of a nucleotide sequence encoding a virus like particle comprising a modified envelope protein E3 for the manufacture of a pharmaceutical composition or a kit for treating or preventing cancer, neurological disease, infectious disease, malaria or lifestyle chronic disease; producing an antibody against the at least one antigen in a mammal; modulating an immune response; immunostimulation; inhibiting function of the at least one antigen; or presenting an antigen on macrophage.

The pharmaceutical composition may be administered to a mammal (e.g. human) intramuscularly (i.m.), intracutaneously (i.c.), subcutaneously (s.c.), intradermally (i.d.) or intraperitoneally (i.p.).

In one embodiment, the pharmaceutical composition is a vaccine, which can be applied to immunotherapy. In one embodiment, when an antigen derived from PD-1, PD-L1, CTLA-4 or BTLA is used for manufacturing the virus like particle, the virus like particle may be used for treating cancer. In one embodiment, when an antigen derived from PD-1 or PD-L1 is used for manufacturing the virus like particle, the virus like particle may be used for treating or preventing an infectious disease. In one embodiment, when an antigen is derived from *Plasmodium falciparum* circumsporozoite protein, the virus like particle may be used for treating or preventing malaria.

Examples of the cancer which may be treated include, but are not limited to, melanoma, renal cancer, prostate cancer, breast cancer, colon cancer and non-small cell lung cancer. Other examples of the cancer include, but are not limited to, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations thereof.

Examples of infectious disease which may be treated include, but are not limited to, HIV, Influenza, Herpes, *Giardia*, Malaria, *Leishmania*, the pathogenic infection by the virus Hepatitis (A, B and C), herpes virus (e.g., VZV, HSV-I, HAV-6, HSV-II, and CMV, Epstein Barr virus), alphavirus, adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus, pathogenic infection by the bacteria chlamydia, rickettsial bacteria, mycobacteria, staphylococci, streptococci, pneumonococci, meningococci and conococci, *klebsiella, proteus, serratia, pseudomonas, legionella*, diphtheria, *salmonella*, bacilli, cholera, tetanus, botulism, anthrax, plague, leptospirosis, and Lymes disease bacteria, pathogenic infection by the fungi *Candida* (*albicans, krusei, glabrata, tropicalis*, etc.), *Cryptococcus neoformans, Aspergillus* (*fumigatus, niger*, etc.), Genus Mucorales (*mucor*, absidia, rhizophus), *Sporothrix schenkii, Blastomyces dermatitidis, Paracoccidioides brasiliensis, Coccidioides immitis* and *Histoplasma capsulatum*, and pathogenic infection by the parasites *Entamoeba histolytica, Balantidium coli*, Naegleriafowleri, *Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis.*

Examples of neurological disease which may be treated include, but are not limited to, Alzheimer disease, Parkinson's disease, epilepsy or Schizophrenia.

Examples of the lifestyle chronic disease which may be treated, but are not limited to, diabetes or hyperlipidemia.

When a pharmaceutical composition comprising a viral structural protein and an antigen (e.g. an antigen derived from *Plasmodium falciparum* circumsporozoite protein, an antigen derived from PD-1, an antigen derived from PD-L1, an antigen derived from CTLA-4, an antigen derived from IL-2, an antigen derived from DISC1, an antigen derived from HER2, an antigen derived from BTLA, an antigen derived from HVEM, an antigen derived from PCSK-9 and an antigen derived from DPP-4) is administered to a mammal (e.g. human), an antibody against the antigen is produced in blood of the mammal. The produced antibody may modulate an immune response; show immunostimulating effects; or inhibit function of the antigen.

The produced antibody may be humanized using a conventional technique. Using the particle provided in a first aspect of the present application, monoclonal antibody or polyclonal antibody can be prepared. In one embodiment, the present application provides a method for producing an antibody comprising administering the particle provided in a first aspect of the present application to a non-human mammal and humanizing non-human mammal produced antibody.

As used herein, the term "antibody" refers to molecules which are capable of binding an epitope or antigenic determinant. The term is meant to include whole antibodies and antigen-binding fragments thereof, including single-chain antibodies. Such antibodies include human antigen binding antibody fragments and include, but are not limited to, Fab, Fab' and F(ab')2, Fd, single-chain Fvs (scFv), single-chain antibodies, disulfide-linked Fvs (sdFv) and fragments comprising either a VL or VH domain. The antibodies can be from any animal origin including birds and mammals. Preferably, the antibodies are mammalian e.g. human, murine, rabbit, goat, guinea pig, camel, horse and the like, or other suitable animals e.g. chicken. As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described, for example, in U.S. Pat. No. 5,939,598, the disclosure of which is incorporated herein by reference in its entirety.

The present application will be described in detail with reference to the following examples, which, however, are not intended to limit the scope of the present application.

EXAMPLES

Example 1: Preparation of Venezuelan Equine Encephalitis Virus (VEEV)-Virus Like Particle (VLP) Comprising Malaria CSP Repeat Antigen Inserted into Envelope Protein E3 of the Viral Structural Protein The following polypeptides of malaria CSP protein were used for preparing a VEEV-VLP comprising malaria CSP repeat antigen. SGG is the N terminal linker and GGS is the C terminal linker for the antigen.

74 (6 repeat of NPNA amino acid sequence)
(SEQ ID NO: 56)
Sggnpnanpnanpnanpnanpnanpnaggs (SEQ ID NO: 60)
(Tccggaggaaacccgaatgccaatcccaacgcgaaccccaatgctaac
ccaaatgccaacccaaacgccaaccccaacgctggtggatcc)

76 (14 repeat of NPNA amino acid sequence)
(SEQ ID NO: 61)
Sggnpnanpnanpnanpnanpnanpnanpnanpnanpnanpnanpnanp
nanpnanpnaggs (SEQ ID NO: 62)
(tccggaggcaaccccaacgccaaccctaatgccaatcccaacgctaat
cccaatgctaaccctaacgcaaatccaaatgcaaaccccaatgccaacc
caaacgctaaccctaacgccaaccctaacgcaaacccaaacgccaatcc
taatgctaacccaaatgcaaaccctaatgctggcggatcc)

78 (25 repeat of NPNA amino acid sequence)
(SEQ ID NO: 63)
Sggnpnanpnanpnanpnanpnanpnvdpnanpnanpnanpnanpnanp
nanpnanpnanpnanpnanpnanpnanpnanpnanpnanpnanpnanpn
anpnaggs (SEQ ID NO: 64)
(tccggaggaaacccgaatgccaatcccaacgcgaaccccaacgctaac
cccaacgccaatccgaatgcaaacccgaacgttgacccaaacgccaacc
cgaatgccaatcccaacgcgaaccccaatgctaacccaaatgccaaccc
aaacgccaaccccaacgctaatccaaacgccaaccctaacgccaatccc
aacgcgaatcctaacgctaatcccaacgcaaatcccaatgctaatccga
acgcgaaccctaatgcaaaccccaacgccaacccgaacgctaacccgaa
cgctaatcccaacgccggtggatcc)

The respective polynucleotides were inserted between the codons encoding Ser at 518-position and Ser at 519-position of SEQ ID NO: 3 to construct a plasmid (hereinafter referred to as pVEEV-74.21, pVEEV-76.21 and pVEEV-78.21, respectively) for expressing VEEV-VLP where the respective antigen is inserted into E2 of Venezuelan equine encephalitis viral structural protein. Likewise, the respective polynucleotides were inserted between the codons encoding Gly at 330-position and Ser at 335-position of SEQ ID NO: 3 to construct a plasmid (hereinafter referred to as pVEEV-74.26, pVEEV-76.26 and pVEEV-78.26, respectively) for expressing VEEV-VLP where the respective antigen is inserted into E3 of Venezuelan equine encephalitis viral structural protein.

293F cells (Lifetechnology) were transfected with 180 μg of each of the plasmid (i.e. pVEEV-74.21, pVEEV-76.21, pVEEV-78.2, pVEEV-74.26, pVEEV-76.26 and pVEEV-78.26, respectively) using PEI (GE Healthcare). 4 days after the transfection, the conditioned medium was collected and centrifuged at 3000 rpm for 15 minutes to separate it from cells. The supernatant was filtrated using 0.45 μm filter to obtain virus like particles. The virus like particles were concentrated using TFF column and purified using QXL column (GE Healthcare) to obtain purified virus like particles. When animals were immunized with virus like particles, the purified virus like particles were further concentrated using spin column (Molecular Weight-cutoff: 100 kDa) to prepare the virus like particles for the immunization.

Figure 3:
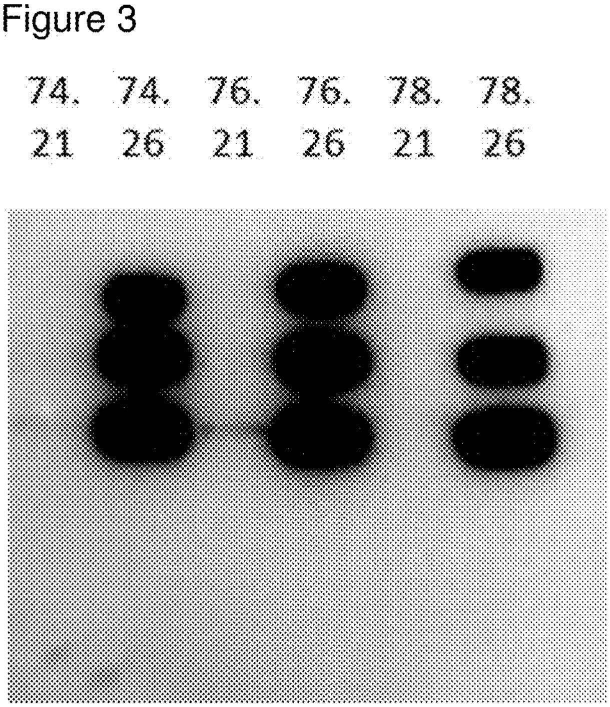
FIG. 3 shows results of western blotting. A CSP repeat sequence of NPNA, which is an antigen derived from *plasmodium falciparum* circumsporozoite protein, was inserted into E2 or E3 of virus like particle of Venezuelan equine encephalitis virus (VEEV) (strain TC-83). The antigen-inserted VEEV virus like particle expressed in 293F cells was confirmed by western blotting using mouse anti-VEEV antibody (1:1000).
74: Malaria CSP repeat antigen (repeat ×6)
76: Malaria CSP repeat antigen (repeat ×14)
78: Malaria CSP repeat antigen (repeat ×25)
In the figure, "74" indicates that inserted antigen is 6×NPNA, "76" indicates that inserted antigen is 14×NPNA, and "78" indicates that inserted antigen is 25×NPNA; and "21" indicates that the antigen is inserted in E2 and "26" indicates that the antigen is inserted in E3.

The production of VLP comprising the CSP repeat antigen 74, 76 or 78 conjugated with VEEV structural polypeptide was confirmed by Western Blot using an anti-VEEV antibody (see FIG. 3). As seen in FIG. 3, antigen-inserted VLP was more efficiently produced when the antigen was inserted into E3 compared to when the antigen was inserted into E2.

Example 2: Preparation of Venezuelan Equine Encephalitis Virus (VEEV)-Virus Like Particle (VLP) Comprising Mouse Malaria CSP Repeat Antigen Inserted into Envelope Protein E3 of the Viral Structural Protein The following polypeptides of mouse malaria CSP protein was used for preparing a VEEV-VLP comprising mouse malaria CSP repeat antigen. SGG is the N terminal linker and GGS is the C terminal linker for the antigen.

261 (repeat of "qgpgap")
(SEQ ID NO: 58)
SGG-qgpgapqgpgapqgpgapqgpgap-GGS (SEQ ID NO: 65)
Tccggaggacagggacctggcgctcctcagggaccaggggcaccaca
gggcccaggcgccccacaggggcctggggcccctgggggatcc The polynucleotides was inserted between the codons encoding Ser at 518-position and Ser at 519-position of SEQ ID NO: 3 to construct a plasmid (hereinafter referred to as pVEEV-261.25) for expressing VEEV-VLP where the antigen was inserted into E2 of Venezuelan equine encephalitis viral structural protein. Likewise, the polynucleotide coding for the peptide was inserted between the codons encoding Gly at 330-position and Ser at 335-position of SEQ ID NO: 3 to construct a plasmid (hereinafter referred to as pVEEV-261.66) for expressing VEEV-VLP where the antigen was inserted into E3 of Venezuelan equine encephalitis viral structural protein.

293F cells (Lifetechnology) were transfected with 180 μg of each of the plasmid (i.e. pVEEV-261.25 and pVEEV-261.66, respectively) using PEI (GE Healthcare). 4 days after the transfection, the conditioned medium was collected and centrifuged at 3000 rpm for 15 minutes to separate it from cells. The supernatant was filtrated using 0.45 μm filter to obtain virus like particles. The virus like particles were concentrated using TFF column and purified using QXL column (GE Healthcare) to obtain purified virus like particles. When animals were immunized with virus like particles, the purified virus like particles were further concentrated using spin column (Molecular Weight-cutoff: 100 kDa) to prepare the virus like particles for the immunization.

Figure 4:
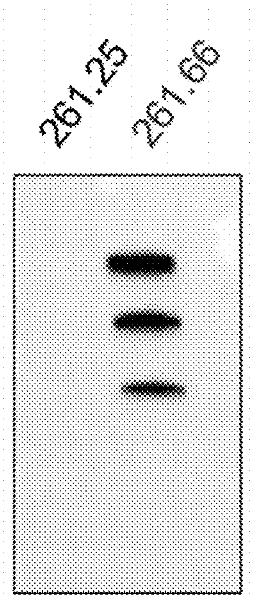
FIG. 4 shows results of western blotting. A mouse malaria CSP repeat antigen was inserted into E2 or E3 of virus like particle of Venezuelan equine encephalitis virus (VEEV) (strain TC-83). The antigen-inserted VEEV virus like particle expressed in 293F cells was confirmed by western blotting using mouse anti-VEEV antibody. In the figure, "261.25" indicates VEEV VLP comprising E2 into which mouse malaria CSP repeat antigen was inserted, and "261.66" indicates VEEV VLP comprising E3 into which mouse malaria CSP repeat antigen was inserted.

The expression of VLP comprising the CSP repeat antigen 261 conjugated with VEEV structural polypeptide was confirmed by Western Blot using an anti-VEEV antibody (see FIG. 4). As seen in FIG. 4, antigen-inserted VLP was more efficiently produced when the antigen was inserted into E3 compared to when the antigen was inserted into E2.

Example 3: Preparation of Venezuelan Equine Encephalitis Virus (VEEV)-Virus Like Particle (VLP) Comprising Malaria Antigen Inserted into Envelope Protein E3 of the Viral Structural Protein The following polypeptides derived from malaria protein were used for preparing a VEEV-VLP comprising malaria CSP repeat antigen. SGG is the N terminal linker (TCCGGAGGA in nuclear sequence) and GGS is the C terminal linker (GGAGGATCC in nuclear sequence) for the antigen.

74 (6 repeat of NPNA amino acid sequence)

(SEQ ID NO: 56)
sggnpnanpnanpnanpnanpnanpnaggs (SEQ ID NO: 60)
(tccggaggaaacccgaatgccaatcccaacgcgaaccccaatgctaacc caaatgccaacccaaacgccaaccccaacgctggtggatcc)

302R (antigen derived from pfs25)

(SEQ ID NO: 66)
SGG-cikidgnpvsyac-GGS 303R (antigen derived from pfs25)

(SEQ ID NO: 67)
tccggagggtgcatcaagatcgacggcaaccccgtgtcctacgcctgcgg gggatcc (SEQ ID NO: 68)
SGG-cildtsnpvktgvc-GGS (SEQ ID NO: 69)
tccggaggctgcatcctggacaccagcaaccccgtgaaaaccggcgtgt gtggcggatcc The respective polynucleotides were inserted between the codons encoding Ser at 518-position and Ser at 519-position of SEQ ID NO: 3 to construct a plasmid (hereinafter referred to as pVEEV-74.21, pVEEV-302R.21 and pVEEV-303R.21, respectively) for expressing VEEV-VLP where the respective antigen is inserted into E2 of Venezuelan equine encephalitis viral structural protein. Likewise, the respective polynucleotides were inserted between the codons encoding Gly at 330-position and Ser at 335-position of SEQ ID NO: 3 to construct a plasmid (hereinafter referred to as pVEEV-74.66, pVEEV-302R.66 and pVEEV-303R.66, respectively) for expressing VEEV-VLP where the respective antigen is inserted into E3 of Venezuelan equine encephalitis viral structural protein.

293F cells (Lifetechnology) were transfected with 180 μg of each of the plasmid (i.e. pVEEV-74.21, pVEEV-302R.21, pVEEV-303R.2, pVEEV-74.66, pVEEV-302R.66 and pVEEV-303R.66, respectively) using PEI (GE Healthcare). 4 days after the transfection, the conditioned medium was collected and centrifuged at 3000 rpm for 15 minutes to separate it from cells. The supernatant was filtrated using 0.45 μm filter to obtain virus like particles. The virus like particles were concentrated using TFF column and purified using QXL column (GE Healthcare) to obtain purified virus like particles. When animals were immunized with virus like particles, the purified virus like particles were further concentrated using spin column (Molecular Weight-cutoff: 100 kDa) to prepare the virus like particles for the immunization.

Figure 5:
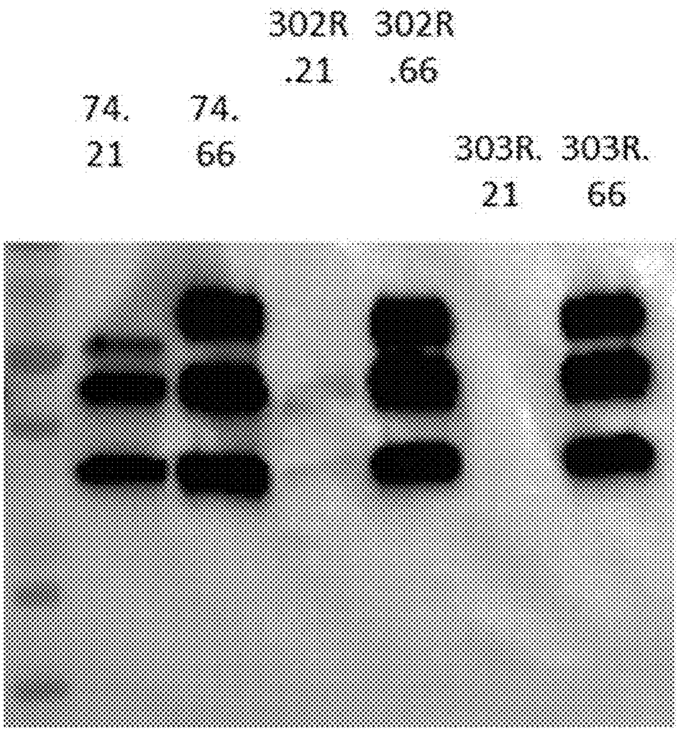
FIG. 5 shows results of western blotting. A CSP repeat sequence, malaria pfs25 domain 1 epitope or malaria pfs25 domain 2 epitope was inserted into E2 or E3 of virus like particle of Venezuelan equine encephalitis virus (VEEV) (strain TC-83). The antigen-inserted VEEV virus like particle expressed in 293F cells was confirmed by western blotting using mouse anti-VEEV antibody. In the figure, "74" indicates that inserted antigen is malaria CSP repeat epitope, "302R" indicates that inserted antigen is malaria pfs25 domain1 epitope, and "303R" indicates that inserted antigen is malaria pfs25 domain2 epitope; and "21" indicates that the antigen is inserted in E2 and "26" indicates that the antigen is inserted in E3.

The expression of VLP comprising antigen 74, 302R or 303R conjugated with VEEV structural polypeptide was confirmed by Western Blot using an anti-VEEV antibody (see FIG. 5). As seen in FIG. 5, antigen-inserted VLP was more efficiently produced when the antigen was inserted into E3 compared to when the antigen was inserted into E2.

Example 4: Preparation of Chikungunya Virus (CHIKV)-Virus Like Particle Comprising a Viral Structural Protein and PD-1 Antigen or PD-1 Ligand Antigen The following polypeptides of PD-1 or PD-L1 were used for preparing a CHIKV-VLP comprising PD-1 antigen or PD-1 ligand antigen. SGG is the N terminal linker (TCCG-GAGGA in nuclear sequence) and GGS is the C terminal linker (GGAGGATCC in nuclear sequence) for the antigen.

1. 299 (mousePD-L1 sequence): A sequence of a fragment of mouse PD-L1 Domain3S attaching linker, which was used for an antigen:

Nuclear Sequence (SEQ ID NO: 70)
tccggaggatgcatcatcagctacggcggagccgactacggaggatcc Amino Acid sequence (SEQ ID NO: 71)
SGG-ciisyggadyC-GGS 2. 274 (mouse PD-1 sequence): A sequence of a fragment of mouse PD-1 domain2short attaching linker, which was used for an antigen:

Nuclear Sequence (SEQ ID NO: 72)
tccggaggaggcgccatcagcctgcaccccaaggccaagatcgaggaa tctggaggatcc Amino Acid sequence (SEQ ID NO: 73)
SGG-gaislhpkakiees-GS The respective polynucleotides was inserted between the codons encoding Ser at 531-position and Asn at 532-position of SEQ ID NO: 2 to construct a plasmid (hereinafter referred to as pCHIKV-299.15 and pCHIKV-274.11, respectively) for expressing Chikungunya viral structural protein where the PD-1-derived peptide or the PD-L1-derived peptide is inserted into E2 of Chikungunya viral structural protein. Likewise, the respective polynucleotides were inserted between the codons encoding H at 321-position and S at 326-position of SEQ ID NO: 2 to construct a plasmid (hereinafter referred to as pCHIKV-299.56 and pCHIKV-274.56, respectively) for expressing Chikungunya viral structural protein where the PD-1-derived peptide or the PD-L1-derived peptide is inserted into E3 of Chikungunya viral structural protein.

293F cells (Lifetechnology) were transfected with 180 μg of each of the plasmid (i.e. pCHIKV-274.11, pCHIKV-299.15, pCHIKV-274.56 and pCHIKV-299.56, respectively) using PEI (GE Healthcare). 4 days after the transfection, the conditioned medium was collected and centrifuged at 3000 rpm for 15 minutes to separate it from cells. The supernatant was filtrated using 0.45 μm filter to obtain virus like particles. The virus like particles were concentrated using TFF column and purified using QXL column (GE Healthcare) to obtain purified virus like particles. When animals were immunized with virus like particles, the purified virus like particles were further concentrated using spin column (Molecular Weight-cutoff: 100 kDa) to prepare the virus like particles for the immunization.

Figure 6:
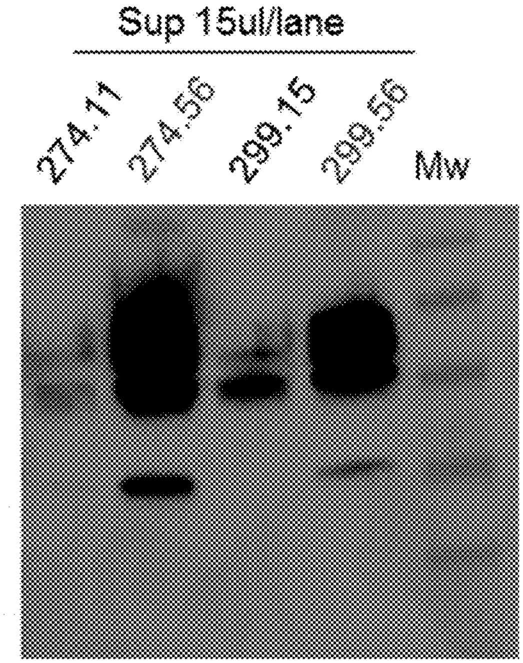
FIG. 6 shows results of western blotting. PD-1 epitope or PD-L1 epitope was inserted into E2 or E3 of virus like particle of Chikungunya virus (CHIKV) (strain 37997). The antigen-inserted CHIKV virus like particle expressed in 293F cells was confirmed by western blotting using mouse anti-CHIKV antibody. In the figure, "274.11" indicates CHIKV VLP comprising E2 into which PD-1 epitope was inserted, "274.56" indicates CHIKV VLP comprising E3 into which mouse PD-1 epitope was inserted, "299.15" indicates CHIKV VLP comprising E2 into which PD-L1 epitope was inserted, and "299.56" indicates CHIKV VLP comprising E3 into which mouse PD-L1 epitope was inserted.

The expression of VLP comprising antigen 274 or 299 conjugated with CHIKV structural polypeptide was confirmed by Western Blot using an anti-CHIKV antibody (see FIG. 6). As seen in FIG. 6, antigen-inserted VLP was more efficiently produced when the antigen was inserted into E3 compared to when the antigen was inserted into E2.

Example 5: Preparation of Chikungunya Virus (CHIKV)-Virus Like Particle Comprising a Viral Structural Protein and Malaria Antigen The following polypeptides of malaria CSP protein was used for preparing a CHIKV-VLP comprising malaria CSP repeat antigen. SGG is the N terminal linker (TCCG-GAGGA in nuclear sequence) and GGS is the C terminal linker (GGAGGATCC in nuclear sequence) for the antigen.

CSP repeat antigen 74 (6 repeat of NPNA amino acid sequence)

(SEQ ID NO: 56)

sggnpnanpnanpnanpnanpnanpnaggs (SEQ ID NO: 60)

(tccggaggaaacccgaatgccaatcccaacgcgaaccccaatgctaacc caaatgccaacccaaacgccaaccccaacgctggtggatcc)

The polynucleotide was inserted between the codons encoding Ser at 531-position and Asn at 532-position of SEQ ID NO: 2 to construct a plasmid (hereinafter referred to as pCHIKV-74.11) for expressing Chikungunya viral structural protein where the malaria CSP repeat antigen is inserted into E2 of Chikungunya viral structural protein. Likewise, the malaria CSP repeat antigen was inserted between the codons encoding H at 321-position and S at 326-position of SEQ ID NO: 2 to construct a plasmid (hereinafter referred to as pCHIKV-74.16) for expressing Chikungunya viral structural protein where the malaria CSP repeat antigen is inserted into E3 of Chikungunya viral structural protein.

293F cells (Lifetechnology) were transfected with 180 μg of each of the plasmid (i.e. pCHIKV-74.11 and pCHIKV-74.16, respectively) using PEI (GE Healthcare). 4 days after the transfection, the conditioned medium was collected and centrifuged at 3000 rpm for 15 minutes to separate it from cells. The supernatant was filtrated using 0.45 μm filter to obtain virus like particles. The virus like particles were concentrated using TFF column and purified using QXL column (GE Healthcare) to obtain purified virus like particles. When animals were immunized with virus like particles, the purified virus like particles were further concentrated using spin column (Molecular Weight-cutoff: 100 kDa) to prepare the virus like particles for the immunization.

Figure 7:
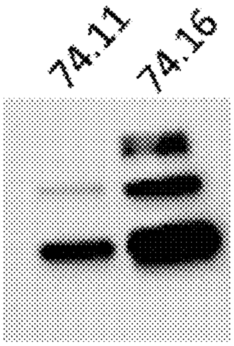
FIG. 7 shows results of western blotting. Malaria CSP repeat epitope was inserted into E2 or E3 of virus like particle of Chikungunya virus (CHIKV) (strain 37997). The antigen-inserted CHIKV virus like particle expressed in 293F cells was confirmed by western blotting using mouse anti-CHIKV antibody. In the figure, "74.11" indicates CHIKV VLP comprising E2 into which malaria CSP repeat epitope was inserted, "74.16" indicates CHIKV VLP comprising E3 into which mouse malaria CSP epitope was inserted.

The expression of VLP comprising VLP74 conjugated with CHIKV structural polypeptide was confirmed by Western Blot using an anti-CHIKV antibody (see FIG. 7). As seen in FIG. 7, antigen-inserted VLP was more efficiently produced when the antigen was inserted into E3 compared to when the antigen was inserted into E2.

Example 6: Preparation of Chikungunya Virus (CHIKV)-Virus Like Particle Comprising a Viral Structural Protein and CTLA-4 Antigen The following polypeptides of CTLA-4 protein was used for preparing a CHIKV-VLP comprising CTLA-4 antigen. SGG is the N terminal linker (TCCGGAGGA in nuclear sequence) and GGS is the C terminal linker (GGAGGATCC in nuclear sequence) for the antigen.

mCTLA4_ver2

(SEQ ID NO: 74)

sggggkvelmypppyfvgmggggs (SEQ ID NO: 78)

tccggaggcggcggcaaggtggaactcatgtacccaccgccatactttg tgggcatgggcggcggcggatcc mCTLA4_ver4

(SEQ ID NO: 79)

sggcattftekntvgfldypfcggs (SEQ ID NO: 80)

tccggaggctgtgccacgacattcacagagaagaatacagtgggcttcc tagattacccettctgcggcggatcc

-continued mCTLA4_ver5

(SEQ ID NO: 81)

sggattftekntvgfldypfggs (SEQ ID NO: 82)

tccggaggcgccacgacattcacagagaagaatacagtgggcttcctag attaccccttcggcggatcc

The polynucleotide was inserted between the codons encoding H at 321-position and S at 326-position of SEQ ID NO: 2 to construct a plasmid for expressing Chikungunya viral structural protein where the mCTLA-4 antigen is inserted into E3 of Chikungunya viral structural protein.

293F cells (Lifetechnology) were transfected with 180 μg of each of the plasmid using PEI (GE Healthcare). 4 days after the transfection, the conditioned medium was collected and centrifuged at 3000 rpm for 15 minutes to separate it from cells. The supernatant was filtrated using 0.45 μm filter to obtain virus like particles. The virus like particles were concentrated using TFF column and purified using QXL column (GE Healthcare) to obtain purified virus like particles. When animals were immunized with virus like particles, the purified virus like particles were further concentrated using spin column (Molecular Weight-cutoff: 100 kDa) to prepare the virus like particles for the immunization.

The expression of VLP comprising each of mCTLA-4_ver2, 4 and 5 conjugated with CHIKV structural polypeptide was confirmed by Western Blot using an anti-CHIKV monkey sera.

Example 7: Preparation of Mature CHIKV VLP

Figure 8:
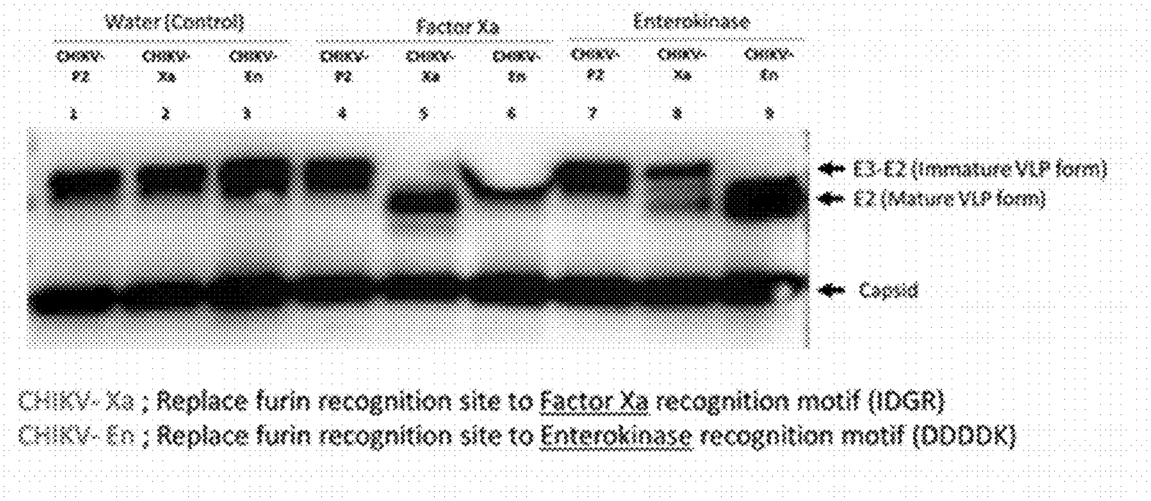
FIG. 8 shows results of western blotting regarding CHIKV immature construct from transient transfection.

CHIKV-P2 VLP expression plasmid that can express a CHIKV viral structural protein whose furin site RQRR at the end of E3 region of CHIKV is replaced with SGGGS; CHIKV-Xa VLP expression plasmid that can express a CHIKV viral structural protein whose furin site RQRR at the end of E3 region of CHIKV is replaced with Factor Xa recognition motif, IDGR and CHIKV-En VLP expression plasmid that can express a CHIKV viral structural protein whose furin site RQRR at the end of E3 region of CHIKV is replaced with Enterokinase recognition motif, DDDDK were used. The all three plasmid 10 ug were transfected into 293F cells and 4 days after the transfection, the supernatants were harvested. 20 ul of supernatants were treated with Water (Control), Factor Xa or Enterokinase for overnight. Then VLPs in the supernatants were measured by Western Blotting using serum against CHIKV. Results are shown in FIG. 8.

Immature VLPs were expressed in the supernatant of the cells transfected with the plasmids, CHIKV-P2, CHIKV-Xa and CHIKV-En. The immature VLP generated from the CHIKV-Xa-transfected cells were digested with Factor Xa. The immature VLP leased E3 and it became mature VLP form (Lane 5). The immature VLP generated from the CHIKV-En-transfected cells were digested with Enterokinase. The immature VLP leased E3 and it became mature VLP form (Lane 9).

Example 8: Preparation of Mature VEEV VLP

Figure 9:
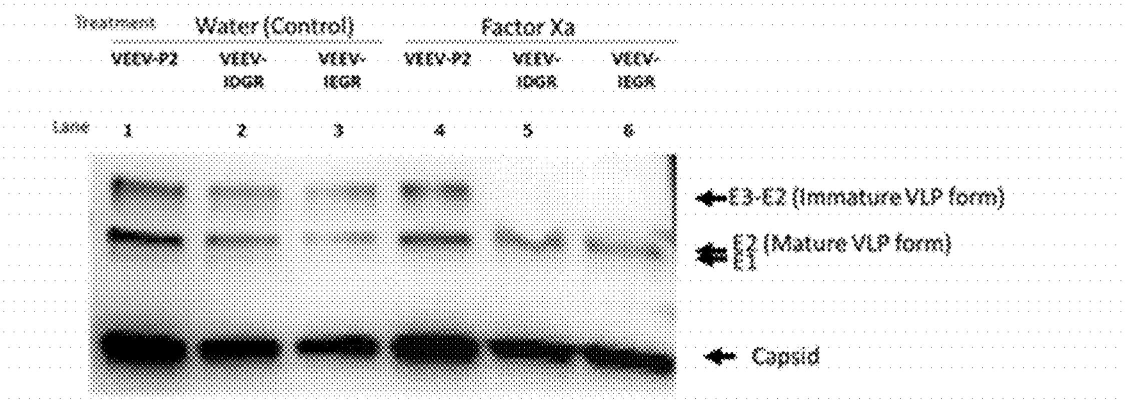
FIG. 9 shows results of western blotting regarding VEEV immature construct from transient transfection.

VEEV-P2 VLP expression plasmid that can express a VEEV viral structural protein whose furin site RQRR at the end of E3 region of VEEV is replaced with SGGGS; VEEV-IDGR VLP expression plasmid that can express a VEEV viral structural protein whose furin site RQRR at the end of E3 region of VEEV is replaced with Factor Xa recognition motif, IDGR; and VEEV-IEGR plasmid that can express a VEEV viral structural protein whose furin site RQRR at the end of E3 region of VEEV is replaced with another Xa recognition motif, IEGR were used. The all three plasmids 10 ug were transfected into 293F cells and 4 days after the transfection, the supernatants were harvested. 20 ul of supernatants were treated with Water (Control), Factor Xa for overnight. Then VLPs in the supernatants were measured by Western Blotting using serum against VEEV. Immature VLP were expressed in the supernatant of the cells transfected with the plasmids, VEEV-P2, VEEV-IDGR and VEEV-IEGR. The immature VLPs generated from the VEEV-IDGR and VEEV-IEGR-transfected cells were digested with Factor Xa. The result is shown in FIG. 9. The immature VLPs generated from the VEEV-IDGR and VEEV-IEGR-transfected cells leased E3 and they became the mature VLP forms (Lane 5 and 6).

Example 9: Preparation of Chikungunya Virus (CHIKV)-Virus Like Particle Comprising DISC1_451, 452 or 454 Inserted into Envelope Protein E3 of the Viral Structural Protein The following polypeptides of DISC1 protein were used for preparing a CHIKV-VLP comprising DISC1 antigen.

| Name | Amino acid sequence |
|---|---|
| DISC1_451 | SGGLLIQSLQLQEARGELSVEDERQMDDLEGGS (SEQ ID NO: 105) |
| DISC1_452 | SGGEARGELSVEDERQMDDLEGGS (SEQ ID NO: 106) |
| DISC1_454 | SGGEARGELSVEGGS (SEQ ID NO: 107) |
| **Name** | **DNA sequence** |
| DISC1_451 | tccggagggctgctgatccagtctctgcagctgcaggaagccagaggc gagctgagcgtggaagatgagcggcagatggacgacctggaaggggga tcc (SEQ ID NO: 117) |
| DISC1_452 | tccggaggggaagccagaggcgagctgagcgtggaagatgagcggcag atggacgacctggaagggggatcc (SEQ ID NO: 118) |
| DISC1_454 | tccggaggggaagccagaggcgagctgagcgtggaagggggatcc (SEQ ID NO: 119) |

SGG is the N terminal linker (TCCGGAGGA in nuclear sequence) and GGS is the C terminal linker (GGAGGATCC in nuclear sequence) for the antigen.

The respective polynucleotides was inserted between the codons encoding Ser at 531-position and Asn at 532-position of SEQ ID NO: 2 as well as inserted between the codons encoding H at 321-position and S at 326-position of SEQ ID NO: 2 to construct a plasmid for expressing Chikungunya viral structural protein where the DISC1-derived peptide is inserted into both E2 and E3 of Chikungunya viral structural protein. The respective polynucleotides was inserted between the codons encoding H at 321-position and S at 326-position of SEQ ID NO: 2 to construct a plasmid (hereinafter referred to as pCHIKV-299.56 and pCHIKV-274.56, respectively) for expressing Chikungunya viral structural protein where the DISC1-derived peptide is inserted into E3 of Chikungunya viral structural protein.
The 293F cells were transfected with the indicated DISC1 expressing VLP. 4 days after transfection, the supernatants were harvested.

Figure 10:
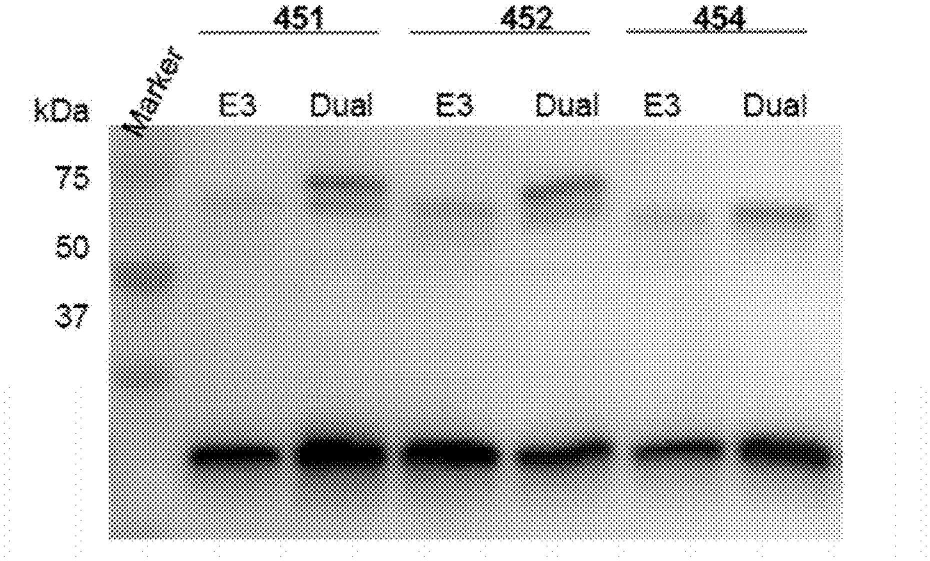
FIG. 10 shows results of western blotting indicating that DISC1_451, _452 and _454-inserted VLPs were produced when those antigens were inserted into E3 and into both E2 and E3 (dual).

The expression of VLP comprising DISC1_451, _452 or _454 conjugated with CHIKV structural polypeptide was confirmed by Western Blot using an anti-CHIKV antibody (see FIG. 10). 1st antibody (1:1000 dilution) was anti-serum against Chikungunya and 2nd antibody (1:5000 dilution) was anti-mouse IgG-HRP antibody. As seen in FIG. 10, DISC1_451, _452 and _454-inserted VLPs were produced when the antigen was inserted into E3 and into both E2 and E3 (dual).

Example 10: Preparation of Chikungunya Virus (CHIKV)-Virus Like Particle Comprising IL-2 Inserted into Envelope Protein E3 of the Viral Structural Protein Human IL-2 mutant was prepared according to the method described in Levin et. al, Nature 484(7395): 529-533, 2012. Mouse IL-2 mutants are F54A (Mott H R et al. J. Mol. Biol. 247, 979-994, 1995) and D34K (Berndt et al. Biochemistry 33, 6571, 1994), the entire contents of those references are herein incorporated by reference.

The respective polynucleotides were inserted between the codons encoding H at 321-position and S at 326-position of SEQ ID NO: 2 to construct a plasmid (hereinafter referred to as pCHIKV-299.56 and pCHIKV-274.56, respectively) for expressing Chikungunya viral structural protein where the IL-2-derived peptide is inserted into E3 of Chikungunya viral structural protein. According to the same manner described in EXAMPLE 6, Chikungunya virus like particle comprising IL-2 were prepared and purified.

Figure 11:
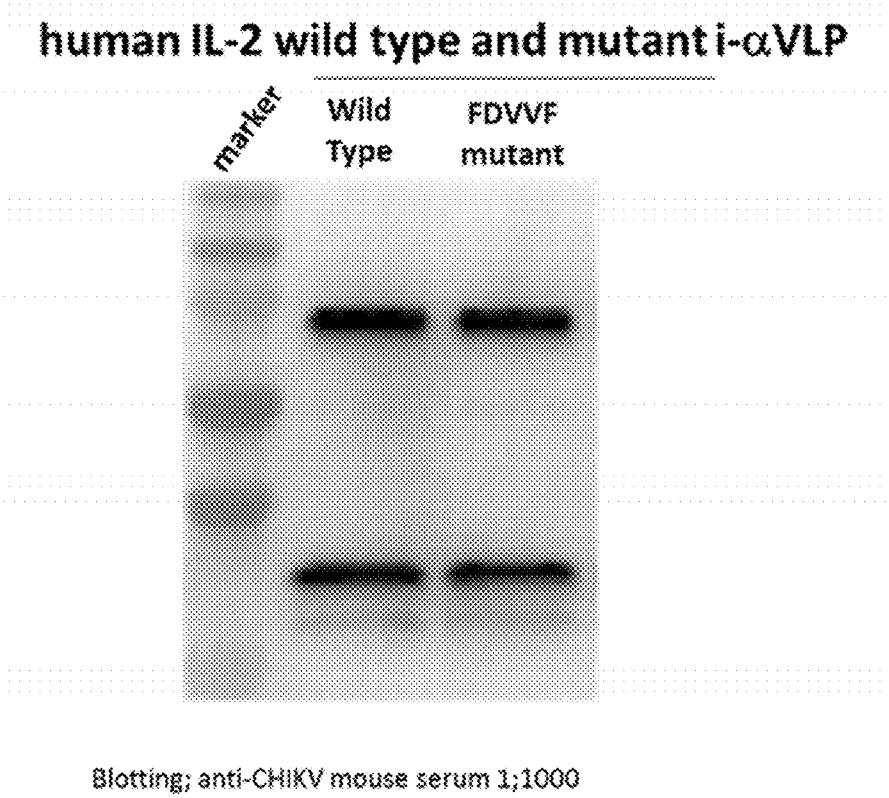
FIGS. 11 and 12 show results of western blotting indicating that human IL-2 wild type, human IL-2 mutant, mouse IL-2 wild type and mouse IL-2 mutant-inserted VLPs were produced when those antigens were inserted into E3.
Figure 12:
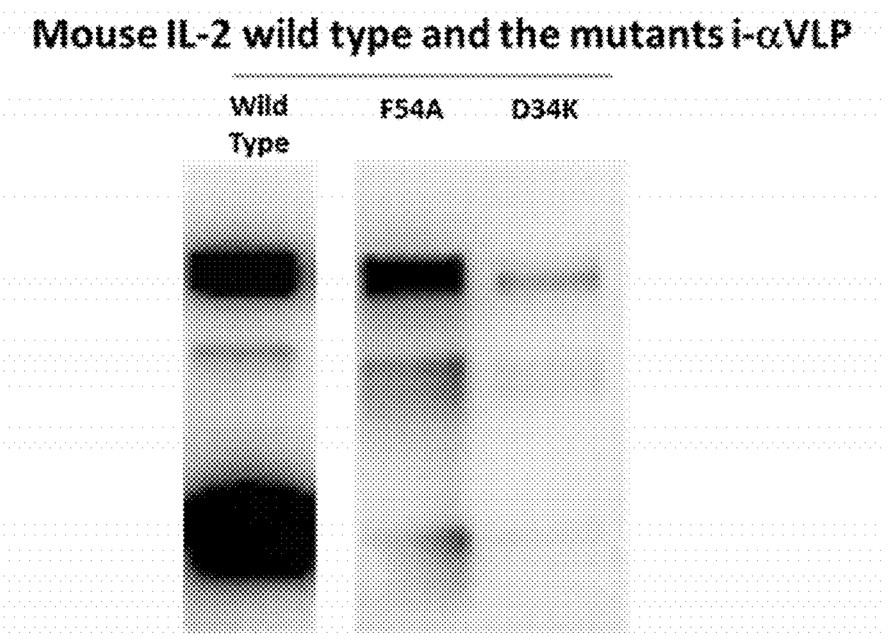

The expression of VLP comprising IL-2 conjugated with CHIKV structural polypeptide was confirmed by Western Blot using mouse anti CHIKV antibody (see FIGS. 11 and 12). As seen in FIGS. 11 and 12, Human IL-2 wild type, human IL-2 mutant, mouse IL-2 wild type and mouse IL-2 mutant-inserted VLPs were produced when those antigens were inserted into E3.

CHIKV viral structural proteins comprising IL-2 derived peptide in their envelope protein E3 provided as well as expression vectors expressing the viral structural proteins are SEQ ID NOs.: 83-92. Those sequences contains the 6K protein but the 6K protein acts as a signal sequence for transporting E1 protein to the endoplasmic reticulum, where it is processed by host signal peptidase and it is not assembled into virus particles.

Example 11: Protection of Mice Against Malaria (*Plasmodium yoelii*) by Intramuscle Injection of CHIKV VLP Comprising Mouse Malaria (*Plasmodium yoelii*) Inserted into Both Envelope Proteins E2 and E3 of the Viral Structural Protein Chikungunya VLP comprising Malaria *Plasmodium yoelii* CSP 4× repeat inserted into both envelop proteins E2 and E3 (261.261 CHIKV VLP) and Chikungunya VLP comprising Malaria *Plasmodium yoelii* CSP 14× repeat inserted into both envelop proteins E2 and E3 (264.264 CHIKV VLP) were prepared and purified in the similar manner as the previous Examples. Amino acid sequences and nucleotide sequences of the repeat antigens with linker used in this example are SEQ ID NOs.: 93-96. CHIKV viral structural proteins containing the antigens in both E2 and E3 and expression vectors for those viral structural proteins are SEQ ID NOs.: 97-100. Those sequences contains the 6K protein but the 6K protein acts as a signal sequence for transporting E1 protein to the endoplasmic reticulum, where it is processed by host signal peptidase and it is not assembled into virus particles.

The mice (n=10) were immunized with the 261.261 CHIKV VLP or 264.264 CHIKV VLP 2 times at week 0 and 3 (20 ug VLP per mouse) by intramuscle injection. VLPs were mixed with alhydrogel adjuvant before the injection. At week 5, the mice immunized with the 261.261 CHIKV VLP, 264.264 CHIKV VLP and CHIKV VLP with no inserted antigen (Control group) were challenged intravenously with 1000 dose of *P. yoelii* sporozoites.

Figure 13:
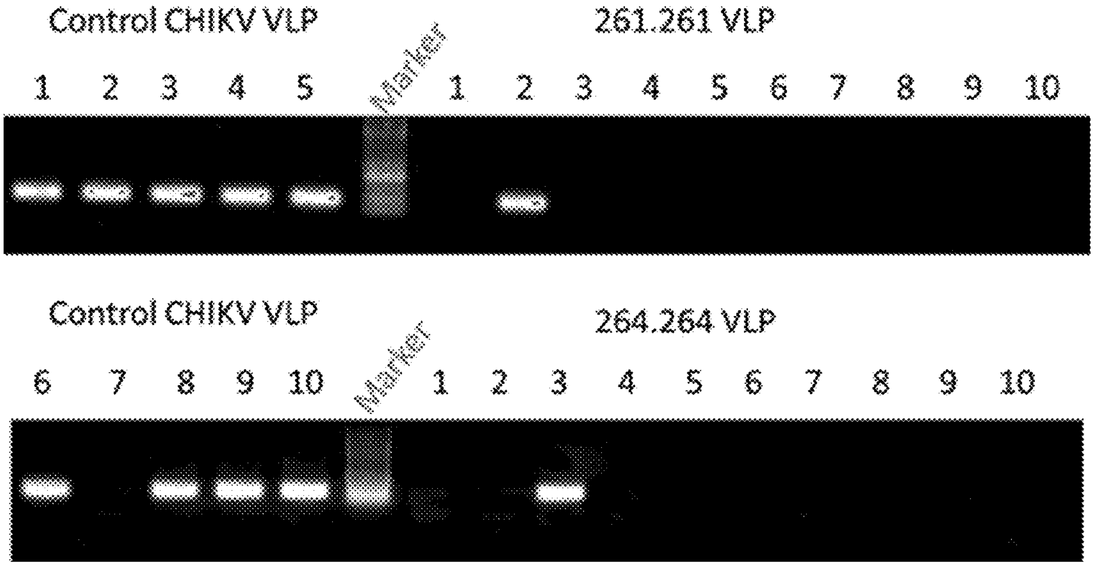
FIG. 13 shows results of the PCR, indicating that among 10 mice immunized with Control VLP, 9 mice were infected with malaria; among 10 mice immunized with Chikungunya VLP comprising Malaria CSP 4× repeat inserted into both envelop proteins E2 and E3 (261.261 VLP), 9 mice were not infected with malaria; and among 10 mice immunized with Chikungunya VLP comprising Malaria CSP 14× repeat inserted into both envelop proteins E2 and E3, 9 mice were not infected with malaria.

Malaria infection was confirmed by PCR. Genomic DNA was purified from the mice blood day 14 after challenge. 18S malaria DNA was amplified by PCR. FIG. 13 shows results of the PCR, indicating that among 10 mice immunized with Control VLP, 9 mice were infected with malaria; among 10 mice immunized with Chikungunya VLP comprising Malaria CSP 4× repeat inserted into both envelop proteins E2 and E3 (261.261 VLP), 9 mice were not infected with malaria; and among 10 mice immunized with Chikungunya VLP comprising Malaria CSP 14× repeat inserted into both envelop proteins E2 and E3, 9 mice were not infected with malaria.

Example 12: Immunogenicity of Chikungunya Virus (CHIKV)-Virus Like Particles Comprising the Viral Structural Protein and Human Malaria CSP Repeat Epitope: 74.74 (E2 and E3 (Dual) Insertion), 74(E2 Insertion) and 74(E3 Insertion)

Chikungunya viral structural protein comprising Malaria CSP 6× repeat antigen (6×NPNA) in its E2 or E3, as well as in both E2 and E3 were prepared in the similar manner as the previous examples. CHIKV viral structural protein comprising CSP 6× repeat antigen in both E2 and E3 is SEQ ID NOs: 101 and expression vector for the viral structural protein is SEQ ID NO: 102(74.74.58). CHIKV VLPs comprising the CSP 6× repeat antigen were prepared and purified in the same manner as Example 6.

The mice (n=4 per group) were immunized with 10 ug of indicated VLPs. 10 days after immunization, the anti-CSP antibody titer in the serum of the immunized mice was measured by ELISA coated with recombinant CSP.

Figure 14:
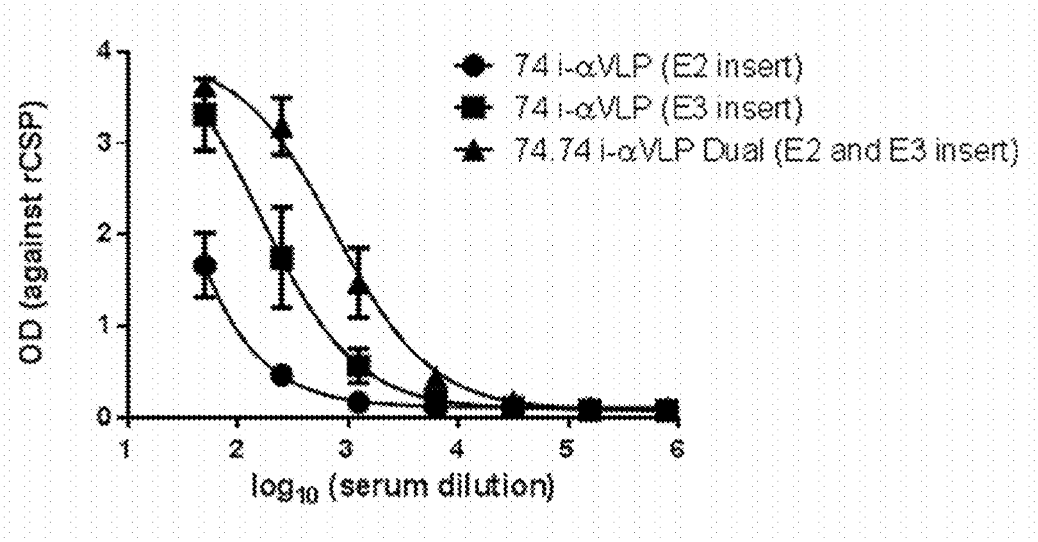
FIG. 14 shows results of ELISA, indicating that E3-inserted as well as E2- and E3-inserted VLPs have higher titer than E2-inserted VLP.

FIG. 14 shows that E3-inserted as well as E2- and E3-(dual) inserted VLP had higher titer than E2-inserted VLP.

Example 13: Preparation of Chikungunya Virus (CHIKV)-Virus Like Particle Comprising a Viral Structural Protein and hHER2 Antigen The following polypeptides derived from hHER2 protein were used for preparing a CHIKV-VLP comprising hHER2 antigen. SGG is the N terminal linker (TCCGGAGGA in nuclear sequence) and GGS is the C terminal linker (GGAGGATCC in nuclear sequence) for the antigen.

| VLP | Amino acid sequence |
|---|---|
| 401 | SGGVTYNTDTFESMPGGS (SEQ ID NO: 108) |
| 403 | SGGYVNARHCLGGS (SEQ ID NO: 110) |
| 404 | SGGYVNARHGLGGS (SEQ ID NO: 111) |
| 405 | SGGKFPDEEGACQPCPIGGS (SEQ ID NO: 112) |
| 406 | SGGKFPDEEGACQPGGS (SEQ ID NO: 113) |
| 407 | SGGKDPPFCVGGS (SEQ ID NO: 114) |
| 408 | SGGYKDPPFCVAGGS (SEQ ID NO: 115) |
| 409 | SGGYKDPPFCVGGS (SEQ ID NO: 116) |

| VLP # | DNA sequence |
|---|---|
| 401 | aaaaaatccggaggcgtcacctacaacacagacacgtttgagtccatgcccggcggatccaaa (SEQ ID NO: 120) |
| 403 | aaaaaatccggaggctatgtgaatgccaggcactgtttgggcggatccaaa (SEQ ID NO: 121) |
| 404 | aaaaaatccggaggctatgtgaatgccaggcacggtttgggcggatccaaa (SEQ ID NO: 122) |
| 405 | aaaaaatccggaggcaagtttccagatgaggagggcgcatgccagccttgccccatcggcggatccaaa (SEQ ID NO: 123) |
| 406 | aaaaaatccggaggcaagtttccagatgaggagggcgcatgccagcctggcggatccaaa (SEQ ID NO: 124) |
| 407 | aaaaaatccggaggcaaggaccctcccttctgcgtgggcggatccaaa (SEQ ID NO: 125) |
| 408 | aaaaaatccggaggctataaggaccctcccttctgcgtggcgggcggatccaaa (SEQ ID NO: 126) |
| 409 | aaaaaatccggaggctataaggaccctcccttctgcgtgggcggatccaaa (SEQ ID NO: 127) |

The respective polynucleotides was inserted between the codons encoding Ser at 531-position and Asn at 532-position of SEQ ID NO: 2 to construct a plasmid for expressing Chikungunya viral structural protein where the hHER2-derived peptide is inserted into E2 of Chikungunya viral structural protein. Likewise, the respective polynucleotides were inserted between the codons encoding H at 321-position and S at 326-position of SEQ ID NO: 2 to construct a plasmid for expressing Chikungunya viral structural protein where the hHER2-derived peptide is inserted into E3 of Chikungunya viral structural protein.

According to the same manner described in EXAMPLE 6, the Chikungunya virus like particle comprising hHER2 was prepared and purified.

Figure 15:
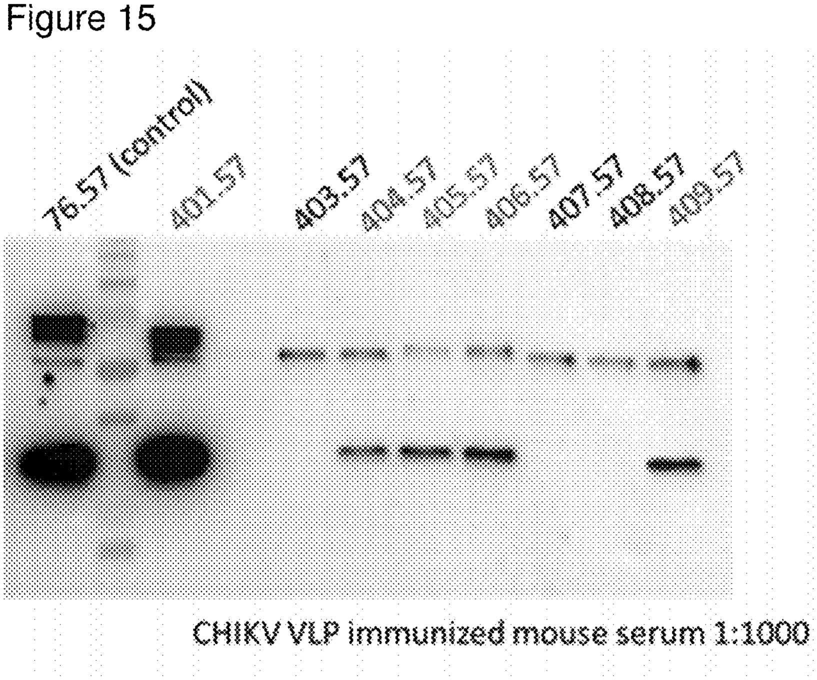
FIG. 15 shows western blotting indicating that hHER2-inserted VLPs were produced.

The expression of VLP comprising hHER2 conjugated with CHIKV structural polypeptide was confirmed by Western Blot using mouse anti CHIKV antibody (see FIG. 15). Among them, 401, 404, 406, and 409 were relatively high expression levels and because they code different epitopes.

Example 14: Immunogenicity

The mice (n=4 per group) were immunized with 10 ug of CHIKV VLP comprising hHER2 antigen #401 inserted into E2 or into both E2 and E3 (dual). The mice (n=10) were immunized with the VLP comprising the hHER2 antigen or CHIKV VLP comprising no antigen 2 times at week 0 and 3 (20 ug VLP per mouse) by intramuscle injection. VLPs were mixed with alhydrogel adjuvant before the injection.

2 weeks after $2^{nd}$ immunization (5 weeks after the $1^{st}$ immunization), the anti-hHER2 antibody titer in the serum of the immunized mice were measured by ELISA plate coated with recombinant hHER2.

Figure 16:
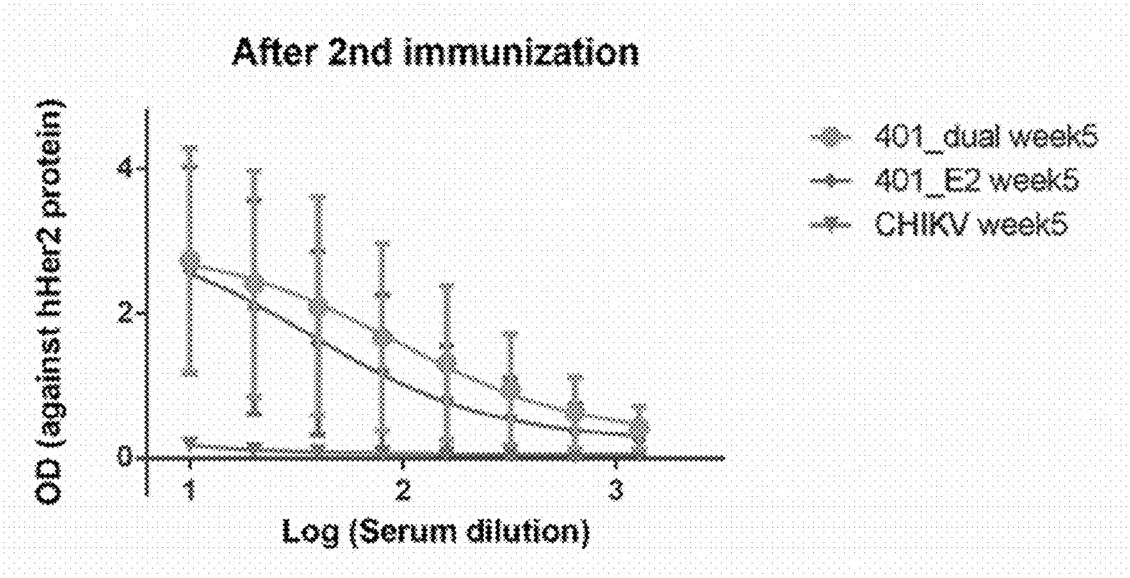
FIG. 16 shows results of ELISA, indicating that E2- and E3-inserted VLP has higher titer than E2-inserted VLP.

FIG. 16 shows that CHIKV VLP comprising hHER2 antigen #401 in E2 or in both E2 and E3 (dual) generated antibody against hHER2 protein, and dual inserted VLP, i.e. antigen was inserted in both E2- and E3-, could provide higher titer than VLP whose antigen was inserted into E2.

Example 15: Preparation of Chikungunya Virus (CHIKV)-Virus Like Particle Comprising a Viral Structural Protein and hHER2 Antigen The following polypeptides derived from hHER2 protein (GENBANK number: NM_001005862) and derivatives were used for preparing a CHIKV-VLP comprising hHER2 antigen.

```
404 (hHer2 original):
sgg yvnarhgl ggs

404-1:
sggcgyvnarhglgcggs

409 (hHer2 original):
sgg ykdppfcv ggs

(409-1):
sgg ykdppfgv ggs
```

Those amino acid sequences are corresponding to SEQ ID NOs. 128, 129, 130 and 131.

SGG is the N terminal linker and GGS is the C terminal linker for the antigen.

The respective polynucleotides were inserted between the codons encoding H at 321-position and S at 326-position of SEQ ID NO: 2 to construct a plasmid for expressing Chikungunya viral structural protein where the hHER2-derived peptide is inserted into E3 of Chikungunya viral structural protein.

The respective polynucleotides was inserted between the codons encoding Ser at 531-position and Asn at 532-position of SEQ ID NO: 2 to construct a plasmid for expressing Chikungunya viral structural protein where the hHER2-derived peptide is inserted into E2 of Chikungunya viral structural protein.

Likewise, the respective polynucleotides were inserted both E2 and E3 of chkungunya viral structural protein.

According to the same manner described in EXAMPLE 6, the Chikungunya virus like particle comprising hHER2 was prepared and purified. The expression of VLP comprising hHER2 that was inserted in E2, E3 or dual (both E2 and E3) of the CHIKV viral structural protein was confirmed by Western Blot using anti CHIKV antibody.

Example 16: Preparation of Chikungunya Virus (CHIKV)-Virus Like Particle Comprising a Viral Structural Protein and BTLA Antigen The polypeptide of hBTLA (383: SGGCKLNGTTCGGS (SEQ ID NO: 132), derived from GENBANK number: NM_001085357) was used for preparing a CHIKV-VLP comprising hBTLA antigen. SGG is the N terminal linker and GGS is the C terminal linker for the antigen.

The polynucleotide coding for the peptide was inserted between the codons encoding H at 321-position and S at 326-position of SEQ ID NO: 2 to construct a plasmid for expressing Chikungunya viral structural protein where the hBTLA-derived peptide is inserted into E3 of the Chikungunya viral structural protein.

According to the same manner described in EXAMPLE 6, the Chikungunya virus like particle comprising hBTLA antigen was prepared and purified.

Figure 17:
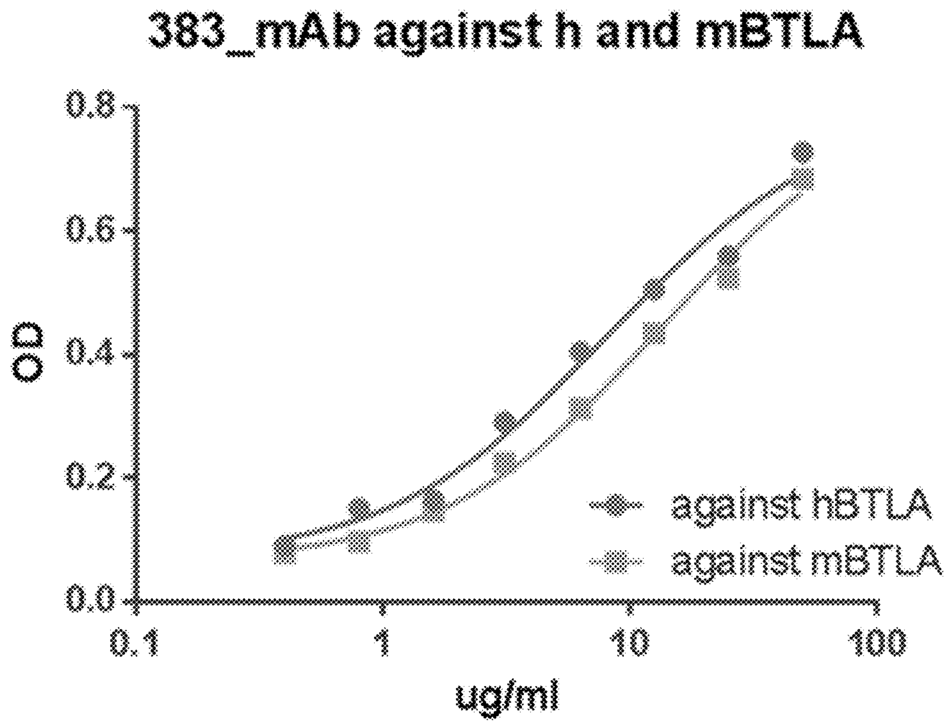
FIG. 17 shows that monoclonal antibody was obtained by using CHIKV-VLP comprising hBTLA antigen.

Monoclonal antibody was prepared by a conventional procedure from mince immunized with thus obtained VLP. The property of the monoclonal antibody to bind the antigen was measured by ELISA coated with BTLA proteins. FIG. 17 shows that CHIKV VLP comprising BTLA antigen could generate monoclonal antibody that binds to both mouse BTLA (mBTLA) and human BTLA (hBTLA) proteins.

Example 17: Preparation of Chikungunya (CHIKV)-Virus Like Particle Comprising a Viral Structural Protein and HVEM Antigen The following of human HVEM peptides (hHVEM, derived from GENBANK number: NM_001297605) were used for preparing a CHIKV-VLP comprising hHVEM antigen.

```
354:
                                    (SEQ ID NO: 133)
SGGCVKEASGELTGTVCGGS

356:
                                    (SEQ ID NO: 134)
SGGCYRVKEASGELTGTVSEPCGGS

362:
                                    (SEQ ID NO: 135)
SGGCSRNSSRTENAVCGGS

372:
                                    (SEQ ID NO: 136)
SGGCQMSDPAMGLRSRNCGGS
```

SGG is the N terminal linker and GGS is the C terminal linker for the antigen. The polynucleotide coding for the peptide was inserted between the codons encoding H at 321-position and S at 326-position of SEQ ID NO: 2 to construct a plasmid for expressing Chikungunya viral structural protein where the hHVEM-derived peptide is inserted into E3 of Chikungunya viral structural protein.

Figure 18:
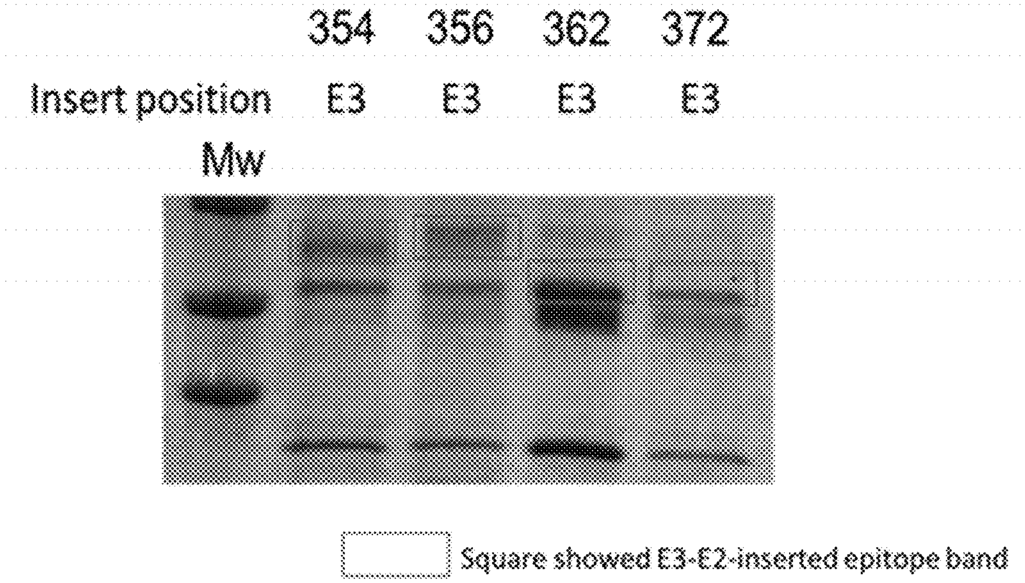
FIG. 18 shows result of western blotting indicating that human hHVEM inserted VLPs were produced when those antigens were inserted into E3.

According to the same manner described in EXAMPLE 6, the Chikungunya virus like particle comprising hHHVEM was prepared and purified. The expression of VLP comprising hHVEM conjugated with CHIKV structural polypeptide was confirmed (see FIG. 18).

Example 18: Expression of Immature CHIKV VLP from Stable Cell Line

The transfected cell line that expresses immature VLP obtained in EXAMPLE 8 was prepared.

1. 293F cells were transfected with an expression vector used in Example 8 that contains a selection marker such as hygromycin B.

2. The transfected cells were incubated for one day. 3. The transfected cells were cultured in a selection medium containing Hygromycin at 150-200 ug/ml for 1-2 weeks.

4. The cells that could grow and be split at least once in the selection medium were chosen.

5. A single cell was isolated and cloned. Then, the cells were confirmed to secrete the VLP in the supernatants by western blotting.

Figure 19:
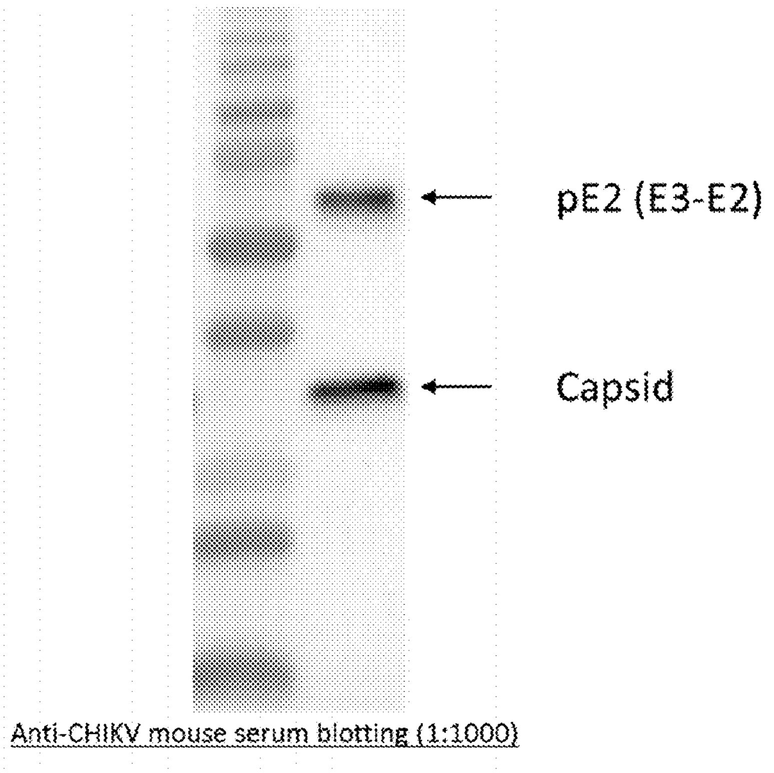
FIG. 19 shows that a cell line that express immature Chikungunya VLP whose furin site in the E3 envelope protein is modified could generate the immature VLP even after 3 months culture.

The cloned cells were cultured for 3 months in a medium comprising sodium butyrate, supernatant of the culture was obtained and the immature VLP in the supernatant was confirmed. Result is shown in FIG. 19. This data shows that the obtained cell line was stable and could continuously generate immature VLP for long term.

Example 19: Protection Against Tumor by PD-L1 VLP

PD-L1 VLP obtained according to Example 4 was used. The mice (n=10 per group) were injected with PBS (control) or PD-L1 VLP at week 0, 3, 6 and 9.

Figure 20:
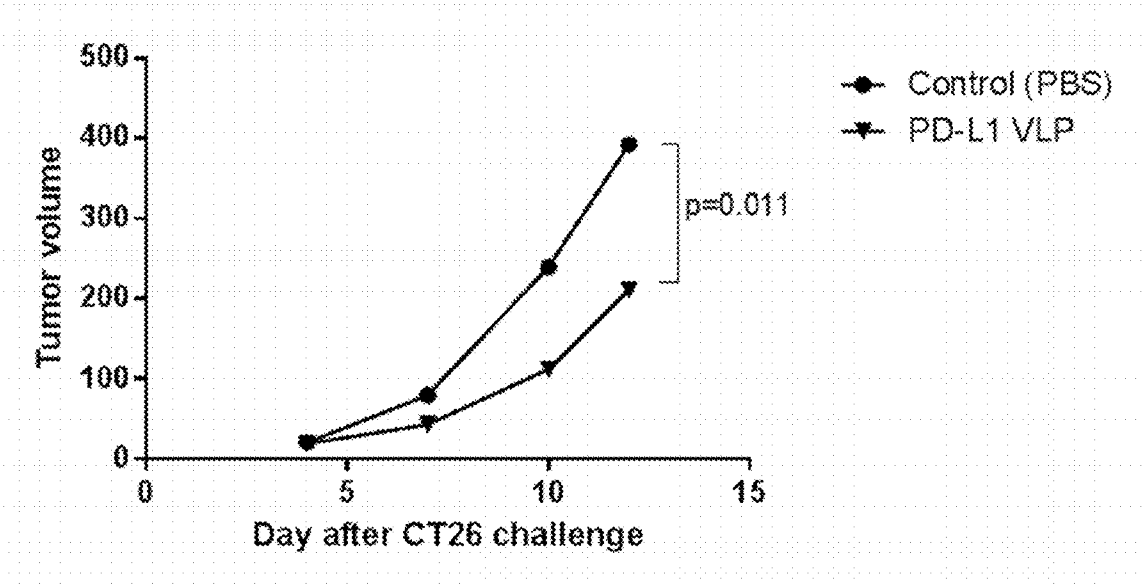
FIG. 20 shows that mouse PD-L1 inserted VLP was effectively protect mouse from tumor.

The mice were challenged with CT26 cell line (1×10^6 cells) at week 8. The tumor sizes were measured. FIG. 20 shows that PD-L1 VLP protects the mice against tumor.

Figure 21:
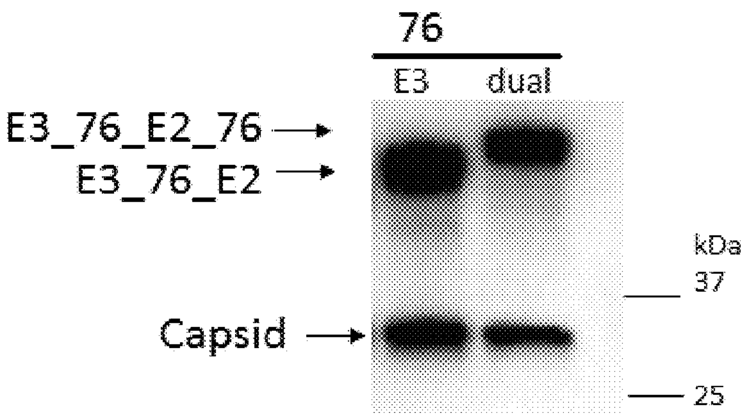
FIG. 21 shows result Western Blot indicating that CHIKV-VLP CSP repeat antigen inserted VLPs were prepared.

Example 20: Preparation of a Pharmaceutical Composition Comprising CHikungunya Virus (CHIKV) Like Particle Comprising a Viral Structural Protein and Malaria Antigen which is Inserted Both in Envelope Protein E2 and E3 of the Viral Structural Protein Chikungunya viral structural protein comprising Malaria CSP 14× repeat antigen 76 (14×NPNA) in only E3 or in both E2 and E3 was expressed in 293F cells in the similar manner according to the previous Examples (CHIKV viral structural protein containing CSP 14× repeat antigen 76 in E2 and E3 is SEQ ID NO: 103 and expression vector for the viral structural protein is SEQ ID NO: 104). The Chikungunya virus like particle was prepared and purified in the similar manner as the previous Examples. The expression of VLP comprising the CSP repeat antigen 76 conjugated with CHIKV structural polypeptide was confirmed by Western Blot against CHIKV-VLP immunized monkey serum. See FIG. 21.

To prepare a pharmaceutical composition which is a vaccine composition, 80 μg of the prepared particles was mixed with 1 ml of Sucrose Phosphate Solution, pH 7.2, Endotoxin Free (Teknova, SP buffer).

Figure 22:
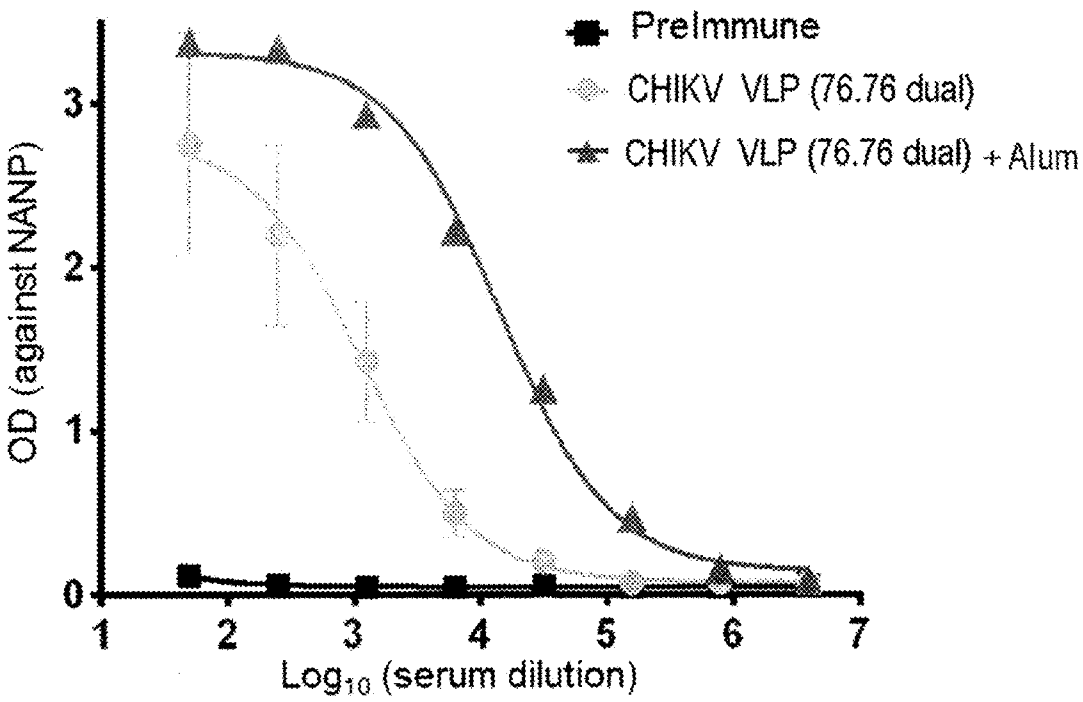
FIG. 22 shows malaria CSP repeat antigen 76 inserted VLP stimulated the production of anti CSP antigen antibodies in mice.

Groups of BALB/c mice (n=4) were immunized intramuscularly three times at a 3 weeks' interval with 15 μg of thus obtained VLP, with or without Alhydrogel 2% adjuvant. The sera were collected 2 weeks after the third dose. The serum anti-CSP NANP titer was measured by ELISA using $(NANP)_6$ peptide for coating. The results of this experiment are presented in FIG. 22. VLP containing CSP epitope NANP stimulated the production of anti-CSP NANP antibodies and the response was enhanced by the use of Alum.

What is claimed is:

1. An alphavirus virus-like particle, wherein said virus-like particle comprises an alphaviral structural protein that comprises an envelope protein E3, wherein said envelope protein E3 is modified to contain at least one foreign antigen inserted into furin cleavage site thereof.

2. The virus-like particle according to claim 1, wherein the alphaviral structural protein is a Chikungunya virus (CHIKV) structural protein or a Venezuelan equine encephalitis virus (VEEV) structural protein.

3. The virus-like particle according to claim 2, wherein the alphaviral structural protein is a viral structural protein of Chikungunya virus strain 37997 or strain OPY-1, or is a viral structural protein of Venezuelan equine encephalitis virus strain TC-83.

4. The virus-like particle according to claim 1, which comprises capsid, envelope protein E1, envelope protein E2 and envelope protein E3.

5. The virus-like particle according to claim 1, which further comprises an envelope protein E2, and wherein the at least one antigen is further inserted into said envelope protein E2.

6. The virus-like particle according to claim 1, wherein the at least one antigen is inserted between residues corresponding to residues 321 and 326 of SEQ ID NO: 1, residues 321 and 326 of SEQ ID NO: 2 or residues 330 and 335 of SEQ ID NO: 3.

7. The virus-like particle according to claim 1, wherein the at least one antigen is an antigen from *Plasmodium falciparum* circumsporozoite protein, PD-1, PD-L1, CTLA-4, DISC1, IL-2, HER2, BTLA or HVEM.

8. The virus-like particle according to claim 7, wherein a peptide selected from (1) and (2) is inserted into the envelope E3 protein:

(1) (NPNA)n (n=4-30) (SEQ ID NO. 140), and (2) an amino acid sequence selected from SEQ ID NOs. 6-9 and 15-29.

9. The virus-like particle according to claim 1, wherein the insertion of said at least one antigen into said furin cleavage site prevents cleavage of said site by furin.

10. An isolated nucleic acid molecule comprising a nucleotide sequence encoding the virus like particle according to claim 1.

11. A vector comprising the nucleic acid molecule according to claim 10, wherein the vector optionally comprises an expression control sequence operably linked to the nucleic acid molecule.

12. A composition comprising:

(a) the virus-like particle according to claim 1; and (b) a pharmaceutically acceptable carrier.

13. A cell line expressing a viral structural protein which comprises an alternation/mutation to the amino acid sequence at the furin site in the envelope protein E3 according to claim 1.

14. The cell line according to claim 13, wherein the cell line is a stable cell line.

15. The cell line according to claim 13, wherein the E3 is removed by a protease.

16. The virus-like particle according to claim 3, wherein the viral structural protein is from one of SEQ ID NOs: 1-3.

* * * * *